(12) United States Patent
Ismagilov et al.

(10) Patent No.: US 11,827,944 B2
(45) Date of Patent: *Nov. 28, 2023

(54) ANTIBIOTIC SUSCEPTIBILITY OF MICROORGANISMS AND RELATED COMPOSITIONS, METHODS AND SYSTEMS

(71) Applicant: CALIFORNIA INSTITUTE OF TECHNOLOGY, Pasadena, CA (US)

(72) Inventors: Rustem F. Ismagilov, Altadena, CA (US); Emily S. Savela, Pasadena, CA (US); Nathan Schoepp, Pasadena, CA (US); Eric J. Liaw, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 590 days.

This patent is subject to a terminal disclaimer.

(21) Appl. No.: 16/158,233

(22) Filed: Oct. 11, 2018

(65) Prior Publication Data

US 2019/0194726 A1   Jun. 27, 2019

Related U.S. Application Data

(60) Provisional application No. 62/722,124, filed on Aug. 23, 2018, provisional application No. 62/571,128, filed on Oct. 11, 2017.

(51) Int. Cl.
   *C12Q 1/689* (2018.01)
   *C12Q 1/6806* (2018.01)
   *C12Q 1/6851* (2018.01)

(52) U.S. Cl.
   CPC .......... *C12Q 1/689* (2013.01); *C12Q 1/6806* (2013.01); *C12Q 1/6851* (2013.01)

(58) Field of Classification Search
   None
   See application file for complete search history.

(56) References Cited

U.S. PATENT DOCUMENTS

| | | |
|---|---|---|
| 5,789,173 A | 8/1998 | Peck et al. |
| 6,153,400 A | 11/2000 | Matsumura et al. |
| 6,391,577 B1 | 5/2002 | Mikkelsen et al. |
| 7,728,119 B2 | 6/2010 | Nakamura et al. |
| 8,476,063 B2 | 7/2013 | Jovanovich et al. |
| 9,133,498 B2 | 9/2015 | Kwon et al. |
| 9,415,392 B2 | 8/2016 | Ismagilov et al. |
| 9,447,461 B2 | 9/2016 | Ismagilov et al. |
| 9,464,319 B2 | 10/2016 | Ismagilov et al. |
| 9,493,826 B2 | 11/2016 | Ismagilov et al. |
| 9,546,358 B2 | 1/2017 | Tanner et al. |
| 9,687,845 B2 | 6/2017 | Weibel et al. |
| 9,803,237 B2 | 10/2017 | Ismagilov et al. |
| 9,808,798 B2 | 11/2017 | Ismagilov et al. |
| 9,822,356 B2 | 11/2017 | Ismagilov et al. |
| 11,168,347 B2 | 11/2021 | Ismagilov et al. |
| 2005/0095665 A1 | 5/2005 | Williams et al. |
| 2009/0181395 A1 | 7/2009 | Becker et al. |
| 2011/0269130 A1 | 11/2011 | Shi et al. |
| 2012/0010091 A1 | 1/2012 | Linnarson |
| 2012/0028342 A1 | 2/2012 | Ismagilov et al. |
| 2012/0100551 A1 | 4/2012 | Kojima et al. |
| 2012/0329038 A1 | 12/2012 | Ismagilov et al. |
| 2013/0052653 A1 | 2/2013 | Stein et al. |
| 2013/0190196 A1 | 7/2013 | Onderdonk et al. |
| 2013/0281316 A1 | 10/2013 | Ismagilov et al. |
| 2013/0288249 A1 | 10/2013 | Gullberg et al. |
| 2013/0309679 A1 | 11/2013 | Ismagilov et al. |
| 2014/0308663 A1 | 10/2014 | Yonekawa et al. |
| 2014/0323340 A1 | 10/2014 | Goldberg et al. |
| 2014/0336064 A1 | 11/2014 | Ismagilov et al. |
| 2015/0104789 A1 | 4/2015 | Haake et al. |
| 2015/0159205 A1 | 6/2015 | Narayanan et al. |
| 2015/0225803 A1 | 8/2015 | Ismagilov et al. |
| 2015/0247190 A1 | 9/2015 | Ismagilov et al. |
| 2015/0267266 A1 | 9/2015 | Soetaert et al. |
| 2016/0138072 A1 | 5/2016 | Talebpour et al. |
| 2016/0160268 A1 | 6/2016 | Haake et al. |
| 2016/0263577 A1 | 9/2016 | Ismagilov et al. |
| 2016/0288121 A1 | 10/2016 | Ismagilov et al. |
| 2016/0362734 A1 | 12/2016 | Ismagilov et al. |
| 2017/0225161 A1 | 8/2017 | Begolo et al. |
| 2018/0105859 A1 | 4/2018 | Ismagilov et al. |
| 2019/0376116 A1 | 12/2019 | Haake et al. |
| 2020/0370087 A1 | 11/2020 | Rangsten et al. |
| 2021/0301326 A1 | 9/2021 | Ismagilov et al. |

(Continued)

FOREIGN PATENT DOCUMENTS

| | | |
|---|---|---|
| CN | 206089692 U | 4/2017 |
| EP | 3695009 A1 | 8/2020 |

(Continued)

OTHER PUBLICATIONS

Hasan, Depletion of Human DNA in Spiked Clinical Specimens for Improvement of Sensitivity of Pathogen Detection by Next-Generation Sequencing, J Clin Microbiol, 54(4): 919-927, 2016. (Year: 2016).*

Bhattacharyya, Rapid Phenotypic Antibiotic Susceptibility Testing through RNA Detection, Open Form Infections Diseases, 4(1): p. S33, Oct. 4, 2017. (Year: 2017).*

Caraguel, Selection of a cutoff value for real-time polymerase chain reaction results to fit a diagnostic purpose: analytical and epidemiologic approaches, J Vet Diagn Invest, 23, 2-14, 2011. (Year: 2011).*

Heera, Efficient extraction of small and large RNAs in bacteria for excellent total RNA sequencing and comprehensive transcriptome, BMC Res Notes, 8:754, pp. 1-11, 2015. (Year: 2015).*

(Continued)

*Primary Examiner* — Angela M. Bertagna
*Assistant Examiner* — Carolyn L Greene
(74) *Attorney, Agent, or Firm* — Steinfl + Bruno LLP

(57) ABSTRACT

Provided herein is an antibiotic susceptibility test and related compositions, methods and systems based on detection of a nucleic acid from a target microorganism in a sample in the presence or absence of a lysis treatment of the sample.

29 Claims, 46 Drawing Sheets

Specification includes a Sequence Listing.

(56) References Cited

U.S. PATENT DOCUMENTS

| | | |
|---|---|---|
| 2022/0282304 A1 | 9/2022 | Ismagilov et al. |
| 2023/0183818 A1 | 6/2023 | Ismagilov et al. |

FOREIGN PATENT DOCUMENTS

| | | |
|---|---|---|
| JP | 2001299388 A | 10/2001 |
| KR | 101779038 B1 | 9/2017 |
| WO | 2010/111265 A1 | 9/2010 |
| WO | 2010/117620 A2 | 10/2010 |
| WO | 2012/148477 A1 | 11/2012 |
| WO | 2013/072069 A1 | 5/2013 |
| WO | 2013/130875 A1 | 9/2013 |
| WO | 2013/159116 A1 | 10/2013 |
| WO | 2013/159117 A1 | 10/2013 |
| WO | 2014/055963 A1 | 4/2014 |
| WO | 2014/172688 A1 | 10/2014 |
| WO | 2015/009967 A1 | 1/2015 |
| WO | 2015/013324 A1 | 1/2015 |
| WO | 2015/058008 A2 | 4/2015 |
| WO | 2015/084458 A2 | 6/2015 |
| WO | 2016/011280 A1 | 1/2016 |
| WO | 2016/085632 A2 | 6/2016 |
| WO | 2017/127727 A1 | 7/2017 |
| WO | 2018/111630 A2 | 6/2018 |
| WO | 2019/075264 A1 | 4/2019 |
| WO | 2019/075624 A1 | 4/2019 |
| WO | 2020/028718 A1 | 2/2020 |
| WO | 2022/183127 A1 | 9/2022 |

OTHER PUBLICATIONS

Schoepp (Rapid pathogen-specific phenotypic antibiotic susceptibility testing using digital LAMP quantification in clinical samples, Science Translational Medicine, 9: 1-12, 2017. (Year: 2017).*

Roth, Bacterial Viability and Antibiotic Susceptibility Testing with SYTOX Green Nucleic Acid Stain, Applied and Environmental Microbiology, 63(6): 2421-2431, 1997. (Year: 1997).*

Aellen S. et al., "Detection of Live Antibiotic-Killed Bacteria by Quantitative Real-Time PCR of Specific Fragments of rRNA" Antimicrobial Agents and Chemotherapy, Jun. 2006, 50(6) pp. 1913-1920.

Chen Y., et al., "Polymeric Sequence Probe for Single DNA Detection." Analytical Chemistry 83.19 (Aug. 2011): 7250-7254.

Extended European Search Report for EP Application No. 18866873.5 filed on Oct. 11, 2018 on behalf of California Institute of Technology dated Jul. 13, 2021 9 pages.

Hebeler, B.H. et al., "Autolysis of Neisseria gonorrhoeae." J Bacteriol., vol. 122, No. 2, 385-392 (May 1975).

Kirkcaldy RD, et al., "Neisseria gonorrhoeae Antimicrobial Susceptibility Surveillance—The Gonococcal Isolate Surveillance Project, 27 Sites, United States, 2014." MMWR Surveill. Summ., Jul. 15, 2016, vol. 65, No. 7, pp. 1-19.

Ota Y, et al., "A rapid and simple detection method for phenotypic antimicrobial resistance in Escherichia coli by loop mediated isothermal amplification" Journal Medical Microbiology, (Jan. 2019); 68:169-177.

PCT International Search Report & Written Opinion, International Application No. PCT/US2015/059344, dated Jul. 12, 2016, 15 Pages.

PCT International Search Report and Written Opinion for PCT/US17/53338, dated Jan. 30, 2018, 19 pages.

PCT International Search Report and Written Opinion for PCT/US2017/061403, dated Feb. 13, 2018, 11 pages.

Savela E. S., et al., "Sufactant-enhanced DNA accessibility to nuclease accelerates phenotypic Beta-lactam antibiotic susceptibility testing of Neisseria gonorrhoeae" PLOS Biology, 18(3): Mar. 2020, 31 pages.

Schoepp N. G., et al., "Differential DNA accessibility to polymerase enables 30-minute phenotypic Beta-lactam antibiotic susceptibility testing of carbapenem-resistant Enterobacteriaceae" PLOS Biology, 18(3): Mar. 2020, 23 pages.

Waldeisen J. R., et al., "A Real-Time PCT Antibiogram for Drug-Resistant Sepsis" PLoS ONE, Dec. 2011, vol. 6, Issue 12, 6 pages.

Advisory Action n for U.S. Appl. No. 15/715,086, filed Sep. 25, 2017 on Behalf of California Institute of Technology. Notification Date: Oct. 14, 2020. 6 Pages.

Ahn H. et al., "Single-Step Recombinase Polymerase Amplification Assay Based on a Paper Chip for Simultaneous Detection of Multiple Foodborne Pathogens." Anal Chem, (2018).

Allan-Blitz L.T. et al., "Wild-Type Gyrase A Genotype of Neisseria gonorrhoeae Predicts In Vitro Susceptibility to Ciprofloxacin: A Systematic Review of the Literature and Meta-Analysis." Sex Transm Dis44, 261-265 (2017).

Allen VG, et al., "Neisseria gonorrhoeae treatment failure and susceptibility to cefixime in Toronto, Canada."JAMA 309, 163-170 (2013).

Assmann, et al., "Identification of vancomycin interaction with Enterococcus faecal is within 30 min of interaction time using Raman spectroscopy", Anal. Bioanal. Chem., vol. 407, 2015, pp. 8343-8352.

Avesar, J., et al., "Rapid phenotypic antimicrobial susceptibility testing using nanoliter arrays." Proceedings of the National Academy of Sciences 114(29): E5787. (2017).

B. Sun, et al., "Measuring fate and rate of single-molecule competition of amplification and restriction digestion, and its use for rapid genotyping tested with hepatitis C viral RNA." Angew. Chem. Int. Ed. Engl. 53, 8088-8092 (2014).

Baker, et al., "Review and re-analysis of domain-specific 16S primers" Journal of Microbiological Methods, 541-555, 2003.

Balashov S. et al., "Multiplex bead suspension array for screening Neisseria gonorrhoeae antibiotic resistance genetic determinants in noncultured clinical samples." J Mol. Diagn 15, 116-129 (2013).

Baltekin, 0., et al., "Antibiotic susceptibility testing in less than 30 min using direct single-cell imaging." Proc Natl Acad Sci US A 114(34): 9170-9175. (2017).

Banoo, S., et al., "Evaluation of diagnostic tests for infectious diseases: general principles." Nat Rev Microbiol 4(9 Suppl): S21-31. (2006).

Barczak, A. K., "RNA signatures allow rapid identification of pathogens and antibiotic susceptibilities," Proc Natl Acad Sci US A, Apr. 17, 2012, vol. 109, No. 16, pp. 6217-6222.

Bard J.D. "Why Can't We Just Use PCR? The Role of Genotypic versus Phenotypic Testing for Antimicrobial Resistance Testing." Clinical Microbiology Newsletter 40, 87-95 (2018).

Baumann, E., et al., "Hemolysis of human erythrocytes with saponin affects the membrane structure." Act Histochem 102(1): 21-35. (2000).

Bernabeu S. et al., "Evaluation of the beta-CARBA test, a colorimetric test for the rapid detection of carbapenemase activity in Gram-negative bacilli." J Antimicrob Chemother 72, 1646-1658 (2017).

Bernhardt, et al. "Detection of Bacteria in Blood by Centrifugation and Filtration" J. Clinical Microbiology, vol. 29, No. 3, 1991, pp. 422-425.

Besant, et al. "Rapid electrochemical phenotypic profiling of antibiotic-resistant bacteria" Lab Chip, vol. 15, May 2015, pp. 2799-2807.

Beuving, et al. "Antibiotic Susceptibility Testing of Grown Blood Cultures by Combining Culture and Real- Time Polymerase Chain Reaction Is Rapid and Effective" PLoS ONE, vol. 6, No. 12, 2011, pp. e27689.

Bhattacharyya, R. P., et al. "Simultaneous detection of genotype and phenotype enables rapid and accurate antibiotic susceptibility determination." Nature Medicine 25(12): 1858-1864. (2019).

Blank, S. et al., "Neisseria gonorrhoeae—Rising Infection Rates, Dwindling Treatment Options." N Engl J Med 379(19): 1795-1797. (2018).

Blattner, et al., "The Complete Genome Sequence of Escherichia coli K-12" Science, vol. 277, 1997, pp. 1453-1462.

Boedicker, et al. "Micofluidic Confinement of Single Cells of Bacteria in Small Volumes Initiates High- Density Behavior of Quorum Sensing and Growth and Reveals Its Variability" Agnew. Chem. Int. Ed., vol. 48, 2009, pp. 5908-5911. Including Supporting Information.

(56) References Cited

OTHER PUBLICATIONS

Boedicker, J. et al., "Detecting Bacteria and Determining Their Susceptibility to Antibiotics by Stochastic Confinement in Nanoliter Droplets Using Plug-Based Microfluidics," Lab on a Chip, vol. 8, No. 8, Jan. 1, 2008, pp. 1265-1272.
Bogaerts P. et al., "Evaluation of the BYG Carba Test, a New Electrochemical Assay for Rapid Laboratory Detection of Carbapenemase-Producing Enterobacteriaceae." J Clin Microbiol 54, 349- 358 (2016).
Bolan G.A., et al., "The emerging threat of untreatable gonococcal infection." N Engl J Med 366, 485-487 (2012).
Bou G, et al. "Fast assessment of resistance to carbapenems and ciprofloxacin of clinical strains of Acinetobacter baumanii." J Clin Microbiol 50, 3609-3613 (2012).
Brunschede, et al. "Establishment of exponential growth after a nutritional shift-up in *Escherichia coli* Bir: Accumulation of deoxyribonucleic acid, ribonucleic acid, and protein" J. Bacteriology, vol. 129, No. 2, 1977, pp. 1020-1033.
Buckley C, et al. "Real-time PCR detection of Neisseria gonorrhoeae susceptibility to penicillin." J Antimicrob Chemother 71, 3090-3095 (2016).
Burnham C.A. et al., "Rapid ertapenem susceptibility testing and Klebsiella pneumoniae carbapenemase phenotype detection in Klebsiella pneumoniae isolates by use of automated microscopy of immobilized live bacterial cells." J Clin Microbiol 52, 982-986 (2014).
Cady N. , "Quantum Dot Molecular Beacons for DNA Detection" Methods Mol Biol 554:367-79, 2009.
Cai S. "Phosphorothioated Primers Leads to Loop-Mediated Isothermal Amplification at Low Temperatures." Anal Chem 90, 8290-8294 (2018).
Cansizoglu, M. F., et al. "Rapid ultrasensitive detection platform for antimicrobial susceptibility testing." PLOS Biology 17(5): e3000291. (2019).
Cartron, et al. "Feo—Transport of ferrous iron into bacteria" BioMetals, vol. 19, 2006, pp. 143-157.
CDC—Agar Dilution Antimicrobial Susceptibility Testing. (2013).
CDC. Antibiotic Resistance Threats in the United States. (2013).
CDC. "Antibiotic/Antimicrobial Resistance: Biggest Threats and Data." (2019).
CDC. Sexually Transmitted Disease Surveillance. (2017).
CDC. Sexually Transmitted Diseases Treatment Guidelines. In: Morbidity and Mortality Weekly Report (2015).
CDDEP. "State of the World's Antibiotics." CDDEP: Washington, DC, (2015).
Cerqueria GC, et al. "Multi-institute analysis of carbapenem resistance reveals remarkable diversity, unexplained mechanisms, and limited clonal outbreaks." Proc Natl Acad Sci U S A 114, 1135-1140 (2017).
Chang YY, et al. "Clinical features of patients with carbapenem nonsusceptible Klebsiella pneumoniae and *Escherichia coli* in intensive care units: a nationwide multicenter study in Taiwan." J Microbiol Immunol Infect 48, 219-225 (2015).
Chantell C., "Multiplexed automated digital microscopy for rapid identification and antimicrobial susceptibility testing of bacteria and yeast directly from clinical samples," Clinical Microbiology Newsletter, Oct. 15, 2015, vol. 37, No. 20, pp. 161-167.
Charalampous, T., et al. "Nanopore metagenomics enables rapid clinical diagnosis of bacterial lower respiratory infection." Nature Biotechnology 37(7): 783-792. (2019).
Chen L. et al., "Direct-qPCR Assay for Coupled Identification and Antimicrobial Susceptibility Testing of Neisseria gonorrhoeae." ACS Infect Dis 4, 1377-1384 (2018).
Chern E.C. et al., "Comparison of quantitative PCR assays for *Escherichia coli* targeting ribosomal RNA and single copy genes." Lett Appl Microbiol 52, 298-306 (2011).
Chesson H. W. et al., "An Illustration of the Potential Health and Economic Benefits of Combating Antibiotic-Resistant Gonorrhea." Sex Transm Dis 45, 250-253 (2018).

Cho S. et al., "Smartphone-based, sensitive microPAD detection of urinary tract infection and gonorrhea." Biosens Bioelectron 74, 601-611 (2015).
Choi, J., et al., "A rapid antimicrobial susceptibility test based on single-cell morphological analysis," Sci Transl Med., Dec. 17, 2014, vol. 6, No. 267, 267ral74, pp. 1-15.
Churski, et al. "Rapid screening of antibiotic toxicity in an automated microdroplet system" Lab Chip, vol. 12, 2012, pp. 1629-1637.
Cirz, et al. "Inhibition of Mutation and Combating the Evolution of Antibiotic Resistance" PLoS Biology, vol. 3, No. 6, 2005, p. e1 76.
Cissell et al., "Resonance energy transfer methods of RNA detection" Anal Bioanal Chem 393(1):125-35, 2009.
Clifford, et al., "Detection of Bacterial 16S rRNA and Identification of Four Clinically Important Bacteria by Real-Time PCR" PLoS ONE, e48558, 2012.
CLSI. "M07-A10; Methods for Dilution Antimicrobial Susceptibility Testing for Bacteria That Grow Aerobically; Approved Standard-Tenth Edition." Clinical and Laboratory Standards Institute, 950 West Valley Road, Suite 2500, Wayne, Pennsylvania 19087 USA (2015).
CLSI. "M100-S25 Performance Standards for Antimicrobial Susceptibility Testing." CLSI 35, (2015).
Communication of European publication number and information on the application of Article 67(3) EPC for EP Application No. 18866873 filed on behalf on California Institute of Technology dated Jul. 22, 2020.
Cortegiani A, et al. "Use of Cepheid Xpert Carba-R(R) for Rapid Detection of Carbapenemase-Producing Bacteria in Abdominal Septic Patients Admitted to Intensive Care Unit." PLoS One 11, e0160643 (2016).
Couturier and Rocha. "Replication-associated gene dosage effects shape the genomes of fast-growing bacteria but only for transcription and translation genes" Molecular Microbiology, vol. 59, No. 5, 2006, pp. 1506-1518.
Craw P. et al., "Isothermal nucleic acid amplification technologies for point-of-care diagnostics: a critical review," Lab Chip, 2012, 12, 2469-2486.
Daher R.K. "Recombinase Polymerase Amplification for Diagnostic Applications." Clin Chem 62, 947-958 (2016).
Davies, J., et al., "Origins and evolution of antibiotic resistance," Microbiol Mol Biol Rev., Sep. 2010, vol. 74, No. 3, pp. 417-433.
Demchick P. et al., "The permeability of the wall fabric of *Escherichia coli* and *Bacillus subtilis*." J Bacteriol 178, 768-773 (1996).
Deshayes S, et al. "Designing Hybrid Antibiotic Peptide Conjugates to Cross Bacterial Membranes." Bioconjug Chem 28, 793-804 (2017).
Dijkstra A.J. "Peptidoglycan as a barrier to transenvelope transport." Journal of Bacteriology 178, 5555-5562 (1996).
Dillard J.P. et al., "A peptidoglycan hydrolase similar to bacteriophage endolysins acts as an autolysin in Neisseria gonorrhoeae." Molecular Microbiology 25, 893-901 (1997).
Dona V, et al. "Mismatch Amplification Mutation Assay-Based Real-Time PCR for Rapd Dection of Neisseria gonorrhoeae and Antimicrobial Resistance Determinants in Clinical Specimens."*J Clin Microbiol*56,(2018).
Donachie and Blakely. "Coupling the initiation of chromosome replication to cell size in *Escherichia coli*" Cur. Opin. Microbioloov, vol. 6, 2003, pp. 146-150.
Douglas, I.S., et al., "Rapid automated microscopy for microbiological surveillance of ventilator- associated pneumonia," Am J Respir Crit Care Med., Mar. 1, 2015, vol. 191, No. 5, pp. 566-573.
Drlica and Zhao. "DNA gyrase, topoisomerase IV, and 4-quinolones" Microbial. Mol. Biology Rev., vol. 61, No. 3, 1997, pp. 377-392.
Dwyer, et al. "Antibiotics induce redox-related physiological alterations as part of their lethality" PNAS, vol. 111, No. 20, May 2014, pp. E1OO-E109.
Ertl, P., et al., "Rapid antibiotic susceptibility testing via electrochemical measurement of ferricyanide reduction by *Escherichia coli* and Clostridium sporogenes," Anal Chem., Oct. 15, 2000, vol. 72, No. 20, pp. 4957-4964.

(56) References Cited

OTHER PUBLICATIONS

Etayash, H., et al., "Microfluidic cantilever detects bacteria and measures their susceptibility to anitbiotics in small confined volumes." Nat Commun 7: 12947. (2016).
Eucast. "European Committee on Antimicrobial Susceptibility Testing: Breakpoint Tables for Interpretation of MICs and Zone Diameters" (ver. 7.1). (2017).
European Patent Office, Extended European Search Report, EP Patent Application No. 15862888.3, dated Jul. 9, 2018, pages.
Eyre DW, et al., "Gonorrhoea treatment failure caused by a Neisseria gonorrhoeae strain with combined ceftriaxone and high-level azithromycin resistance", England, Feb. 2018. Euro Surveill 23.
Faria-Ramos I, et al. "A Novel flow cytometric assay for rapid detection of extended-spectrum beta-lactamases." Clin Microbiol Infect 19, E8-E15 (2013).
FDA. "Evaluation of Automatic Class III Designation for T2Candida Panel and T2Dx Instrument." (2014).
Felix H. "Permeabilized cells." Anal Biochem 120, 211-234 (1982).
Fifer H, et al. "Failure of Dual Antimicrobial Therapy in Treatment of Gonorrhea." N Engl J Med 374, 2504-2506 (2016).
Final Office Action of U.S. Appl. No. 15/715,086, filed Sep. 25, 2017 on behalf of University of California dated May 26, 2020 23 pages.
Fingerhuth S M. et al., "Detection of antibiotic resistance is essential for gonorrhoea point-of-care testing: a mathematical modelling study." BMC Med 15, 142 (2017).
Foerster S,. et al., "A new rapid resazurin-based microdilution assay for antimicrobial susceptibility testing of Neisseria gonorrhoeae." *J Antimicrob Chemother*72, 1961-1968 (2017).
Foerster S. et al., "Time-kill curve analysis and pharmacodynamic modelling for in vitro evaluation of antimicrobials against Neisseria gonorrhoeae." BMC Microbiol 16, 216 (2016).
Fossum, et al. "Organization of sister origins and replisomes during multifork DNA replication in *Escherichia coli*" EMBO Journal, vol. 26, 2007, pp. 4514-4522.
Fredborg, M., et al., "Real-time optical antimicrobial susceptibility testing," J Clin Microbiol., Jul. 2013, vol. 51, No. 7, pp. 2047-2053.
Gaydos CA, et al. "Performance of the Cepheid CT/NG Xpert Rapid PCR Test for Detection of Chlamydia trachomatis and Neisseria gonorrhoeae." *J Clin Microbiol*51, 1666-1672 (2013).
Geiss, et al. "Direct multiplexed measurements of gene expression with color-coded probe pairs" Nature Biotech., vol. 26, No. 3, 2008, pp. 317-325. Including Corrigendum.
Gianecini RA, et al. "Genome-based epidemiology and antimicrobial resistance determinants of Neisseria gonorrhoeae isolates with decreased susceptibility and resistance to extended-spectrum cephalosporins in Argentina in 2011-16." J Antimicrob Chemother, (2019).
Glossary entry for "base pair" in Lodish H, Berk A, Zipursky SL, et al. Molecular Cell Biology. 4th edition. New York: W. H. Freeman; 2000. Available from: https://www.ncbi.nlm.nih.gov/books/NBK21475/, printed as p. 1/1. (Year: 2000).
Glossary entry for "Dalton" in Lodish H, Berk A, Zipursky SL, et al. Molecular Cell Biology. 4th edition. New York: W. H. Freeman; 2000. Available from: https://www.ncbi.nlm.nih.gov/books/NBK21475/, printed as p. 1/1. (Year: 2000).
Glossary entry for "replication origin" in Lodish H, Berk A, Zipursky SL, et al. Molecular Cell Biology. 4th edition. New York: W. H. Freeman; 2000. Available from: https://www.ncbi.nlm.nih.gov/books/NBK21475/, printed as p. 1/1. (Year: 2000).
Grad YH. et al., "Genomic Epidemiology of Gonococcal Resistance to Extended-Spectrum Cephalosporins, Macrolides, and Fluoroquinolones in the United States, 2000-2013." J Infect Dis 214, 1579-1587 (2016).
Guh A.Y. et al. "Epidemiology of Carbapenem-Resistant Enterobacteriaceae in 7 US Communities," 2012-2013. JAMA 314, 1479-1487 (2015).

Hagiwara, et al. "A Genome-Wide View of *Escherichia coli* BasS-BasR Two-component System Implicated in Iron-responses" Bioscience, Biotechnology and Biochemistry, vol. 68, No. 8, 2004, pp. 1758-1767.
Halford, et al. "Rapid Antimicrobial Susceptibility Testing by Sensitive Detection of Precursor rRNA Using a Novel Electrochemical Biosensing Platform" Antimicrobial Agents and Chemotherapy, vol. 57, No. 2, 2013, pp. 936-943.
Hansen, et al., "A Real-Time PCR-Based Semi-Quantitative Breakpoint to Aid in Molecular Identification of Urinary Tract Infections" PLoS ONE, e61439, 2013.
Harrison ST. "Bacterial cell disruption: a key unit operation in the recovery of intracellular products." Biotechnol Adv 9, 217-240 (1991).
Hawkey PM et al., "Carbapenem antibiotics for serious infections." BMJ 344, e3236 (2012).
Hicks J.M. et al., "Recommendations and opinions for the use of point-of-care testing for hospitals and primary care: summary of a 1999 symposium." Clinica Chimica Acta 303, 1-17 (2001).
Hou, et al. "Direct detection and drug-resistance profiling of bacteremias using inertial microfluidics" Lab Chip, vol. 15, 2015, pp. 2297-2307.
Hu C, et al. "Ultra-fast electronic detection of antimicrobial resistance genes using isothermal amplification and Thin Film Transistor sensors." Biosens Bioelectron 96, 281-287 (2017).
Ikeuchi, T., et al. "PCR-based method for rapid and minimized electrochemical detection of mecA gene of methicillin-resistant *Staphylococcus aureus* and methicillin-resistant *Staphylococcus epidermis*," General Medicine: Open Access. 2015, vol. 3, No. 6, pp. 1-5.
Intellectual Property Office of Singapore, Search Report and Invitation to Respond to Written Opinion, Singapore Patent Application No. 11201703695V, dated May 8, 2018, 10 pages.
International Preliminary Report on Patentability for International PCT Application No. PCT/US2019/044748 filed on Aug. 1, 2019 on behalf on California Institute of Technology. dated Feb. 11, 2021. 7 pages.
International Report on Patentability for International Application No. PCT/US2018/055501 filed Oct. 11, 2018, on behalf of California Institute of Technology. dated Apr. 23, 2020. 10 pages.
Iovleva A. et al., "Carbapenem-Resistant Enterobacteriaceae." Clin Lab Med 37, 303-315 (2017).
Jeon, et al. "RstA-Promoted Expression of the Ferrous Iron Transporter FeoB under Iron-Replete Conditions Enhances Fur Activity in Salmonella enterica" J. Bacteriology, vol. 190, No. 2, 2008, pp. 7326-7334.
Jorgensen, J.H., et al., "Antimicrobial susceptiblity testing: a review of general principles and contemporary practices," Clin Infect Dis., Dec. 2009, vol. 49, No. 11, pp. 1749-1755.
Joshi, et al. "*Escherichia coli* sister chromosome separation includes an abrupt global transition with concomitant release of late-splitting intersister snaps" PNAS, vol. 108, No. 7, 2011, pp. 2765-2770.
Kalsi et al. Rapid and sensitive detection of antibiotic resistance on a programmable digital microfluidic platform. Lab on a Chip, vol. 15, pp. 3065-3075, Jun. 18, 2015, including pp. 1/2-2/2 of Supplementary Material. (Year: 2015).
Kang, et al. "An extracorporeal blood-cleansing device for sepsis therapy" Nature Med., vol. 20, No. 10, Oct. 2014, pp. 1211-1216.
Kang, et al. "Rapid detection of single bacteria in unprocessed blood using Integrated Comprehensive Droplet Diqital Detection" Nature Communications, Nov. 2014, pp. 1-10.
Kang, W., et al.. "Ultrafast Parallelized Microfluidic Platform for Antimicrobial Susceptibility Testing of Gram Positive and Negative Bacteria." Analytical Chemistry 91(9): 6242-6249. (2019).
Katz AR, et al. "Cluster of Neisseria gonorrhoeae Isolates With High-level Azithromycin Resistance and Decreased Ceftriaxone Susceptibility," Hawaii, 2016. Clin Infect Dis 65, 918-923 (2017).
Kempf, et al. "Fluorescent In Situ Hybridization Allows Rapid Identification of Microorganisms in Bloods Cultures" J. Clin. Microbial., vol. 38, No. 2, 2000, pp. 830-838.
Kirkcaldy RD, et al. "Antimicrobial Drug Prescription and Neisseria gonorrhoeae Susceptibility, United States, 2005-2013." Emerg Infect Dis 23, 1657-1663 (2017).

(56) References Cited

OTHER PUBLICATIONS

Kohanski M.A. et al., "How antibiotics kill bacteria: from targets to networks." Nat Rev Microbiol 8, 423-435 (2010).
Kostic, et al. "Thirty-minute screening of antibiotic resistance genes in bacterial isolates with minimal sample preparation in static self-dispensing 64 and 384 assay cards" Appl Microbial Biotechnol, vol. 99, No. 18, Jul. 2015, pp. 7711-7722.
Kubitschek and Freedman "Chromosome Replication and the Division Cycle of *Escherichia coli* B/r" J. Bacteriology, vol. 107, No. 1, 1971, pp. 95-99.
Kumar, A., et al., "Duration of hypotension before initiation of effective antimicrobial therapy is the critical determinant of survival in human septic shock," Crit Care Med. 2006, vol. 34, No. 6, pp. 1589-1596.
Kurosaki, Y., et al., "Development and Evaluation of Reverse Transcription-Loop-Mediated Isothermal Amplification (RT-LAMP) Assay Coupled with a Portable Device for Papid Diagnosis of Ebola Vims Diseases in Guinea," PLoS Negl Trop Dis., Feb. 22, 2016, vol. 10, No. e0004472, pp. 1-12.
Lange C. et al., "Quantitative matrix-assisted laser desorption ionization-time of flight mass spectrometry for rapid resistance detection." J Clin Microbiol 52, 4155-4162 (2014).
Lasserre C, et al. "Efficient Detection of Carbapenemase Activity in Enterobacteriaceae by Matrix-Assisted Laser Desorption Ionization-Time of Flight Mass Spectrometry in Less Than 30 Minutes." J Clin Microbiol 53, 2163-2171 (2015).
Lee SG, et al. "Various penA mutations together with mtrR, porB and ponA mutations in Neisseria gonorrhoeae isolated with reduced susceptibility to cefixime or ceftriaxone." J Antimicrob Chemother 65, 669-675 (2010).
Lehmann, et al. "A multiplex real-time PCR assay for rapid detection and differentiation of 25 bacterial and fungal pathogens from whole blood samples" Med Microbial Immunol, vol. 197, 2008, pp. 313-324.
Li et al., "Molecular beacons: An optimal multifunctional biological probe" Biochem Biophys Res Comm 373(4):457-61, 2008.
Li et al. Picoliter well array chip-based digital recombinase polymerase amplification for abolute quantification of nucleic acids. PLOS ONE, vol. 11, No. 4, E0153359, Apr. 13, 2016, printed as pp. 1/15-15/15, including 1/3-3/3 of Supporting Information. (Year: 2016).
Li L. et al., "User-loaded SlipClip for equipment-free multiplexed nanoliter-scale experiments." J Am Chem Soc 132, 106-111 (2010).
Li Z. et al., "Rapid detection of quinolone resistanceassociated gyrA mutations in Neisseria gonorrhoeae with a LightCycler." J Infect Chemother 8, 145-150 (2002).
Liu, T., et al. "Rapid antimicrobial susceptibility testing with electrokinetics enhanced biosensors for diagnosis of acute bacterial infections." Ann Biomed Eng 42(11): 2314-2321. (2014).
Lobritz, et al. "Antibiotic efficacy is linked to bacterial cellular respiration" PNAS, vol. 12, No. 27, Jul. 2015, pp. 8173-8180.
Longo, G., et al. "Rapid detection of bacterial resistance to antibiotics using AFM cantilevers as nanomechanical sensors." Nat Nanotechnol 8(7): 522-526. (2013).
Ma, et al. "Gene-targeted microfluidic cultivation validated by isolation of a gut bacterium listed in Human Microbiome Project's Most Wanted taxa" PNAS, vol. 111, No. 27, Jul. 2014, pp. 9768-9773.
Ma, et al. "Individually addressable arrays of replica microbial cultures enabled by splitting SlipChips" Integr Biol, vol. 6, 2014, pp. 796-805. Including Supporting Information.
Mach, K.E., et al., "A biosensor platform for rapid antimicrobial susceptibility testing directly from clinical samples," J Urol., Jan. 2011, vol. 185, No. 1, pp. 148-153.
Magill SS, et al. "Prevalence of antimicrobial use in US acute care hospitals, May-Sep. 2011." JAMA 312, 1438- 1446 (2014).
Mann et al., "Antibiotic Susceptibility Testing at a Screen-Printed Carbon Electrode Array" Anal Chem, vol. 80, 2008, pp. 843-848.
Marston, H.D., et al., "Antimicrobial Resistance," JAMA. Sep. 20, 2016, vol. 316, No. 11, pp. 1193-1204.

Matsuda K. et al., "Sensitive quantitative detection of commensal bacteria by rRNA targeted reverse transcription-PCR." Appl Environ Microbiol 73, 32-39 (2007).
Mezger, A. et al., "A General Method for Rapid Determination of Antibiotic Susceptibility and Species in Bacterial Infections," Journal of Clinical Microbiology, Feb. 2015, vol. 53, No. 2, pp. 425-432. 8 Pages.
Millar, et al. "A simple and sensitive method to extract bacterial, yeast and fungal DNA from blood culture material" J Microbial Methods, vol. 42, 2000, pp. 139-147.
Mo, M., et al. "Rapid Antimicrobial Susceptibility Testing of Patient Urine Samples Using Large Volume Free Solution Light Scattering Microscopy." Analytical Chemistry 91(15): 10164-10171. (2019).
Morse, S. A. and B. H. Hebeler "Effect of pH on the growth and glucose metabolism of Neisseria gonorrhoeae." Infect Immun 21(1): 87-95. (1978).
Mu X, et al."Loop-mediated isothermal amplification: Rapid and sensitive detection of the antibiotic resistance gene ISAba1-blaOXA-51-like in Acinetobacter baumannii." J Microbiol Methods 121, 36-40 (2016).
Murata-Kamiya, N., et al. "Helicobacter pylori exploits host membrane phosphatidylserine for delivery, localization, and pathophysiological action of the CagA oncoprotein." Cell Host Microbe 7(5): 399-411. (2010).
Musta, A. C., et al. "Vancomycin MIC plus heteroresistance and outcome of methicillin-resistant *Staphylococcus aureus* bacteremia: trends over 11 years." J Clin Microbiol 47(6): 1640-1644. (2009).
Nadkarni, et al., "Determination of bacterial load by real-time PCR using broad-range (universal) probe and primers set" Microbiology, 257-266, 2002.
Nakano R, et al. "Rapid detection of the Klebsiella pneumoniae carbapenemase (KPC) gene by loop-mediated isothermal amplification (LAMP)." J Infect Chemother 21, 202-206 (2015).
Newman L, et al. "Global Estimates of the Prevalance and Incidence of Four Curable Sexually Transmitted Infections on 2012 Based on Systematic Review and Global Reporting." PLoSOne 10, e0143304 (2015).
Newman L. M. et al., "Update on the management of gonorrhea in adults in the United States."*Clin Infect Dis 44 Suppl*3, S84-101 (2007).
Nikaido H. "Molecular basis of bacterial outer membrane permeability revisited." Microbiol Mol Biol Rev 67, 593-656 (2003).
Non-Final Office Action for U.S. Appl. No. 15/715,086, filed Sep. 25, 2017 on behalf of California Institute of Technology. dated Feb. 3, 2021. 11 Pages.
Non-Final Office Action for U.S. Appl. No. 15/715,086, filed Sep. 25, 2017 on behalf of University of California dated Sep. 20, 2019 40 pages.
O'Neill J. "Tackling Drug-Resistant Infections Globally: Final Report and Recommendations." (2016).
Papp JR, et al. "Azithromycin Resistance and Decreased Ceftraxone Susceptibility in Neisseria Gonorrhoeae," Hawaii, USA. Emerg Infect Dis 23, 830-832 (2017).
Park K. et al., "FRET probe-based antibacterial susceptibility testing (F-AST) by detection of bacterial nucleases released by antibiotic-induced lysis." Biosensors and Bioelectronics, (2019).
Peterson, L.R., et al., "Methicillin-Resistant *Staphylococcus aureus* Control in the 21st Century: Laboratory Involvement Affecting Disease Impact and Economic Benefit from Large Population Studies," J Clin Microbiol., Nov. 2016, vol. 54, No. 11, pp. 2647-2654.
Phaneuf C.R. et al., "Rapid, Portable, Multiplexed Detection of Bacterial Pathogens Directly from Clinical Sample Matrices." Biosensors (Basel) 6, (2016).
Phillips E.A. "Strand Displacement Probes Combined with Isothermal Nucleic Acid Amplification for Instrument-Free Detection from Complex Samples." Anal Chem 90, 6580-6586 (2018).
Pholwat et al.,"Digital PCR to Detect and Quantify Heteroresistance in Drig Resistant Mycobacterium tuberculosis", PLoS One, Feb. 2013, vol. 8, No. 2, e57238, pp. 1-10.
Piddock LJ. "Assess drug-resistance phenotypes, not just genotypes." Nat Microbiol 1, 16120 (2016).

(56) References Cited

OTHER PUBLICATIONS

Pidgeon S.E. et al., "Vancomycin-Dependent Response in Live Drug-Resistant Bacteria by Metabolic Labeling." Angew Chem Int Ed Engl 56, 8839-8843 (2017).
Pink D. et al., "On the architecture of the gram-negative bacterial murein sacculus." J Bacteriol 182, 5925-5930 (2000).
Pollett S. et al., "Phenotype and molecular characteristics of carbapenem-resistant Enterobacteriaceae in a health care system in Los Angeles, California, from 2011 to 2013." J Clin Microbiol 52, 4003-4009 (2014).
Poritz MA, et al. "FilmArray, an automated nested multiplex PCR system for multi-pathogen detection: development and application to respiratory tract infection." PLoS One 6, e26047 (2011).
Premasiri, W. R., et al. "Rapid urinary tract infection diagnostics by surface-enhanced Raman spectroscopy (SERS): identification and antibiotic susceptibilities." Anal Bioanal Chem 409(11): 3043-3054. (2017).
Qian et al., "Scaling Up Digital Circuit Computation with DNA Strand Displacement Cascades," Science 2011; 6034: 1196-1201.
Rahimi F, et al. "Direct urine polymerase chain reaction for chlamydia and gonorrhoea: a simple means of bringing high-throughput rapid testing to remote settings?" Sex Health 10, 299-304 (2013).
Raja B. et al., "Development of a Panel Recombinase Polymerase Amplification Assays for Detection of Common Bacterial Urinary Tract Infection Pathogens." J Appl Microbiol, (2017).
Reid M.S. "Exponential Isothermal Amplification of Nulceic Acids Assays for Proteins, Cells, Small Molecules, and Enzyme Activities: An EXPAR Example." Agnew Chem Int Ed Engl 57, 11856-11866 (2018).
Renner LD, et al. "Detection of ESKAPE Bacterial Pathogens at the Point of Care Using Isothermal DNA-Based Assays in a Portable Degas-Actuated Microfluidic Diagnostic Assay Platform." Appl Environ Microbiol 83, (2017).
Restriction Requirement for U.S. Appl. No. 15/715,086, filed Sep. 25, 2017 on behalf of University of California dated Jun. 21, 2019 6 pages.
Robinson A.M. et al., "The rapid detection of cefotaxime-resistant Enterobacteriaceae by HPLC." Future Sci OA 2, FSO142 (2016).
Rojas E.R. et al. "The outer membrane is an essential load-bearing element in Gram-negative bacteria." Nature 559, 617-621 (2018).
Rolain, J.M., et al., "Real-time PCR for universal antibiotic susceptibility testing," J Antimicrob Chemother., Jul. 2004, vol. 54, No. 2, pp. 538-541.
Rolando J.C. "Real-Time, Digital LAMP with Commercial Microfluidic Chip Reveals the Interplay of Efficiency, Speed, and Background Amplification as a Function of Reaction Temperature and Time." Anal Chem, (2018).
Rowley, J., et al. "Chlamydia, gonorrhoea, trichomoniasis and syphilis: global prevalence and incidence estimates, 2016." Bulletin of the World Health Organization (2019).
Rui P. et al., "National Ambulatory Care Survey: 2015 State and National Summary Tables." (2015).
Sadiq S.T. et al., "Rapid accurate point-of-care tests combining diagnostics and antimicrobial resistance prediction for Neisseria gonorrhoeae and Mycoplasma genitalium." Sex Transm Infect 93, S65-S68 (2017).
Santiso R. et al., "A rapid in situ procedure for determination of bacterial susceptibility or resistance to antibiotics that inhibit peptidoglycan biosynthesis." BMC Microbiol 11, 191 (2011).
Satlin MJ, et al. "Multicenter Clinical and Molecular Epidemiological Analysis of Bacteremia Due to Carbapenem-Resistant Enterobacteriaceae (CRE) in the CRE Epicenter to the United States." Antimicrob Agents Chemother 61, e02349-02316 (2017).
Schlappi, T., et al., "Flow-through Capture and in Situ Amplification Can Enable Rapid Detection of a Few Single Molecules of Nucleic Acids from Several Milliliters of Solution." Analytical Chemistry, Jul. 2016, vol. 88, No. 15, pp. 7647-7653.
Schoepp N.G. "Differential Accessibility to Polymerase During Isothermal Nucleic Acid Amplification Enables 30-Minute Phenotypic Beta-lactam Antibiotic Susceptibility Testing of Carbapenem-resistant Enterobacteriaceae (CRE)." In Preparation, (2018).
Schoepp NG, et al. "Digital Quantification of DNA Replication and Chromosome Segregation Enables Determination of Antimicrobial Susceptibility after only 15 Minutes of Antibiotic Exposure." Angew Chem Int Ed Engl 55, 9557-9561 (2016).
Selck D.A. et al., "Instrument for Real-Time Digital Nucleic Acid Amplification on Custom Microfluidic Devices." PLoS One 11, e0163060 (2016).
Shawar, R. "510(k) Premarket Notification for K160901 Cepheid Xpert Carba-R Assay." Silver Spring, MD, USA Food and Drug Administration, Department of Health and Human Services. (2016).
Shen, et al. "Digital PCR on a SlipChip" Lab Chip, vol. 10, 2010, pp. 2666-2672.
Shen, F., et al., "Digital Isothermal Quantification of Nucleic Acids via Simultaneous Chemical Initiation of Recombinase Polymerase Amplification Reactions on SlipChip," Analytical Chemistry, Apr. 8, 2011, vol. 83, pp. 3533-3540.
Shen, F, et al. "Multiplexed quantification of nucleic acids with large dynamic range using multivolume digital RT-PCR on a rotational SlipChip tested with HIV and hepatitis C viral load." J Am Chem Soc 133, 17705-17712 (2011).
Shen, F., et al., "Nanoliter multiplex PCR arrays on a SlipChip," Analytical chemistry, Jun. 1, 2010, vol. 82, No. 11, pp. 4606-4612.
Shishkin, et al. "Simultaneous generation of many RNA-seq libraries in a single reaction." Nat Meth, vol. 12, 2014, pp. 323-325.
Siedner MJ, et al. "Real-time PCR assay for detection of quinolone-resistant Neisseria gonorrhoeae in urine samples." J Clin Microbiol 45, 1250-1254 (2007).
Silhavy T.J. et al., "The bacterial cell envelope." Cold Spring Harbor perspectives in biology 2, a000414 (2010).
Singh V. et al., "Comparative assessment of CDS, CLSI disc diffusion and E-test techniques for antimicrobial susceptibility testing of Neisseria gonorrhoeae: a 6-year study." BMJ Open2, e000969 (2012).
Slager, et al. "Antibiotic-induced replication stress triggers bacterial competence by increasing gene dosage near the origin." Cell, vol. 157, 2014, pp. 395-406.
Spilker, et al., "PCR-Based Assay for Differentiation of Pseudomonas aeruginosa from Other Pseudomonas Species Recovered from Cystic Fibrosis Patients" Journal of Clinical Microbiology, 2074-2079, 2004.
Steinberger-Levy, I., et al., "A Rapid Molecular Test for Determining Yersinia pestis Susceptibility to Ciprofloxacin by the Quantification of Differentially Expressed Marker Genes," Frontiers in Microbiology, May 2016, vol. 7, pp. 1-13.
Stone M.R.L. "Fluorescent Antibiotics: New Research Tools to Fight Antibiotic Resistance." Trends Biotechnol, (2018).
Su IH, et al. "A dielectrophoresis system for testing antimicrobial susceptibility of Gram-negative bacteria to betalactam antibiotics." Anal Chem, (2017).
Tamayo, et al. "Rapid assessment of the effect ofciprofloxacin on chromosomal DNA from *Escherichia coli* using an in situ DNA fragmentation assay." BMC Microbial, vol. 9, 2009, p. 69.
Tamma PD, et al. "Comparing the Outcomes of Patients With Carbapenemase-Producing and Non-Carbapenemase- Producing Carbapenem-Resistant Enterobacteriaceae Bacteremia." Clin Infect Dis 64, 257-264 (2017).
Tobiason, D. M. et al., "The obligate human pathogen, Neisseria gonorrhoeae, is polyploid." PLoS Biology 4(6): 1069-1078. (2006).
Toley BJ, et al. "Isothermal strand displacement amplification (iSDA): a rapid and sensitive method of nucleic acid amplification for point-of-care diagnosis." Analyst 140, 7540-7549 (2015).
Touati, et al. "Lethal oxidative damage and mutagenesis are generated by iron in delta-fur mutants of *Escherichia coli*: Protective role of superoxide dismutase." J Bacter, vol. 177, 1995, pp. 2305-2314.
Tsongalis, Branched DNA Technology in Molecular Diagnostics, Am J Clin Pathol 2006; 126: 448-453.
Tuite A.R. et al., "Impact of Rapid Susceptibility Testing and Antibiotic Selection Strategy on the Emergence and Spread of Antibiotic Resistance in Gonorrhea." J Infect Dis 216, 1141-1149 (2017).

(56) References Cited

OTHER PUBLICATIONS

Turner KM, et al. "Analysis of the potential for point-of-care test to enable individualised treatment of infections caused by antimicrobial-resistant and susceptible strains of Neisseria gonorrhoeae: a modelling study." BMJ Open, e015447 (2017).
Tyagi et al., "Multicolor molecular beacons for allele disrimination" Nature Biotechnology 16:49-53 (1998).
UCLA Health System. "Antimicrobial Susceptibility Summary 2019;." Clinical Microbiology; Department of Pathology & Laboratory Medicine, (2019).
Unemo M. et al., "Antimicrobial resistance in Neisseria gonorrhoeae in the 21st century: past, evolution, and future." Clin Microbiol Rev 27, 587-613 (2014).
Valiadi, M., et al. "Simple and rapid sample preparation system for the molecular detection of antibiotic resistant pathogens in human urine." Biomedical Microdevices 18(1). (2016).
van Belkum A, et al. "Developmental roadmap for antimicrobial susceptibility testing systems." Nature Reviews Microbiology, (2018).
Van Boeckel T.P. et al., "Global antibiotic consumption 2000 to 2010: an analysis of national pharamaceutical sales data." The Lancet Infectious Diseases 14, 742-750 (2014).
van den Bogaart G. et al., "Protein mobility and diffusive barriers in *Escherichia coli*: consequences of osmotic stress." Mol Microbiol 64, 858-871 (2007).
Van der Zee, A., et al., "Review of a major epidemic of methicillin-resistant *Staphylococcus aureus*: the costs of screening and consequences of outbreak management," Am J Infect Control. 2013, vol. 41, No. 3, pp. 204-209.
Vazquez-Laslop N. et al., "Molecule sieve mechanism of selective release of cytoplasmic proteins by osmotically shocked *Escherichia coli*." J Bacteriol 183, 2399-2404 (2001).
Versporten A, et al. "Antimicrobial consumption and resistance in adult hospital inpatients in 53 countries: results of an internet-based global point prevalence survey." Lancet Glob Health 6, e619-e629 (2018).
Wade J.J. et al., "A fully defined, clear and protein-free liquid medium permitting dense growth of Neisseria gonorrhoeae from very low inocula." FEMS Microbiol Lett 273, 35-37 (2007).
Wadsworth C.B. et al., "Impact of population structure in the design of RNA-based diagnostics for antibiotic resistance in Neisseria gonorrhoeae." bioRxiv (2019).
Wang et al., "Molecular Engineering of DNA: Molecular Beacons" Angew Chem Int Ed Engl, 48(5):856-870 2009.
Weaver, et al., "Taking qPCR to a higher level: Analysis of CNV reveals the power of high throughput qPCR to enhance quantitative resolution." Methods, vol. 50, 2010, pp. 271-276.
Wecke et al., "Antibiotic research in the age of omics: from expression profiles to interspecies communication." J. Antimicrob Chemo, vol. 66, 2011, pp. 2689-2704.
Wegener W.S. et al., "Cell envelope of Neisseria gonorrhoeae: penicillin enhancement of peptidoglycan hydrolysis." Infect Immun 18, 717-725 (1977).
Weiner LM, et al. "Antimicrobial-Resistant Pathogens Associated With Healthcare-Associated Infections: Summary of Data Reported to the National Healthcare Safety Network at the Centers for Disease Control and Prevention, 2011-2014." Infection Control & Hospital Epidemiology 37, 1288-1301 (2016).
Weston E.J. et al.,. "Strengthening Global Surveillance for Antimicrobial Drug-Resistant Nerisseria gonorrhoeae through the Enhanced Gonococcal Antimicrobial Surveillance Program." Emerg Infect Dis23,(2017).
Whale, A. S., et al., "Comparison of microfluidic digital PCR and conventional quantitative PCR for measuring copy number variation." Nucleic Acids Res., Feb. 28, 2012, vol. 40, No. 11, e82, pp. 1-9.
Whiley D.M. et al., "Genetic characterisation of Neisseria gonorrhoeae resistant to both ceftriaxone and azithromycin." Lancet Infectious Diseases 18, 717-718 (2018).
White House. "National Action Plan for Combating Antibiotic-Resistant Bacteria." (2015).

WHO—Antimicrobial Resistance in Neisseria gonorrhoeae. In: World Health Organization, Department of Communicable Disease Surveillance and Response (2001).
WHO—Global Action Plan on Antimicrobial Resistance. (2015).
WHO—Global Action Plan to Control the Spread of and Impact of Antimicrobial Resistance in Neisseria gonorrhoeae. (2012).
WHO—Global Priority List of Antibiotic-resistant Bacteria to Guide Research, Discovery, and Development of New Antibiotics. (2017).
WHO—"No time to wait: Securing the future from drug-resistant infections Report to the Secretary-General of the United Nations." (2019).
WHO—WHO Guidelines for the treatment of Neisseria gonorrhoeae. (2016).
Wi T, et al. "Antimicrobial resistance in Neisseria gonorrhoeae: Global surveillance and a call for international collaborative action." PLoS Med 14, e1002344 (2017).
Wiesinger-Mayr et al. "Establishment of a semi-automated pathogen DNA isolation from whole blood and comparison with commercially available kits" J Microbial Methods, vol. 85, 2011, pp. 206-213.
Wong L.K. et al., "Real-Time PCT Targeting the penA Mosaic XXXIV Type for Prediction of Extended-Spectrum-Cephalosporin Susceptibility in Clinical Neisseria gonorrhoeae Isolates." *Antimicrob Agents Chemother*61,(2017).
Zankari E, et al., "Identification of acquired anitmicrobial resistance genes." J Antimicrob Chemother 67. 2640-2644 (2012).
Zboromyrska, Y., et al., "Rapid detection of beta-lactamases directly from positive blood cultures using a loop-mediated isothermal amplification (LAMP)-based assay," Int J Antimicrob Ag., Mar. 4, 2015, vol. 46, No. 3, pp. 355-356.
Zgurskaya H.I. et al., "Permeability Barrier of Gram-Negative Cell Envelopes and Approaches to Bypass It." ACS Infect Dis 1, 512-522 (2015).
Zhang Y, et al. "Epidemiology of Carbapenem-Resistant Enterobacteriaceae Infections: Report from the China CRE Network." Antimicrob Agents Chemother 62, e01882-01817 (2018).
Zhang Y, et al. "Label-Free Visualization of Carbapenemase Activity in Living Bacteria." Angew Chem Int Ed Engl 57, 17120-17124 (2018).
Zhao S. et al., "Genetics of chromosomally mediated intermediate resistance to ceftriaxone and cefixime in Neisseria gonorrhoeae." Antimicrob Agents Chemother 53, 3744-3751 (2009).
Zierdt, et al. "Development of lysis-filtration blood culture technique." J Clin Microbial, vol. 5, 1977, pp. 46- 50.
Zierdt "Simplified Lysed-Blood Culture Technique" J Clin Microbial, vol. 23, No. 3, 1986, pp. 452-455.
Zou K.H. et al., "Receiver-operating characteristic analysis for evaluating diagnostics tests and predictive models." Circulation 115, 654-657 (2007).
FDA-CDC "Antibiotic Resistance Isolate Bank." *American Society for Microbiology*, Feb. 2018, vol. 56, Issue 2, 7 pages.
Notice of Allowance for U.S. Appl. No. 15/715,086, filed Sep. 25, 2017 on behalf of California Istitute of Technology. dated Jul. 29, 2021. 30 Pages.
Rizzo K. et al., "Carbapenem and Cephalosporin Resistance among Enterobacteriaceae in Healthcare-Associated Infections" *Emerging Infectious Diseases*, vol. 25, No. 7, Jul. 2019, pp. 1389-1393.
Tapsall J. "Antimicrobial Resistance in Neisseria Gonorrhoeae" *World Health Organization*, WHO/CDS/CSR/DRS/2001.3 2001, 65 pages.
Gelband H. et al. "The State of the World's Antibiotics." *Center of Diseases Dynamics, Economics & Policy*, Washington, D.C, HHS (2015) 84 pages.
Alschul S.F. et al., "Basic local alignment search tool." *J Mol Biol*, 1990. 215(3); p. 403-410.
Altschul S.F. et al., "Gapped BLAST and PSI-BLAST: a new generation or protein database search programs." *Nucleic Acids Res*, 1997. 25(17): p. 3389-3402.
Badshah S.L. et al., "New developments in non-quinolone-based antibiotics for the inhibition of bacterial gyrase and topoisomerase IV." *Eur J Med Chem*, 2018. 152: p. 393-400.

(56) References Cited

OTHER PUBLICATIONS

Collin F. et al., "Exploiting bacterial DNA gyrase as a drug target: current state and perspective." *Appl Microbial Biotechnol*, 2011. 92(3): p. 479-497.
Davidsen T. et al., "Genetic interactions of DNA repair pathways in the pathogen Neisseria meningitidis." *J Bacteriol*, 2007. 189(15): p. 5728-5737.
Davidsen T. et al., "Meningococcal genome dynamics" *Nat Rev Microbiol*, 2006. 4(1): p. 11-22.
Fernandez L. et al., "Adaptive and mutational resistance: role of porins and efflux pumps in drug resistance." *Clinical Microbiology Reviews*, 2012. 25(4): p. 661-681.
Gao Q. et al., "Gene expression diversity among *Mycobacterium tuberculosis* clinical isolates." *Microbiology*, 2005. 151(1): p. 5-14.
Gomez J.E. et al., "Ribosomal mutations promotes the evolution of antibiotic resistance in a multidrug environment." *Elife*, 2017. 6. e20420. 25 pages.
Honda S. et al., "Four-leaf clover qRT-PCR: A convenient method for selective quantification of mature tRNA." *RNA Biol*, 2015. 12(5): p. 501-508.
International Search Report for International Application No. PCT/US2019/044748 filed on Aug. 1, 2019 on behalf of California Institute of Technology dated Nov. 29, 2019 5 pages.
Johnson L.S. et al., "Hidden Markov model speed heuristic and iterative HMM search procedure." *BMC Bioinformatics*, 2010. 11: p. 431. 8 pages.
Khazaei T. et al., "RNA markers enables phenotype test of antibiotic susceptibility in Neisseria gonorrhoeae after 10 minutes of ciprofloxacin exposure" *Nature*, 2018, pp. 1-10.
Marin M.A. et al., "The invasive Neisseria meningitidis MenC CC103 from Brazil is characterized by an accessory gene repertoire." *Sci Rep*, 2017. 7(1): p. 1617. 11 pages.
Mezger A. et al., "A general method for rapid determination of antibiotic susceptibility and species in bacterial infections" *Journal of Clinical Microbiology*, Feb. 2015, vol. 53, No. 2, pp. 425-432.
Pearson W.R. et al., "Improved tools for biological sequence comparison." *Proc Natl Acad Sci USA*, 1988. 85(8): p. 2444-2448.
Pearson W.R. "Searching protein sequence libraries: comparison of the sensitivity and selectivity of the Smith-Waterman and FASTA algorithms." *Genomics*, 1991. 11(3): p. 635-650.
Quillin S.J. et al., "Neisseria gonorrhoeae host adaptation and pathogenesis" *Nature Reviews Microbiology*, 2018. vol. 16, 226-240.
Schook P.O. et al., "The DNA-binding activity of the Neisseria gonorrhoeae LexA orthologue NG1427 is modulated by oxidation." *Molecular Microbiology*, 2011. 79(4): p. 846-860.
Smith T.F. et al., "Identification of common molecular subsequences." *J Mol Biol*, 1981. 147(1): p. 195-197.
Stohl E.A. et al., "Purification and characterization of the RecA protein from Neisseria gonorrhoeae" *PloS One*, 2011. 6(2): p. e17101. 13 pages.
Tatusova T.A. et al., "BLAST 2 Sequences, a new tool for comparing protein and nucleotide sequences." *FEMS Microbiol Lett*, 1999, 174. 247-250.
*The European Commitee on Antimicrobial Susceptibility Testing*"Ciprofloxacin/Neisseria gonorrhoeae International MIC Distribution-Reference Database" Apr. 2, 2018 https://mic.eucast.org/Eucast2/regShow.jsp?Id=35702.
Written Opinion for International Application No. PCT/US2019/044748 filed on Aug. 1, 2019 on behalf of California Institute of Technology dated Nov. 29, 2019 5 pages.
Zheng G. et al., "Efficient and quantitative high-throughput tRNA sequencing." *Nat Methods*, 2015, 12(9): p. 835-837. 5 pages.
Cacciapuoti, A F. et al., "Cell envelope of Neisseria gonorrhoeae: phospholipase activity and its relationship to autolysis." Infection and Immunity, vol. 2, No. 2, pp. 418-420 (1978).
Chakravorty, S., et al., "A detailed analysis of 16S ribosomal RNA gene segments for the diagnosis of pathogenic bacteria." J Microbiol Methods, 69(2): p. 330-339. 2007.

Chen, C.Y. et al., "A 6 × 6 drop plate method for simultaneous colony counting and MPN enumeration of Campylobacter jejuni, Listeria monocytogenes, and *Escherichia coli*." J Microbiol Methods, 55(2): p. 475-479. 2003.
Conesa, A., et al., "A survey of best practices for RNA-seq data analysis." Genome Biol, 17: p. 13. 2016. 19 pages.
Elmros, T. et al., "Autolysis of Neisseria gonorrhoeae." Journal of Bacteriology, pp. 969-976 (May 1976).
Garcia, D.L. et al., "AmiC functions as an N.acetylmuramyl-L-alanine amidase necessary for cell separation and can promote autolysis in Neisseria gonorrhoeae." Journal of Bacteriology, vol. 188, No. 20, pp. 7211-7221 (Oct. 2006).
Gootenberg, J.S., et al., "Multiplexed and portable nucleic acid detection platform with Cas13, Cas12a, and Csm6." Science, 360(6387): p. 439-444. Apr. 2018.
Gootenberg, J.S., et al., "Nucleic acid detection with CRISPR-Cas13a/C2c2." Science, 356(6336): p. 438-442. Apr. 2017.
Hamilton, H.L. et al., "Natural transformation of Neisseria gonorrhoeae: From DNA donation to homologous recombination." Molecular Microbiology, 59(2), pp. 376-385 (2006).
International Search Report for International Application No. PCT/US2018/055501 filed Oct. 11, 2018, on behalf of California Institute of Technology. dated Jan. 31, 2019. 4 pages.
Jackman, J.E. et al., "Transfer RNA modifications: Nature's combinatorial chemistry playground." Wiley interdisciplinary reviews. RNA, 4(1): p. 35-48. 2013.
Kruetz, J.E., et al., "Theoretical design and analysis of multivolume digital assays with wide dynamic range validated experimentally with microfluidic digital PCR." Anal Chem 83(21): p. 8158-68. 2011.
Lee, S.R. et al., "Rapid one step detection of pathogenic bacteria in urine with sexually transmitted diseases (STD) and prostatitis patient by multiplex PCR assay (mPCR)." J Microbiol, 45(5): p. 453-459. Oct. 2007.
Matsuda, K., et al., "Sensitive quantitative detection of commensal bacteria by rRNA targeted reverse transcription-PCR." Appl Environ Microbiol, 73(1): p. 32-39. Jan. 2007.
Myhrvold, C., et al., "Field-deployable viral diagnostics using CRISPR-Cas13." Science, . 360(6387): p. 444-448. Apr. 2018.
Schoepp, N.G., et al., "Rapid pathogen-specific phenotypic antibiotic susceptibility testing using digital LAMP quantification in clinical samples." Sci Transl Med, 9(410) eaal3693. Oct. 2017. 13 pages.
Song, J. et al., "Chemical Modifications to RNA: A New Layer of Gene Expression Regulation." ACS Chem Biol 12(2): p. 316-325. 2017.
Wagner, G.P. et al., "Measurement of mRNA abundance using RNA-seq data: RPKM measure is inconsistent among sample." Theory Biosci, 131(4): p. 281-2855. 2012.
Wegener, W. et al. "Cell envelope of Neisseria gonorrhoeae: relationship between autolysis in buffer and the hydrolysis of peptidolycan." Infection and Immunity, vol. 18, No. 1, pp. 210-219 (Oct. 1977).
Written Opinion for International Application No. PCT/US2018/055501 filed Oct. 11, 2018, on behalf of California Institute of Technology. dated Jan. 31, 2019. 8 pages.
Ye, J., et al., "Primer-BLAST: a tool to design target-specific primers for polmerase chain reaction." BMC bioinformatics, 13(1): p. 134. 2012. 11 pages.
CLSI. "M100—Performance Standards for Antimicrobial Susceptibility Testing." 30th Edition, (2020), 332 pages.
EUCAST: Clinical breakpoints and dosing of antibiotics https://www.eucast.org/clinical_breakpoints/ , Feb. 26, 2021. 1 pages.
Guzman S. et al., "Stimfit: quantifying electrophysiological dated with python" *Frontiers in Neuroinformatics*, vol. 8, Feb. 21, 2014. 10 pages.
Hori Y. et al., "Cell-free extract based optimization of biomolecular circuits with droplet microfluidics" *Lab Chip*, vol. 17 No. 18, Sep. 2017, pp. 3037-3042.
International Preliminary Report on Patentability for PCT/US2019/044748 filed on Aug. 1, 2019 on behalf of California Institute of Technology dated Feb. 2, 2021 6 pages.
Kaminski M.M. et al., "CRISPR-based diagnostics" *Nat Biomed Eng*, vol. 5, No. 7, Jul. 2021, pp. 643-656. 14 pages.

(56) References Cited

OTHER PUBLICATIONS

Kim S. et al., "CRISPR as a diagnostic tool" *Biomolecules*, vol. 11 No. 8, p. 1162, Aug. 2021.
Leonard H. et al., "Recent Advances in the Race to Design a Rapid Diagnostic Test for Antimicrobial Resistance," *ACS Sens*. vol. 3 No. 11, Aug. 2018, pp. 2202-2217.
Li Y. et al., "Emerging microtechnologies and automated systems for rapid bacterial identification and antibiotic susceptibility testing" *SLAS TECHNOLOGY: Translating Life Sciences Innovation*, vol. 22 No. 6, 2017, pp. 585-608.
Logan L.K. et al., "The Epidemiology of Carbapenem-Resistant Enterobacteriaceae: The Impact and Evolution of a Global Menace" *J Infect Dis*, vol. 215, Feb. 2017. 9 pages.
Nguyen T.N.A. et al., "Molecular Diagnosis of Drug-Resistant Tuberculosis; A Literature Review" *Frontiers in Microbiology*, vol. 10, Article 794. Apr. 16, 2019. 12 pages.
Obande G.A. et al., "Current and Future Perspectives on Isothermal Nucleic Acid Amplification Technologies for Diagnosing Infections" *Infect Drug Resist*, vol. 13, Feb. 2020, pp. 455-483.
Savela E.S. et al., "Surfactant-enhanced DNA accessibility to nuclease accelerated phenotypic B-lactum antibiotic susceptibility testing of Neisseria gonorrhoeae" *PLOS Biology*, vol. 18 No. 3, Mar. 19, 2020. 31 pages.
Sekerli M. et al., "Estimating action potential thresholds from neuronal time-series: new metrics and evaluation of methodologies" *IEEE Transactions on Biomedical Engineering*, vol. 51 No. 9, Sep. 2004, pp. 1665-1672.
Shahi P. et al., "Abseq: Ultrahigh-throughput single cell protein profiling with droplet microfluidic barcoding" *Scientific Reports*, vol. 7 No. 1, Mar. 2017. 12 pages.
The European Commitee on Antimicrobial Susceptibility Testing. "Breakpoint tables for interpretation of MICs and zone diameters." Version 12.0, 2022. Published online 2022. Accessed Feb. 27, 2022. 110 pages.
Van Belkum A. et al., "Innovative and rapid antimicrobial susceptibility testing systems" *Nat Rev Microbiol*, vol. 18 No. 5, May 2020. 13 pages.
Altun, O. et al., "Clinical evaluation of the FilmArray blood culture identification panel in identification of bacteria and yeasts from positive blood culture bottles", J. Clin. Microbiol., Dec. 2013, 51 (12), 4130-4136.
Anderson, C. M. & Pitt, W. G. "Effects of dilution on sedimentational separation of bacteria from blood". Biotechnol Prog 36, e3056, 10 pages. doi:10.1002/btpr.3056 (2020).
Andrews, J.M., "Determination of minimum inhibitory concentrations", J. Antimicrob. Chemother. Jul. 2001, vol. 48 Suppl 1, 5-16.
Baker, S. et al., "Fitness benefits in fluoroquinolone-resistant Salmonella Typhi in the absence of antimicrobial pressure", eLife, Dec. 10, 2013, 2, e01229. 17 pages.
Barber, A.E., et al. "Urinary tract infections: current and emerging management strategies". Clin Infect Dis 57, 719-724 (2013).
Beal, S.G. et al., "Evaluation of the nanosphere verigene grampositive blood culture assay with the VersaTREK blood culture system and assessment of possible impact on selected patients", J. Clin. Microbiol. Dec. 2013, 51 (12), 3988-3992.
Biolunch presentation (weekly seminar for Caltech Biology grads) Feb. 20, 2019 Eric Law Oral presentation: "Characterizing a rapid phenotypic diagnostic assay for β-lactam antibiotic resistance" 44 pages. (D4).
Blaschke, A.J. et al., "Rapid identification of Pathogens from Positive Blood Cultures by Multiplex PCR using FilmArray System", Diagn. Microbiol. Infect. Dis., Dec. 2012, 74 (4), 349-355. 17 pages.
Boardman, A. K., et al., Rapid Microbial Sample Preparation from Blood Using Novel Concentration Device. PloS one 10, e0116837, doi:10.1371/journal.pone.0116837 (Feb. 2015). 13 pages.
Broeren, M.A., et al., Antimicrobial susceptibility testing in 90 min by bacterial cell count monitoring. Clin Microbial Infect 19, 286-291 (2013).
Buchanon, C. M. et al. Rapid separation of very low concentrations of bacteria from blood. J Microbiol Methods 139, 48-53, doi:10.1016/j.mimet.2017.05.004 (Aug. 2017). 15 pages.
Buhlmann, A. et al. "Erwina amylovora loop-mediated isothermal amplification (LAMP) assay for rapid pathogen detection and on-site diagnosis of fire blight". J Microbial Methods 92, 332-339 (2013).
Buser, J.R. et al., "Electromechanical cell lysis using a portable audio device: enabling challenging sample preparation at the point-of-care", Lab Chip 2015, 15, pp. 1994-1997.
Bush, K. and Bradford, P.A., "β-Lactams and β-Lactamase Inhibitors: An Overview", Cold Spring Harbor Perspectives in Medicine, 6: a026247 (2016), pp. 1-22.
Bush, K. and J. F. Fisher, "Epidemiological expansion, structural studies, and clinical challenges of new Beta-lactamases from gram-negative bacteria", Annu. Rev. Microbiol. 2011, 65, 455-478.
Caltech Chemical Signaling Center Seminar presentation Oct. 18, 2018 Eric Liaw Oral presentations: "A mechanism for a rapid diagnostic assay of the activity of beta-lactam antibiotics against pathogenic bacteria" 47 pages. (D2).
Caltech MicroMorning Seminar presentation Dec. 12, 2018 Emily Savela Oral Presentation: "Measuring cell envelope damage after 15 min β-lactam exposure in N. gonorrhoeae to enable phenotypic diagnostics" 30 pages. (D3).
CBD S&T conference. Cincinnati, Ohio. Nov. 18-21, 2019. Poster Presentation: Alex Winnett. "30-min Phenotypic Antimicrobial Susceptibility Testing (AST) via Measurement of Nucleic Acid Quantity and State" (Nathan G. Schoepp, et al.) 1 page. (D9).
CDC—2012 "Cephalosporin-Resistant Neisseria gonorrhoeae Public Health Response plan", Aug. 2012, 44 pages.
CDC, "Sexually Transmitted Disease Surveillance, STDs 2015", National Center for HIV/AIDS, Viral Hepatitis, STD, and TB Prevention, Division of STD Prevention, (2015) 177 pages. website: cdc.gov/std/stats15/gisp2015/GISP-Supplement-AggrFigs_AggrTables_Clinic-Profiles_2015.
Chan, Y.A., Hackett, K.T., Dillard, J.P. "The Lytic Transglycosylases of Neisseria gonorrhoeae." Microbial Drug Resistance. 2012. 18(3) p. 271-279.
Chen, C.H. et al., "Rapid Antimicrobial susceptibility testing using high surface-to-volume ratio microchannels". Anal Chem 82 (3), 1012-1019 (Feb. 2010). 17 pages.
Cooper, R. M. et al. "A microdevice for rapid optical detection of magnetically captured rare blood pathogens". Lab on a chip 14, 182-188, doi:10.1039/C3LC50935D (2014).
Cosgrove, S.E., "The relationship between antimicrobial resistance and patient outcomes: mortality, length of hospital stay, and health care costs". Clin Infect Dis 42 Suppl 2, S82-89 (2006).
Dow, P., et al., "Acoustic separation in plastic microfluidics for rapid detection bacteria in blood using engineered bacteriophage". Lab on a chip 18, 923-932, doi:10.1039/C7LC01180F (2018).
Drlica, K. and X. Zhao, "DNA Gyrase, Topoisomerase IV, and the 4-Quinolones", Microbial. Mol. Biol. Rev. Sep. 1997, vol. 61, No. 3, 377-392.
Elmros, T., G. Sandstrom & L. Burman—"Autolysis of Neisseria gonorrhoeae. Relation between mechanical stability and viability", 1976—Brit. J. Vener Dis—52(4), pp. 246-249.
"Ertapenem", Wikipedia.com. Last edited: May 4, 2018. 5 pages. (Downloaded through the Wayback Machine on Jul. 18, 2023).
Fabrega, A. et al., "Review: Mechanism of action and resistance to quinolones", Microbial Biotechnology, 2009, 2 (1), 40-61.
Faridi, M. A. et al. Elastro-inertial microfluidics for bacteria separation from whole blood for sepsis diagnostics. Journal of Nanobiotechnology 15, 3, doi:10.1186/s12951-016-0235-4 (2017). 9 pages.
FDA, Guidance for Industry and FDA, Class II Special Controls Guidance Document: Antimicrobial Susceptibility Test (AST) Systems, 2007. 43 pages.
FDA, Guidance for Industry and FDA Staff Statistical Guidance on Reporting Results from Studies Evaluating Diagnostic Tests. Guidance for Industry and FDA Staff, 1-39. (Mar. 2007).
Foxman, B., "Epidemiology of urinary tract infections: incidence, morbidity, and economic costs", Am. J. Med. Jul. 8, 2002, 113 Suppl 1A: 5S-13S (5-13).

(56) References Cited

OTHER PUBLICATIONS

Fredborg, M. et al., "Rapid antimicrobial susceptibility testing of clinical isolates by digital time-lapse microscopy". Eur J Clin Microbial Infet Dis 34, 2385-2394 (2015).
Gansen, A. et al., "Digital LAMP in a sample self-digitization (SD) chip", Lab Chip 2012, 12 (12), 2247-2254. 15 pages.
Ghosal, A. et al., "The extracellular RNA complement of *Escherichia coli*", Microbiology Open, 2015; 4 (2): 252-266 Website: pubmed. ncbi.nlm.nih.gov/25611733/.
Ghosal, A. "Secreted bacterial RNA: an unexpected avenue", FEMS Microbiology Letters, 365, 2018, fny036. 3 pages. Website: academic. oup.com/femsle/article/365/7/fny036/4867967.
Gillespie, D.T., "Stochastic Simulation of Chemical Kinetics". Annu. Rev. Phys. Chem 58, 35-55 (2007). 23 pages.
Gordon Research Conference GRC Tropical Infectious Diseases, Galveston, TX. Mar. 27-28, 2019. Poster Presentation: Emily Savela "Measuring cell envelope damage of Neisseria gonorrhoeae after 15-min beta-lactam exposure enables rapid antimicrobial susceptibility testing" (Emily S. Savela, et al.) 1 page. (D7).
Gupta, K. et al., "International clinical practice guidelines for the treatment of acute umcomplicated cystitis and pyelonephritis in women: A 2010 updated by the Infectious Diseases Society of America and teh European Society for Microbiology and Infectious Diseases". Clin Infect Dis 52 (5), e103-120 (Mar. 2011).
Guymon, L.F. and Sparling, P.F., Altered Crystal Violet Permeability and Lytic Behavior in Antibiotic-Resistant and -Sensitive Mutants of Neisseria gonorrhoeae, Journal of Bacteriology, Nov. 1975, vol. 124, No. 2, pp. 757-763.
Hatch, A.C. et al., "1-Million droplet array with wide-field fluourescence imaging for digital PCR", Lab Chip 2011, 11, 3838-3845.
Hooton, T.M. "Clinical practice. Uncomplicated urinary tract infection". N Engl J Med 366, 1028-1037 (Mar. 2012).
Huang, Y., Yao, X. et al., Mediator Complex Regulates Alternative mRNA Processing via the MED23 Subunit, (Feb. 24, 2012) Molecular Cell. 45, pp. 459-469.
Huggett, J.F. et al "The digital MIQE guidelines: Minimum Information for Publication Quantitative Digital PCR Experiments", Clin. Chem. Jun. 2013, 59 (6), 892-902.
Hwang, K.-Y. et al. Bacterial DNA Sample Preparation from Whole Blood Using Surface-Modified Si Pillar Arrays. Analytical chemistry 80, 7786-7791, doi:10.1021/ac8012048 (2008).
Ibanez de Aldecoa, A. et al., "Mechanisms and Regulation of Extracellular DNA Release and Its Biological Roles in Microbial Communities" Frontiers in Microbiology, vol. 8, article 1390, Jul. 26, 2017, 19 pages.
Imai, M., et al., "Development of H5-RT-LAMP (loop-mediated isothermal amplification) system for rapid diagnosis of H5 avian influenza virus infection". Vaccine vol. 21, Issues 44-46, 6679-6682 (Nov. 2006).
International Search Report and Written Opinion for International PCT Application No. PCT/US2022/018208 filed on Feb. 28, 2022 on behalf of California Institute of Technology. dated Jun. 15, 2022. 12 Pages.
Ivancic, V. et al., "Rapid antimicrobial susceptibility determination of uropathogens in clinical urine specimens by use of ATP bioluminescence". J Clin Microbiol, vol. 46, No. 4, 1213-1219 (Apr. 2008).
Jarvius, J. et al. "Digital quantification using amplified single-molecule detection", Nature Methods, 2006, vol. 3, No. 9, 725-727.
Kalinina, O. et al., "Nanoliter scale PCR with TaqMan detection", Nucleic Acids Res. 1997, vol. 25, No. 10, 1999-2004.
Kallen, A.J., et al., Current antibiotic therapy for isolated urinary tract infections in women. Arch intern Med, vol. 166, 635-639 (Mar. 27, 2006).
Kang, J. H. et al. "Optimization of Pathogen Capture in Flowing Fluids with Magnetic Nanoparticles". Small 11, No. 42, 5657-5666, doi:10.1002/smll.201501820 (2015).
Khazaei T. et al., "RNA markers enable phenotypic test of antibiotic susceptibility in Neisseria gonorrhoeae after 10 minutes of ciprofloxacin exposure." Supplementary Information, *Nature*, 2018, 2 pages.

Khorosheva, E.M. et al. "Lack of correlation between reaction speed and analytical sensitivity in isothermal amplification reveals the value of digital methods for optimization: validation using digital real-time RT-LAMP", Nucleic Acids Res., vol. 44, No. 2, p. e10. 2016. Published Sep. 2015. 12 pages.
Kim, S. et al., "Miniaturized Antimicrobial Susceptibility Test by Combining Concentration Gradient Generation and Rapid Cell Culturing", Antibiotics, 2015, 4, 455-466.
Kim, Y., Lee, J. & Park, S. A 3D-Printed Millifluidic Platform Enabling Bacterial Preconcentration and DNA Purification for Molecular Detection of Pathogens in Blood. Micromachines (Basel) 9, 472. 12 pages. doi:10.3390/mi9090472 (2018).
Ku, H.H., "Notes on the use of propagation of error formulas". Journal of Research of the National Bureau of Standards, Section C: Engineering and Instrumentation, vol. 70C, No. 4, 263-273 (Oct.-Dec. 1966).
Lattuada, M. et al. Theranostic body fluid cleansing: rationally designed magnetic particles enable capturing and detection of bacterial pathogens. Journal of Materials Chemistry B 4, 7080-7086, doi:10.1039/C6TB01272H (2016).
Laxminarayan, R. et al. Antibiotic resistance—the need for global solutions. Lancet Infect Dis 13, 1057-1098, (2013). 42 pages.
Lee, J.-J. et al. Synthetic Ligand-Coated Magnetic Nanoparticles for Microfluidic Bacterial Separation from Blood. Nano Letters 14, 1-5, doi:10.1021/nl3047305 (2014).
Levine, C. et al., "DNA gyrase and topoisomerase IV: biochemical activities, physiological roles during chromosome replication, and drug sensitivities", Biochim Biophys Acta, Oct. 1, 1998, 1400 (1-3), 29-43.
Liu, C.Y., et al. "Rapid bacterial antibiotic susceptibility test based on simple surface enhanced Raman spectroscopic biomarkers". Sci Rep 6, 23375 (Mar. 2016). 15 pages.
Liu, T.T., et al., "A high speed detection platform based on surface-enhanced Raman scattering for monitoring antibiotic-induced chemical changes in bacteria cell wall". PLoS One, vol. 4, Issue 5, e5470 (May 2009). 10 pages.
Logan, L.K. et al., Carbapenem-Resistant Enterobacteriaceae in Children, United States, 1999-2012, (Nov. 2015) Emerging Infectious Diseases, vol. 21, No. 11, pp. 2014-2021.
Lu, Y., et al., "Single cell antimicrobial susceptibility testing by confined microchannels and electrokinetic loading". Anal Chen 85 (8), 3971-3976 (Apr. 16, 2013). 16 pages.
"M100: Performance Standards for Antimicrobial Susceptibility Testing," *Clinical and Laboratory Standards* Institute. 28th Edition. Jan. 2018. Excerpt, 2 Pages.
Mahalanabis, M. et al., "Cell lysis and DNA extraction of gram-positive and gram-negative bacteria from whole blood in a disposable chip", Lab Chip 2009, 9, 2811-2817.
Martin, A. Ultimate Single-Copy DNA Detection Using Real-Time Electrochemical LAMP:. ACS Sensors 1, 904-912 (2016).
Mazzulli, T., "Diagnosis and management of simple and complicated urinary tract infections (UTIs)", Canadian. J. Urology. Oct. 2012, 19 (Suppl 1), 42-48.
McCalla, D.R., "Nitrofuran Derivatives as Radiomimetic Agents: Cross-Resistance Studies with *Escherichia coli*", Can. J. Microbial. 1965, 11, No. 2, 185-191.
Molecular Med Tri-Con, San Francisco, CA, Mar. 10-15, 2019. Abstract only. Eric Liaw. "A Rapid Phenotypic Test for Beta Lactam Antibiotic Susceptibility" (Nathan Schoepp, Eric Liaw, Emily Savela, Rustem Ismagilov) 1 page. (D6).
Nagler, M. et al. "Extracellular DNA in natural environments: features, relevance and applications" Applied Microbiology and Biotechnology (2018) 102: 6343-6356. Website: www.ncbi.nlm.nih. gov/pmc/articles/PMC6061472/.
Nickel, J.C., "Management of Urinary Tract Infections: Historical Perspective and Current Strategies: Part 2—Modern Management", J. Urol. Jan. 2005, vol. 2005, vol. 173, Issue 1, 27-32.
Notomi, T. et al., "Minireview: Loop-mediated isothermal amplification (LAMP): principle, features, and future prospects". J Microbial vol. 53, No. 1, 1-5 (2015).
Ohlsson, P. et al. "Integrated Acoustic Separation, Enrichment, and Microchip Polymerase Chain Reaction Detectin of Bacteria from

(56) References Cited

OTHER PUBLICATIONS

Blood for Rapid Sepsis Diagnostics". Analytical chemistry 88, 9403-9411, doi:10.1021/acs.analchem.6b00323 (2016).
O'Neill, J. "Rapid Diagnostics: Stopping Unnecessary Use of Antibiotics". Review on Antimicrobial Resistance. Oct. 2015. 39 pages. Website: amr-review.org/Publication.html, Dec. 1, 2016.
Pallett, A., and K. Hand, "Complicated urinary tract infections: practical solutions for the treatment of multiresistant Gram-negative bacteria", J. Antimicrob. Chemother. 2010, 65 Suppl 3, iii25-33.
PCAST, "Report to the President on Combating Antibiotic Resistance", Executive Office of the President, President's Council of Advisors on Science and Technology, Sep. 2014. 78 pages.
Perez, K.K. et al., "Integrating rapid pathogen identification and antimicrobial stewardship significantly decreases hospital costs". Arch Pathol Lab Med, vol. 137, 1247-1254 (Sep. 2013).
Peterson, L.R., and C. J. Shanholtzer, "Tests for Bactericidal Effects of Antimicrobial Agents: Technical Performance and Clinical Relevance", Clin. Microbial. Rev. Oct. 1992, vol. 5, No. 4, 420-432.
Pitt, W. G. et al. "Factors affecting sedimentational separation of bacteria from blood". Biotechnol Prog 36, e2892, doi:10.1002/btpr.2892 (2020). 13 pages.
Pulido, M.R. et al., "Progress on the development of rapid methods for antimicrobial susceptibility testing", J. Antimicrob. Chemother. 2013, 68, 2710-2717.
Rane, T.D. et al., "Microfluidic continuous flow digital loop-mediated isothermal amplification (LAMP)". Lab Chip 15 (3), 776-782 (Feb. 2015). 14 pages.
Reddy, B. Jr. et al., "Point-of-care sensors for the management of sepsis", Nature Biomedical Engineering, (Sep. 2018), vol. 2 (9), 640-648.
Roberts, R.R. et al., "Hospital and societal cost of antimicrobial-resistant infections in a Chicago teaching hospial: implications for antibiotic stewardship" Clin. Infect. Dis. Oct. 2009, 49(8), 1175-1184.
Rodriguez-Manzano, J. et al., "Reading Out Single-Molecule Digital RNA and DNA Isothermal Amplification in Nanoliter Volumes with Unmodified Camera Phones". ACS Nano, 10, 3102-3113, (2016).
Rossmanith, P., et al. "Development of matrix lysis for concentration of gram positive bacteria from food and blood". J Microbiol Methods 69, 504-511, doi:10.1016/j.mimet.2007.03.003 (2007).
Roth, B.L., "Bacterial viability and antibiotic susceptibility testing with SYTOX green nucleic acid stain". Appl Environ Microbiol, vol. 63, No. 6, 2421-2431 (Jun. 1997).
Savela, Emily. Caltech Center for the Chemistry of Cellular Signaling Seminar presentation Oct. 12, 2017 "Designing a phenotype antimicrobial susceptibility test for N. gonorrhoeae at the point of care." (D1).
Schappert SM, et al., Ambulatory medical care utilization estimates for 2006. National health statistics reports; No. 8. (Eds.: Hyattsville, M. N. C. f. H. Statistics;), Aug. 2008. 30 pages.
Schoepp, N. G. et al., "Differential DNA accessibility to polymerase enables 30-minute phenotypic β-lactam antibiotic susceptibility testing of carbapenem-resistant Enterobacteriaceae", *PLoS Biology*, vol. 18, No. 3, Article No. e3000652. Mar. 19, 2020. 22 Pages.
Schuler, F. et al, "Centrifugal step emulsification applied for absolute quantification of nucleic acids by digital droplet RPA". Lab on a chip 15, 2759-2766 (2015).
Schuler, F., et al., Digital droplet LAMP as a microfluidic app on standard laboratory devices. Anal. Methods 8, 2750-2755 (2016).
Seiler, B. T. et al. Broad-spectrum capture of clinical pathogens using engineered Fc-mannose-binding lectin enhanced by antibiotic treatment. F1000Res 8, 108, doi:10.12688/f1000research/17447.1
Selck, D.A., et al. "Increased robustness of single-molecule counting with microfluidics, digital isothermal amplification, and a mobile phone versus real-time kinetic measurements". Anal Chem 85 (22), 11129-11136 (Nov. 19, 2013). 19 pages.
Shrestha, N.K., et al., Rapid differentiation of methicillin-resistant and methicillin-susceptible *Staphylococcus aureus* by flow cytometry after brief antibiotic exposure. J Clin Microbial, vol. 49, No. 6, 2116-2120 (Jun. 2011).
Sigma. Buffer Reference Center. Download Jan. 18, 2023. 16 pages. Website: www.sigmaaldrich.com/US/en/technical-documents/protocol/protein-biology/protein-concentration-and-buffer-exchange/buffer-reference-center.
Silva, R. et al. "Rapid prototyping and parametric optimization of plastic acoustofluidic devices for blood-bacteria separation". Biomed Microdevices 19, 70, 14 pages. doi:10.1007/s10544-017-0210-3 (2017).
Simerville, J.A., et al., "Urinalysis: a comprehensive review". Am Fam Physician vol. 71, No. 6, 1153-1162 (Mar. 15, 2005).
Sinn, I. et al. "Asynchronous magnetic bead rotation (AMBR) biosensor in microfluidic droplets for rapid bacterial growth and susceptibility measurements". Lab Chip 11, 2604-2611 (2011).
Spanu, T. et al., "Evaluation of the New NucliSENS EasyQ KPC Test for Rapid Detection of Klebsiella pneumoniae Carbapenemase Genes (bla kpc)" J. Clin. Microbiol. Aug. 2012, vol. 50, No. 8, 2783-2785.
Spellberg, B. et al. Infectious Diseases Society of America (ISDA), "Combating antimicrobial resistance: policy recommendations to save lives". Clin Infect Dis 52 Suppl 5, S397-428 (2011).
Spencer, M. et al. A primer on on-demand polymerase chain reaction technology. Am J Infect Control 43, 1102-1108 (2015).
Stenholm, T. et al. "High-throughput screening of colonization samples for methicillin-resistant *Staphylococcus aureus*". Scand J Infect Dis 45 (12), 922-929 (Dec. 2013).
Stevens, D.L. et al., Practice Guidelines for the Diagnosis and Management of Skin and Soft Tissue Infections: 2014 Update by the Infectious Diseases Society of America, ISDA Guideline. CID 2014:59. E10-E52. 43 pages.
STI & HIV 2019 World Congress, Vancouver, BC, Canada. Jul. 15-18, 2019. Poster Presentation: Emily Savela "Cell envelope damage of Neisseria gonorrhoeae after 15-min beta-lactam exposure enables rapid antimicrobial susceptibility testing" (Emily S. Savela, et al.) 1 page. (D8).
Stuck, A.K., et al., "Determinants of Quinolone versus Trimethoprim-Sulfamethoxazole Use for Outpatient Urinary Tract Infection", Antimicrob. Agents and Chemother. 2012, 56, 1359-1363.
Suay-Garcia, B., and Perez-Garcia, M.T., "Review: Drig-resistant Neisseria gonorrhoeae: latest developments", Eur J Clin Microbiol Infect Dis, (2017), 36: 1065-1071.
Sun, B. et al., "Mechanistic evaluation of the pros and cons of digital RT-LAMP for HIV-1 viral load quantification on a microfluidic device and improved efficiency via a two-step digital protocol". Anal Chem 85 (3), 1540-1546 (Feb. 2013). 14 pages.
Takagi, R. et al., "A microfluidic microbial culture device for rapid determination of the minimum inhibitory concentration of antibiotics", J. Analyst, 2013, 138, 1000-1003.
Tang, Y. et al., "Rapid antibiotic susceptibility testing in a microfluidic pH sensor". Anal Chem 85, 2787-2794 (2013).
Tanner, N.A. and T. C. Evans, Jr., "Loop-mediated isothermal amplification for detection of nucleic acids". Current Protocols in Molecular Biology, Supplement 105, Unit 15 14, 15.14.1-14.14-14 (Jan. 2014).
Tanner, N.A. et al., Simultaneous multiple target detection in real-time loop-mediated isothermal amplification. Biotechniques, vol. 53, No. 2, 81-89 (2012). 7 pages.
Tanner, N.A. et al. "Visual detection of isothermal nucleic acid amplification using pH-sensitive dyes". Biotechniques vol. 58, No. 2, 59-68 (Feb. 2015). 8 pages.
Tomasz, A. "The Mechanism of the Irreversible Antimicrobial Effects of Penicllllins", 1979, Ann. Rev. Microbiol., 33:113-137.
Tsatsaronis, J.A. et el. "Extracellular Vesicle RNA: A Universal Mediator of Microbial Communication?" Trends in Microbiology, vol. 26, Issue 5, P401-410, May 1, 2018 Website: www.cell.com/trends/microbiology/comments/S0966-842X(18)30045-3.
Tuite, N. et al., "Rapid nucleic acid diagnostics for the detection of antimicrobial resistance in Gram-negative bacteria: is it time for pagdigm shift?" J. Antimicrob. Chemother. 2014, 69, 1729-1733.

(56) References Cited

OTHER PUBLICATIONS

Typas, A. et al. "From the regulation of peptidoglycan synthesis to bacterial growth and morphology", (Feb. 2012) Nat Rev Microbiology, vol. 10, pp. 123-136.
UCLA MSTP Annual Research Conference. Westwood, CA Sep. 13, 2019. Poster Presentation: Eric Liaw. "Characterizing performance at low cell numbers of nucleic acid amplification-based phenotypic antimicrobial susceptibility assays for β-lactams and fluoroquinolones" (Eric Liaw et al.) 1 pages. (D10).
Unemo M. et al., "Antimicrobial Resistance Expressed by Neisseria gonorrhoeae: A Major Global Public Health Problem in the 21st Century". Microbiology spectrum, vol. 4, issue 3 (Jun. 2016), pp. 1-18.
Vogelstein, B. and K. W. Kinzler, "Digital PCR", Proc. Natl. Acad. Sci. U. S. A., Aug. 1999, vol. 96, 9236-9241.
Wadsworth, C.B. et al., "Impact of species diversity on the design of RNA-based diagnostics for antibiotic resistance in Neisseria gonorrhoeae", Antimicrob. Agents Chemotherap., Aug. 2019, vol. 63, Issue 8, e00549-19. 13 pages. Doi:101128/AAC.00549-19.
Wagenlehner, F.M. et al. "Therapeutic challenges of urosepsis", Eur. J. Clin. Invest. Oct. 2008, vol. 38, Issue s2 (Suppl 2), 45-49.
Wagenlehner, F.M, et al. "Urosepsis—from the view of the urologist", Int. J. Antimicrob. Agents, Dec. 2011, 38 Suppl, 51-57.
Walsh, A.L., M. D. Smith, V. Wuthiekanun, Y. Suputtamongkol, W. Chaowagul, D. A. B. Dance, B. Angus, N. J. White, Prognostic significance of quantitative bacteremia in septicemic melioidosis. Clinical Infectious Diseases, vol. 21, Issue 6, 1498-1500 (Dec. 1995).
Walsh, C., "Molecular mechanisms that confer antibacterial drug resistance", Nature, Aug. 2000, vol. 406, 775-781.
Webber, M.A. and L. J. V. Piddock, "The Importance of efflux pumps in bacterial antibiotic resistance", J. Antimicrob. Chemother. 2003, 51, 9-11.
White House, Executive Order—Combating Antibiotic Resistant Bacteria, Washington, D.C., Sep. 18, 2014. 294-299. 6 pages.
White III, R.A. et al., "Digital PCR provided sensitive and absolute calibration for hight throughput sequencing", BMC Genomics, Mar. 19, 2009, 10, 116. 12 pages.
White III, R.A. et al., "Digital PCR provides absolute quantitation of viral load for an occult RNA virus", J. Viral. Methods Jan. 2012, vol. 179, Issue 1, 45-50.
WHO, Antimicrobial Resistance: Global Report on Surveillance 2014, World Health Organization, France, 2014, p. 256.
WHO, Global Antimicrobial Resistance Surveillance System—Manual for Early Implementation. 2015. 44 pages. Website: apps.who.int/iris/bitstrearn/1066S/188783/1/9789241549400 enq.pdf; Dec. 1, 2016.
Witters, D., B. Sun, S. Begolo, J. Rodriguez-Manzano, W. Robles. R. F. Ismagilov, Digital biology and chemistry. Lab Chip 14, 3225-3232 (2014).
Wu, G.P, and S. H. Chen, R. E. Levin, Application of ethidium bromide monoazide for quantification of viable and dead cells of Salmonella enterica by real-time loop-mediated isothermal amplification. J Microbial Methods, vol. 117, 41-48 (Oct. 2015).
Xu, P. et al., "Cross-Interface Emulsification for Generating Size-Tuneable Droplets". Anal Chem, 88, 3171-3177. (2016).
Yi, J. et al. "Identification of pathogenic bacteria in human blood using IgG-modified Fe(3)O(4) magnetic beads as a sorbent and MALDI-TOF MS for profiling". Microchimica Acta 185, 542, 10 pages. doi:10.1007/s00604-018-3074-1 (2018).
Zhu, C. et al. "Rapid, Simple and High-Throughput Antimicrobial Susceptibility Testing and Antibiotics Screening", Angew. Chem. Int. Ed. Engl. Oct. 2011, vol. 50, Issue 41, 9607-9610.
Zweig, M, et.al. "Secreted single-stranded DNA is involved in the initial phase of biofilm formation by Neisseria gonorrhoeae." Environmental Microbiology, (2014) 16(4), pp. 1040-1052.
Zweig, M.H. and G. Campbell, "Receiver-operating characteristic (ROC) plots: A fundamental evaluation tool in clinical medicine". Clinical Chemistry vol. 39, No. 39, No. 4, 561-577 (1993).
Bos, M.P. et al., Function of Neisserial Outer Membrane Phospholipase A in Autolysis and Assessment of Its Vaccine Potential. Infection and Immunity, Apr. 2005, vol. 73, No. 4, pp. 2222-2231.
Clinical and Laboratory Standards Institutes (CLSI), Performance Standards for Antimicrobial Susceptibility Testing; Seventeenth Informational Supplement, 2007. Filing CLSI edition, 2013, as an equivalent.
Longitude Prize 2014, "Antibiotics", Nesta, (2014), 44 pages. www.longitudeprize.org.
"Loop-Mediated Isothermal Amplification", Mar. 2023, 4 pages. Internet: www.neb.com/applications/dna-amplification-pcr-and-qpcr/isothermal-amplification/loop-mediated-isothermal-amplification-lamp.
MSTP seminar presentation (weekly seminar for UCLA Medical Scientist Training Program Students) Sep. 9, 2019 Oral presentation: Eric Liaw "Mechanistic modeling of fluoroquinolone antimicrobial susceptibility" 57 pages. (D5).
Communication pursuant to Article 94(3) EPC (First Substantive Examination Report) for European application No. 18866873.5 filed on Aug. 19, 2020 on behalf of California Institute of Technology. dated Aug. 16, 2023. 6 pages.

* cited by examiner

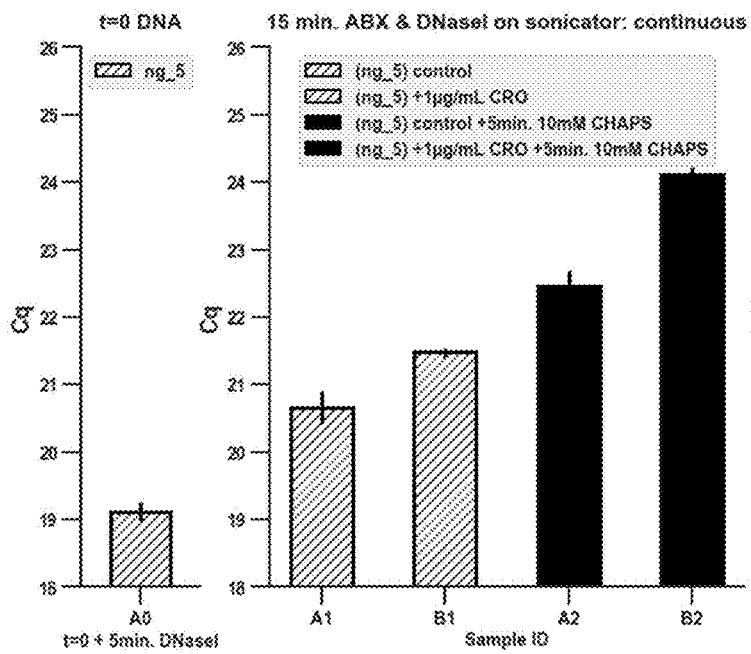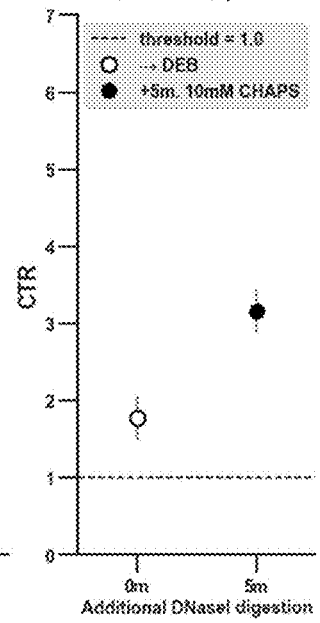
FIG. 20A  FIG. 20B  FIG. 20C

ANTIBIOTIC SUSCEPTIBILITY OF MICROORGANISMS AND RELATED COMPOSITIONS, METHODS AND SYSTEMS

CROSS-REFERENCE TO RELATED APPLICATION

The present application claims priority to U.S. Provisional Application No. 62/571,128, entitled "Antibiotic Susceptibility Testing (AST) Via Measurement of Nucleic Acid Accessibility" filed on Oct. 11, 2017, and to U.S. Provisional Application No. 62/722,124, entitled "Antibiotic Susceptibility Testing (AST) Via Measurement of Nucleic Acid Accessibility" filed on Aug. 23, 2018, the contents of each of which is incorporated by reference in its entirety.

STATEMENT OF GOVERNMENT GRANT

This invention was made with government support under Grant No. HR0011-11-2-0006 awarded by DARPA and under Grant No. EB012946 and Grant No. GM007616 awarded by the National Institutes of Health. The government has certain rights in the invention.

FIELD

The present disclosure relates to microorganisms and related biology as well as to diagnosis and treatment of related conditions in individuals. In particular, the present disclosure relates to antibiotic susceptibility of microorganisms and related markers, compositions, methods and systems.

BACKGROUND

Antibiotic susceptibility is an important feature of the biology of various microorganisms, which can be used in identifying approaches to treat or prevent bacterial infections.

Ideal antibiotic therapy is based on determination of the etiological agent for a particular condition and determination of the antibiotic sensitivity of the identified agent. In particular, the effectiveness of individual antibiotics varies with various factors including the ability of the microorganism to resist or inactivate the antibiotic.

Despite progress in identifying methods and systems to test antibiotic susceptibility for various microorganisms, as well as the identification of related markers, determination of antibiotic susceptibility can still be challenging.

In particular, determination of antibiotic susceptibility when a rapid and accurate detection is desired for microorganisms such as *Neisseria gonorrhoeae* which are slow growing and lack the classic transcriptional SOS response to DNA damage.

SUMMARY

Provided herein is an antibiotic susceptibility test (sometimes abbreviated as AST) and related compositions, methods and systems based on nucleic acid detection which in several embodiments allows determination of antibiotic susceptibility of microorganisms as well as the diagnosis and/or treatment of related infections in individuals.

According to a first aspect, a method is described to detect a nucleic acid of a microorganism in a sample comprising the microorganism. The method comprises detecting in an antibiotic treated sample a nucleic acid of the microorganism, the detecting performed quantitatively detecting in the antibiotic treated sample a nucleic acid of the microorganism, the detecting performed or in absence of a lysis treatment of the antibiotic treated sample targeting the microorganism;

in presence of a lysis treatment of the antibiotic treated sample targeting the microorganism, the lysis treatment following pre-lysis separation of nucleic acid from the microorganism in the antibiotic treated sample, or in presence of a lysis treatment of the antibiotic treated sample targeting the microorganism, the lysis treatment following pre-lysis separation of microorganism from the nucleic acid in the antibiotic treated sample, to obtain a detected antibiotic treated nucleic acid concentration value of the microorganism in the antibiotic treated sample. to obtain a detected nucleic acid in an antibiotic treated sample.

According to a second aspect, a method to perform an antibiotic susceptibility test for a microorganism is described. The method comprises detecting susceptibility to an antibiotic of the microorganism, by quantitatively detecting in a sample comprising the microorganism a nucleic acid of the microorganism following contacting the sample with the antibiotic:

in absence of a lysis treatment of the antibiotic treated sample targeting the microorganism;

or in presence of a lysis treatment of the antibiotic treated sample targeting the microorganism, the lysis treatment following pre-lysis separation of nucleic acid from the microorganism in the antibiotic treated sample, or in presence of a lysis treatment of the antibiotic treated sample following pre-lysis separation of microorganism from the nucleic acid in the antibiotic treated sample.

According to a third aspect, a method is described to detect a marker of susceptibility to an antibiotic in a microorganism. The method comprises contacting with the antibiotic a sample comprising the microorganism, the contacting performed in absence of a lysis treatment of the antibiotic treated sample targeting the microorganism;

or in presence of a lysis treatment of the antibiotic treated sample targeting the microorganism, the lysis treatment following pre-lysis separation of nucleic acid from the microorganism in the antibiotic treated sample, or in presence of a lysis treatment of the antibiotic treated sample targeting the microorganism, the lysis treatment following pre-lysis separation of microorganism from the nucleic acid in the antibiotic treated sample, to obtain an antibiotic treated sample.

The method further comprises quantitatively detecting in the antibiotic treated sample a nucleic acid of the microorganism to obtain an antibiotic treated concentration value, The method also comprises detecting a nucleic acid concentration ratio in the sample by comparing the detected antibiotic treated nucleic acid concentration value with a detected reference nucleic acid concentration value of the nucleic acid of the microorganism in the sample, the nucleic acid concentration ratio is indicative of resistance or susceptibility of the microorganism to the antibiotic.

According to a fourth aspect, a method to diagnose susceptibility to an antibiotic of a microorganism infection in an individual is described. The method comprises contacting with the antibiotic a sample from the individual, the sample including the microorganism, the contacting performed
in absence of a lysis treatment of the antibiotic treated sample targeting the microorganism;
or
in presence of a lysis treatment of the antibiotic treated sample targeting the microorganism, the lysis treatment following pre-lysis separation of nucleic acid from the microorganism in the antibiotic treated sample, or
in presence of a lysis treatment of the antibiotic treated sample targeting the microorganism, the lysis treatment following pre-lysis separation of microorganism from the nucleic acid in the antibiotic treated sample, to obtain an antibiotic treated sample;

The method further comprises detecting in the antibiotic treated sample a nucleic acid of the microorganism to obtain a detected antibiotic treated concentration value.

The method also comprises detecting a nucleic acid concentration ratio in the sample of the individual by comparing the detected antibiotic treated nucleic acid concentration value with a detected reference nucleic acid concentration value of the nucleic acid of the microorganism in the sample of the individual, and comparing the detected nucleic acid concentration ratio in the sample with a threshold to diagnose the antibiotic susceptibility of the microorganism infection in the individual.

According to a fifth aspect, a method is described to detect antibiotic susceptibility of a microorganism and treat an infection of the microorganism in an individual. The method comprises contacting a sample from the individual with an antibiotic, the contacting performed
in absence of a lysis treatment of the antibiotic treated sample targeting the microorganism;
or
in presence of a lysis treatment of the antibiotic treated sample targeting the microorganism, the lysis treatment following pre-lysis separation of nucleic acid from the microorganism in the antibiotic treated sample, or
in presence of a lysis treatment of the antibiotic treated sample targeting the microorganism, the lysis treatment following pre-lysis separation of microorganism from the nucleic acid in the antibiotic treated sample,
to obtain an antibiotic treated sample.

The method further comprises detecting in the antibiotic treated sample, a nucleic acid of the microorganism to obtain an antibiotic treated concentration value.

The method also comprises detecting a nucleic acid concentration ratio in the sample of the individual by comparing the detected antibiotic treated nucleic acid concentration value with a detected reference nucleic acid concentration value of the nucleic acid of the microorganism in the sample of the individual.

The method further comprises diagnosing antibiotic susceptibility of the microorganism infection in the individual by comparing the nucleic acid concentration ratio with a threshold.

The method additionally comprises administering an effective amount of the antibiotic to an individual diagnosed with a microorganism susceptible to the antibiotic.

According to a sixth aspect, a system is described for performing at least one of the methods herein described to detect a nucleic acid of a microorganism in a sample, to detect antibiotic susceptibility of a microorganism, to perform an antibiotic susceptibility test for the microorganism, and/or to diagnose and/or treat a microorganism infection in an individual. The system comprises an antibiotic, at least a probe specific for a nucleic acid of the microorganism or for a polynucleotide complementary thereto, and reagents for detecting the at least one probe. The system can optionally comprise reagents to perform a lysis treatment, a separation treatment and/or mechanical separation of the sample for concurrent sequential or combined use in any one of the methods of the disclosure.

The antibiotic susceptibility test and related compositions, methods and systems herein described allow in several embodiments phenotypic measurements of antibiotic susceptibility and resistance of a microorganism (e.g. *N gonorrhoeae*).

The antibiotic susceptibility test and related compositions, methods and systems allow in several embodiments to perform an accurate and rapid antibiotic susceptibility test for microorganisms such as *N. gonorrhoeae* and carbapenem-resistant Enterobacteriaceae (CRE) based on quantification of DNA and/or RNA.

The antibiotic susceptibility test and related compositions, methods and systems herein described allow in several embodiments to provide an assay with a duration that shorter than the gold standard, through the short antibiotic exposure times and rapid nucleic acid quantification, enabling point of care timescales.

The antibiotic susceptibility test and related compositions, methods and systems herein described can be used in connection with various applications wherein identification and/or detection of antibiotic susceptibility for a microorganism is desired. For example, antibiotic susceptibility test and related compositions, methods and systems herein described can be used in drug research and to develop diagnostic and therapeutic approaches and tools to counteract infections, and to enable development and commercialization of narrow-spectrum antimicrobial therapeutics, such as antimicrobial therapeutics with a narrower spectrum than the therapeutic that would have been prescribed in the absence of the test. Additional exemplary applications include uses of the antibiotic susceptibility test and related compositions, methods and systems herein described in several fields including basic biology research, applied biology, bio-engineering, etiology, medical research, medical diagnostics, therapeutics, and in additional fields identifiable by a skilled person upon reading of the present disclosure.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description and example sections, serve to explain the principles and implementations of the disclosure. Exemplary embodiments of the present disclosure will become more fully understood from the detailed description and the accompanying drawings, wherein:

FIG. 11A shows that total nucleic acid concentration (NA=DNA+RNA) measured from the extraction FIG. 11B shows the total DNA concentration measured from the extraction. FIG. 11C shows the C:T ratio computed from the total nucleic acid measurement (ddRT-PCR of extractions in the presence of a reverse-transcription enzyme), right. The concentrations are quantified in digital PCR.

FIG. 12A shows a diagram illustrated the RNA concentrations computed from the subtraction of the DNA from the total NA as described in Example 6. FIG. 12B shows a diagram illustrating a CT ratio to differentiate between the susceptible and resistant isolates, giving a very similar readout to the CT ratio computed from the total RNA measurement. And conclusions made as with previous DNA accessibility CT ratios.

FIG. 17A shows the raw qPCR measurements of *N. gonorrhoeae* 16S DNA with error bars of triplicate qPCR measurements. Sample ID of A1 corresponds to susceptible isolate ng_17 (untreated sample). Sample ID of B1 corresponds to susceptible isolate ng_17 treated with the antibiotic penicillin. Sample ID of A3 corresponds to the susceptible isolate ng_17 (untreated sample) with 30 s of covaris sonication at 15 W peak incident power. Sample ID of B3 corresponds to susceptible isolate ng_17 treated with the antibiotic penicillin with 30 s of covaris sonication at 15 W peak incident power. Sample ID of A5 is the sample as A3 but with 5 W peak incident power. Sample ID of B5 is the same as sample B3 but with 5 W peak incident power. FIG. 17B shows the corresponding conversion to a CT ratio from each condition. The x-axis is sorted by the peak incident power of sonication, showing the relationship between changing this parameter and the efficacy of sonication as an enhancer. The power of 15 W for 30 s after antibiotic treatment enhances the ability of the DNaseI to degrade accessible DNAs and decrease the amount of inaccessible nucleic acids in the antibiotic-treated sample.

FIG. 18A shows the untreated (A1, B1, C1) samples and treated samples (A3, B3, C3) for three conditions with a DNaseI treatment after sonication. Samples A1 and A3 did not undergo a sonication treatment after a 15-minute antibiotic exposure. Samples B1 and B3 underwent 30 seconds of sonication after the same 15-minute antibiotic exposure as A1 and A3. Samples C1 and C3 are the same as Samples B1 and B3 but with a 12-second of sonication. FIG. 18B shows the same samples as in FIG. 18A, but with an additional enhancer. Samples B2, B4, C2, and C4 all experienced two enhancers (1) sonication enhancer and (2) surfactant enhancer of 5 mM TNP for 5 minutes after sonication. FIG. 18C shows the conversion of these qPCR measurements into CT ratios. The open black circles represent the data from FIG. 18A, with DNaseI only and the black-filled-in circles represent data from FIG. 18B with the combination of both sonication and surfactant incubation.

FIGS. 20A-20C show diagrams illustrating the results of an exemplary AST according to the disclosure in which mechanical disruption by sonication is used as an enhancer for beta-lactam incubation, in combination with DNaseI as a degrader.

FIG. 22A illustrates the qPCR measurements, shown as Cqs with an error bar of a 95% confidence interval based on triplicate measurements. The "t0" measurements (the first bar of each pair) represent the initial amount of inaccessible nucleic acids in a sample. These samples have undergone a 5-minute DNaseI treatment, but no antibiotic exposure or enhancement treatments. The treated measurements are from the sonication enhancement and antibiotic incubation. FIG. 22B shows t0/TREATED ratio for isolates ng_19 treated with CRO, ng_30 treated with CRO, and ng_19 treated with PEN.

FIG. 44A shows the LAMP data for susceptible, labeled "S" on the x-axis and shown as open circles, and resistant, labeled "R" on the x-axis and shown as black circles isolates of *E. coli* exposed to four different antibiotics. The antibiotics include ampicillin (AMP), ceftriaxone (CRO), ertapenem (ETP), and meropenem (MEM). The y-axis shows the time-to-positive (TTP) measurement of the treated-sample adjusted for the TTP of the reference sample, which in this example is the DEB extracted nucleic acids quantified with a separate LAMP measurement. FIG. 44B shows the same measurements as FIG. 44A, but for a *K. pneumoniae* instead of *E. coli*. and with a different set of antibiotics. FIG. 44B shows *K. pneumoniae* responses to the antibiotics ceftriaxone (CRO), ertapenem (ETP), and meropenem (MEM).

In FIG. 45A *N. gonorrhoeae* isolates are tested with the antibiotic penicillin (PEN), with at least three biological replicates of each isolate. On the x-axis, a prefix of "S" refers to antibiotic-susceptible isolates and a prefix of "R" refers to an antibiotic-resistant isolate. In FIG. 45B *N. gonorrhoeae* isolates are tested with the antibiotic ceftriaxone (CRO), with at least three biological replicates of each isolate. On the x-axis, a prefix of "S" refers to antibiotic-susceptible isolates, a prefix of "E" refers to an isolate with an elevated MIC, and a prefix of "R" refers to an antibiotic-resistant isolate or an isolate with reduced-susceptibility to ceftriaxone. In FIG. 45C *N. gonorrhoeae* isolates are tested with the antibiotic cefixime (CFM), with at least three biological replicates of each isolate. On the x-axis, a prefix of "S" refers to antibiotic-susceptible isolates and a prefix of "R" refers to an antibiotic-resistant isolate.

DETAILED DESCRIPTION

Figure 1:
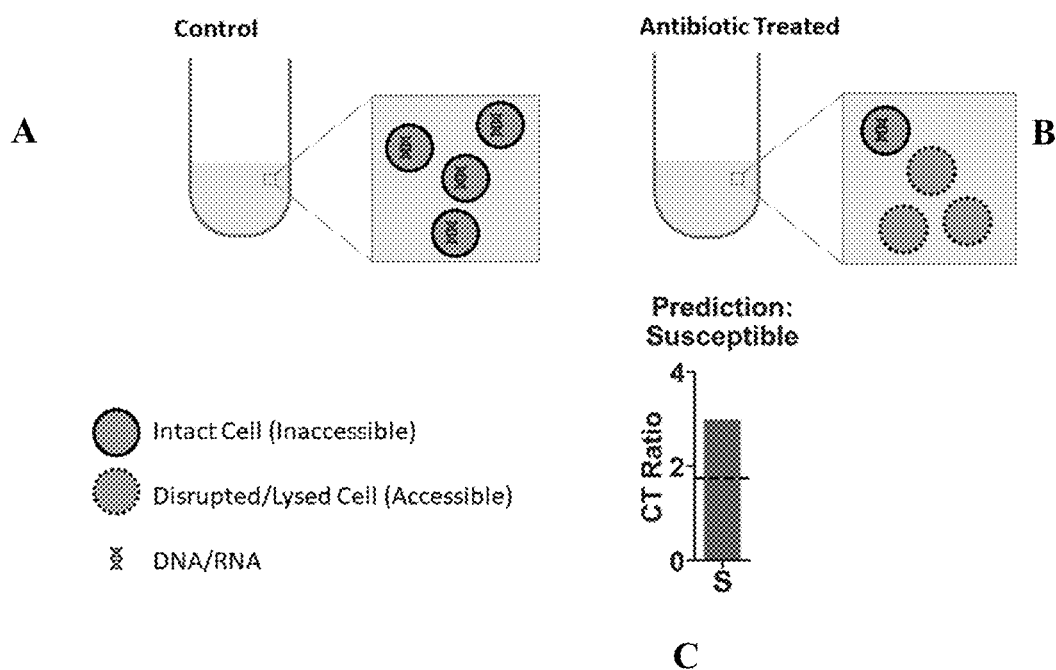
FIG. 1 shows a schematic representation of an exemplary outcome of an exemplary antibiotic susceptibility test for a susceptible microorganism of the instant disclosure. In particular, Panel A shows a schematic representation of a control sample comprising the microorganism not treated with antibiotic and showing inaccessible DNA in an intact cell. Panel B shows a schematic representation of an antibiotic-treated sample showing a disrupted or lysed susceptible microorganism cell with DNA accessible to nuclease. Panel C shows a diagram illustrating the CT ratio of the control sample of Panel A and the antibiotic-treated sample of Panel B. A threshold control-treated (CT) ratio (the dashed line with a prediction of the cell being antibiotic susceptible (S).

Provided herein is an antibiotic susceptibility test for microorganisms and related compositions, methods and systems which is based on quantitative detection of nucleic acids of the microorganism following administration of the antibiotic to the microorganism.

The term "nucleic acid" or "polynucleotide" as used herein indicates an organic polymer composed of two or more monomers including nucleotides, nucleosides or analogs thereof. The term "nucleotide" refers to any of several compounds that consist of a ribose or deoxyribose sugar joined to a purine or pyrimidine base and to a phosphate group and that is the basic structural unit of nucleic acids. The term "nucleoside" refers to a compound (such as guanosine or adenosine) that consists of a purine or pyrimidine base combined with deoxyribose or ribose and is found especially in nucleic acids. Accordingly, the term "polynucleotide" includes nucleic acids of any length, and in particular DNA, RNA, and fragments thereof. A polynucleotide of three or more nucleotides is also called "nucleotidic oligomer" or "oligonucleotide."

The term "DNA" or Deoxyribonucleic acid" as used herein indicates a polynucleotide composed of deoxiribonucleotide bases or an analog thereof to form an organic polymer. The term "deoxyribonucleotide" refers to any compounds that consist of a deoxyribose (deoxyribonucleotide) sugar joined to a purine or pyrimidine base and to a phosphate group, and that are the basic structural units of a deoxyribonucleic acid, typically adenine (A), cytosine (C), guanine (G), and thymine (T). In an DNA adjacent ribose nucleotide bases are chemically attached to one another in a chain typically via phosphodiester bonds. The term "deoxyribonucleotide analog" refers to a deoxyribonucleotide in which one or more individual atoms have been replaced with a different atom with a different functional group. For example, deoxyribonucleotide analogues include chemically modified deoxyribonucleotides, such as methylation hydroxymethylation glycosylation and additional modifications identifiable by a skilled person.

The term "RNA" or "Ribonucleic acid" as used herein indicates a polynucleotide composed of ribonucleotide bases: or an analog thereof linked to form an organic polymer. The term "ribonucleotide" refers to any compounds that consist of a ribose (ribonucleotide) sugar joined to a purine or pyrimidine base and to a phosphate group, and that are the basic structural units of a ribonucleic acid, typically adenine (A), cytosine (C), guanine (G), and uracil (U). In an RNA adjacent ribose nucleotide bases are chemically attached to one another in a chain typically via phosphodiester bonds. The term "ribonucleotide analog" refers to a ribonucleotide in which one or more individual atoms have been replaced with a different atom with a different functional group. For example, ribonucleotide analogues include chemically modified ribonucleotides, such as methylation hydroxymethylation glycosylation and additional modifications identifiable by a skilled person. Examples of chemical modifications of RNA comprise dynamic modifications to RNA identified in the transcriptome, including $N^6$-methyladenosine ($m^6A$), inosine (I), 5-methylcytosine ($m^5C$), pseudouridine (Ψ), 5-hydroxymethylcytosine ($hm^5C$), and $N^1$-methyladenosine ($m^1A$), and related epitranscriptome which are described in Song and Yi 2017. [1] Additional chemical modifications of transfer RNA (tRNA) are described in Jackman and Alfonzo 2013 [2] Accordingly, the term RNA includes ribonucleic acids of any length including analogs or fragments thereof.

The term "antibiotic" sometimes abbreviated as ABX, as used herein refers to a type of antimicrobial used in the treatment and prevention of bacterial infection. Some antibiotics can either kill or inhibit the growth of bacteria. Others can be effective against fungi and protozoans. The term "antibiotic" can be used to refer to any substance used against microbes. Antibiotics are classified based on their mechanism of action, chemical structure, or spectrum of activity. Most antibiotics target bacterial functions or growth processes. Antibiotics having bactericidal activities target the bacterial cell wall, such as penicillins and cephalosporins, or target the cell membrane, such as polymyxins, or interfere with essential bacterial enzymes, such as rifamycins, lipiarmycins, quinolones and sulfonamides. Antibiotics having bacteriostatic properties target protein synthesis, such as macrolides, lincosamides and tetracyclines. Antibiotics can be further categorized based on their target specificity. "Narrow-spectrum" antibacterial antibiotics target specific types of bacteria, such as Gram-negative or Gram-positive bacteria or a specific genus of bacteria. "Broad-spectrum" antibiotics affect a wide range of bacteria. Antibiotics can also be used in combinations with each other or with adjuvant substances (such as cilastatin or beta-lactamase inhibitors) that enhance their antimicrobial activity. These combinations are often approved by the Food and Drug Administration as distinct drug names.

In preferred embodiments, this method is used to analyze susceptibility and resistant antibiotics that directly or indirectly interact with cell envelope, structure and function, and integrity. Exemplary antibiotics include beta-lactam antibiotics, and consisting of all antibiotic agents that contain a beta-lactam ring in their molecular structures. Including penicillin derivatives (penams), cephalosporins (cephems), monobactams, and carbapenems. Penams include narrow-spectrum penems such as, benzathine penicillin (benzathine & benzylpenicillin), benzylpenicillin (penicillin G), phenoxymethylpenicillin (penicillin V), Procaine penicillin (procaine & benzylpenicillin), and Pheneticillin. Broad spectrum penams include amoxicillin and ampicillin. Extended spectrum penems include mecillinam, nafcillin, oxacillin, dicloxacillin, carboxypenicillins (including carbenicillin and ticarcillin), and ueidopenicillins (including azlocillin, mezlocillin, and piperacillin). Cephems include first, second, third, fourth, and fifth generation cephalosporins; including cefazolin, cephalexin, cephalosporin C, cephalothin, cefaclor, cefamandole, cefuroxime, cefotetan, cefoxitin, cefixime, cefdinir, cefoperazone, cefotaxime, cefpodoxime, ceftazidime, ceftriaxone, cefepime, cefpirome, and ceftaroline. Carbapenems include biapenem, doripenem, ertapenem, faropenem, imipenem, meropenem, panipenem, razupenem, tebipenem, and thienamycin. Monobactams include aztreonam, tigemonam, nocardicin A, and tabtoxinine b-lactam. Exemplary combinations of antibiotics and adjuvant substances include ampicillin/sulbactam, amoxicillin/clavulanate, ticarcillin/clavulanate, piperacillin/tazobactam, ceftazidime/avibactam, imipenem/cilastatin, and meropenem/vaborbactam. Other antibiotics that may impact the cell wall directly or indirectly include polymixin B, colistin, depolarizing antibiotics such as daptomycin, antibiotics that hydrolyze NAM-NAG, tyrothricin (Gramicidin or Tyrocidine), isoniazid, and teixobactin. Antibiotics that inhibit peptidoglycan chain elongation including vancomycin (Oritavancin Telavancin), teicoplanin (Dalbavancin), and ramoplanin. Antibiotics that inhibit peptidoglycan subunit synthesis and transport include NAM synthesis inhibition (fosfomycin), DADAL/AR inhibitors (Cycloserine), and bactoprenol inhibitors (bacitracin).

The wording "antibiotic susceptibility" or "antibiotic sensitivity" as used herein indicates the susceptibility of bacteria to antibiotics and the antibiotic susceptibility can vary within a species. Antibiotic susceptibility testing (AST) can be carried out to predict the clinical response to treatment and guide the selection of antibiotics as will be understood by a person skilled in the art. In some embodiments, AST categorizes organisms as susceptible, resistant, or intermediate to a certain antibiotic.

Microorganisms can be classified as susceptible (sensitive), intermediate or resistant based on breakpoint minimum inhibitory concentration (MIC) values that are arbitrarily defined and reflect the achievable levels of the antibiotic, the distribution of MICs for the organism and their correlation with clinical outcome. MIC value of a microorganism is the lowest concentration of an antibiotic that will inhibit its growth. Methods that can be used to measure the MIC of a microorganism comprise broth dilution, agar dilution and gradient diffusion (the 'E test'), where twofold serial dilutions of antibiotic are incorporated into tubes of broth, agar plates or on a paper strip, respectively, as will be understood by a person skilled in the art. The disk diffusion method defines an organism as susceptible or resistant based on the extent of its growth around an antibiotic-containing disk. MIC values are influenced by several laboratory factors.

Laboratories follow standard for parameters such as incubation temperature, incubation environment, growth media, as well as inoculum and quality control parameters. In the U.S. Standards for performing AST as well as breakpoint MIC values for various bacteria can be found in Clinical & Laboratory Standards Institute (CLSI) publications, with an example also enclosed herein as Appendix C, as will be understood by the skilled person. In Europe, standards for performing AST as well as breakpoint MIC values for bacteria can be found in European Committee on Antimicrobial Susceptibility Testing (EUCAST) see the web page eucast.org/clinical_breakpoints/ at the time of filing of the instant disclosure) as will be understood by the skilled person.

The term "microorganism", or "microbe" as used herein indicates a microscopic living organism, which may exist in its single-celled form or in a colony of cells, such as prokaryotes and in particular bacteria, and including fungi (yeast and molds), and protozoal parasites. Microorganisms include human and animal pathogens. Microorganisms can comprise one or more prokaryotes or individual genera or species of prokaryotes.

The term "prokaryotic" is used herein interchangeably with the terms "cell" and refers to a microbial species which contains no nucleus or other membrane-bound organelles in the cell. Exemplary prokaryotic cells include bacteria and archaea.

The term "bacteria" or "bacterial cell", used herein interchangeably with the term "cell" indicates a large domain of prokaryotic microorganisms. Typically a few micrometers in length, bacteria have a number of shapes, ranging from spheres to rods and spirals, and are present in most habitats on Earth, such as terrestrial habitats like deserts, tundra, Arctic and Antarctic deserts, forests, savannah, chaparral, shrublands, grasslands, mountains, plains, caves, islands, and the soil, detritus, and sediments present in said terrestrial habitats; freshwater habitats such as streams, springs, rivers, lakes, ponds, ephemeral pools, marshes, salt marshes, bogs, peat bogs, underground rivers and lakes, geothermal hot springs, sub-glacial lakes, and wetlands; marine habitats such as ocean water, marine detritus and sediments, flotsam and insoluble particles, geothermal vents and reefs; man-made habitats such as sites of human habitation, human dwellings, man-made buildings and parts of human-made structures, plumbing systems, sewage systems, water towers, cooling towers, cooling systems, air-conditioning systems, water systems, farms, agricultural fields, ranchlands, livestock feedlots, hospitals, outpatient clinics, health-care facilities, operating rooms, hospital equipment, long-term care facilities, nursing homes, hospice care, clinical laboratories, research laboratories, waste, landfills, radioactive waste; and the deep portions of Earth's crust, as well as in symbiotic and parasitic relationships with plants, animals, fungi, algae, humans, livestock, and other macroscopic life forms. Bacteria in the sense of the disclosure refers to several prokaryotic microbial species which comprise Gram-negative bacteria, Gram-positive bacteria, Proteobacteria, Cyanobacteria, Spirochetes and related species, *Planctomyces, Bacteroides, Flavobacteria, Chlamydia*, Green sulfur bacteria, Green non-sulfur bacteria including anaerobic phototrophs, Radioresistant micrococci and related species, *Thermotoga* and *Thermosipho* thermophiles as would be understood by a skilled person. Taxonomic names of bacteria that have been accepted as valid by the International Committee of Systematic Bacteriology are published in the "Approved Lists of Bacterial Names" [3] as well as in issues of the International Journal of Systematic and Evolutionary Microbiology. More specifically, the wording "Gram positive bacteria" refers to cocci, nonsporulating rods and sporulating rods that stain positive on Gram stain, such as, for example, *Actinomyces, Bacillus, Clostridium, Corynebacterium, Cutibacterium* (previously *Propionibacterium*), *Erysipelothrix, Lactobacillus, Listeria, Mycobacterium, Nocardia, Staphylococcus, Streptococcus, Enterococcus, Peptostreptococcus*, and *Streptomyces*. Bacteria in the sense of the disclosure refers also to the species within the genera *Clostridium, Sarcina, Lachnospira, Peptostreptococcus, Peptoniphilus, Helcococcus, Eubacterium, Peptococcus, Acidaminococcus, Veillonella, Mycoplasma, Ureaplasma, Erysipelothrix, Holdemania, Bacillus, Amphibacillus, Exiguobacterium, Gracilibacillus, Halobacillus, Saccharococcus, Salibacillus, Virgibacillus, Planococcus, Kurthia, Caryophanon, Listeria, Brochothrix, Staphylococcus, Gemella, Macrococcus, Salinococcus, Sporolactobacillus, Marinococcus, Paenibacillus, Aneurinibacillus, Brevibacillus, Alicyclobacillus, Lactobacillus, Pediococus, Aerococcus, Abiotrophia, Dolosicoccus, Eremococcus, Facklamia, Globicatella, Ignavigranum, Carnobacterium, Alloiococcus, Dolosigranulum, Enterococcus, Melissococcus, Tetragenococcus, Vagococcus, Leuconostoc, Oenococcus, Weissella, Streptococcus, Lactococcus, Actinomyces, Arachnia, Actinobaculum, Arcanobacterium, Mobiluncus, Micrococcus, Arthrobacter, Kocuria, Nesterenkonia, Rothia, Stomatococcus, Brevibacterium, Cellulomonas, Oerskovia, Dermabacter, Brachybacterium, Dermatophilus, Dermacoccus, Kytococcus, Sanguibacter, Jonesia, Microbacteirum, Agrococcus, Agromyces, Aureobacterium, Cryobacterium, Corynebacterium, Dietzia, Gordonia, Skermania, Mycobacterium, Nocardia, Rhodococcus, Tsukamurella, Micromonospora, Propioniferax, Nocardioides, Streptomyces, Nocardiopsis, Thermomonospora, Actinomadura, Bifidobacterium, Gardnerella, Turicella, Chlamydia, Chlamydophila, Borrelia, Treponema, Serpulina, Leptospira, Bacteroides, Porphyromonas, Prevotella, Flavobacterium, Elizabethkingia, Bergeyella, Capnocytophaga, Chryseobacterium, Weeksella, Myroides, Tannerella, Sphingobacterium, Flexibacter, Fusobacterium, Streptobacillus, Wolbachia, Bradyrhizobium, Tropheryma, Megasphera, Anaeroglobus*.

The term "proteobacteria" as used herein refers to a major phylum of Gram-negative bacteria. Many move about using flagella, but some are nonmotile or rely on bacterial gliding. As understood by skilled persons, taxonomic classification as proteobacteria is determined primarily in terms of ribosomal RNA (rRNA) sequences. The Proteobacteria are divided into six classes, referred to by the Greek letters alpha through epsilon and the Acidithiobacillia and Oligoflexia, including the alphaproteobacteria, betaproteobacteria and gammaproteobacteria as will be understood by a skilled person. Proteobacteria comprise the following genera: in the Alphaproteobacteria, *Rickettsia, Ehrlichia, Anaplasma, Sphingomonas, Brevundimonas, Agrobacterium, Bartonella, Brucella, Ochrobactrum, Afipia, Methylobacterium*, and *Roseomonas*; in the Betaproteobacteria, *Burkholderia, Ralsonia, Alcaligenes, Achromobacter, Chromobacterium, Bordetella, Taylorella, Comamonas, Neisseria, Alysiella, Eikenella, Kingella*, and *Spirillum*; in the Gammaproteobacteria, *Xanthomonas, Stenotrophomonas, Cardiobacterium, Suttonella, Francisella, Legionella, Coxiella, Ricketsiella, Pseudomonas, Chryseomonas, Flavimonas, Oligella, Moraxella (Branhamella), Acinetobacter, Psychrobacter, Shewanella, Vibrio, Photobacterium, Aeromonas, Succinivibrio, Anaerobiospirillum, Ruminobacter, Succinimonas, Enterobacter, Brenneria, Budvicia, Buttiauxella, Calymmatobacterium, Cedeceae, Citrobacter, Edwardsiella, Erwinia, Escherichia, Ewingella, Hafnia, Klebsiella, Kluyvera, Leclercia, Leminorella, Moellerella, Morganella, Obesumbacterium, Pantoea, Plesiomonas, Proteus, Providencia, Rahnella, Salmonella, Serratia, Shigella, Tatumella, Trabulsiella, Yersinia, Yokenella, Pasteurella, Actinobacillus (Aggregatibacter), Haemophilus*, and *Mannheimia*; in the Deltaproteobacteria, *Desulfovibrio* and *Biophila*; in the Epsilonproteobacteria, *Campylobacter, Arcobacter, Helicobacter*, and *Wolinella*. [4]. The Proteobacteria also comprise the species which are classified within the aforementioned genera. Within the Proteobacteria are the species *Neisseria gonorrhoeae* and *Neisseria meningitidis* within the class Betaproteobacteria, the order Neisseriales the family Neisseriaceae, and the genus *Neisseria*. It should be understood by the skilled practitioner that the classification and nomenclature of formal bacterial species is subject to revision as new scientific knowledge is discovered. Changes in name are performed according to rules in the International Code of Nomenclature of Bacteria, and future name changes can be found by consulting the International Journal of Systematic and Evolutionary Microbiology.

The term Enterobacteriaceae in the sense of the disclosure refers to members of the Proteobacteria that fall within the family Enterobacteriaceae, Class Gammaproteobacteria, as defined by the International Committee of Systematic Bacteriology. These bacteria are Gram-negative rods that can inhabit the gastrointestinal tracts of animals as well as environmental surfaces. Many species are pathogenic in humans and other animals. Many species are commensals that become pathogenic when their hosts immune barriers are breached. Enterobacteriaceae are frequently encountered in clinical specimens. [4] Enterobacteriaceae include the following taxa and clinical entities: *Escherichia coli* (*E. coli*), uropathogenic *E. coli*, enterotoxigenic *E. coli*, enteroaggregative *E. coli*, enteropathogenic *E. coli*, enteroinvasive *E. coli*, enterohemorrhagic *E. coli*, Shiga toxin-producing *E. coli*, diffusely adherent *E. coli*, *Klebsiella pneumoniae* subsp. *ozaenae*, *Klebsiella pneumoniae* subsp. *pneumoniae*, *Klebsiella pneumoniae* subsp. *rhinoscleromatis*, *Klebsiella oxytoca*, *Enterobacter aerogenes*, *Enterobacter cloacae*, *Citrobacter freundii*, *Citrobacter koseri* (*Citrobacter diversus*), *Salmonella enterica* subsp. *enterica* and its serovars, *Salmonella enterica Typhi*, *Salmonella enterica Paratyphi*, *Salmonella bongori*, *Shigella dysenteria*, *Shigella flexneri*, *Shigella boydii*, *Shigella sonnei*, *Proteus mirabilis*, *Proteus vulgaris*, *Serratia marcescens*, *Yersinia pestis*, *Yersinia enterocolitica*, *Yersinia pseudotuberculosis*, *Providencia stuartii*, *Edwardsiella hoshinae*, *Raoultella ornithinolytica*, *Raoultella planticola*, *Raoultella terrigena*, *Arizona hinshawii*, *Budvicia aquatica*, *Buttiauxella agrestis*, *Buttiauxella brennerae*, *Buttiauxella ferragutiae*, *Buttiauxella gaviniae*, *Buttiauxella izardii*, *Buttiauxella noackiae*, *Buttiauxella warmboldiae*, *Cedecea davisae*, *Cedecea lapagei*, *Cedecea neteri*, *Cedecea* species 3, *Cedecea* species 5, *Citrobacter amalonaticus*, *Citrobacter braakii*, *Citrobacter farmer*, *Citrobacter gillenii*, *Citrobacter murliniae*, *Citrobacter rodentium*, *Citrobacter sedlakii*, *Citrobacter werkmanii*, *Citrobacter youngae*, *Edwardsiella ictaluri*, *Edwardsiella tarda*, *Edwardsiella tarda* biogroup 1, *Enterobacter amnigenus*, *Enterobacter asburiae*, *Enterobacter cancerogenus* (*Enterobacter taylorae*), *Enterobacter cowanii*, *Enterobacter dissolvens*, *Enterobacter gergoviae*, *Enterobacter hormaechei*, *Enterobacter intermedius*, *Enterobacter kobei*, *Enterobacter nimipressuralis*, *Enterobacter pyrinus*, *Enterobacter sakazakii*, *Erwinia* spp., *Ewingella americana*, *Hafnia alvei*, *Kluyvera ascorbate*, *Kuyvera cryocrescens*, *Kluyvera georgiana*, *Leclercia adecarboxylata*, *Leminorella grimontii*, *richardii*, *Moellerella wisconsensis*, *Morganella morganii*, *Obesumbacterium proteus*, *Pantoea agglomerans*, *Pantoea dispersa*, *Photorhabdus luminescens*, *Photorhabdus asymbiotica*, *Pragia fontium*, *Proteus hauseri*, *Proteus myxofaciens*, *Proteus penneri*, *Providencia alcalifaciens*, *Providencia heimbachae*, *Providencia rettgeri*, *Providencia rustigianii*, *Rahnella aquatilis*, *Serratia entomophilia*, *Serratia ficaria*, "*Serratia fonticola*", *Serratia liquifaciens* group, *Serratia odorifera*, *Serratia plymuthica*, *Serratia rubidea*, *Tatumella ptyseos*, *Trabulsiella guamensis*, *Xenorhabdus nematophilus*, *Yersinia aldovae*, *Yersinia bercoviera*, *Yersinia frederiksenii*, *Yersinia intermedia*, *Yersinia kristensenii*, *Yersinia mollaretii*, *Yersinia rohdei*, "*Yersinia ruckeri*", *Yokenella regensburgei*.

The term carbapenem-resistant Enterobacteriaceae in the sense of this disclosure refers to any member of the family Enterobacteriaceae, defined earlier, that exhibit resistance to at least one member of the carbapenem class of antibiotics, defined earlier. The term carbapenem-resistant Enterobacteriaceae can be abbreviated as "CRE". CRE isolates are frequently resistant to classes of beta-lactam antibiotics besides the carbapenems, namely the penicillins, cephalosporins, and monobactams. CRE isolates also frequently carry resistance toward other classes of antibiotics. Some CRE isolates are susceptible very few antibiotics, and some CRE isolates have been found to be resistant to all antibiotics available for use in humans in the USA or Europe. CRE achieve antibiotic resistance through a variety of resistance mechanisms, including the expression of enzymes that degrade beta-lactam antibiotics (carbapenemases, extended-spectrum beta-lactamases, and beta-lactamases), alterations in expression of their porin genes, and by unknown mechanisms. CRE prevalence has increased worldwide and in the USA in the past three decades. CRE cause a significant fraction of health-care associated infections. CRE infections have an estimated 50% mortality rate in the USA.

In embodiments of the instant disclosure, methods and systems are described that are based on detection of a nucleic acid of a microorganism in a sample of an isolate or specimen treated with the antibiotic and in a sample of the isolate or specimen not treated with antibiotic.

The microorganism tested with methods and systems of the disclosure is generally referred in the present disclosure as target microorganism, and the nucleic acid detected in methods and systems of the instant disclosure is generally referred as target nucleic acid.

Accordingly, the term "target microorganism", or "target microbe" as used herein indicates one or more microorganisms in the sample targeted specifically by the methods described herein. For example, when a sample contains a mixture of pathogens and commensal organisms, the target microorganism of methods and system herein described can be one or more of the pathogens in the mixture.

The term "target nucleic acid" as used herein indicates a nucleic acid of a target microorganism detected by methods described herein. In particular in the nucleic acid detection methods described herein, one or more nucleic acids from the target organism may be targeted for detection.

The term "sample" as used herein indicates a limited quantity of something that is indicative of a larger quantity of that something, including but not limited to fluids from an isolate or a specimen such as biological environment, cultures, tissues, commercial recombinant proteins, synthetic compounds or portions thereof. In particular biological sample can comprise one or more cells of any biological lineage, as being representative of the total population of similar cells in the sampled individual. Exemplary biological samples comprise the following: whole venous and arterial blood, blood plasma, blood serum, dried blood spots, cerebrospinal fluid, lumbar punctures, nasal secretions, sinus washings, tears, corneal scrapings, saliva, sputum or expectorate, bronchoscopy secretions, transtracheal aspirate, endotracheal aspirations, bronchoalveolar lavage, vomit, endoscopic biopsies, colonoscopic biopsies, bile, vaginal fluids and secretions, endometrial fluids and secretions, urethral fluids and secretions, mucosal secretions, synovial fluid, ascitic fluid, peritoneal washes, tympanic membrane aspirate, urine, clean-catch midstream urine, catheterized urine, suprapubic aspirate, kidney stones, prostatic secretions, feces, mucus, pus, wound draining, skin scrapings, skin snips and skin biopsies, hair, nail clippings, cheek tissue, bone marrow biopsy, solid organ biopsies, surgical specimens, solid organ tissue, cadavers, or tumor cells, among others identifiable by a skilled person. Biological samples can be obtained using sterile techniques or non-sterile techniques, as appropriate for the sample type, as identifiable by persons skilled in the art. Some biological samples can be obtained by contacting a swab with a surface on a human body and removing some material from said surface, examples include throat swab, nasal swab, nasopharyngeal swab, oropharyngeal swab, cheek or buccal swab, urethral swab, vaginal swab, cervical swab, genital swab, anal swab, rectal swab, conjunctival swab, skin swab, and any wound swab. Depending on the type of biological sample and the intended analysis, biological samples can be used freshly for sample preparation and analysis, or can be fixed using fixative. Preferably, in methods and systems herein described, the sample contains live target microorganisms.

The term "isolate" as used herein indicates a portion of matter resulting from a separation of a strain of a microorganism from a natural, usually mixed population of living microbes, as present in a natural or experimental environment, for example in water or soil flora, or from living beings with skin flora, oral flora or gut flora.

The word "specimen" as used herein indicates a portion of matter from an environment for use in testing, examination, or study. The environment can comprise individuals and in particular human beings. In these instances, a specimen can include a portion of tissues, organs or other biological material from the living being such as urethra, urine, cervix, vagina, rectum, oropharynges, conjunctiva, or any body fluids.

When referred to as a noun, the term "individual" as used herein in the context of treatment refers to a single biological organism, including but not limited to, animals and in particular higher animals and in particular vertebrates such as mammals and in particular human beings.

In particular, in embodiments of the instant disclosure, methods and systems are described that are based on detection of a differential concentration of nucleic acid of a target microorganism in a sample of an isolate or specimen treated with the antibiotic and in a sample of the isolate or specimen not treated with antibiotic.

In embodiments herein described, a differential concentration of a nucleic acid can be expressed with fold change approach. In the fold-change approach, a nucleic acid is considered to have a differential concentration if the ratio of a nucleic acid concentration value, possibly normalized, between two nucleic acids exceeds a certain threshold. The two nucleic acid concentration value can be obtained from a sample under different conditions (e.g. antibiotic treated and untreated conditions) or at different times under a same or different condition (e.g. on a same treated sample at different times or on a treated sample and an untreated sample at different times).

For a sample wherein detection of a nucleic acid concentration value is performed according to a set method, a nucleic acid concentration value is a value obtained by quantitively detecting a target nucleic acid in the sample within the set method. A nucleic acid concentration value in the sense of the disclosure is a value proportional to the true concentration of the target nucleic acid in the sample Any positive number can be used as the proportionality constant, preferably the proportionality constant equals to 1.

In some embodiments, the nucleic acid concentration value is a true concentration. In these embodiments, the nucleic acid concentration value can be detected by a digital quantification method such as digital PCR (dPCR).

In some embodiments, the nucleic acid concentration value is not the true concentration but proportionally reflects the amount of nucleic acid in the sample. That is, for a higher amount of true nucleic acid concentration in the sample, a higher nucleic acid concentration value will be obtained.

In some of these embodiments, the nucleic acid concentration value can be a direct measurement from experiments. For example, the nucleic acid concentration can be estimated by detecting a nucleic acid with a digital quantification method such as digital PCR (dPCR), or with correction for amplification efficiency by digital LAMP or digital RPA or other digital isothermal amplification chemistries, or calculated from the number of reads corresponding to the target nucleic acids as measured by many high throughput sequencing methods.

Alternatively, digital methods and other methods could be used to provide a concentration parameter that is proportional to concentration, such as raw concentration or positive counts obtained from digital LAMP or digital RPA or other digital isothermal amplification chemistries, from the number of reads corresponding to the target nucleic acids as measured by many high throughput sequencing methods. In some of the digital methods, correction for Poisson loading of nucleic acid molecules is used to obtain the concentration parameter from the raw data, as would be known to those skilled in the art.

In other embodiments, the nucleic acid concentration value can be obtained by detecting a concentration parameter such as Cq, reaction time, fluorescence intensity, and comparing the detected concentration parameter with a standard calibration curve to obtain the nucleic acid concentration value.

In one exemplary embodiment, a nucleic acid concentration value can be obtained from a detected Cq value by using the formula "nucleic acid concentration value"=$2^{(-Cq)}$.

In another exemplary embodiment, a nucleic acid concentration value can be obtained from a concentration parameter such as detected reaction time of an exponential quantification method, such as an isothermal amplification method, by using the formula "nucleic acid concentration value"=$n^{(-\text{reaction time})}$ where n has typically a value larger than 1, and reflects the properties of the detecting reaction. For example, if the isothermal exponential amplification doubles the concentration of the product nucleic acid every 20 seconds, then the relative concentration=$2^{(-\text{reaction time in seconds}/20 \text{ seconds})}$. For a reaction with inverse linear dependence of reaction time on starting target nucleic acid concentration, "nucleic acid concentration value"=1/(reaction time).

In yet another exemplary embodiment, a nucleic acid concentration value can be obtained from a detected florescence by using the formula relative concentration=$n^{*}$(fluorescence intensity) where n is a normalization factor determined by constructing a standard calibration curve.

When two samples derived from the same sample are measured by the same method, the proportionality constant connecting nucleic acid concentration value and true concentration is approximately the same and therefore it does not need to be known to calculate the nucleic acid concentration ratio.

In methods herein described, detection of a differential concentration of nucleic acid is performed by detecting a concentration parameter of the nucleic acid in samples of isolates or specimens with and without antibiotic treatment and then obtaining a nucleic acid concentration value for the treated and a nucleic acid concentration value for a reference sample such untreated samples respectively. In some embodiments, when the detection technique is a digital quantification method, the nucleic acid concentration value is the detected value of the parameter.

The terms "detect" or "detection" as used herein indicates the determination of the existence, presence or fact of a target in a limited portion of space, including but not limited to a sample, a reaction mixture, a molecular complex and a substrate. The "detect" or "detection" as used herein can comprise determination of chemical and/or biological properties of the target, including but not limited to ability to interact, and in particular bind, other compounds, ability to activate another compound and additional properties identifiable by a skilled person upon reading of the present disclosure. The detection can be quantitative or qualitative. A detection is "qualitative" when it refers, relates to, or involves identification of a quality or kind of the target or signal in terms of relative abundance to another target or signal, which is not quantified. A detection is "quantitative" when it refers, relates to, or involves the measurement of quantity or amount of the target or signal (also referred as quantitation), which includes but is not limited to any analysis designed to determine the amounts or proportions of the target or signal. A quantitative detection in the sense of the disclosure comprises detection performed semi-quantitatively, above/below a certain amount of nucleic acid molecules as will be understood by a skilled person and/or using semiquantitative real time isothermal amplification methods including real time loop-mediated isothermal amplification (LAMP) (see e.g. semi quantitative real-time PCR). For a given detection method and a given nucleic acid input, the output of quantitative or semiquantitative detection method that can be used to calculate a nucleic acid concentration value or nucleic acid concentration ratio (NACR) is a "concentration parameter"

In methods herein described where the target nucleic acid comprises DNA and/or RNA, quantitative detection of nucleic acid concentration can be performed with various techniques (commonly in combination with reverse transcription for RNA) such as by RNA-seq, DNA-seq, qPCR, digital PCR, and isothermal techniques such as LAMP or digital isothermal, microarrays signals, Nanostring as well high throughput DNA and RNA sequencing as reads per kilobase per million reads (RPKM) or transcripts per million (TPM) for RNA-seq data and additional nucleic acid quantification techniques identifiable to a skilled person. It should be understood that in such methods quantitative detection of expression of a gene is commonly combined with a reverse transcription step to convert the RNA sequence into a cDNA sequence which can be quantified by methods described herein and/or identifiable by a skilled person. Either sequence-specific or sequence-non-specific primers can be used to initiate reverse transcription of a target gene as will be understood by a skilled person.

In some embodiments where the target nucleic acid comprises RNA, detecting nucleic acid concentrations can be performed at the transcription level by performing RNA-seq and calculating RNA concentration values based on the sequence data.

In some embodiments where the target nucleic acid comprises RNA, the RNA concentration values can be detected and provided as transcripts per million (TPM) as will be understood by a person skilled in the art. In particular, to calculate TPM, read counts are first divided by the length of each gene in kilobases, which gives reads per kilobase (RPK). RPKs for all genes are added and the sum is divided by 1,000,000. This gives the "per million" scaling factor. Finally, the RPK value for each genes is divided by the "per million" scaling factor to give TPM. [5]

In particular, in embodiments herein described, method and systems herein described, quantitatively detecting the nucleic acid concentration is performed in treated samples of the isolate or specimen following treatment of the samples with the antibiotic and in reference samples of the isolate or specimen without treatment with the antibiotic.

"Reference samples" as used herein often indicates samples providing a standard for comparison against an antibiotic treated sample where the factor being tested (here antibiotic treatment) is applied during a testing procedure. Reference samples are used to produce reference nucleic acids.

A part of the treated sample can be used as a reference sample, obtained for example by splitting and processing the treated sample. A second sample treated under the same or different conditions as the first treated sample may also be used as a reference sample.

Reference samples can be control samples, which are samples subjected to the same testing procedure as another corresponding sample, except that the factor being tested is not applied. Reference samples and treated samples can be derived by splitting and manipulating the original sample being tested by the methods herein.

Total target nucleic acid refers to total intracellular and extracellular nucleic acid from the target microorganisms in a sample. In some embodiments, when gene-specific detection methods are used, such as nucleic acid amplification methods, total target nucleic acid refers to the total detectable target nucleic acid by the method used. It may include DNA or the sum of DNA and RNA amounts for some quantification methods used, such as RT-PCR. A reference sample may be different from a treated sample in the way it is handled prior to detection of nucleic acids, such as in the incubation conditions, or it might differ from a treated sample in the detection methods (such as a different target molecule in the same extraction). A reference sample may provide the total target nucleic acid in a sample (no treatment, no degradation) by undergoing complete lysis through a lysis treatment (as in Example 21).

A reference sample may be a quantification of the total inaccessible nucleic acid target molecules in a sample (no treatment with antibiotic, but includes a degrader or a separation step to remove the accessible nucleic acids), (as in Example 10). A reference sample may be nucleic acid molecules in a treated sample, but a molecule which is not targeted by a degrader (see example 6; RNase is included to degrade accessible target RNA molecules but not target DNA molecules; therefore, DNA can be an appropriate reference sample that comes from the same sample as the treated sample).

In some of these embodiments, providing a treated sample and a reference sample of the isolate or specimen can comprise contacting a first sample of the isolate or specimen with a treatment media to obtain a control sample and contacting a second sample of the isolate or specimen from the same source or host with the same treatment media and an antibiotic to obtain a treated sample. The contacting time (referring to the duration of the contact) with the treatment media can differ from the treated sample and the reference sample by more than 30%. Additionally, the treatment medias can differ between the reference and the treated samples by one or more components, such as the presence or absence of degrading molecules such as nucleases. Some embodiments include a lysis treatment of the reference sample but not necessarily in the treated sample, such as in Example 21. A method which uses three or more sample measurements for a ratio includes any scenario normalized to another normalization nucleic acid. For example, control samples and treated samples can be used to generate a CT ratio, which can then be normalized to a ratio of starting nucleic acid concentrations in the respective control and treated samples. This can be used to correct for technical or biological variability, such as uneven division of a sample containing the microorganism before antibiotic exposure, by normalizing to a third (or reference) condition.

Some embodiments include a lysis treatment of a reference sample to obtain total nucleic acid but not necessarily in the treated sample, such as in Example 21. For example, treated samples can be compared to the total nucleic acid concentrations in the respective control sample. This can be used to correct for technical variability, such as uneven division of a sample containing the microorganism before antibiotic exposure.

In some particular treatment of a sample with a treatment media is performed to create a controlled environment that would minimize the impact of biochemical parameters of a sample, such as pH or salt concentration or presence of molecules other than RNA or cells (human cells or other microorganisms other than target microorganism) on the RNA and DNA and cell-envelope response of the target microorganism to an external stimulus such as an antibiotic treatment and/or quantitative detection of gene expression. Treatment media can be used to create a more controlled environment for obtaining a more reliable response and/or gene expression. For example, treatment media can be composed of commercially available broths designed for the cultivation of microorganisms (such as Fastidious Broth from Hardy Diagnostics) or prepared using chemically defined components. In some cases, commercial broths can be diluted to create the desired treatment environment. For example, a specific osmolarity (for example in the range 0.0-0.5 osmols) or pH (for example in the range 5-9). Treatment media can be modified to contain specific factors to increase or decrease the metabolism of the target microorganism (such as carbon source or specific anions or cations). Gentle or vigorous mixing can be performed at specific time intervals after the addition of microorganisms to the treatment media in order to maintain homogeneity and reliable gene expression.

In some embodiments, a control sample and/or treated sample of the isolate or specimen or sample can preferably be pretreated to enrich said sample with nucleic acids or with the target microorganism, and/or to remove human nucleic acid or nucleic acid of other microorganisms. The removal of human nucleic acid can be performed via hybridization to beads or columns with probes specific for human nucleic acid. The removal of human nucleic acid can also be performed via selective lysis of human cells and degradation of released human nucleic acid. The sample may also be pretreated to enrich or deplete, as desired, nucleic acid via size selection. The removal of human DNA can be performed with treatment with DNases.

In embodiments, treatment or exposure with antibiotic can be performed by adding antibiotics to the microorganism and incubating the sample under certain condition preferably following and/or upon contacting the sample with a treatment media.

Treatment media used in connection with antibiotic exposure in accordance to methods herein described, can be designed to support physiological processes of the target microorganism, enable or accelerate remodeling or modification or disruption of the cell envelope, and promote interaction of the microorganism and antibiotic. Accordingly, the treatment media can be selected to include a source of energy and nourishment specific for the target microorganism, such as providing elements such as carbon, hydrogen, oxygen, nitrogen phosphorus, Sulphur, potassium, magnesium, calcium, iron, trace elements and organic growth factors which can be provided as organic sources such as simple sugars e.g. glucose, acetate or pyruvate, amino acids, nitrogenous bases or extracts such as peptone, tryptone, yeast extract and additional identifiable by a skilled person. Inorganic sources such as; carbon dioxide ($CO_2$) or hydrogen carbonate salts ($HCO_3$)$NH_4Cl$, $(NH_4)_2 SO_4$, $KNO_3$, and for dinitrogen fixers $N_2$, $KH_2PO_4$, $Na_2HPO_4$, $Na_2SO_4$, $H_2S$, $KCl$, $K_2HPO_4$, $MgCl_2$, $MgSO_4$, $CaCl_2$, $Ca(HCO_3)_2$, $NaCl$, $FeCl_3$, $Fe(NH_4)(SO_4)_2$, Fe-chelates1), $CoCl_2$, $ZnCl_2$, $Na_2MoO_4$, $CuCl_2$, $MnSO_4$, $NiCl_2$, $Na_2SeO_4$, $Na_2WO_4$, $Na_2VO_4$, as well as vitamins, amino acids, purines, pyrimidines (see the website sigmaaldrich.com/technical-documents/articles/microbiology/microbiology-introduction.html at the filing date of the present disclosure). Additional parameters considered to select the proper treatment media for a target microorganism comprise osmotic pressure, pH, oxygen content, water content, carbon dioxide content as will be understood by a skilled person to support physiological processes of the target microorganism, enable or accelerate DNA replication and translation, maintain cellular uniformity and homogeneity in suspension, and promote interaction of the microorganism and antibiotic. For example in some of the experiments described herein with reference to *N. gonorrhoeae* the treatment media used was Fastidious Broth from Hardy Diagnostics (cat no. $K_{31}$) which comprise pancreatic Digest of Casein, Yeast Extract, Dextrose, Peptic Digest of Animal Tissue, Sodium Chloride, Brain Heart Infusion, TRIS, Pancreatic Digest of Gelatin, Agarose, L-Cysteine HCl, Magnesium Sulfate, Ferrous Sulfate, Hematin, NAD, Pyridoxal and Tween® 80 (see the website catalog.hardydiagnostics.com/cp_prod/content/hugo/fbbroth.htm at the filing date of the present disclosure) Additional treatment media suitable to support physiological processes of *N. gonorrhoeae, E. coli, K. pneumoniae*, or other target microorganisms to enable or accelerate DNA replication and translation, maintain cellular uniformity and homogeneity in suspension, and promote interaction of the microorganism and the antibiotic are identifiable by a skilled person (see also Example 23).

In methods herein described, incubation of a sample with an antibiotic can be performed at a temperature such that a physiological response to the antibiotic is generated in the target microorganism. Incubation temperature is within ±0.5 degrees, ±1 degree, ±2 degrees, ±3 degrees Celsius from the physiological (for the organism) conditions. For example, for many human pathogens the physiological T is 37 C and the antibiotic incubation will be carried out at 37 degrees Celsius±0.5 degrees, ±1 degree, ±2 degrees, ±3 degrees Celsius). Also, adding the antibiotics can be performed throughout incubation or at set intervals during incubation to increase or decrease the physiological response of the microorganism to the antibiotic. In some embodiments, temperatures varying from 37 degrees Celsius might be used as a viability preserving enhancer or enhancer as an enhancing treatment alone, or with another enhancer. Temperature as a viability preserving enhancing treatment creates stress but preserves viability according to the definition of the viability preserving enhancing treatment provided herein. More generally, enhancing treatments that are more than 5 degrees, more than 10 degrees, more than 15 degrees, more than 20 degrees, more than 25 degrees, more than 30 degrees Celsius, can be used as enhancing treatments. For example, a viability preserving treatment for *E. coli* can be up to 75 degrees Celsius.

In some embodiments, concentrations of antibiotics above the resistance breakpoint are used, see Example 2. In particular in some embodiments, the antibiotic for treating the sample herein described can be provided at a concentration equal to or above the breakpoint MIC for the susceptible isolate or specimen to the antibiotic. In particular, the antibiotic for treating the sample herein described can be provided at a concentration lower than the breakpoint MIC for the resistant isolate or specimen to the antibiotic, for example 1.5 times (or 1.5×) lower, 2 times (or 2×) lower, 3 times (or 3×) lower, 4 times (or 4×) lower, 8 times (or 8×) lower, or 16 times (or 16×) lower than the breakpoint MIC for a resistant isolate. In some embodiments, the antibiotic for treating the sample herein described is provided at a concentration higher than the breakpoint MIC for the resistant isolate or specimen to the antibiotic, for example 1.5 times (or 1.5×) higher, 2 times (or 2×) higher, 3 times (or 3×) higher, or 4 times (or 4×) higher, 8 times higher (8×), 16 times higher (or 16×) than then breakpoint MIC. The breakpoint MIC of the antibiotic can be obtained from the Clinical & Laboratory Standards Institute (CLSI) guidelines, European Committee of Antimicrobial Susceptibility Testing (EUCAST) or other sources identifiable to a skilled person. In some embodiments, samples can be treated at several concentrations of the antibiotics for example, to measure the MIC of an organism before identifying the marker of antibiotic susceptibility as will be understood by a skilled person. One antibiotic susceptibility test can include exposing one or more aliquots of the sample to more than one antibiotic concentration.

These concentrations include multiple dilutions below the susceptible MIC breakpoint, dilutions between the susceptible and resistant MIC breakpoints (including intermediate breakpoint concentrations), as well as a dilution above the resistant MIC breakpoint. To determine, degree of susceptibility, the sample can be exposed to three concentrations of antibiotic: a concentration equal to the susceptible MIC breakpoint, a concentration equal to the concentration of the resistant MIC breakpoint, and a concentration equal to the average of the maximum and minimum of the intermediate MIC breakpoint range. Susceptibility can then be determined, for example, by measuring the slope obtained by fitting a curve or line to the three points on the T:R ratio vs treatment concentration plot, and/or by comparing the relative difference in T:R ratio between the low and intermediate concentration of antibiotic and the difference in T:R ratio between the intermediate and high concentration, and/or by comparing the magnitude of the value relative to a predefined threshold, or a combination of these analyses.

In some embodiments of the methods of the instant disclosure, the time period of contacting the sample with an antibiotic can be up to 5 minutes, up to 10 minutes, up to 15 minutes, up to 20 minutes, 25 minutes, 30 minutes, up to 45 minutes, up to 60 up to 90 up to 120 up to 360 or higher, inclusive of any value therebetween or fraction thereof.

In some embodiments of the methods of the instant disclosure, the time period of contacting the sample with an antibiotic is shorter than the doubling time of the target organism. For example, the time of contacting could be less than 1× doubling time, less than 0.75× doubling time, less than 0.5 doubling time, less than 0.35 doubling time, less than 0.25 doubling time, less than 0.2 doubling time, less than 0.15 doubling time, less than 0.1 doubling time, less than 0.075 doubling time, less than 0.05 doubling time. In one example of this disclosure, example 7, antibiotic exposure times greater than the doubling time, or many doubling times can be used, but in the absence of growth-sustaining media for the target microorganism where substantial (greater than or equal to one doubling of the initial detected target nucleic acid) replication of DNA is not observed in the untreated sample.

In embodiments herein described, the detection of a nucleic acid specific for the microorganism is performed either
- in absence of a lysis treatment of the antibiotic treated sample targeting the target microorganism; or
- in presence of a lysis treatment of the antibiotic treated sample targeting the microorganism, the lysis treatment performed following pre-lysis separation of nucleic acid from the microorganism in the antibiotic treated sample, or
- in presence of a lysis treatment of the antibiotic treated sample targeting the microorganism, the lysis treatment performed following pre-lysis separation of microorganism from the nucleic acid in the antibiotic treated sample, to obtain a detected antibiotic treated nucleic acid concentration value of the microorganism in the antibiotic treated sample.

The wording "lysis," "lyse," and "lysing" as used herein indicates disruption of the cell membranes and release of intracellular contents which results in death of the cell. As will be understood by a skilled person, cell death can be measured by measuring of cell death or cell viability according to one or more measurement methods such as serial dilution on plate to quantify CFU/mL [6] most probable number (MPN) assays [7], LIVE/DEAD flow cytometry (such as kits available through ThermoFisher scientific), Live/Dead viability staining assays cytometry (such as kits available through ThermoFisher scientific), and automated cell counters (such as the QUANTOM Tx Microbial Cell Counter from Logos Biosystems), metabolic assays and metabolic stains and additional methods identifiable by a skilled person.

A skilled person will understand that that cells of different organisms can undergo lysis under different conditions, and that lysis conditions for mammalian cells can be different that lysis conditions of the microorganism cells. Accordingly, a treatment directed to lyse one or more cell in a sample can be set up based on the type of cells targeted (e.g. bacterial or mammalian) and the composition of the reference mixture as well as reaction conditions such as pH temperature and osmolarity of the reaction mixture.

Lysis in the sense of the disclosure can occur by mechanisms including natural cell death, as well lytic agents produced by cells or added exogenously, or environmental stresses.

A "lytic agent" in the sense of the disclosure indicates any substance or energy that that results in lysis of a target cell if applied to the target.

Lytic agents in the sense of the disclosure comprise chemical lytic agent such as detergents and/or enzyme capable of catalyzing disassembly of cell walls, mechanical methods capable of disrupting the cell wall or membrane such as sonication at Covaris M220 soincation parameters 75 W peak incident power, >15% duty cycle, >200 cycles per burst, and >30 minutes in a volume of 50 uL such as high pH or high temperature (see Examples 3). Examples of chemical lytic agents suitable to perform a lysis of the disclosure Triton X-100, Tween-20, SDS, NP-40, and Lysozyme. Examples of mechanical lytic agents suitable to perform a lysis of the disclosure include sonication.

Lytic agents in the sense of the disclosure can be used to perform a lysis treatment of a sample and/or an enhancing treatment of a sample.

A "lysis treatment" in the sense of the disclosure is a concurrent combined or sequential administration of lytic agents that results in lysis of >90%, preferably >95%, more preferably >97%, and even more preferable >99% target cells in a control sample. Depending on the target organism, a lysis treatment can be obtained by exposing the organisms to high and low extremes incubation condition, which will depend on the type and features of the target cells. Exemplary lysis treatment in the sense of the disclosure for some target microorganism comprises high pH, such as pHs greater than 11 for 30 minutes or more, high temperatures such as >90 C for 10 minutes or more. A skilled person will be able to identify the correct conditions for a lysis treatment depending on the taxonomy of the target cell. For example, lytic treatment of gram positive cell can performed with additional enzymatic treatment of the cell wall in combination or in parallel with the above listed conditions. Lytic treatment of a gram negative like $N.$ $gonorrhoeae$ can be performed by any one of the conditions above.

Accordingly, lysis treatment of target microorganism in the sense of the disclosure can be performed using lytic agents at conditions directed to result in the lysis of ≥90% or microorganism in the sample. For example, the ionic detergents such as SDS or BAC at concentrations above their critical micelle concentrations (CMC) and/or sonication at powers greater than (Covaris M220 soincation parameters 75 W peak incident power, >15% duty cycle, >200 cycles per burst, and >30 minutes in a volume of 50 uL) for gram negative organism and at higher powers such as 5×, 10×, 100× the power used for gram-negative organisms. Examples of conditional lytic agents suitable to perform a lysis treatment of the disclosure include pHs greater than 8 (see Examples 3) and temperatures greater than 90 C for >1 min.

In some embodiments, lysis treatment of target microorganism in the sense of the disclosure can be performed, for example, with a commercial lysis kits such as that provided by Zymo or Qiagen. For gram-negative microorganisms, such kit can include highly denaturing lysis agents containing guanidinium salts in combination with buffers and enzymes to promote complete disruption of all cell envelope and denaturation of cellular proteins.

A "stressor" is a reagent of a form of energy that acts synergistically with antibiotic to disrupt cell envelope.

An "enhancement treatment" or an "enhancing treatment" in the sense of the disclosure refers to a concurrent combined or sequential administration of lytic agents and or stressors that results in in lysis of <90%, preferably ≤60%, more preferably ≤30%, and even more preferable ≤35%, more preferably ≤15% most preferably ≤5% target cells in a control sample. An enhancing treatment used together with the antibiotic exposure in the antibiotic treated sample is directed to preserve the viability of at least 10% of microorganism in a sample.

Exemplary enhancing treatment in the sense of the disclosure for most target microorganism comprises pH above optimal physiological conditions for the cell, such as pHs greater or equal to 7.5 and lower than 9, or equal or less than 6.5 and greater than 5 for 30 minutes or less, high temperatures such as >38 C and <80 C for 30 minutes or less depending on the temperature selected, or high or low osmolarity values deviating from the physiological osmolarity by up to 250 mOsmole for 30 minutes or less, in some embodiments applied in a form of osmotic shock, in some embodiments approaching zero osmolarity. A skilled person will be able to identify the correct conditions for a lysis treatment depending on the taxonomy of the target cell. For example, lytic treatment of Gram-positive cells can be performed with additional enzymatic treatment of the cell wall in combination or in parallel with the above listed conditions. Lytic treatment of a Gram-negative like $N.$ $gonorrhoeae$ can be performed by any one of the conditions above.

A lysis treatment in the sense of the disclosure typically results in conversion of ≥90%, ≥95%, ≥97%, ≥99% of the total intracellular nucleic acids of the target cell to extracellular nucleic acids of the target cell.

Thus in embodiments of the disclosure where the method comprises a lysis treatment and/or an enhancing treatment results in an increase in accessible nucleic acid of the target cells and in a decrease in the inaccessible nucleic acid of the sample as will be understood by a skilled person upon reading of the disclosure.

The wording "accessibility" in the sense of the disclosure refers to the capability of a nucleic acid comprised in a referenced mixture, to react with a referenced reagent in the referenced mixture (typically a sample) under referenced conditions (the conditions of a steps or assay of a method).

The wording "accessibility" in the sense of the disclosure refers to the capability of a nucleic acid comprised in a referenced mixture, to react with a referenced reagent in the referenced mixture (typically a sample) under referenced conditions (the conditions of a steps or assay of a method).

Accordingly, "an accessible nucleic acid" in the sense of the disclosure is a nucleic acid capable of reacting with a referenced reagent capable within a referenced mixture under referenced conditions. Conversely an "inaccessible nucleic acid" in the sense of the disclosure is a nucleic acid incapable of reacting with a referenced reagent within a referenced mixture under referenced conditions.

Reagents added in samples or other referenced mixtures of methods of the instant disclosure typically include degrading reagents (including exonucleases and endonucleases, RNases, DNases, restriction enzymes, and other enzymes that cleave or degrade nucleic acids), detecting reagents (including enzymes used in detection of nucleic acids, including reverse transcriptases, polymerases, primers, probes), or binding reagents (including primers, probes, affinity reagents, nucleic acid binding proteins, surfaces for binding nucleic acids such as silica surfaces). Reacting includes binding as will be understood by a skilled person.

In methods herein described a key factor impacting accessibility is cell permeability of the nucleic acid and the reagent under the conditions of a certain step or assay performed in accordance with the method.

Cell permeability in the sense of the disclosure indicates the collection of mechanisms that regulate the passage of a referenced solute and in particular nucleic acid through biological membranes and/or a cell envelope as will be understood by a skilled person depending on the cell at issue.

A cell membrane indicates lipid bilayers that can contain proteins embedded. A cell envelope indicates the inner cell membrane and the cell wall of a bacterium. In gram-negative bacteria the cell envelope can comprise an outer membrane. Bacterial cell envelopes fall into two major categories: a Gram-positive type and a Gram-negative type, distinguished by Gram staining as will be understood by a skilled person.

Accordingly, in methods herein described cell permeability and refers to the ability of the majority of a nucleic acid or an externally added reagent to pass through the envelope of target cells in the sample. For example, a reagent can be considered cell impermeable when intracellular concentration of the added reagent is less than 5% of the extracellular concentration, less than 1% of the extracellular concentration, less than 0.1% of extracellular concentration, less than 0.01% of the extracellular concentration. Typically, intracellular nucleic acids are not accessible to cell-impermeable reagents. Typically, extracellular nucleic acids are accessible to cell-impermeable reagents.

Lysis of cells performed in accordance with a lysis treatment and/or an enhancing treatment in the sense of the disclosure affect the target nucleic acid accessibility in the methods of the disclosure as will be understood by a skilled person upon reading of the present disclosure.

In some embodiments of the methods herein described the detection of nucleic acid of a target microorganism is performed in absence of a lysis treatment in the sense of the disclosure or in presence of a lysis treatment of the antibiotic treated sample following pre-lysis separation of microorganism from the nucleic acid in the antibiotic treated sample. In those embodiments, the method is directed to detect a nucleic acid of the target microorganism that is accessible to detection reagents in the sample following the contacting and before the detecting.

In some embodiments of the methods herein described detection of nucleic acid of a target microorganism is performed in presence of a lysis treatment in the sense of the disclosure of the antibiotic treated sample following pre-lysis separation of nucleic acid from the target microorganism in the antibiotic treated sample. In those embodiments the method is directed to detect a nucleic acid of the target microorganism that is inaccessible to detection reagents in the sample following the contacting and before the lysing treatment.

In some embodiments of all the methods herein described wherein the method comprises performing an enhancing treatment of the sample concurrently or after contacting the sample with the antibiotics.

In some embodiments herein described directed to detect accessible or inaccessible nucleic acid, the method can comprise isolating the nucleic acid from the antibiotic treated sample before detecting.

In those embodiments, in methods wherein detection of nucleic acid of a target microorganism is performed in absence of a lysis treatment in the sense of the disclosure, the isolating is performed by purifying the nucleic acid from the sample in absence of lysis in the sense of the present disclosure. Exemplary methods for isolating nucleic acids without lysis include isothermal amplification techniques such as qLAMP; methods that separate cells from liquid by non-lysing mechanical forces or particle size such as filtration by membranes, sieves, or microfluidic devices, centrifugation, sedimentation, flocculation, gel electrophoresis, dielectrophoresis, and size-exclusion chromatography; methods that separate cells from liquid by chemical affinity for bacterial cells such as affinity chromatography; and other approaches identifiable by a skilled person upon reading of the present disclosure.

In embodiment methods wherein detection of nucleic acid of a target microorganism is performed in presence of a lysis treatment in the sense of the disclosure of the antibiotic treated sample following pre-lysis separation, (either directed to remove the microorganism from the nucleic acid in the sample to detect accessible nucleic acid, or to remove nucleic acid from the microorganism in the sample to detect inaccessible nucleic acid) the isolating is performed by extracting the nucleic acid from the sample with procedure which may comprise lysis in the sense of the disclosure. Exemplary nucleic acid isolating methods include combinations of techniques that lyse—such as alkaline lysis with SDS [6], bead beating, centrifugation, French presses, Dounce homogenizers, rotor homogenizers, ultrasonic homogenizers, and pressure homogenizers—and techniques which separate nucleic acids out of a liquid phase, such as phenol-chloroform extraction, incubation with nucleases, precipitation and concentration by alcohols, gel electrophoresis followed by gel dissolution; affinity chromatography; commercial nucleic acid extraction kits (e.g. Qiagen Miniprep Kit, Lucigen DNA Extraction Buffer); and other approaches identifiable by a skilled person upon reading of the present disclosure.

In embodiments herein described directed to detect accessible or inaccessible nucleic acid, the method can comprise separation to remove either the accessible nucleic acid or the inaccessible nucleic acid from the sample.

The wording "separate" or "separation" as used herein indicates an action performed on a sample such that two desired components of the sample (such as nucleic acid and cells of a target microorganism) are no longer able to come into molecular contact. One example of such separation include filtration through a filter with a pore size (such as 0.2 um) such that cells are removed from surrounding liquid and any components of the surrounding liquid smaller than the pore size of the filter. One example of such separation includes selective degradation of a selected component (such as degradation of extracellular nucleic acids (NAs) with DNase I) such that the component is removed from the sample.

In some embodiments of methods directed to detect accessible nucleic acid and comprising a separation, the separation is directed to remove the microorganism from the nucleic acid in the sample. The separation can be performed mechanically e.g. by filtrating the sample to remove the retentate from the sample formed by the filtrate, or by centrifugation followed by selective removal of the pellet from the supernatant, sedimentation followed by selective removal of the sediment, chromatography followed by selective of the target fraction. Other approaches identifiable by a skilled person upon reading this disclosure may be used to separate the microorganism from nucleic acids in the sample.

In some embodiments of methods directed to detect inaccessible nucleic acid, the separation is directed to remove the nucleic acid from the microorganism in the sample the separation can be performed mechanically e.g. by filtrating the sample to remove the filtrate from the sample formed by the retentate, or by centrifugation followed by selective removal of the supernatent from the pellet, sedimentation followed by selective removal of the supernatent, chromatography followed by selective of the target fraction. Other approaches identifiable by a skilled person upon reading this disclosure may be used to separate the nucleic acids from microorganisms in the sample.

In some embodiments of methods directed to detect inaccessible nucleic acid, when the separation is directed to remove the nucleic acid from the microorganism in the sample the separation can be performed chemically by performing a nuclease treatment of the sample.

In those embodiments of methods directed to detect inaccessible nucleic acid, the method can further comprise adding nucleases, such as DNase (Examples 1-4) or RNase (Examples 5-6) to the antibiotic treated sample. In some embodiments, for example when beta lactam antibiotics are used, antibiotic susceptibility is indicated by increased accessibility of the pathogen's nucleic acids to the nuclease in the treated sample relative to the control sample.

In some of those embodiments of methods directed to detect inaccessible nucleic acid, nucleases can be added during the ABX exposure step (Examples 1-2, 4-6). In some of those embodiments, nucleases can be added during the exposure to lytic agents (Examples 1-6).

In methods herein described, to during the incubation, the sample can be collected at different time interval for further analysis. In addition to collecting samples during the incubation with antibiotics, samples can be collected for analysis before treatment or exposure. Such samples can be used as controls in analysis. Detection of response of the target microorganism to the antibiotic can be performed one or more times at any time after antibiotic treatment or exposure. In some embodiments, rapid detection, for example detection completed within 10 minutes, 15 minutes, 20 minutes, 30 minutes, 40 minutes during or after exposure.

In some of embodiments providing a treated sample and a control sample of the isolate or specimen can comprise enriching a first sample and a second sample of the isolate or specimen from the same source or host with the microorganism to obtain control, or reference, samples respectively, and contacting the second sample with an antibiotic to obtain an antibiotic treated sample respectively.

In embodiments of the method and systems herein described, providing a treated sample and a control sample of the isolate or specimen can comprise enriching a first sample and a second sample of the isolate or specimen from the same source or host with the microorganism, contacting the first sample with a treatment media following the enriching to obtain the control samples respectively and contacting the second sample of the isolate or specimen from the same source or host with the same treatment media and an antibiotic to obtain an antibiotic treated sample respectively. The sample may be split into two or more parts, such as a scenario wherein many antibiotic treatments are compared to one control, or reference, sample. Multiple treated samples can be setup and sampled at different times, or, a treated sample can be split during treatment and analyzed.

In methods herein described enriching a sample with the target microorganisms can be performed between sample collection (and optionally elution from a collection tool such as a swab) and exposure. In particular enriching a sample with target microorganisms and in particular bacteria (such as *Neisseria gonorrhoeae* or *Escherichia coli*) can be performed by capturing the target microorganism using a solid support (e.g. a membrane, a filtration membrane, an affinity membrane, an affinity column) or a suspension of a solid reagent (e.g. microspheres, beads). Capture of a target microorganism can improve the assay and the response to antibiotic. Capture can be used to enrich/concentrate low-concentration samples. Capture followed by washing can be used to remove inhibitors or components that may interfere with the method described here. Capture followed by washing may be used to remove inhibitors of nucleic acid amplification or inhibitors of other quantitative detection assays. Enrichment can also be performed using lysis-filtration techniques to lyse host cells and dissolve protein and/or salt precipitates while maintaining bacterial cell integrity then capturing target bacteria on filters (e.g. mixed cellulose ester membranes, polypropylene and polysulfone membranes). Enrichment can also be performed by binding target bacteria to membranes of microspheres, optionally coated with an affinity reagent (e.g. an antibody, an aptamer) specific to the target bacteria's cell envelope. When microspheres or beads are used for capture, they can be filtered, centrifuged, or collected using a magnet to enrich bacteria. AST in the format described here can then be performed directly on captured bacteria, or the bacteria can be released before performing the method.

In some embodiments, the methods herein described further comprise detecting a nucleic acid concentration ratio in the sample by comparing the detected antibiotic treated nucleic acid concentration value with a detected reference nucleic acid concentration value of the nucleic acid of the target microorganism in the sample.

A reference nucleic acid concentration value as used herein indicates a target nucleic acid concentration value obtained from a reference sample. Reference nucleic acids may be obtained from a reference sample, which differs from a treated sample in one or more of the following: handling prior to detection of nucleic acids (such as in the incubation conditions, or the presence or absence of lysis treatments) or it might differ from a treated sample in the detection methods (such as a different target molecule in the same extraction). A reference nucleic acid may be the total target nucleic acid in a sample (no treatment, degradation) which has undergone complete lysis through a lysis treatment (as in Example 21). A reference nucleic acid may be a quantification of the total inaccessible nucleic acid target molecules in a sample (no treatment with antibiotic, but includes a degrader or a separation step to remove the accessible nucleic acids), (as in Example 10). A reference nucleic acid may be nucleic acid in a treated sample, but a molecule which is not targeted by a degrader (see example 6; RNase is included to degrade accessible target RNA molecules but not target DNA molecules; therefore, DNA can be an appropriate reference nucleic acid that comes from the same extraction as the treated nucleic acid).

A reference sample can have target nucleic acids quantified and compared to the target nucleic acids treated sample to generate a T:R ratio (also may be referred to as T:R) to assess susceptibility compared to a threshold of T:R ratio under those conditions.

In some embodiments the reference nucleic acid concentration value is a control nucleic acid concentration value obtained in a control sample of the isolate or specimen comprising the target microorganism not treated with the antibiotic.

In particular, in embodiments of the methods performed in absence of a lysis treatment of the antibiotic treated sample, the control acid concentration value can be obtained following detection in the control sample performed in absence of a lysis treatment of the control sample.

In embodiments of the methods performed in presence of a lysis treatment of the antibiotic treated sample, the control acid concentration value can be obtained following detection in the control sample performed in presence of a lysis treatment of the control sample. In particular, in some of these embodiments wherein the lysis treatment is performed following pre-lysis separation of nucleic acid from the microorganism in the antibiotic treated sample, the detection of nucleic acid in the control sample is also performed following pre-lysis separation of the nucleic acid from the microorganism in the control treated sample.

In those embodiments instead wherein the lysis treatment is performed following pre-lysis separation of microorganism from the nucleic acid in the antibiotic treated sample, the detection of nucleic acid in the control sample is also performed following pre-lysis separation of the microorganism from the nucleic acid in the control treated sample as will be understood by a skilled person.

Accordingly, in all embodiments comprises methods herein described, quantitative detection of a nucleic acid concentration can be performed to provide a control nucleic acid concentration value C in a control sample not treated with the antibiotic and a corresponding nucleic acid treated concentration value T in a treated sample treated with the antibiotic for a specimen or isolate.

In particular, in embodiments of the methods herein described wherein a reference (or control) nucleic acid concentration is performed, quantitative detection of the concentration value of a nucleic acid in method herein described can be performed to provide a (T:R) value for a nucleic acid concentration in a an isolate or specimen. the T:R ratio can be defined as the ratio of the nucleic acid readout of the control sample divided by the nucleic acid readout of the antibiotic-treated sample. The T:R ratio is compared to a threshold ratio, to differentiate between the susceptible (S) and resistant (R) ratios, see CT ratios in Examples 4-5.

In particular providing a (T:R) value for a nucleic acid in an isolate or specimen can be performed by
  providing a treated sample treated with the antibiotic and a control sample not treated with the antibiotic,
  quantitatively detecting a control nucleic acid concentration value C in the control susceptible sample,
  quantitatively detecting a treated nucleic acid concentration value T for the nucleic acid in the treated sample, and
  providing a (T:R) value for the nucleic acid concentration by dividing C for the nucleic acid by T for the nucleic acid.

In methods herein described a susceptible strain of a target microorganism is identified by detecting a T:R ratio lower than a threshold.

In some embodiments the treated-reference T:R ratio, control-treated C:T ratio, or reference nucleic acid concentration value can be provided by RPKM (reads per kilobase per million mapped reads). The use of RPKM and comparison to TPM is described for example in Wagner et al 2012 [5]. In some embodiments the T:R or C:T ratio is provided by FPKM (fragments per kilobase per million), the use of FPKM is described for example in Conesa, Ana, et al. 2016 [8]. These units normalize for sequencing depth and transcript length. In some embodiments RPM (reads per million mapped reads; RPM does not normalize for transcript length) or raw sequencing read counts can be used. Typically, to calculate RPM (reads per million), the total reads from a sample are divided by 1,000,000 to obtain the "per million scaling factor". The read counts for each gene are then divided by the "per million scaling factor" to give RPM. Also typically to calculate RPKM (for single-end RNA-seq), the RPM values are divided by the gene length in kilobases. FPKM (for paired-end RNA-seq), is calculated the same way as RPKM, taking into account that with paired-end RNA-seq, two reads can correspond to a single fragment, or, if one read in the pair did not map, one read can correspond to a single fragment as will be understood by a skilled person.

In some embodiments, to qualify for a differential concentration in the treated sample of the isolate or specimen, the difference between the C value and T value or R value and T value is statistically significant.

In preferred embodiments, the difference between the C and T value is statistically significant over the related biological variability (variability due to physiologic differences among a biological unit of a same microorganism such as between different strains of the microorganism and/or between different individual microorganism of a same strains) and/or technical variability (variability within identically performed measurements of a same biological unit due to random noise in the performance of the measuring device), more preferably over both biological and technical variability. To measure technical variability a T:R or C:T ratio is measured from a given sample multiple times with the method of choice and statistical analysis is performed on the resulting data. Technical variability would depend on the measurement method chosen. To measure biological variability, a T:R or C:T ratio is measured from multiple samples with a method that has minimal technical variability. Statistical analysis of the data comprises testing the null hypothesis that the C and T values obtained arose from the same distribution, the choice of distribution being informed according to standard statistical theory as the skilled practitioner should know [5], and rejecting the null hypothesis if the probability of generating the observed data is less than the p-value, a threshold for statistical significance chosen by the practitioner according to standards of the field. Common choices for the p-value would be 0.05, 0.025, and 0.01 (for relevant descriptions see Devore 2017 [9]). Additional description of statistical analysis used in single-molecule (digital) measurements to resolve differences between two distributions is provided in Kreutz et al 2011 [10].

In some embodiment, the reference concentration value is a total nucleic acid concentration value obtained from detection of total nucleic acid in antibiotic treated sample or in control sample (untreated with the antibiotics)

A total nucleic acid of a sample in the sense of the disclosure indicates the combined intracellular and extracellular nucleic acids in the sample. Quantification of total nucleic acids of a sample can be done following a lysis treatment of the sample and subsequent quantitative detection with methods to detect nucleic acids, after optional nucleic acid purification, including: nucleic acid amplification, gel electrophoresis, spectrophotometric detection, fluorescence detection.

Total nucleic acid of a microorganism in a sample comprise a total intracellular nucleic acid and a total extracellular nucleic acid.

The wording "total intracellular nucleic acid" as used herein refers to the portion of the total nucleic acids that are within an intact cell prior to treatment of the sample with any reagents. Accordingly, intracellular nucleic acid molecules are not able to interact will cell-impermeable reagents as will be understood by a skilled person and are detectable by detecting reagents that are impermeable to the cell. Total intracellular nucleic acid can be quantitatively detected with exemplary methods comprising filtrating the sample with a 0.2 μm filter, removing substantially all (at least 90%) extracellular nucleic acid in the sample, followed by quantifying the nucleic acids in the material retained on a filter. In addition, these methods can include incubating cell suspension with a nucleic-acid degrading reagent to degrade extracellular nucleic acids accessible to the degrading agent, followed by inactivating or removing the degrading reagent, followed by amplifying nucleic acid. For example, an RNase can be selected as a degrader to remove extracellular RNAs. The remaining RNAs are the intracellular RNA. For example, a DNase enzyme can be selected as a degrader to remove extracellular DNA. In that the remaining DNAs are the intracellular DNA.

The wording "total extracellular nucleic acid" as used herein refers to the portion of the total nucleic acids that are outside an intact cell prior to treatment of the sample with any reagents. Extracellular nucleic acid molecules are able to interact will cell-impermeable reagents as will be understood by a skilled person. Nucleic acids might be extracellular from any cells that undergo lysis, exported genetic material from a living cell, DNA in bacterial biofilms, and other means of nucleic acids exiting the cell. Methods one may use to quantify intracellular nucleic acid include cell-permeable fluorescent stains targeting nucleic acids used in combination with washing or degradation protocols to remove extracellular nucleic acids. Intracellular nucleic acids may also be quantified by subtracting extracellular nucleic acids from total nucleic acids.

In particular, in embodiments of the methods herein described wherein a total nucleic acid concentration value is detected, quantitative detection of the concentration value of a nucleic acid in method herein described can be performed to provide a value for a total nucleic acid concentration in a an isolate or specimen. The treated-total (T:tNA) ratio can be defined as the nucleic acid readout of the antibiotic-treated sample divided by the total nucleic acid readout of the sample. The T:tNA ratio is compared to a threshold, to differentiate between the susceptible (S) and resistant (R) microorganism in the sample, see Example 21.

In particular, providing a (T:tNA) value for a nucleic acid in a sample can be performed by
  providing a treated sample treated with the antibiotic,
  quantitatively detecting a total nucleic acid concentration value tNA in the sample treated or untreated with antibiotics,
  quantitatively detecting a treated nucleic acid concentration value T for the nucleic acid in the treated sample, and
  providing a (T:tNA) value for the nucleic acid concentration by dividing T for the nucleic acid by tNA for the nucleic acid.

In methods herein described a susceptible strain of a microorganism is identified by detecting a T:tNA lower than a threshold.

In some embodiments the T:tNA ratio can be provided by RPKM (reads per kilobase per million mapped reads). The use of RPKM and comparison to TPM is described for example in Wagner et al 2012 [3]. In some embodiments the T:tNA ratio is provided by FPKM (fragments per kilobase per million), the use of FPKM is described for example in Conesa, Ana, et al. 2016 [4]. These units normalize for sequencing depth and transcript length. In some embodiments RPM (reads per million mapped reads; RPM does not normalize for transcript length) or raw sequencing read counts can be used. Typically, to calculate RPM (reads per million), the total reads from a sample are divided by 1,000,000 to obtain the "per million scaling factor". The read counts for each gene are then divided by the "per million scaling factor" to give RPM. Also, typically to calculate RPKM (for single-end RNA-seq), the RPM values are divided by the gene length in kilobases. FPKM (for paired-end RNA-seq), is calculated the same way as RPKM, taking into account that with paired-end RNA-seq, two reads can correspond to a single fragment, or, if one read in the pair did not map, one read can correspond to a single fragment as will be understood by a skilled person.

In some embodiments, to qualify for a differential concentration in the treated sample of the isolate or specimen, the difference between the T value and tNA value is statistically significant.

In preferred embodiments, the difference between the T and tNA value is statistically significant over the related biological variability (variability due to physiologic differences among a biological unit of a same microorganism such as between different strains of the microorganism and/or between different individual microorganism of a same strains) and/or technical variability (variability within identically performed measurements of a same biological unit due to random noise in the performance of the measuring device), more preferably over both biological and technical variability. To measure technical variability, a T:TNA ratio is measured from a given sample multiple times with the method of choice and statistical analysis is performed on the resulting data. Technical variability would depend on the measurement method chosen. To measure biological variability, a T:TNA ratio is measured from multiple samples with a method that has minimal technical variability. Statistical analysis of the data comprises testing the null hypothesis that the C and T values obtained arose from the same distribution, the choice of distribution being informed according to standard statistical theory as the skilled practitioner should know [5], and the practitioner rejects the null hypothesis if the probability of generating the observed data is less than the p-value, a threshold for statistical significance chosen by the practitioner according to standards of the field. Common choices for the p-value would be 0.05, 0.025, and 0.01 (for relevant descriptions see Devore 2017 [5]. Additional description of statistical analysis used in single-molecule (digital) measurements to resolve differences between two distributions is provided in Kreutz et al 2011 [6]

In some embodiments herein described, a susceptible threshold and a resistant threshold can be defined. There are various methods to define susceptible and resistant threshold as will be understood by a person skilled in the art.

In some of the embodiments for detecting accessible nucleic acids, such as in the absence of a lysis treatment or in the presence of a lysis treatment of the antibiotic treated sample following pre-lysis mechanical separation of the microorganism, a susceptible threshold and a resistant threshold can be calculated. The susceptibility or resistance of the microorganism is determined based on whether the obtained nucleic acid concentration ratio is above or below these thresholds.

As a person skilled in the art will understand, these threshold pairs are specific to each combination of bacterial species, antibiotic, concentration of antibiotic, the specific embodiment of the methods herein described, but independent of the number of samples included in the training sets.

In some embodiments, a susceptible threshold and a resistant threshold can be calculated as follows. Two sets of training sample bacteria are prepared, one with known antibiotic susceptibility and one with known antibiotic resistance, to serve as training sets, i.e. a susceptible training set and a resistant training set. Each set can have at least three training samples, preferably at least five training samples, preferably at least ten training samples, preferably at least twenty training samples, preferably at least fifty training samples, or preferably at least one hundred training samples. The susceptibility and resistance of the two training sets of sample bacteria can be pre-determined by an AST method recognized by a gold standard (e.g. the microdilution broth assay) such as by Centers for Disease Control and Prevention, by Clinical & Laboratory Standards Institute or by Food and Drug Administration or other professional organizations such as Infectious Disease Society of America as will be understood by a skilled person.

Two cutoff percentages will be designated, one referred to as "purity cutoff percentage" and the other referred to as "sensitivity cutoff percentage". The purity cutoff percentage can be any value of at least 50% up to 100%. In particular, the purity cutoff percentage can be a value equal to or greater than 80%, 85%, 90%, 93%, 95%, 96% 97%, 98%, or 99%. The sensitivity cutoff percentage can be any value of at least 50% up to 100%. In particular, the sensitivity cutoff percentage can be a value equal to or greater than 50%, 60%, 70%, 80%, 85%, 90%, 93%, 95%, 96% 97%, 98%, or 99%.

For a given susceptible threshold, a purity percentage of that threshold is the percentage of true susceptible organisms found among organisms determined as susceptible by the method. For example, if 100 organisms were determined to be susceptible by the method herein described, and 97 of these organisms are true susceptible, then susceptible purity percentage is 97%.

For a given resistant threshold, a purity percentage is the percentage of true resistant organisms found among organisms determined as resistant by the method herein described for a given resistant threshold. For example, if 100 organisms were determined to be resistant by the method herein described, and 97 of these organisms are true resistant, then resistant purity percentage is 97%.

For a given susceptible threshold, a sensitivity percentage is the percentage of all susceptible organisms in the training set that are determined as susceptible by the method. For example, if the training set has 100 true susceptible organisms, and 96 of them were determined to be true susceptible by the method herein described, the sensitivity percentage is 96%.

For a given resistant threshold, a sensitivity percentage is the percentage of all resistant organisms in the training set that are determined as resistant by the method herein described.

The desired purity cutoff percentage and the desired sensitivity percentages can be selected based on current regulatory guidelines such as those set by the Food and Drug Administration. In addition, purity cutoff percentage and the sensitivity percentages can be selected based on commercial and business considerations as will be understood by a person skilled in the art.

A nucleic acid concentration ratio ("NACR") is then measured using the embodiments herein described for each of the training sample in the susceptible training set and the resistant training set with a given choice of antibiotic, an antibiotic concentration and antibiotic exposure time. All the obtained NACRs will be ranked in descending order (largest to smallest).

The following steps are performed to calculate the susceptible threshold.

First is to find the lowest NACR whose purity percentage is greater than or equal to the purity cutoff percentage. For any NACR value between the lowest NACR and the largest NACR, a purity percentage is calculated by first counting the number of susceptible training samples whose NACR is greater than or equal to the given NACR, then counting the number of training samples—including both the susceptible and resistant training samples—whose NACR is greater than or equal to the given NACR, and lastly dividing the former count by the latter count.

If no such NACR is found with a purity percentage greater than or equal to the purity cutoff percentage, then a threshold that satisfies the desired cutoff percentage is unavailable, and the method can be modified by modifying the antibiotic exposure time, changing the antibiotic concentration, selecting a different cutoff percentage, and/or modifying the enhancers.

Once the lowest NACR is found, the sensitivity percentage of that NACR will be calculated. The sensitivity percentage is calculated by first counting the number of susceptible training samples whose NACR is greater than or equal to the lowest NACR, then counting the total number of susceptible training samples in the susceptible training set, and then dividing the former count by the latter count.

If the lowest NACR found does not have a sensitivity percentage above the sensitivity cutoff percentage, then a threshold that satisfies the desired cutoff percentage is unavailable, and the method will be modified by modifying the antibiotic exposure time, changing the antibiotic concentration, selecting a different cutoff percentage, and/or modifying the enhancers.

The lowest NACR whose purity percentage and sensitivity percentage are above the respective cutoff percentages will serve as the susceptibility threshold. Accordingly, any given microorganism with unknown susceptibility or resistance having a NACR value above the susceptible threshold will be identified as "susceptible".

In some embodiments, the calculation of the susceptibility threshold described above can be repeated with higher purity cutoff percentages and/or higher susceptibility cutoff percentages.

The following steps are performed to calculate the resistant threshold.

First is to find the highest NACR whose purity percentage is greater than or equal to the purity cutoff percentage. For any NACR value between the lowest NACR and the largest NACR, a purity percentage is calculated by first counting the number of susceptible training samples whose NACR is less than or equal to the given NACR, then counting the number of training samples—including both the susceptible and resistant training samples—whose NACR is less than or equal to the given NACR, and lastly dividing the former count by the latter count.

If no such NACR is found with a purity percentage greater than or equal to the purity cutoff percentage, then a threshold that satisfies the desired cutoff percentage is unavailable, and the method will be modified by modifying the antibiotic exposure time, changing the antibiotic concentration, selecting a different cutoff percentage, and/or modifying the enhancers.

Once the highest NACR is found, the sensitivity percentage of that NACR will be calculated. The sensitivity percentage is calculated by first counting the number of susceptible training samples whose NACR is less than or equal to the highest NACR, then counting the total number of susceptible training samples in the susceptible training set, and then dividing the former count by the latter count.

If the highest NACR found does not have a sensitivity percentage above the sensitivity cutoff percentage, then a threshold that satisfies the desired cutoff percentage is unavailable, and the method will be modified by modifying the antibiotic exposure time, changing the antibiotic concentration, selecting a different cutoff percentage, and/or modifying the enhancers.

The highest NACR whose purity percentage and sensitivity percentage are above the respective cutoff percentages will serve as the resistant threshold. Accordingly, any given microorganism with unknown susceptibility or resistance having a NACR value below the resistant threshold will be identified as "resistant".

In some embodiments, the calculation of the resistant threshold described above can be repeated with higher purity cutoff percentages and/or higher susceptibility cutoff percentages.

In some of the embodiments for detecting inaccessible target nucleic acids, such as in presence of a lysis treatment of the antibiotic treated sample following pre-lysis separation of nucleic acid from the microorganism, a susceptible threshold and a resistant threshold can be calculated. The susceptibility or resistance of the microorganism is determined based on whether the obtained nucleic acid concentration ratio is above or below these thresholds.

Similar to the steps described above with reference to the embodiments for detecting accessible target nucleic acids, two sets of training sample bacteria are prepared, one with known antibiotic susceptibility and one with known antibiotic resistance, to serve as training sets, i.e. a susceptible training set and a resistant training set. Each set can have at least three training samples, preferably at least five training samples, preferably at least ten training samples, preferably at least twenty training samples, preferably at least fifty training samples, or preferably at least one hundred training samples. The susceptibility and resistance of the two training sets of sample bacteria can be pre-determined by an AST method recognized by a gold standard (e.g. the microdilution broth assay) such as by Centers for Disease Control and Prevention, by Clinical & Laboratory Standards Institute or by Food and Drug Administration or other professional organizations such as Infectious Disease Society of America as will be understood by a skilled person.

A "purity cutoff percentage" and a "sensitivity cutoff percentage" as described above will be designated. The desired purity cutoff percentage and the desired sensitivity percentages can be selected based on current regulatory guidelines such as those set by the Food and Drug Administration. In addition, purity cutoff percentage and the sensitivity percentages can be selected based on commercial and business considerations as will be understood by a person skilled in the art.

The purity cutoff percentage can be any value of at least 80% up to 100%. In particular, the purity cutoff percentage can be a value equal to or greater than 80%, 85%, 90%, 93%, 95%, 96% 97%, 98%, or 99%. The sensitivity cutoff percentage can be any value of at least 50% up to 100%. In particular, the sensitivity cutoff percentage can be a value equal to or greater than 50%, 60%, 70%, 80%, 85%, 90%, 93%, 95%, 96% 97%, 98%, or 99%.

A nucleic acid concentration ratio ("NACR") is then measured using the embodiments herein described for each of the training sample in the susceptible training set and the resistant training set with a given choice of antibiotic, an antibiotic concentration and antibiotic exposure time. All the obtained NACRs will be ranked in descending order (largest to smallest).

The following steps are performed to calculate the susceptible threshold.

First is to find the highest NACR whose purity percentage is greater than or equal to the purity cutoff percentage. For any NACR value between the lowest NACR and the largest NACR, a purity percentage is calculated by first counting the number of susceptible training samples whose NACR is less than or equal to the given NACR, then counting the number of training samples—including both the susceptible and resistant training samples—whose NACR is less than or equal to the given NACR, and lastly dividing the former count by the latter count.

If no such NACR is found with a purity percentage greater than or equal to the purity cutoff percentage, then a threshold that satisfies the desired cutoff percentage is unavailable, and the method can be modified by modifying the antibiotic exposure time, changing the antibiotic concentration, selecting a different cutoff percentage, and/or modifying the enhancers.

Once the highest NACR is found, the sensitivity percentage of that NACR will be calculated. The sensitivity percentage is calculated by first counting the number of susceptible training samples whose NACR is less than or equal to the highest NACR, then counting the total number of susceptible training samples in the susceptible training set, and then dividing the former count by the latter count.

If the highest NACR found does not have a sensitivity percentage above the sensitivity cutoff percentage, then a threshold that satisfies the desired cutoff percentage is unavailable, and the method will be modified by modifying the antibiotic exposure time, changing the antibiotic concentration, selecting a different cutoff percentage, and/or modifying the enhancers.

The highest NACR whose purity percentage and sensitivity percentage are above the respective cutoff percentages will serve as the susceptibility threshold. Accordingly, any given microorganism with unknown susceptibility or resistance having a NACR value below the susceptible threshold will be identified as "susceptible".

In some embodiments, the calculation of the susceptibility threshold described above can be repeated with higher purity cutoff percentages and/or higher susceptibility cutoff percentages.

The following steps are performed to calculate the resistant threshold.

First is to find the lowest NACR whose purity percentage is greater than or equal to the purity cutoff percentage. For any NACR value between the lowest NACR and the largest NACR, a purity percentage is calculated by first counting the number of susceptible training samples whose NACR is greater than or equal to the given NACR, then counting the number of training samples—including both the susceptible and resistant training samples—whose NACR is greater than or equal to the given NACR, and lastly dividing the former count by the latter count.

If no such NACR is found with a purity percentage greater than or equal to the purity cutoff percentage, then a threshold that satisfies the desired cutoff percentage is unavailable, and the method will be modified by modifying the antibiotic exposure time, changing the antibiotic concentration, selecting a different cutoff percentage, and/or modifying the enhancers.

Once the lowest NACR is found, the sensitivity percentage of that NACR will be calculated. The sensitivity percentage is calculated by first counting the number of susceptible training samples whose NACR is greater than or equal to the highest NACR, then counting the total number of susceptible training samples in the susceptible training set, and then dividing the former count by the latter count.

If the lowest NACR found does not have a sensitivity percentage above the sensitivity cutoff percentage, then a threshold that satisfies the desired cutoff percentage is unavailable, and the method will be modified by modifying the antibiotic exposure time, changing the antibiotic concentration, selecting a different cutoff percentage, and/or modifying the enhancers.

The lowest NACR whose purity percentage and sensitivity percentage are above the respective cutoff percentages will serve as the resistant threshold. Accordingly, any given microorganism with unknown susceptibility or resistance having a NACR value above the resistant threshold will be identified as "resistant".

In some embodiments, the calculation of the resistant threshold described above can be repeated with higher purity cutoff percentages and/or higher susceptibility cutoff percentages.

In lieu of the algorithm described above, there exist other mathematical algorithms to find a NACV threshold, some equivalent to each other when applied to 1-dimensional data. The algorithms all take as their input the same training set of NACVs and their corresponding gold-standard AST calls as the above algorithm. These other mathematical algorithms include algorithms in which a receiver operating characteristic curve is calculated, and thresholds are chosen that maximize the area under the curve (AUC), maximize the sensitivity, maximize the specificity, or are found by a weighted sum or other combination of these metrics; supervised machine learning techniques for binary or multi-class classification, including support vector machines with soft margins, linear regression, logistic regression, and ordinal regression; probabilistic methods in which the distributions of susceptible and resistant samples are each modeled as probability density functions of random variables, and then thresholds are drawn which correspond to a probability, chosen by the practitioner as desired, that incorrect calls will be made; clustering algorithms. Descriptions of these algorithms are found in reference [11].

Nucleic acid concentration ratio can be obtained by dividing nucleic acid concentration values. It can also be described as a mathematically equivalent operation, for example for an exponential amplification process by taking a difference of concentration parameters, such as the difference of Cq values (cycle threshold values) from qPCR. As described herein, a nucleic acid concentration value can be calculated from a Cq by equation (1). A ratio can be computed from two nucleic acid concentration values from Cq measurements as seen in equation (2). This expression can be rearranged to include a difference term, as seen in equation (3).

$$\text{Nucleic acid concentration value} = 2^{\wedge}(-Cq) \quad (1)$$

$$T{:}R \text{ ratio} = (2^{\wedge}-Cq \text{ treated})/(2^{\wedge}-Cq \text{ reference}) \quad (2)$$

$$T{:}R \text{ ratio} = 2^{\wedge}(Cq \text{ reference} - Cq \text{ treated}) \quad (3)$$

When using concentration parameters, the concentration parameters obtained by the nucleic acid detecting method may be converted to an equivalent nucleic acid concentration value using the formulas described herein or by constructing and consulting a standard curve. Then, the nucleic acid concentration ratio can be calculated from the equivalent nucleic acid concentration values. However, as illustrated herein, NACR can be calculated directly from the concentration parameters, for example for an exponential amplification process by taking a difference of concentration parameters, such as the difference of Cq values (cycle threshold values) from qPCR, or by analogous mathematical transformations that convert reaction times of exponential isothermal amplification directly into a ratio. For detection methods with linear dependence of concentration parameter on concentration (results of digital amplification and number of reads of the target nucleic acids obtained from high throughput sequencing), ratio of concentration parameters can be obtained directly without converting them into nucleic acids concentration values.

In some embodiments of methods of the disclosure, antibiotic susceptibility in a target microorganism of the instant disclosure can comprise selecting the sample with a detected high fold-change in detected nucleic acid concentration upon antibiotic exposure. In those embodiments, the fold-change is calculated based on nucleic acid quantification results. in particular, fold-change may be computed from qPCR Cq values or from digital PCR concentrations. When representing a decreasing fold-change, it may also be visualized as the reciprocal 1/FC, see Example 3. Fold change is compared to a threshold fold change to differentiate between the susceptible (S) and resistant (R) fold changes. If the fold-change comprises a treated nucleic acid concentration value divided by a reference nucleic acid concentration value, then the fold-change is equivalent to a NACR.

A high fold change is defined as at least two folder change or higher. In particular, in some embodiments, a significant shift of fold change (larger than 4) in concentration levels can be observed within 5 min, 10 min, or 15 min of antibiotic exposure.

In preferred embodiments, the R and T value is adjusted to reduce the impact of biological variability and/or technical variability, more preferably of both biological and technical variability. Accordingly, in some embodiments, the methods herein described, further comprises normalizing the (T:R) value prior to detecting a differential concentration of nucleic acid in the treated samples.

The wording "normalizing" and "normalization" as used herein refer to adjustments of a value related to a quantified amount to account for variations. In particular normalization of a value can be performed to account for a variation in a parameter associated with the detection of the quantified amount, such as variations in an amount of starting material, variations in an amount of sample, variations in bacterial concentration of sample, variations due to biological variability and variations due to technical variability.

Normalizing the T:R value can be performed with a reference measurement of cell number, the number of samples, the volume of sample used, the concentration of sample used, the effective amount of sample used and/or a related ratio in a reference and in a treated sample. Effective amount of sample can be calculated by for example measuring the volumes and concentration of the sample used. Normalizing the T:R value can be performed by dividing the control nucleic acid concentration by a reference measurement in the control sample and dividing the treated nucleic acid concentration by the reference measurement in the treated sample. Normalizing the (T:R) value can be performed by dividing the (T:R) value by a normalization ratio. The normalization ratio for the sample can be calculated by dividing the control reference measurement by the treated reference measurement.

In some embodiments of these embodiments, the normalizing measurement is a measurement that reflects the number of target cells. For example, prior to the calculation of a CT ratio, the detected nucleic acids in the untreated control sample and the detected nucleic acids in the treated sample would be divided by a cell normalization ratio between number of target cells in the treated sample and number of target cells in the control sample which can be calculated from other measurements such as optical density, turbidity, increase in intensity of a colorimetric, fluorogenic, or luminescent metabolic indicator or a live/dead indicator, colony counting after plating, amount of pathogen-specific DNA and amount of pathogen-specific RNA as will be understood by a skilled person.

In some embodiments the number of cells of the target microorganism present in a treated or control experiment can be estimated from a number of detected pathogen-specific DNA or RNA copies. In some embodiments of methods directed to detect inaccessible nucleic acid, two detected nucleic acids from a single sample are compared. These comparisons, ideally, are between one changing nucleic acid (such as changes in accessibility with addition of a targeting nuclease) and one unchanging nucleic acid (such as DNA in a sample which is known not to undergo substantial DNA replication under incubation conditions, such as *N. gonorrhoeae* in MHB media). In some methods, the extracted sample can be split only for the detection step two different primer sets are used. In other methods/examples, an incubation method includes RNase, nucleic acid quantification results can be used to calculate a DNA target and an RNA target from the same sample. The ratio of inaccessibility T:R ratio (e.g. the treated RNA sample with a degrading RNase divided by the reference RNA sample with a degrading RNase) can be normalized (by division of the ratios) to a ratio of DNA T:R ratio (without a degrader targeting the DNA, this number will be equal to 1.0 in a situation without any biological or technical noise). DNA and RNA concentrations can be quantified with qPCR, digital PCR, digital isothermal amplification, real-time isothermal amplification, digital LAMP, real-time LAMP. To differentiate between DNA and RNA concentrations reactions with and without reverse transcriptase are performed. The DNA/RNA ratio can be defined as the ratio of DNA readout, such as concentration of copies/µL, divided by the RNA readout, such as concentration of copies/µL, see Example 6.

In some embodiments the number of cells of the target microorganism present in a treated or control experiment can be estimated from a number of detected pathogen-specific DNA or RNA copies. In some methods, a reference measurement will be done of the initial detectable inaccessible target nucleic acids. This is similar to the estimation of total amount of cells, but uses a degrading treatment of nucleic acids to remove any background, nucleic acid molecules from a target microorganism. This reference sample is sometimes referred to as a time-zero reference or "t0" reference as the total amount of inaccessible target molecules before treatment begins. In some methods, the T:R ratio can be used alone, refer to Example 10 for experimental methods and data. In other methods, the t0 ratio of the untreated and treated samples can be used to normalize the comparison between the untreated and treated samples to normalize for aforementioned biological and technical variability.

In some embodiments of methods directed to detect accessible nucleic acid, two detected nucleic acids from a single sample are compared. Before detection, a sample may be split into two or more sub-samples. One sample may undergo a lysis treatment, to obtain a sample containing total nucleic acids from the target microorganism. The other part of the sample may not undergo any lysis treatment. Both samples can be quantified using a non-lysing amplification method such as qLAMP; only the accessible target nucleic acid molecules are detected in sample without lysis, which are compared to the total nucleic acid molecules from the sample which undergoes lysis prior to detection. Refer to Example 21 for experimental methods and data.

In some embodiments, quantitatively detecting T:R, C:T, or total nucleic acid can be performed on a treated sample and corresponding control sample under several sets of conditions (e.g. varying treatment times, different experimental settings and/or using a plurality of isolates or specimen and/or a plurality of related control and/or treated sample) to provide a nucleic acid concentration pattern for the nucleic acid in each treated and corresponding control samples under each set of conditions. In those embodiments, the differential concentration of the nucleic acid is detected with respect to the corresponding gene expression pattern or nucleic acid concentration value according to approaches identifiable by a skilled person upon reading of the present disclosure.

In some embodiments of the method of the instant disclosure, the target microorganism is a slow growing microorganism, a microorganism with a transcriptome which is not characterized and/or a microorganism that lacks a transcriptional SOS response to DNA damage.

The term "slow growing" as used herein indicates an organism with a doubling time longer than 30 minutes.

In some embodiments of the methods of the instant disclosure, the antibiotic is an antibiotic which interacts directly or indirectly with the cell envelope, cell envelope biosynthesis, cell structural remodeling, or overall cell integrity. For example, beta lactam antibiotics and antibiotic agents that contain a beta-lactam ring in their molecular structures. Including penicillin derivatives (penams), cephalosporins (cephems), monobactams, and carbapenems. Exemplary beta-lactam antibiotics include penicillin, ceftriaxone, cefixime, ampicillin, amoxicillin, meropenem, imipenem, and ertapenem.

In some of these embodiments, the antibiotic for treating the sample herein described, the concentration of the antibiotic can be provided at a concentration between 0.015 microgram/mL and 16.0 microgram/mL.

In some of these embodiments, the beta-lactam is penicillin. In some of these embodiments, the concentration of antibiotic used during exposure or treatment can be any concentration between the susceptible and resistant MIC breakpoints of the target organism. For example, for exposure or treatment of Ng with ciprofloxacin, the concentration of antibiotic used could be any concentration ≥0.06 microgram/mL (the susceptible MIC breakpoint for penicillin for *Neisseria gonorrhoeae*) and ≤2.00 microgram/mL (the resistant MIC breakpoint for penicillin for *Neisseria gonorrhoeae*). In some embodiments, for example when faster responses are desired, higher than breakpoint concentrations can be used.

In some embodiments, methods herein described can be performed on a treated sample only, without need of a control sample and related incubation. An incubation method can include a degrading molecule, such as an RNase, to degrade accessible RNAs (or complementarily, DNase to degrade accessible DNAs) followed by nucleic acid quantification of the accessible nucleic acids. Quantification can be performed on nucleic acids split after a single, antibiotic-treated sample. The reference measurement of an unchanging nucleic acid may refer to DNA, unchanging mRNA transcript, or the initial total amount of that nucleic acid target prior, during, or after treatment can be used to calculate a T:R ratio. The treated (T) part of that ratio is a nucleic acid target and the reference (R) refers to the reference target nucleic acid, which may differ in primer target, nucleic acid type (e.g. DNA or RNA), which can be measured from the same sample for nucleic acid detection. For example, a DNA/RNA ratio alone can be used to differentiate susceptible and resistant strains. See Example 6.

In some embodiments of methods herein described a specimen does not need to be split equally between treated and control sample. For example, when DNA/RNA ratio is used to predict susceptibility. This aforementioned DNA/RNA ratio can be used as a normalization factor or as a ratio for the susceptibility readout. Advantages of using two nucleic acid targets of amplification in the same sample include unequal numbers of cells between the reference sample and the treated sample that may occur. When the quantifiable nucleic acids are targeted from the same extraction of the treated sample, there is no longer a concern that the sample containing microorganisms. See Example 6, only the treated sample is required for the susceptibility call.

In some embodiments, nucleic acid extraction methods are used to inactivate nucleases. Extraction methods include but are not limited to Epicentre DNA Extraction Buffer and Zymo Research Viral DNA/RNA kit. In the instance in which nuclease treatments are used, such as the aforementioned exogenous degrading nucleases or sample pre-treatment of host nucleic acids, these degraders are desired to be inactivated prior to ucleic acid detection, as they may interfere with the measurement. The extraction methods described in experiments containing nucleases (DNaseI, RNaseA, or RNase cocktail) are inactivated with the corresponding nucleic acid extraction and lysis treatment of the sample, including the Lucigen DNA extraction buffer (DEB) and the Zymo Viral DNA/RNA lysis kit through the use of proteases and heat (DEB) and the use of denaturing agents in the Zymo kits, as is the case with the examples provided. If other nucleic acid extraction methods are used, then the method must be assessed for the ability to also inactivate the exogenous nucleases or add an additional treatment or step, such as including inhibitors, proteases, or quenching molecules to stop the nucleases. Other options include conjugation of nucleases to beads to enable physical, magnetic, or other targeted separation of the nucleases from the sample prior to nucleic acid quantification.

In some embodiments of the methods herein described, the target microorganism is *N. gonorrhoeae*.

*Neisseria gonorrhoeae* is one type of proteobacteria that causes the sexually transmitted genitourinary infection gonorrhea, as well as other forms of gonococcal disease including oropharyngeal gonorrhea, rectal gonorrhea, disseminated gonococcemia, gonococcal septic arthritis, and gonococcal ophthalmia neonatorum. The term "*Neisseria gonorrhea*" includes all strains of *N. gonorrhoeae* identifiable by a person skilled in the art. *Neisseria gonorrhoeae* also includes genetic variants of different strains. One may determine whether the target organism is *N. gonorrhoeae* by a number of accepted methods, including sequencing of the 16S ribosomal RNA (rRNA) gene, as described in Chakravorty et al (2007) for *N. gonorrhoeae*. [12].

In some embodiments of the method herein described the target microorganism is of the family Enterobacteriaceae, for example *Escherichia coli, Klebsiella pneumoniae*, and *Enterobacter* spp. Organisms in the family Enterobacteriaceae are Gram-negative bacteria that can cause multiple types of infections (such as urinary tract infections, enteritis, dysentery, pneumonia, meningitis, bacteremia, and sepsis), especially in healthcare settings.

In some embodiments of the methods of the instant disclosure wherein the target microorganism is *N. gonorrhoeae*, the time period of contacting the sample with an antibiotic is shorter than the doubling time of the *N. gonorrhoeae* strain in the sample. For example, for conditions with *N. gonorrhoeae* doubling time of 45 minutes, 1 hour, 1.5 hours, or 2 hours, antibiotic exposure contacting time could be less than the time indicated in Table 1 below

TABLE 1 time of contacting *N. gonorrhoeae* with antibiotic

| factor X | 45 minute doubling | 60 min doubling | 90 min doubling | 120 doubling |
|---|---|---|---|---|
| | | contacting time, less than (minutes): | | |
| 1 | 45 | 60 | 90 | 120 |
| 0.75 | 33.75 | 45 | 67.5 | 90 |
| 0.5 | 22.5 | 30 | 45 | 60 |
| 0.35 | 15.75 | 21 | 31.5 | 42 |
| 0.25 | 11.25 | 15 | 22.5 | 30 |
| 0.2 | 9 | 12 | 18 | 24 |
| 0.15 | 6.75 | 9 | 13.5 | 18 |
| 0.1 | 4.5 | 6 | 9 | 12 |
| 0.075 | 3.375 | 4.5 | 6.75 | 9 |
| 0.05 | 2.25 | 3 | 4.5 | 6 |

In methods of the instant disclosure wherein the target microorganism is *N. gonorrhoeae*, incubation of a sample with an antibiotic can be performed at a temperature such that a physiological response to the antibiotic is generated in *N. gonorroheae*. The contacting is performed typically in an incubation temperature at 37° C., in an incubation temperature within the range of 36-38 degrees ° C., in an incubation temperature within the range of 35-39 degrees ° C.

In methods of the instant disclosure wherein the target microorganism is incubated with antibiotics, the incubation can be performed by adding antibiotics to the microorganism and incubating the sample under certain condition preferably following and/or upon contacting the sample with a treatment media designed to support physiological processes of the target microorganism, and/or enable or accelerate DNA replication and translation, and/or enable or accelerate cell wall biosynthesis, maintenance, or repair, and/or maintain cellular uniformity and homogeneity in suspension, and/or promote interaction of the target microorganism and antibiotic herein described.

In some embodiments of the methods of the instant disclosure, quantitatively detecting a nucleic acid concentration value can be performed using probes specifically targeting any one sequence of the nucleic acids of the target microorganism.

The term "probe" as described herein indicates a molecule or computer support tool capable of specifically detecting a target molecule such as nucleic acids herein described. The wording "specific" "specifically" or "specificity" as used herein with reference to the binding of a first molecule to second molecule refers to the recognition, contact and formation of a stable complex between the first molecule and the second molecule, together with substantially less to no recognition, contact and formation of a stable complex between each of the first molecule and the second molecule with other molecules that may be present. Exemplary specific bindings are antibody-antigen interaction, cellular receptor-ligand interactions, polynucleotide hybridization, enzyme substrate interactions and additional interactions identifiable by a skilled person. The wording "specific" "specifically" or "specificity" as used herein with reference to a computer supported tool, such as a software indicates a tool capable of identifying a target sequence (such as the nucleic acids of the target organism herein described) among a group of sequences e.g. within a database following alignment of the target sequence with the sequences of the database. Exemplary software configured to specifically detect target sequences comprise Primer-1 PerlPrimer and PrimerBlast.

In some embodiments of the methods of the instant disclosure, the probe specific for the sequence of the target nucleic acid is selected from a primer having a sequence specific for the target nucleic acid, or an antibody specific for the target nucleic acid.

In particular, probes usable in methods herein described can include primers for nucleic acid amplification reactions (such as polymerase chain reaction (PCR), loop mediated isothermal amplification (LAMP), helicase-dependent amplification (HDA), recombinase polymerase reaction (RPA), nucleic acid sequence-based amplification (NASBA), rolling circle amplification (RCA), strand displacement amplification (SDA), nicking enzyme amplification reaction (NEAR), and additional reactions identifiable by a skilled person), including digital single molecule versions of these reactions and including real-time versions of these reactions, molecular beacons that include dyes, quenchers, or combinations of dyes and quenchers.

Nucleic acid probes preferably have sequences that complementarily bind to the DNA and/or RNA sequences of the nucleic acids from target organisms described herein, and can be used to target RNA molecules directly, or DNA molecules that result, for example, from reverse transcription of the target RNA molecules (such molecules may be referred to as cDNA). In embodiments of the present disclosure when two polynucleotide strands, sequences or segments are noted to be binding to each other through complementarily binding or complementarily bind to each other, this indicate that a sufficient number of bases pairs forms between the two strands, sequences or segments to form a thermodynamically stable double-stranded duplex, although the duplex can contain mismatches, bulges and/or wobble base pairs as will be understood by a skilled person.

In embodiments herein described primers and/or other nucleic acid probes can be designed to complementarily bind nucleic acids of the target microorganism herein described with methods described in [13].

Probes usable in methods herein described include probes used in guiding CRISPR-based detection of nucleic acids. e.g. CRISPR-associated protein-9 nuclease; CRISPR-associated nucleases. An example of a CRISPR-based method is described in references [14] [15] [16]. Such probes can be synthesized using naturally occurring nucleotides including deoxylnosine, or include unnatural nucleotides such as locked nucleic acid (LNA). Probes can comprise dyes, quenchers, or combinations of dyes and quenchers attached to the probe. Hybridization probes, including those used in fluorescent in situ hybridization and hybridization chain reaction. Probes can also comprise electrochemically active redox molecules attached to the probe. Probes can be provided in a dry state. Probes can also include probes bound to beads, such beads may be fluorescently labeled. Probes can also include probes bound to nanoparticles, such nanoparticles may include gold nanoparticles. Probes can include probes disposed in arrays of wells with volumes less than 50 microliters, and/or wells within plastic substrates.

In some embodiments, of the methods of the instant disclosure, quantitatively detecting of a nucleic acid can be performed by detecting a detectable portion thereof. Exemplary detectable portions comprise to regions of at least 14 base pair, at least 16 base pair, at least 18 base pair, at least 19 base pair, at least 20 base pair, at least 21 base pair, at least 22 base pair, at least 23 base pair, at least 24 base pair, at least 30 base pair, at least 40 base pair, at least 50 base pair, at least 60 base pair, at least 70 base pair, at least 80 base pair, at least 90 base pair, or at least 100 base pair, The specific portion can be identified by a skilled person based on the length of the nucleic acid to be detected as will be understood by a skilled person.

In some embodiments of the methods of the instant disclosure, the methods comprise detecting whether there is an increase in the nucleic acid concentration value, in a sample treated with an antibiotic with respect to a sample not treated with antibiotic.

In particular in embodiments of the methods of the instant disclosure, the methods comprise detecting whether there is an upshift of a detected increase in a treated nucleic acid concentration value detected following treatment with antibiotic with respect to an untreated nucleic acid concentration value in absence of antibiotic treatment.

In some embodiments of the methods of the instant disclosure using any target organisms herein described, the sample can be stored until sample preparation and analysis, for example at room temperature, 4° C., −20° C., or −80° C., as appropriate, identifiable by those skilled in the art. When biological specimens are stored, ideally they remain equivalent to freshly-collected specimens for the purposes of analysis. In some embodiments, of the methods of the instant disclosure using any one of target organisms herein described, the sample can be pre-incubated with growth media for a short period of time to increase the number of viable bacterial cells or to increase the level of nucleic acids in such cells. The temperature and media for such pre-incubation can be performed as described herein for incubation. The duration of such pre-incubation can range, for example, from 5 minutes to 20 minutes to 1 hour to 2 hours.

Methods of the present disclosure can be performed with a corresponding system comprising at least one probe specific for a nucleic acid of the target microorganism and reagents for detecting the at least one probe. The at least one probe and reagents are included in the system for simultaneous combined or sequential use in any one of the methods of the present disclosure.

In some embodiments of the system herein described the system comprises primers configured to specifically hybridize with a sequence of nucleic acid from the target organism.

In some embodiments, the systems of the disclosure to be used in connection with methods herein described can further comprise an antibiotic formulated for administration to a sample in combination with the at least one probe.

In some embodiments, the systems of the disclosure, the system further comprises an antibiotic formulated for administration to an individual in an effective amount to treat a microorganism infection in the individual.

In some embodiments, the systems of the disclosure to be used in connection with methods herein described, the reagents comprise DNA extraction, RNA extraction kit and amplification mix. The system can also include one or more antibiotics and/or exposure media with or without the antibiotics. The system can also include reagents required for preparing the sample, such as one or more of buffers e.g. lysis, stabilization, binding, elution buffers for sample preparation, enzyme for removal of DNA e.g. DNase I, and solid phase extraction material for sample preparation, reagents required for quantitative detection such as intercalating dye, reverse-transcription enzyme, polymerase enzyme, nuclease enzyme (e.g. restriction enzymes; CRISPR-associated protein-9 nuclease; CRISPR-associated nucleases as described herein) and reaction buffer. Sample preparation materials and reagents may include reagents for preparation of RNA and DNA from samples, including commercially available reagents for example from Zymo Research, Qiagen or other sample preparations identifiable by a skilled person. The system can also include means for performing DNA or RNA quantification such as one or more of: container to define reaction volume, droplet generator for digital quantification, chip for digital detection, chip or device for multiplexed nucleic acid quantification or semi-quantification, and optionally equipment for temperature control and detection, including optical detection, fluorescent detection, electrochemical detection.

In some embodiments, the system can comprise a device combining all aspects required for an antibiotic susceptibility test.

The systems herein disclosed can be provided in the form of kits of parts. In kit of parts for performing any one of the methods herein described, the probes and the reagents for the related detection can be included in the kit alone or in the presence of one or more antibiotic as well as any one of the RNA markers, corresponding cDNA and/or probes for one or more reference RNAs and/or corresponding cDNAs. In kit of parts for the treatment of an individual the probes and reagents for the related detection can be comprised together with the antibiotic formulated for administration to the individual as well as additional components identifiable by a skilled person.

In a kit of parts, the probes and the reagents for the related detection, antibiotics, RNA markers, and/or reference RNA and additional reagents identifiable by a skilled person are comprised in the kit independently possibly included in a composition together with suitable vehicle carrier or auxiliary agents. For example, one or more probes can be included in one or more compositions together with reagents for detection also in one or more suitable compositions.

Additional components can include labeled polynucleotides, labeled antibodies, labels, microfluidic chip, reference standards, and additional components identifiable by a skilled person upon reading of the present disclosure.

The terms "label" and "labeled molecule" as used herein refer to a molecule capable of detection, including but not limited to radioactive isotopes, fluorophores, chemiluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and the like. The term "fluorophore" refers to a substance or a portion thereof which is capable of exhibiting fluorescence in a detectable image. As a consequence, the wording "labeling signal" as used herein indicates the signal emitted from the label that allows detection of the label, including but not limited to radioactivity, fluorescence, chemoluminescence, production of a compound in outcome of an enzymatic reaction and the like.

In embodiments herein described, the components of the kit can be provided, with suitable instructions and other necessary reagents, in order to perform the methods here disclosed. The kit will normally contain the compositions in separate containers. Instructions, for example written or audio instructions, on paper or electronic support such as tapes, CD-ROMs, flash drives, or by indication of a Uniform Resource Locator (URL), which contains a pdf copy of the instructions for carrying out the assay, will usually be included in the kit. The kit can also contain, depending on the particular method used, other packaged reagents and materials (i.e. wash buffers and the like).

Further details concerning the identification of the suitable carrier agent or auxiliary agent of the compositions, and generally manufacturing and packaging of the kit, can be identified by the person skilled in the art upon reading of the present disclosure.

EXAMPLES

The methods of the disclosure and related composition, and systems herein described are further illustrated in the following examples, which are provided by way of illustration and are not intended to be limiting.

In particular, the following examples illustrate exemplary methods and protocols for performing methods directed to detect accessible or inaccessible nucleic acid. A person skilled in the art will appreciate the applicability and the necessary modifications to adapt the features described in detail in the present section, to additional methods and related compositions and systems according to embodiments of the present disclosure.

The following general materials and methods were used unless specified.

Clinical isolates referenced, minimum inhibitory concentrations (MIC s), and categorical susceptibility based on CLSI breakpoints The below list of organisms are examples of clinically-relevant susceptible and resistant Enterobacteriaceae clinical isolates. Minimum inhibitory concentrations (MICs) are provided in µg/mL for the antibiotics listed. Any number with an inequality sign ≤, or >indicates that an endpoint measurement was not made.

|  |  | Antibiotic MICs | | |
| --- | --- | --- | --- | --- |
| ID | Organism | AMP | CRO | ETP |
| Ec_1 | Escherichia coli | 4* | <=1* | <=.5* |
| Ec_2 | Escherichia coli | <=2* | <=1* | <=.5* |
| Ec_3 | Escherichia coli | <=2* | <=1* | <=.5* |
| Ec_4 | Escherichia coli | <=2* | <=1* | <=.5* |
| Ec_38 | Escherichia coli | ND | >32# | >4# |
| Ec_39 | Escherichia coli | >=32# | >32# | 2# |
| Ec_40 | Escherichia coli | >=32# | >=64# | 2# |
| Ec_41 | Escherichia coli | ND | >32# | 2# |
| Kp_1 | Klebsiella pneumoniae | ND | <=1* | <=.5* |
| Kp_2 | Klebsiella pneumoniae | ND | <=1* | <=.5* |
| Kp_7 | Klebsiella pneumoniae | >32# | >32# | >8# |
| Kp_8 | Klebsiella pneumoniae | >32# | >3 2 | >8# |

*the organism is susceptible (also referred to herein as "S"),
the organism is resistant (also referred to herein as "R")
ND = not determined The below list of organisms are examples of clinically-relevant susceptible and resistant *Neisseria gonorrhoeae* clinical isolates. Minimum inhibitory concentrations (MICs) are provided in µg/mL for the antibiotics listed. Any number with an inequality sign ≤, or >indicates that an endpoint measurement was not made.

|  |  | Antibiotic MICs | | | |
| --- | --- | --- | --- | --- | --- |
| ID | Organism | CIP | CRO | CFM | PEN |
| ng_1 | Neisseria gonorrhoeae | ≤0.015* | ≤0.008* | ≤0.015* | 0.250 |
| ng_2 | Neisseria gonorrhoeae | ≤0.015* | ≤0.008* | ≤0.015* | 0.250 |
| ng_3 | Neisseria gonorrhoeae | ≤0.015* | ≤0.008* | ≤0.015* | 0.250 |
| ng_4 | Neisseria gonorrhoeae | 16.000# | 0.030* | 0.060* | 0.500 |
| ng_5 | Neisseria gonorrhoeae | ≤0.015* | 0.015* | 0.030* | 1.000 |
| ng_6 | Neisseria gonorrhoeae | 4.000# | ≤0.008* | 0.015* | 0.250 |

-continued

| | | Antibiotic MICs | | | |
|---|---|---|---|---|---|
| ID | Organism | CIP | CRO | CFM | PEN |
| ng_12 | Neisseria gonorrhoeae | 2.000# | 0.015* | 0.030* | 0.500 |
| ng_15 | Neisseria gonorrhoeae | ≤0.015* | ≤0.008* | ≤0.015* | 0.015* |
| ng_16 | Neisseria gonorrhoeae | ≤0.015* | ≤0.008* | ≤0.015* | 0.015* |
| ng_17 | Neisseria gonorrhoeae | ≤0.015* | ≤0.008* | ≤0.015* | 0.060* |
| ng_18 | Neisseria gonorrhoeae | 16.000# | 0.030* | 0.060* | 2.000# |
| ng_19 | Neisseria gonorrhoeae | 4.000# | 0.015* | 0.030* | 2.000# |
| ng_20 | Neisseria gonorrhoeae | ≤0.015* | ≤0.008* | ≤0.015* | 0.060* |
| ng_30 | Neisseria gonorrhoeae | 0.015* | 0.500# | 1.000# | 1.000 |
| ng_41 | Neisseria gonorrhoeae | 16.000# | 0.125* | 0.250* | 2.000# |
| ng_44 | Neisseria gonorrhoeae | 4.000# | ≤0.008* | ≤0.015* | 8.000# |

*the organism is susceptible (also referred to herein as "S"),
the organism is resistant (also referred to herein as "R")
ND = not determined MHB Media Preparation: Mueller Hinton Broth (MHB) prepared from BBL Mueller Hinton II Broth Cation Adjusted (BBL cat no. 212322) according to manufacturer instructions (autoclaved to sterilize)

HFB Media Preparation: Hardy fastidious broth (HFB) purchased from Hardy Diagnostics (Hardy cat no. K31) and used as received (stored at 4° C.)

BHI Media Preparation Brain-heart Infusion Media (BHI) prepared from BD Bacto Brain Heart Infusion (BD cat no. 237500) according to instructions (autoclaved to sterilize)

GWM Media Preparation M199 cell culture medium was prepared by dissolving M199 salts (Sigma cat no. M3769, lot no. SLBW4106) in 1 L milliQ H2O. Graver-Wade salt additions to 667 mL M199 cell culture medium (final volume 1.0 L) are shown below. All concentrations based on volumes and reported concentration in Wade et al. 2007 paper. Final media is filter-sterilized with a 0.2 μm filter and stored at 4° C.

| Component (stock concentration) | Volume (final concentration) |
|---|---|
| Glucose (1000 mM) | 3.7 mL (37 mM) |
| Ammonium bicarbonate (1000 mM) | 1.7 mL (17 mM) |
| Sodium acetate (1000 mM) | 0.49 mL (4.9 mM) |
| L-glutamine (50 mM) | 6.8 mL (3.4 mM) |
| Spermidine (500 mM) | 0.18 mL (0.92 mM) |
| L-arginine (100 mM) | 0.38 mL (0.38 mM) |
| Hypoxanthine (100 mM) | 0.25 mL (0.25 mM) |
| Uracil (850 mM) | 0.35 mL (0.30 mM) |
| Oxaloacetate (100 mM) | 0.25 mL (0.25 mM) |
| Thiamine hydrochloride (100 mM) | 0.10 mL (0.10 mM) |
| L-ornithine (100 mM) | 0.04 mL (0.04 mM) |
| Nicotinamide adenine dinucleotide, NAD+ (50 mM) | 0.02 mL (0.01 mM) |
| DL-lactate (60% w/w, ~7500 mM) | 2.5 mL (~13 mM) |
| NF-H2O | 316.24 mL |

Preparation and storage of antibiotic stocks: All antibiotic (ABX) stocks are prepared from solids of the listed antibiotic or solid salts of the listed antibiotic. ABX stocks are prepared such that the final concentration of antibiotic (not including counterion salts) is as listed. ABX stocks were prepared at 1 mg/mL in either nuclease-free H2O (NF—H2O) unless listed otherwise. 50-100 uL aliquots of ABX stocks were stored frozen at −80 celsius. Aliquots are thawed only once on day of experiment before use, and used to prepare listed working stock.

NG Stock and Resuspension: the following procedure is carried out:
1. Isolates are plated from glycerol stocks onto BBL ChocII Agar—Pre-poured plates (Cat no. 221267) and grown overnight in a 37° C., 5% $CO_2$ incubator. (Referred to as "pass 0" or "p0" plates).
2. Isolates are passed by streaking a colony or a clump of colonies on a new, pre-warmed BBL Chocolate II Agar plate. The passage number is increased each time the plates are streaked this way; cells from a p0 plate streaked onto a fresh BBL Chocolate II Agar plate are now labeled p1 cells.
    a. Note: cultures started for resuspensions for experiment prep use pass 1 (p1), pass 2 (p2), or pass 3 (p3) plates.
3. Prewarm media before adding cells for at least 30-60 minutes in a 37° C., 5% $CO_2$ incubator on a shaking block (500-1000 rpm) before adding cells (step 4).
    a. Media is either MHB with an addition of $NaHCO_3$ to a final concentration of 5 mM or GWM. Each cell pellet is resuspended in 2 mL of pre-warmed media.
4. Resuspend cell pellets. Scrape cell pellet from the chocolate agar plate with inoculating loop and twirl in 2 mL pre-warmed media. incubate on shaker (1000 rpm) in 37° C., 5% $CO_2$ incubator
    a. Break apart the cell pellet by pipetting the cell pellet up and down with a P1000 until large pieces are no longer seen.
    b. Resuspension time can vary from 10 minutes-8 hours, depending on the objective of the experiment.

EC, KP, Stock and Resuspension All Ec and Kp stocks were handled in the same fashion as Ng stocks, except plates used to grow Ec and Kp were TSA II plates with 5% sheep's blood. Media used for resuspension was typically BD brain heart infusion media or mueller hinton broth unless listed otherwise. Media used for incubation was typically MHB unless listed otherwise.

DEB Extraction: the extraction can be performed with the following materials: Lucigen QuickExtract DNA Extraction Soln. 1.0. Cat #QE09050, and according to the following procedure:
1. In the BioSafety Cabinet (BSC), dilute sample 1/10 into Lucigen DNA Extraction Buffer (DEB). Such as 10 μL from exposure tube into 90 μL DEB, in a 1.5 mL Eppendorf tube or a 200 μL PCR tube.
    a. Gently close tubes
    b. Vortex for 2-3 seconds
    c. Quickly centrifuge tubes to remove the droplets from the caps d. Spray gloves and tubes with 70% ethanol before moving to the thermocycler from the BSC (If using Eppendorf tubes, move to a glass bead bath set to 65° C.)

2. On thermocylcer or heat blocks:
   a. Heat to 65° C. for 6 minutes
   b. Heat to 98° C. for 4 minutes
   c. Hold at 12° C. (PCR tubes on thermocylcer) or move to ice bath (Eppendorf tubes) to cool The heating can be done on the BioRad thermocylcer in PCR tubes, or in sequential heating steps on heat-blocks in Eppendorf tubes.

Zymo Column Extraction (RNA): the extraction can be performed with the following materials: bacterial suspension to extract RNA and DNA (referred to as "sample"), Zymo Research DNA/RNA Shield, Zymo Research Viral DNA/RNA kit, and according to the following procedure:

1. Add 1 volume of DNA/RNA Shield to 1 volume sample (50 µL:50 µL)
2. Add 2 volumes Viral DNA/RNA Buffer to sample and mix (200 µL buffer+100 µL sample+shield)
3. Transfer sample to Zymo Spin column in a collection tube and centrifuge for 1-2 minutes. Discard flow-through
4. Add 500 µL viral wash buffer to column and centrifuge for 2 minutes.
5. Transfer column to a DNase/RNase-Free Tube.
6. Elute: Add 50-100 µL Nuclease-Free Water and centrifuge for 30 seconds.

qPCR qPCR mixes were prepared according to the table below.

| qPCR | | |
|---|---|---|
| Component (stock concentration) | Volume (final concentration) | Initial Melt (1X) |
| BioRad SsoFast EvaGreen Supermix (2X) | 5.0 uL (1X) | 95° C. 3.0 min |
| PCR primer mix (10 uM each) | 0.5 uL (0.5 uM each) | Cycle (40X) |
| NF-H20 | 3.5 uL | 95° C. 10 sec |
| Template | 1.0 uL | 60° C. 10 sec |
| | | 72° C. 15 sec |
| | | Melt Curve (1X) |
| | | 95° C. 15 sec |
| | | 50° C. 15 sec |
| | | 50-95° C. cont. read |

PCR primers used for detection and quantification of Ec and Kp consisted of forward and reverse primers with sequence TGCCGTAACTTCGGGAGAAGGC (SEQ ID NO: 1) and TCAAGGCTCAATGTTCAGTGTC (SEQ ID NO: 3)_respectively, and were obtained from Matsuda et al. 2007 [17]. PCR primers used for detection and quantification of Ng consisted of forward and reverse primers with sequence ACTGCGTTCTGAACTGGGTG (SEQ ID NO: 4) and GGCGGTCAATTTCACGCG (SEQ ID NO: 2) respectively, and were obtained from Lee et al. 2007 [18].

The thermocycling can be performed according to the following procedure

1. If possible, run triplicate wells for each nucleic acid sample in 10 µL volumes according to the table below of the qPCR master mix:

| qPCR Master Mix ($V_f$ = 10 µL) | |
|---|---|
| Reagent | Volume |
| BioRad sso fast (contains EvaGreen) 2X | 5.0 µL (1X) |
| Primer Mix (10 µM forward and reverse) | 0.5 µL (0.5 µM) |
| Template: Extracted DNA | 1.0 µL |
| Nuclease-Free Water | 3.5 µL |

2. Vortex and centrifuge each of the PCR tubes with three volumes of the Master Mix prior to aliquoting into the Roche Light Cycler 96 plate.
3. With the PCR plate on a −20° C. cold block, pipette 9.5 µL into each well of the PCR well plate.
4. Seal the well plate with film.
5. Centrifuge the well plate
6. Place the well plate back to the −20° C. ice block until it is placed on the machine. Run the protocol as follows:
7. An example of PCR settings are reported in the table below

| | | |
|---|---|---|
| Initial Melt | 95° C. | 3:00 |
| 35X | 95° C. | 0:15 |
| | 62° C. | 0:15 |
| | 72° C. | 0:20 |
| Melt Curve 1X | 95° C. | 0:15 |
| | 50° C. | 0:15 |
| | 95° C. | |

8. Export the data from the Roche LightCylcer 96 software to a .csv or .xlsx file. Perform the analysis on the Cq data (plotting the raw Cq data and processing the Cqs to get a C:T ratio)

qRT-PCR: the qRT PCR can be performed with the mix and conditions summarized in the tables below.

| RT-qPCR mix (10 µL) For-RT samples, WarmStart RTx and RiboGuard volume was replaced with NF-water. | |
|---|---|
| Component (stock concentration) | Volume (final concentration) |
| 2X BioRad ssoFast EvaGreen Supermix | 5.0 µL (1X) |
| WarmStart RTx (15,000 U/mL) | 0.1 µL (150 U/mL) |
| RiboGuard (40,000 U/mL) | 0.2 µL (800 U/mL) |
| Primer Mix (10 µM each) | 0.5 µL (0.5 µM each) |
| Template | 1.0 µL |
| NF water | 3.2 µL |

| RT-qPCR rxn conditions | |
|---|---|
| RT/Initial Melt (1X) | |
| 55° C. | 10 min |
| 95° C. | 3 min |
| Cycle (30X) | |
| 95° C. | 15 s |
| 62° C. | 15 s |
| 72° C. | 15 s |
| Melt Curve (1X) | |
| 95° C. | 15 s |
| 50° C. | 15 s |
| 95° C. | 5 s | ddPCR: ddPCR can be performed with the material and conditions summarized in the table below

| Component (stock concentration) | Volume (final concentration) | RT (1X) | |
|---|---|---|---|
| BioRad Droplet Generation Mix for EvaGreen (2X) | 5.0 uL (1X) | 55° C. | 10.0 min |
| Primer mix (10 uM each) | 0.5 uL (0.5 uM each) | Initial Melt (1X) | |
| NF-H2O | 3.5 uL | 95° C. | 5.0 min |
| Template | 1.0 uL | Cycle (40X) | |
| | | 95° C. | 30 sec |
| | | 60° C. | 30 sec |
| | | 68° C. | 30 sec |
| | | Dye Stabilization (1X) | |
| | | ⇐4° C. | 5.0 min |
| | | 90° C. | 5.0 min |
| | | 12° C. | Ho ld | ddRT-PCR the ddRT PCR can be performed with the mix and conditions summarized in the tables below.

| RT-ddPCR mix (10 µL). For-RT samples, WarmStart RTx and RiboGuard volume was replaced with NF-water. | |
|---|---|
| Component (stock concentration) | Volume (final concentration) |
| 2X BioRad Droplet Generation Mix for EvaGreen | 5.0 µL (1X) |
| WarmStart RTx (15,000 U/mL) | 0.1 µL (150 U/mL) |
| RiboGuard (40,000 U/mL) | 0.2 µL (800 U/mL) |
| Primer Mix (10 µM each) | 0.5 µL (0.5 µM each) |
| Template | 1.0 µL |
| NF water | 3.2 µL |

| RT-ddPCR rxn conditions 2° C./s ramp on all cycling steps. | |
|---|---|
| RT/Initial Melt (1X) | |
| 55° C. | 10 min |
| 95° C. | 3 min |
| Cycle (30X) | |
| 95° C. | 15 s |
| 60° C. | 15 s |
| 68° C. | 15 s |
| Dye Stabilization (1X) | |
| 4° C. | 5 min |
| 90° C. | 5 min |
| 12° C. | hold | qLAMP without enhancer present in amplification mix; the qLAMP can be performed with the material and conditions summarized in the table below

| LAMP | | | |
|---|---|---|---|
| Component (stock concentration) | | Cycle (120X) | |
| IsoAmp Butter II (10X, (—) Tween 20) | 1.0 uL (1X) | 70° C. | 10 sec |
| MgSO4 (100 mM) | 0.3 uL (5 mM) | Melt Curve (1X) | |
| KCl (1.0M) | 1.5 uL (150 mM) | 95° C. | 15 sec |
| dNTPs (10 mM each) | 1.4 uL (1.4 mM each) | 50° C. | 15 sec |
| Primer mix (20 X) | 0.5 uL (1X) | 50-95° C. | cont. read |
| Bst 3.0 (8000 U/mL) | 0.4 uL (320 U/mL) | | |
| Syto-9 (50 uM) | 0.4 uL (2 uM) | | |
| Template | 1.0 uL | | |
| NF-H2O | 3.5 uL | | | wherein the Iso Amp Buffer II (10×, (–) Tween 20)=200 mM Tris-HCl, 20 mM MgSO4, 100 mM $(NH_4)_2SO_4$, pH 8.8. Primers for detection and quantification of Ec and Kp was same as that listed in Schoepp et al. 2017 [19].

qLAMP with enhancer present in amplification mix: can be performed with the material and conditions summarized in the table below

| Component (stock concentration) | Volume (final concentration) | Cycle (120X) | |
|---|---|---|---|
| NEB IsoAmp Butter II | 1.0 uL (1X) | 70° C. | 10 sec |
| MgSO4 (100 mM) | 0.3 uL (5 mM) | Melt Curve (1X) | |
| dNTPs (10 mM each) | 1.4 uL (1.4 mM each) | 95° C. | 15 sec |
| Primer mix (20X) | 0.5 uL (1X) | 50° C. | 15 sec |
| Bst 3.0 (8000 U/mL) | 0.4 uL (320 U/mL) | 50-95° C. | cont. read |
| Syto-9 (50 uM) | 0.4 uL (2 uM) | | |
| Template | 1.0 uL | | |
| NF-H2O | 5.0 uL | | | wherein the NEB Iso Amp Buffer II=200 mM Tris-HCl, 20 mM MgSO4, 100 mM (NH4)2SO4, pH 8.8. Primers for detection and quantification of Ec and Kp was same as that listed in Schoepp et al. 2017 [19].

Example 0: Modification of Nucleic Acid Accessibility in a Cell Following Administration of an Antibiotic The general methods and material indicated above were used in ASTs in which detection of accessible and inaccessible nucleic acid is set up based on the modification in nucleic acid accessibility of nucleic acid associated with antibiotic administration schematically illustrated in FIGS. 1 and 2.

In particular the schematic illustration of FIG. 1 shows difference in accessibility and a corresponding exemplary outcome of an exemplary antibiotic susceptibility test for a susceptible microorganism of the instant disclosure. In particular, FIG. 1 Panel A shows a schematic representation of a control sample comprising the microorganism not treated with antibiotic and showing inaccessible DNA in an intact cell. FIG. 1 Panel B shows a schematic representation of an antibiotic-treated sample showing a disrupted or lysed susceptible microorganism cell with DNA accessible to nuclease. FIG. 1 Panel C shows a diagram illustrating the CT ratio of the control sample of Panel A and the antibiotic-treated sample of FIG. 1 Panel B. A threshold control-treated (CT) ratio (the dashed line with a prediction of the cell being antibiotic susceptible (S).

Figure 2:
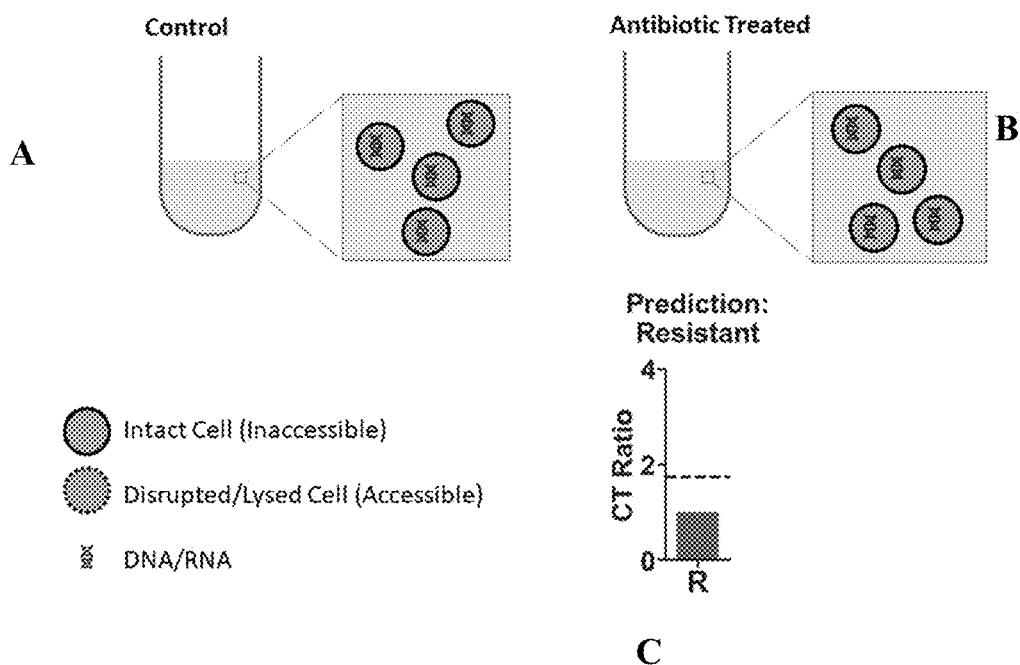
FIG. 2 shows a schematic representation of an exemplary outcome of an exemplary antibiotic susceptibility test for a resistant microorganism of the instant disclosure. In particular, Panel A shows a schematic representation of a control sample comprising the microorganism not treated with antibiotic and showing inaccessible DNA in an intact cell. Panel B shows a schematic representation of an antibiotic-treated sample showing intact resistant microorganism cell. Panel C shows a diagram illustrating the CT ratio of the control sample of Panel A and the antibiotic-treated sample of Panel B. A threshold control-treated (CT) ratio (the dashed line with a prediction of the cell being antibiotic resistant (R).

The illustration of FIG. 2 shows instead a schematic representation of difference in nucleic acid accessibility and a corresponding exemplary outcome of an exemplary antibiotic susceptibility test for a resistant microorganism of the instant disclosure. In particular, FIG. 2, Panel A shows a schematic representation of a control sample comprising the microorganism not treated with antibiotic and showing inaccessible DNA in an intact cell. FIG. 2, Panel B shows a schematic representation of an antibiotic-treated sample showing intact resistant microorganism cell. FIG. 2, Panel C shows a diagram illustrating the CT ratio of the control sample of Panel A and the antibiotic-treated sample of Panel B. A threshold control-treated (CT) ratio (the dashed line with a prediction of the cell being antibiotic resistant (R).

Example 1: AST Performed by Detecting Inaccessible DNA with 1 Incubation Step (Media with Enhancing Treatment; Followed by Cell Lysis and NA Extraction) with DNA Quantification Performed by gPCR An antibiotic susceptibility test can be performed with methods herein described comprising 15-minute co-incubation of the sample with antibiotics and an enhancing treatment followed by cell lysis, and detection of differences in amounts of detected DNA between the antibiotic-susceptible and a corresponding control but not in antibiotic-resistant NG isolates with respect to a corresponding control.

In particular this example shows a detection of a difference in amounts of DNA in a treated incubation for an antibiotic-susceptible (ng_3, ceftriaxone susceptible) clinical isolate with respect to a corresponding control, but not in antibiotic-resistant (ng_30, ceftriaxone resistant/reduced-susceptible) clinical isolate.

In particular, the detection was performed in outcome of to the following procedure.

1. Provide incubation media containing enhancer, with and without antibiotic for each isolate Several milliliters of media were prewarmed in a 37° C., 5% $CO_2$ incubator (media is MHB, see media preparation in general methods) for ≥30 minutes prior to use.

For each isolate, two incubation tubes were prepared in 2 mL purple cap tubes (VWR Cat #89004-298), following the indication in table x below, titled "Antibiotic Exposure per 500 µL". Add Triton X (enhancer), DNaseI (Cat: M0303L) (degrader), $NaHCO_3$ (conditioner).

Antibiotic was added when bacteria cells were incubating, so that the time from thawing the antibiotic stock was minimized before exposure (see step 3). In particular antibiotic dilutions were prepared from pre-made and frozen antibiotic stocks: Diluted 1 mg/mL ceftriaxone stock, prepared according to "Preparing Antibiotic Stocks" description above, see ceftriaxone. The stocks used had short-term storage of the 1 mg/mL stocks in −20° C. storage instead of −80° C. storage, but were only thawed once. To Prepare 50× stocks of the antibiotic follow the following dilutions in nuclease-free (NF) water:

50× Stock (1×4 µg/mL cro→200 µg/mL=0.2 mg/mL cro)
   400 µL of 0.2 mg/mL=80 µL (1 mg/mL stock)+320 µL NF water
50× Stock (1×0.25 µg/mL cro→12.5 µg/mL=0.0125 mg/mL cro)
   400 µL of 0.0125 mg/mL=62.5 mg/mL dilution)+337.5 µL NF water The resulting mixture was thus provided

| Antibiotic Exposure per 500 µL. (2 mL purple cap tubes setup) | |
| --- | --- |
| Component | Volume |
| Ng Suspension (OD = 0.5) | 50 µL (OD = 0.05) |
| MHB (Prewarmed) (media) | 360 µL |
| 10X detergent (10% TritonX) (enhancer) | 50 µL (1X, 1%) |
| NEB DNaseI (2000 U/mL) (degrader) | 25 µL (100 U/mL) |
| Ceftriaxone (50X), see ABX dilutions above (treated) or replace with nuclease-free (NF) Water in controls (untreated) | 10 µL (1X) |
| $NaHCO_3$ (100 mM) (conditioner) | 5 µL (1 mM) |

This step can be performed before or after steps 2-4 of this example as will be understood by a skilled person upon reading of the present disclosure.

2. Provide a sample containing bacteria

The bacteria were prepared according to the "NG Stock and Resuspension" description above with the following changes: MHB+5 mM $NaHCO_3$ was shaken at 800 rpm for 55 min in the incubator, p0 cells were used, 50 minutes of resuspension in MHB at 37° C., 5% CO2, 1000 rpm, and the cell clumps were not manually broken apart with a pipette.

While cell pellet was suspending, the antibiotic exposure condition (everything except Ng suspension and ABX) was prepared.

Right before measuring OD, of step 3 of this example, the antibiotic exposure tubes prepared in step 1 were set on the shaking heat block (set to 38° C. and 1000 rpm shaking)

3. Add the antibiotic to the exposure tube

In variation of this set of experiments where the antibiotic was not added during step 1, the antibiotic exposure tubes was brought from the shaking heat block (set to 38° C. and 1000 rpm shaking) to the BSC. 10 µL of the appropriate antibiotic dilution was added to the exposure tubes. For the exposure tubes which was set to go "untreated" 10 µL of NF water was added.

4. Optionally, pre-process the sample containing the bacteria to modify the bacterial concentration in the sample In a variation of the set of experiments herein described the OD600 of each of the suspensions prepared in step 2 can be adjusted to OD600=0.5. Measure the OD600 (dilute 1/10 in pre-warmed media) and dilute accordingly in pre-warmed media.

5. Split the sample into two or more parts

50 μL of the Ng suspension (such as the OD 0.5 suspensions prepared in step 4) was withdrawn.

6. Combine the sample with incubation media

50 μL of the Ng suspension was added into "treated" media, and 50 μL of the Ng suspension was added into untreated media. This addition can be performed sequentially or in parallel (using multichannel pipet) as will be understood by a skilled person upon reading of the present disclosure 7. Incubate the treated and untreated samples at a controlled temperature for a short amount of time.

The antibiotic exposure tubes prepared in step 1 were returned on the shaking heat block (set to 38° C. and 1000 rpm shaking).

The antibiotic incubation/exposure was performed on a heat-shake block fit to 2 mL purple cap tubes (VWR Cat #89004-298). The particular shake-block was measured with a thermocouple to ensure the temperature inside the tubes with 500 μL of media is 37° C. (settings 38° C. and 1000 rpm shaking). qPCR was used for NA amplification The liquid temperature of this particular heat/shake block was measured with a thermocouple to ensure the temperature inside the tubes with 500 μL of media is 37° C. (settings: 38° C. and 1000 rpm shaking).

8. Extraction (at 15 minutes) of treated and untreated samples to purify DNA

Extraction was performed following "DEB Extraction" description in the general methods using Eppendorf tubes. Vortex samples briefly (2 seconds) and centrifuge before transferring 10 μL of the sample to 90 μL of the extraction buffer.

9. Optionally, continue incubation of the treated and untreated samples for a control of the antibiotic efficacy over >15 minute exposures After desired incubation time >60 minutes, Silt droplets were plated on a pre-warmed BBL Chocolate Agar plate as a positive control of the antibiotic.

10. Measurement of DNA by qPCR

The "qPCR" description in the general methods was followed. All DEB-extracted DNA were quantified using a primer mix=(10 μM forward and reverse) targeting *N. gonorrhoeae* porA gene. Samples were run in qPCR triplicates (10 μL reactions) at an annealing temperature 62° C. The primers target the porA gene.

Figure 3:
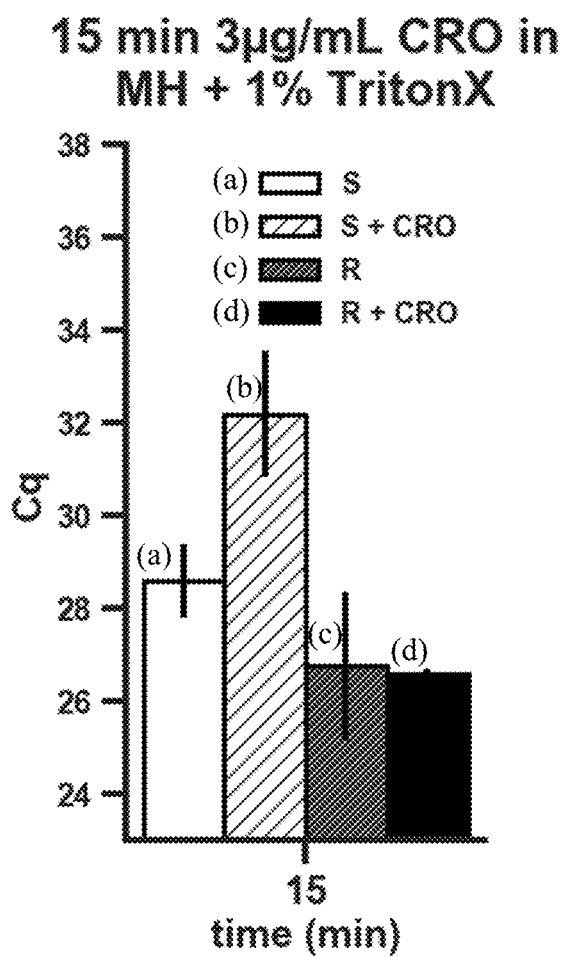
FIG. 3 shows a diagram illustrating the results of experiments, described in Example 1, directed to detect the effects of antibiotic ceftriaxone (CRO) on DNA accessibility for ceftriaxone-susceptible Ng isolates (ng_3) and ceftriaxone-resistant Ng isolates (ng_30) in comparison to a control sample, with an increase in Cq corresponding to decrease in accessible DNA. Error bars represent 95% confidence intervals of the qPCR measurement.

11. Data analysis is performed on the raw Cq measurements obtained from the qPCR instrument The related results are illustrated in FIG. 3 which illustrates the results for one ceftriaxone-susceptible Ng isolates (ng_3) (se FIG. 3, (a) and (b) bars) and one ceftriaxone-resistant Ng isolate (ng_30) (see FIG. 3, (c) and (d) bars). Cq's detected plotted with error bars of 95% confidence intervals based on the qPCR triplicate measurements.

As can be seen from the illustration of FIG. 3, upon incubation with 1% TritonX-100, NEB DNaseI, and ceftriaxone ABX in cell culture media (MH), the susceptible isolates showed a decrease in DNA concentration. This is likely due to an increased accessibility of the DNA due to lysed or disrupted cells. The DNaseI added to the incubation digests the accessible DNA. The increase in Cq corresponds to decreased quantity of detectable inaccessible nucleic acids. These data also show that increasing antibiotic concentration can enhance the effect of a beta-lactam treatment after a short (15-minute) incubation time. This effect is not seen in the resistant isolate, as the Cqs are not distinguishable from the control (no ABX). Note that 3.5 Cq difference between FIG. 3 bars (a) and (b) on the exponential scale represents an 11-fold difference in relative concentrations.

The results exemplified in FIG. 3, support the conclusion that a 15-minute co-incubation with antibiotics and an enhancer of 1% Triton X-100 show differences in DNA accessibility (as seen by the difference in Cq) between the antibiotic-susceptible but not antibiotic-resistant NG isolates.

The results exemplified in FIG. 3, also supports the conclusion that the difference in Cqs (detectable difference) is sufficient to differentiate between the antibiotic-susceptible and antibiotic-resistant isolates of NG.

The results exemplified in FIG. 3, further support the conclusion that same protocol can be run on isolates on different days, and the results can be compared between days.

Example 2: AST Performed by Detecting Inaccessible DNA with 1 Incubation Step (Media with Enhancer; Followed by Cell Lysis and NA Extraction) with DNA Quantified with gPCR and Treatment with Antibiotic Concentration Above Breakpoint to Shorten the Exposure Time Experiments were performed to show that antibiotic concentration above the resistance breakpoints can be used with short antibiotic exposures in AST performed with methods herein described. In particular in this example AST was performed by 30-minute co-incubation with antibiotics and an enhancer followed by cell lysis, nucleic acid extraction and detection in detectable differences in DNA between the antibiotic-susceptible but not antibiotic-resistant NG isolates.

The procedure used in this example is identical to the one of Example 1, except for the fact that the isolates here are one ceftriaxone-susceptible Ng isolates (ng_17) and one ceftriaxone-resistant Ng isolate (ng_30), and for the fact that the antibiotic exposure is 30 minutes instead of 15 minutes.

Figure 4:
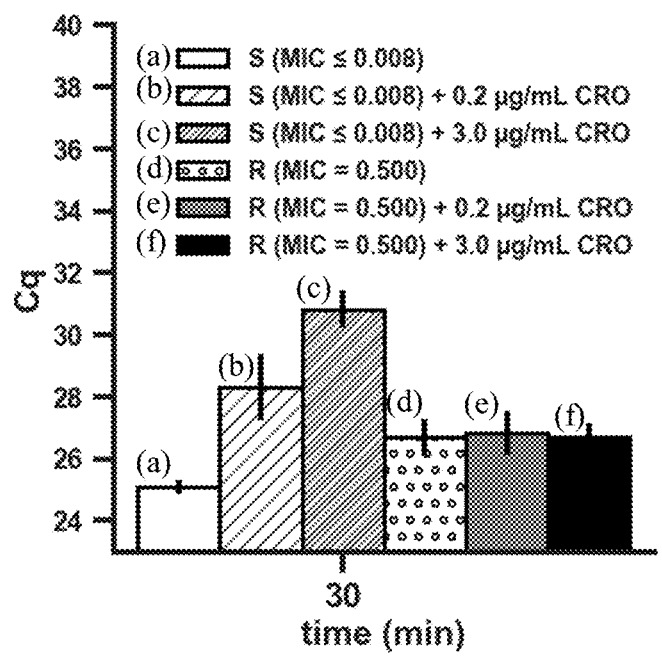
FIG. 4 shows a diagram illustrating the results of experiments, described in Example 2, directed to detect effects of antibiotics CRO concentration on DNA accessibility for ceftriaxone-susceptible Ng isolates (ng_17) and ceftriaxone-resistant Ng isolate (ng_30). Error bars represent 95% confidence intervals. The diagram of FIG. 4 shows one untreated measurement of each isolate and two treated measurements.

The related data are shown in FIG. 4 which illustrates the results for the ne ceftriaxone-susceptible Ng isolates (ng_17) (see FIG. 4, (a) (b) and (c) bars) and the one ceftriaxone-resistant Ng isolate (ng_30) (see FIG. 4, (d) (e) and (f) bars). Primers target the porA gene. Cq's are plotted with error bars of 95% confidence intervals based on the qPCR triplicate measurements.

As can be seen from the illustration of FIG. 4, upon incubation with 1% TritonX-100, NEB DNaseI, and ceftriaxone ABX in cell culture media (MH), the susceptible isolates showed a decrease in DNA concentration.

The exemplary results illustrated in FIG. 4, show that treating with a concentration of antibiotic even one that is higher than the breakpoint of ceftriaxone can enhance the effect seen at an exposure times without observing an increase in DNA accessibility for the resistant isolate. This figure shows that the method herein described allow a measurable effect from the susceptible-treated condition with a shorter treatment.

The exemplary results illustrated in FIG. 4, show that 30-minute co-incubation with antibiotics and an enhancer of 1% Triton X-100 show differences in DNA accessibility (as seen by the difference in Cq) between the antibiotic-susceptible but not antibiotic-resistant NG isolates. The increase in Cq corresponds to decreased quantity of detectable inaccessible nucleic acids. The differences are larger in the ceftriaxone-susceptible isolate when the antibiotic concentration was increased without having a complimentary effect in the antibiotic-resistant isolate. Accordingly, the difference in Cqs as measured with qPCR is sufficient to differentiate between the antibiotic-susceptible and antibiotic-resistant isolates of NG.

The exemplary results illustrated in FIG. 4, support the conclusion that with a given antibiotic-exposure time, increasing the antibiotic concentrations can yield a larger difference in nucleic acid accessibility (shown with the difference of Cqs between the treated and untreated samples) as will be understood by a skilled person.

Example 3: AST Performed by Detecting Inaccessible DNA with 2 Incubation Steps (Media; Dilute into Enhancing Buffer; Followed by Cell Lysis and NA Extraction) with DNA Quantified by qPCR Antibiotic susceptibility test was performed with methods herein described comprising 2 sequential incubation steps, and in particular
- a primary incubation in which a sample is contacted with media, antibiotic (or water in untreated sample), and a nuclease (such as DNaseI), and optionally an enhancer (such as 1% Triton X-100); and
- a secondary incubation in which a cell suspension from primary incubation is contacted with enhancers such as 50 mM TRIS buffer at pH 8.5 and/or 1% Triton X-100, possibly using dilution of the cell suspension from the antibiotic exposure by 90-95% (such as 50 µL into 450 µL, 25 µL into 475 µL) removing most antibiotic, culture media, and other components from the primary incubation for the enhancer condition.

In particular this example shows a detection of a difference in amounts of DNA in a treated incubation for an antibiotic-susceptible (ng_17, ng_3, penicillin-susceptible) clinical isolate with respect to a corresponding control, but not for a antibiotic-resistant (ng_44, penicillin resistant) clinical isolate.

In particular, the detection was performed in outcome of the following procedure.

1. Provide incubation media containing enhancer, with and without antibiotic for each isolate Several milliliters of media were prewarmed in a 37° C., 5% $CO_2$ incubator (media is HFB, see "HFB media preparation" in general methods) for ≥15 minutes prior to use. Two milliliter aliquots were used for each isolate and addition media is needed for OD600 measurements and dilutions (see step 4 of this example)

For each isolate, incubation tubes were prepared in 2 mL purple cap tubes (VWR Cat #89004-298), following the chart below, titled Primary incubation 1 or 2. For each of the desired incubation conditions, an untreated and treated tube were used (all comparisons are made from identical handling conditions; e.g. the same primary and secondary incubation conditions and dilutions). Add Triton X (enhancer), DNaseI (Cat: M0303L) (degrader) as instructed by the tables below. Antibiotic was added when bacteria cells were incubating, so that the time from thawing the antibiotic stock was minimized before exposure (see step 3 of this example).

| Primary incubation (option 1) Antibiotic Exposure per 500 µL. (2 mL purple cap tubes setup) | |
|---|---|
| Component | Volume |
| Ng Suspension (OD600 = 0.5 in HFB, media) | 465 µL |
| NEB DNaseI (2000 U/mL) (degrader) | 25 µL (100 U/mL) |
| Penicillin (50X), see ABX dilutions in step 3 (treated) or replace with nuclease-free (NF) Water in controls (untreated) | 10 µL (1X) |

| Primary incubation (option 2) Antibiotic Exposure per 500 µL (±) Triton X-100. Volume from Triton X-100 replaced with NF water in this control (2 mL purple cap tubes setup) | |
|---|---|
| Component | Volume |
| Ng Suspension (OD600 = 0.5 in HFB, media) | 50 µL |
| 10X detergent (10% TritonX) (enhancer) or replace with nuclease-free (NF) water in controls (control, in place of enhancer) | 50 µL (1X, 1%) |
| NEB DNaseI (2000 U/mL) (degrader) | 25 µL (100 U/mL) |
| Ceftriaxone (50X), see ABX dilutions above (treated) or replace with nuclease-free (NF) Water in controls (untreated) | 10 µL (1X) |

For each isolate, incubation tubes were prepared in 2 mL purple cap tubes (VWR Cat #89004-298), following the chart below, titled Secondary incubation 1, 2, or 3. These conditions were set up for a sequential incubation containing enhancers.

| Secondary incubation (option 1) Enhancer per 500 µL TRIS pH 8.5. (2 mL purple cap tubes setup) | |
|---|---|
| Component | Volume |
| Ng Suspension from antibiotic exposure | 25 µL |
| 10X TRIS pH 8.5 (500 mM) (enhancer) | 50 µL (1X, 50 mM) |
| NEB DNaseI (2000 U/mL) (degrader) | 25 µL (100 U/mL) |
| $CaCl_2$ (50 mM) | 5 µL (1X, 0.5 mM) |
| $NaHCO_3$ (100 mM) | 5 µL (1 mM) |
| NF water | 390 µL |

| Secondary incubation (option 2) Enhancer per 500 µL TRIS pH 8.5. (2 mL purple cap tubes setup) | |
|---|---|
| Component | Volume |
| Ng Suspension from antibiotic exposure | 50 µL |
| 10X TRIS pH 8.5 (500 mM) (enhancer) | 50 µL (1X, 50 mM) |
| NEB DNaseI (2000 U/mL) (degrader) | 25 µL (100 U/mL) |
| $CaCl_2$ (50 mM) | 5 µL (1X, 0.5 mM) |
| $NaHCO_3$ (100 mM) | 5 µL (1 mM) |
| NF water | 365 µL |

| Secondary incubation (option 3) Enhancer per 500 µL TRIS pH 8.5 + 1% Triton X-100. (2 mL purple cap tubes setup) | |
|---|---|
| Component | Volume |
| Ng Suspension from antibiotic exposure | 50 µL |
| 10X TRIS pH 8.5 (500 mM) (enhancer) | 50 µL (1X, 50 mM) |
| 10X detergent (10% TritonX) (enhancer) or replace with nuclease-free (NF) water in controls (control, in place of enhancer) | 50 µL (1X, 1%) |
| NEB DNaseI (2000 U/mL) (degrader) | 25 µL (100 U/mL) |
| $CaCl_2$ (50 mM) | 5 µL (1X, 0.5 mM) |

-continued

Secondary incubation (option 3) Enhancer per 500 µL TRIS pH 8.5 + 1% Triton X-100. (2 mL purple cap tubes setup)

| Component | Volume |
|---|---|
| NaHCO$_3$ (100 mM) | 5 µL (1 mM) |
| NF water | 315 µL |

This step 1 can be performed before or after steps 2-4 of this example as will be understood by a skilled person upon reading of the present disclosure.

2. Providing a sample containing bacteria

The bacteria were prepared according to the "NG Stock and Resuspension" description in the General Methods section with the following changes: media used was HFB shaken at 1000 rpm for 54-65 min in the incubator, p0 cells were used, 30-80 minutes of resuspension in HFB at 37° C., 5% CO2, 1000 rpm, and the cell clumps were not manually broken apart with a pipette.

While cell pellet was suspending, the antibiotic exposure condition (everything except Ng suspension and ABX) was prepared.

Right before measuring OD, step 3, the primary incubation and secondary incubation tubes prepared in step 1 were set on the shaking heat block (set to 38° C. and 1000 rpm shaking) to warm the contents to 37° C.

3. Add the antibiotic to the exposure tube

Antibiotic dilutions were prepared from pre-made and frozen antibiotic stocks: Diluted 1 mg/mL ceftriaxone stock, according to "Preparing Antibiotic Stocks" description in the general methods, see ceftriaxone. The stocks used in this example had short-term storage of the 0.05 mg/mL stocks in −20° C. storage instead of −80° C. storage. No further dilutions needed to be made, since this concentration is at 50× working concentration.

The antibiotic incubation/exposure was performed on a heat-shake block fit to 2 mL purple cap tubes (VWR Cat #89004-298). The particular shake-block was measured with a thermocouple to ensure the temperature inside the tubes with 500 µL of media is 37° C. (settings 38° C. and 1000 rpm shaking).

The primary incubation (antibiotic exposure) tubes were brought from the shaking heat block (set to 38° C. and 1000 rpm shaking) to the BSC. Add 10 µL of the appropriate antibiotic dilution to the exposure tubes. For the exposure tubes which will go "untreated" add 10 µL of NF water.

The secondary incubation (enhancer) tubes were set on the shaking heat block (set to 38° C. and 1000 rpm shaking).

4. Optionally, pre-process the sample containing the bacteria to modify the bacterial concentration in the sample In a variation of this set of experiment the OD600 of each of the suspensions prepared in step 2 can be adjusted to OD600=0.5. Measure the OD600 (dilute 1/10 in pre-warmed media) and dilute accordingly in pre-warmed media.

5. Split the sample into two or more parts

50 µL or 465 µL of the Ng suspension (such as the OD 0.5 suspensions prepared in step 4 of this example) were withdrawn. The incubation charts in step 1 was followed to set up the volumes to be added to the corresponding tubes.

6. Combine the sample with incubation media

50 µL or 465 µL of the Ng suspension were added into "treated" media, add 50 µL or 465 µL of the Ng suspension into untreated media. Note this addition can be performed sequentially or in parallel (using multichannel pipet).

7. Incubate the treated and untreated samples at a controlled temperature for a short amount of time.

The antibiotic exposure tubes prepared in step 1 were returned on the shaking heat block (set to 38° C. and 1000 rpm shaking). T the liquid temperature of this particular heat/shake block was measured with a thermocouple to ensure the temperature inside the tubes with 500 µL of media is 37° C. (settings: 38° C. and 1000 rpm shaking).

8. Dilution of treated and untreated samples (at 30 minutes) into a secondary incubation for a short amount of time The samples were mixed before transferring 25 µL or 50 µL of the sample to the prepared secondary incubation (enhancer) tubes. The charts in step 1 were followed to add the appropriate volume of cells to each tube. Mix the tubes and proceed to step 9 immediately 9. Extraction (at 30 minutes) of treated and untreated samples to purify DNA Extraction was performed following the "DEB Extraction" description in the general methods using Eppendorf tubes. Mix the samples that have just been diluted into the secondary incubation tubes in step 8 before transferring 10 µL of the contents to 90 µL of the extraction buffer.

The secondary incubation (enhancer) tubes were returbed to the shaking heat block to continue incubation at 37° C.

10. Extraction (at 50 minutes) of treated and untreated samples to purify DNA

Extraction was performed following the "DEB Extraction" description in the general methods using Eppendorf tubes. The samples from the secondary incubation tubes in step 9 of this example were mixed before transferring 10 µL of the contents to 90 µL of the extraction buffer 11. Optionally, continue incubation of the treated and untreated samples from the primary incubation for a control of the antibiotic efficacy over >30 minute exposures In a variation of the procedure exemplified herein after desired incubation time >60 minutes, Silt droplets can be plated on a pre-warmed BBL Chocolate Agar plate as a positive control of the antibiotic.

12. Measurement of DNA by qPCR

Detection of DNA was performed following the "qPCR" description in the general methods. Quantify all DEB-extracted DNA using the Primer mix=(10 µM forward and reverse) targeting *N. gonorrhoeae* porA gene. Samples were run in qPCR triplicates (10 µL reactions) at an annealing temperature 62° C. The primers did target the porA gene.

Figure 5:
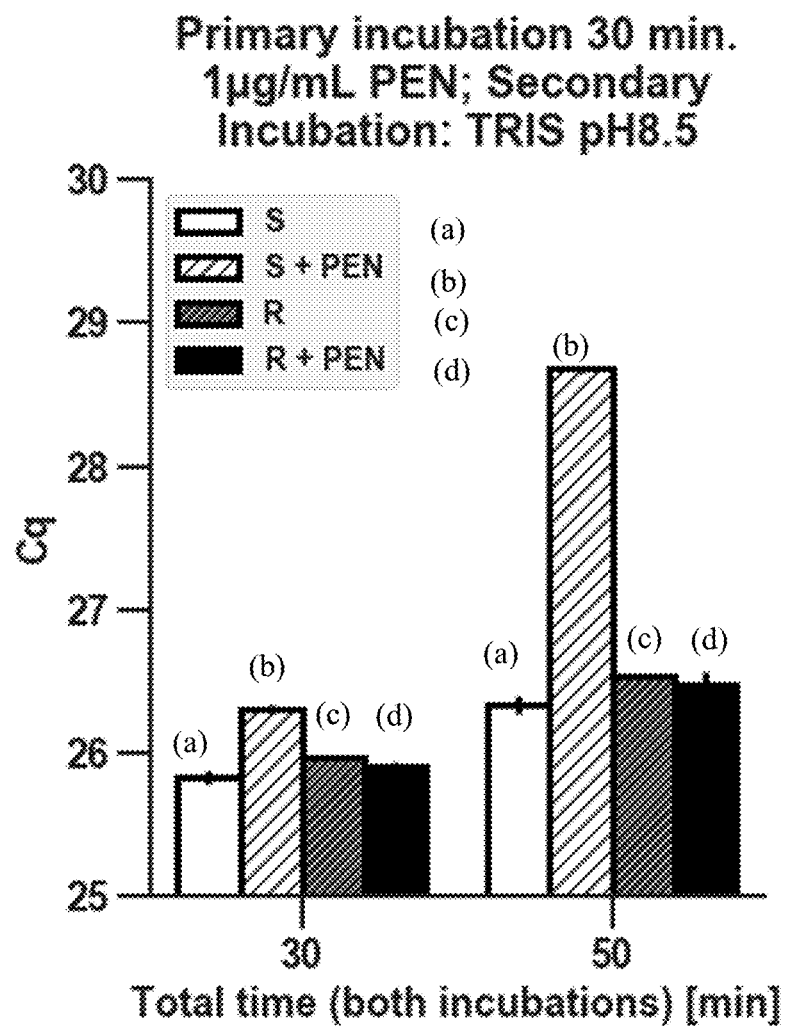
FIG. 5 shows a diagram illustrating the results of experiments, described in Example 3, directed to detect time effect in a two-step incubation including a 30 or 50-minute incubation in a buffer for autolysis on DNA accessibility represented as Cq for S, a penicillin-susceptible Ng isolate (ng_17) and R, a penicillin-resistant Ng isolate (ng_44). Error bars represent 95% confidence intervals.

13. Data analysis is performed on the raw Cq measurements obtained from the qPCR instrument The results illustrated in FIG. 5 show differences in responses which can be seen by comparing the time 30 and time 50 measurements from the second incubation step in TRIS buffer pH 8.5. All samples are expected to have an increased rate of lysis (represented here as the reciprocal of the fold change, to visualize positive values). Cq's are plotted with error bars of 95% confidence intervals based on the qPCR triplicate measurements. The increase in Cq corresponds to decreased quantity of detectable inaccessible nucleic acids.

Figure 6:
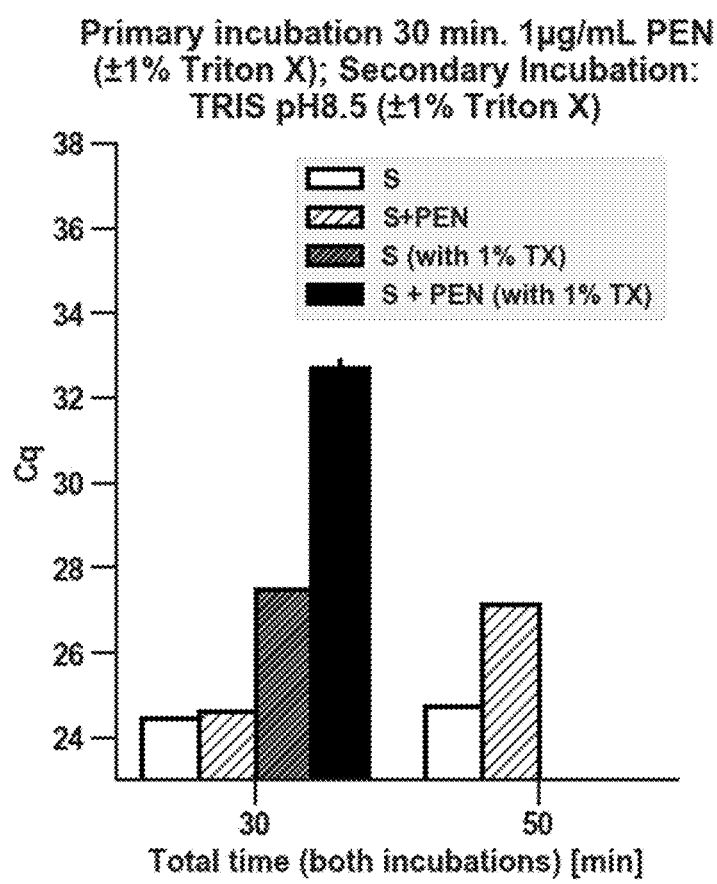
FIG. 6 shows a diagram illustrating the results of experiments, described in Example 3, directed to detect effect of an additional lysis agent Triton X in a two-step incubation including a 30 or 50-minute incubation in a TRIS buffer pH 8.5 on DNA accessibility represented as Cq for S, a penicillin-susceptible Ng isolate (ng_17), and R, a penicillin-resistant Ng isolate (ng_44).

This observation is confirmed by data obtained by the exemplified method with the inclusion of an additional enhancer (1% Triton X-100 in this example) during both the primary incubation and secondary incubation are shown in FIG. 6. FIG. 6 shows how enhancers might be combined to get a larger change in detectable nucleic acids, since an increase in Cq in the antibiotic-treated sample corresponds to decreased quantity of detectable inaccessible nucleic acids.

The illustration of FIG. 5 and FIG. 6 clearly illustrate the increase in partial lysis, measured by DNA accessibility, after 50 minutes of incubation (30 min ABX exposure in cell culture media followed by 20 minutes of an enhancing treatment in TRIS buffer), nucleic acid extraction follows this exposure, and quantification is done with qPCR. Quantification could be done with several different methods. One could draw a threshold line for future comparisons of susceptible and resistant responses.

These data are obtained from steps 1-13 of this example with primary incubation #2 and secondary incubations #2 and #3. The interpretation of susceptibility could be determined from the magnitude of the 1/FC plots by the treated samples only. (In the above example the fold change of the susceptible-treated samples is >5 and the fold change of the resistant, and each of the controls is approximately 1.5)

The results shown in FIG. 5 and FIG. 6 supports the conclusion that the two-step incubations with enhancers in the secondary incubation only increase DNA accessibility in the susceptible-treated isolate after short beta-lactam exposures. Accordingly, the results of these examples support the conclusion that two-step incubation with enhancers in both the primary and secondary incubations increase DNA accessibility in the susceptible-treated samples.

Example 4: AST Performed by Detecting Inaccessible DNA with 1 Step Incubation with an Enhancer and β-Lactams Followed by Cell Lysis and DNA Extraction with DNA Quantified with Digital PCR Antibiotic susceptibility test was performed with methods herein described comprising one-step incubation with an enhancer with three different beta-lactam antibiotics.

In particular, this example shows a detection of a difference in amounts of DNA in a treated incubation for an antibiotic-susceptible clinical isolate with respect to a corresponding control, but not for an antibiotic-resistant clinical isolate.

In particular, the isolates ng_3, ng_15, ng_17, ng_18, and ng_30 were used (see the "Clinical Isolate MICs" table for $N.$ $gonorrhoeae$ for MICs in the General Methods). Penicillin was tested on isolates ng_15 (PEN-S) and ng_18 (PEN-R) and used the media HFB. Ceftriaxone was tested on isolates ng_17 (CRO-S) and ng_30 (CRO-R) and used the media MHB. Cefixime was tested on isolates ng_3 (CFM-S) and ng_30 (CFM-R) and used the media MHB.

The DNA detection was performed in outcome of the following procedure.

1. provide incubation media containing enhancer, accessibility, with and without an antibiotic for each isolate Several milliliters of media were pre-warmed in a 37° C., 5% $CO_2$ incubator (media is MHB, see media preparation in general methods; or HFB) for ≥30 minutes prior to use. The bacteria were prepared according to the "NG Stock and Resuspension" description in the General Methods section with the following changes: In this example, the penicillin exposures used HFB and the ceftriaxone and cefixime exposures used MHB.

For each isolate, two incubation tubes were prepared in 2 mL purple cap tubes (VWR Cat #89004-298), following the chart below, titled "Antibiotic Exposure per 500 µL". Add Triton X (enhancer), DNaseI (degrader), $NaHCO_3$ (conditioner, if using MHB as the media). Antibiotic was added when bacteria cells were incubating, so that the time from thawing the antibiotic stock is minimized before exposure (see step 4 of this example).

Table of components for media preparation and antibiotic Exposure per 500 µL (2 mL purple cap tubes setup)

| Component | Volume |
| --- | --- |
| Media (Prewarmed HFB or MHB) (media) | 360 µL |
| Triton X-100 detergent (10X, 10%) (enhancer) | 50 µL (1X, 1%) |
| NEB DNaseI (2000 U/mL) (degrader) | 25 µL (100 U.mL) |
| Antibiotic (50X), see ABX dilutions in step 4 (treated) (OR replace with NF Water in controls, (untreated) | 10 µL (1X) |
| $NaHCO_3$ (100 mM) | 5 µL (1 mM) |
| Ng Suspension (OD = 0.5) | 50 µL (OD = 0.05) |

2. Providing a sample containing bacteria

Cell pellets were resuspended and in particular cell pellet were scraped with inoculating loop, twirled in 2 mL media and incubated on shaker (1000 rpm) in 37° C., 5% $CO_2$ incubator (≥30 minutes).

While cell pellet was suspending, the antibiotic exposure condition (everything except Ng suspension and ABX) was prepared.

Right before measuring OD, these tubes were set on the shaking heat block (set to 38° C. and 1000 rpm shaking)

3. Optionally, pre-process the sample containing bacteria

In a variation of the procedure exemplified in this example, the OD600 (dilute 1/10 in media) was measured, OD's below were corrected for the 1/10 dilution for the measurement. ng_30 OD=1.1 (before dilution). Adjust OD of suspension to OD=0.5 in prewarmed MHB+5 mM $NaHCO_3$ media 4. Add antibiotic to the exposure tubes Antibiotic dilutions were prepared from pre-made and frozen antibiotic stocks as follows: Diluted 1 mg/mL ceftriaxone stock, was prepared according to "Preparing Antibiotic Stocks" description in the general methods, see ceftriaxone. To Prepare 50× stocks of the antibiotic the following dilutions were performed: Dilutions from 1 mg/mL Penicillin stock (aliquot from ES −20° C. box 2 as prepared on 20170822_1) to (50× antibiotic) as indicated below for each antibiotic.

Penicillin: 4 µg/mL (1×)→200 µg/mL (50×)=0.2 mg/mL
  200 µL of 50× stock=40 µL 1 mg/mL stock+160 µL NF water in nuclease-free (NF) water Ceftriaxone: 4 µg/mL (1×)→200 µg/mL (50×)=0.2 mg/mL
  200 µL of 50× stock=40 µL 1 mg/mL stock+160 µL NF water in nuclease-free (NF) water Cefixime: 1×3 µg/mL→50× Stock (1×3 µg/mL cro→150 µg/mL=0.15 mg/mL cro)
  500 µL of 0.150 mg/mL=75 µL (1 mg/mL stock)+425 µL NF water Antibiotic was added to the "treated" sample. Nuclease free water was added to the untreated sample.

5. Split the sample into two or more parts 50 uL of the Ng suspension were withdrawn into a pipette 6. Combine sample with incubation media 50 uL of the Ng suspension were added into "treated" media, and 50 uL of the Ng suspension were added into the untreated media. This addition can be performed sequentially or in parallel (using multichannel pipet) as will be understood by a skilled person 7. Incubate the treated and untreated samples at a controlled temperature for a short amount of time The treated and untreated samples were incubated at 37 C for 15 minutes 8. Extraction (at 15 minutes) of treated and untreated samples to purify RNA and DNA Extraction was performed following the procedure outlined herein "DEB Extraction" in the general methods section, using 10 μL of sample and 90 μL DEB in Eppendorf tubes.

9. Measurement of DNA qPCR

Detection of DNA was performed by preparing qPCR mix. (see the "qPCR" protocol in the General Methods). Primers were for the Ng porA gene in each amplification. Samples were quantified to obtain a Cq for concentration estimation before the samples were run in digital PCR (see step 10)

10. Measurements of DNA by ddPCR

Detection of DNA was performed ddPCR following the "ddPCR" protocol in General Methods. Use the Cq obtained from qPCR in step 9 to determine the dilution before quantification with droplet digital PCR (ddPCR). Primers were for the Ng 16S gene 11. Digital PCR analysis The ddPCR concentrations reported are corrected for dilutions prior to any CT ratio calculation. The CT ratio is calculated by dividing the DNA concentration in copies/μL of the untreated (control) sample by the treated sample. The ddPCR raw concentration values in copies of target molecule/μL are not shown, but the ratio of these concentrations is shown as the CT ratio in FIG. 7A, FIG. 7B, and FIG. 7C. A CT ratio>1 can occur when the denominator (treated sample concentration) is less than the numerator (untreated/control concentration). A smaller detected concentration in the antibiotic-treated sample corresponds to decreased quantity of detectable inaccessible nucleic acids, as a result of the antibiotic exposure, enhancing treatment, and degradation of nucleic acids with a molecule such as DNaseI.

Figure 7A:
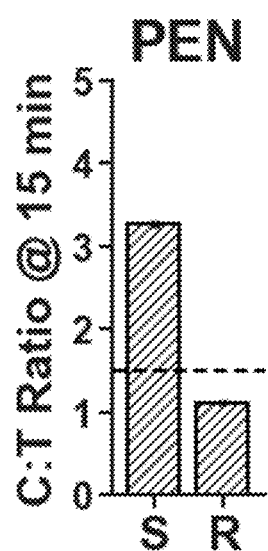
FIGS. 7A-C show diagrams illustrating the results of experiments, described in Example 4, directed to detect effect of β-lactams PEN (penicillin, FIGS. 7A), CFM (cefixime, FIGS. 7B), and CRO (ceftriaxone, FIG. 7C) on DNA accessibility represented as CT ratio and quantified with digital PCR. Error bars represent 95% confidence intervals
Figure 7B:
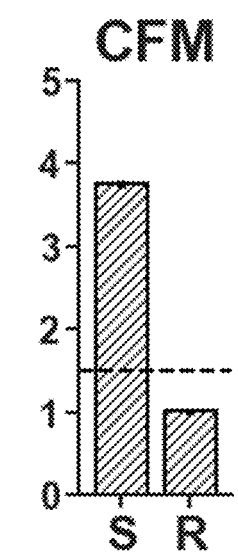
Figure 7C:
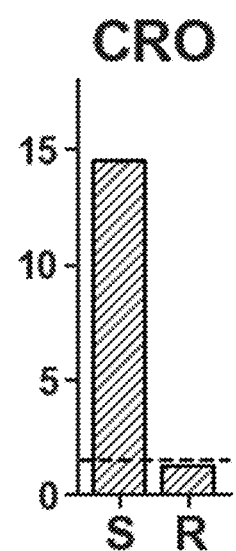

The results illustrated in FIGS. 7A-7C show the generality of DNA accessibility method with one-step incubation with an enhancer, since differentiable CT ratios between susceptible and resistant isolates are obtained through this exposure Digital PCR use for NA amplification and to obtain DNA concentrations here is performed to compare the untreated and treated samples (shown above in the results section as a CT ratio, dividing the concentrations of nucleic acid in one sample by the other). This metric is enough to differentiate between the isolates screened.

The exemplary results of FIGS. 7A-7C, support the conclusion that Antibiotic concentrations greater than the clinical MIC breakpoint will be used for exposures. This is the case for each resistant isolate above; since the CT ratios for the resistant isolates in each antibiotic screen are not significantly greater than 1.0, this concentration does not seem to add background signal in the resistant isolates at these antibiotic incubation timescales (15 minute exposure).

Example 5: AST Performed by Detecting Inaccessible RNA Quantified with ddPCR, LAMP Antibiotic susceptibility test was performed with methods herein described wherein detection of inaccessible RNA is performed in an AST comprising adding an RNA degrading enzyme to a sample before cell lysis and detection of RNA in the sample.

In particular this example shows a detection of a difference in amounts of DNA in a treated incubation for an antibiotic-susceptible clinical isolate with respect to a corresponding control, but not for a antibiotic-resistant clinical isolate. The isolates used in this example were ng_3 and ng_30 (see the "Clinical Isolate MICs" table for *N. gonorrhoeae* for MICs in the General Methods).

In particular, in this example detection of RNA was performed in outcome of the following procedure.

1. Provide incubation media containing enhancer, accessibility, with and without an antibiotic for each isolate Several milliliters of media were prewarmed in a 37° C., 5% $CO_2$ incubator (media is MHB, see media preparation in general methods) for ≥30 minutes prior to use.

For each isolate, two incubation tubes were prepared in 2 mL purple cap tubes (VWR Cat #89004-298), following the chart below, titled "Antibiotic Exposure per 500 μL". Add Triton X (enhancer), RNase cocktail (Catalog AM2286) (degrader), $NaHCO_3$ (conditioner). Antibiotic was added when bacteria cells are incubating, so that the time from thawing the antibiotic stock is minimized before exposure (see step 3 of this example).

Antibiotic dilutions were prepared from pre-made and frozen antibiotic stocks: Diluted 1 mg/mL ceftriaxone stock, was prepared according to "Preparing Antibiotic Stocks" description in the general methods, see ceftriaxone. To Prepare 50× stocks of the antibiotic follow the following dilutions in nuclease-free (NF) water Antibiotic was added to the "treated" sample Nuclease free water was added to the untreated sample.

| Table of components for media preparation and antibiotic Exposure per 500 μL. (2 mL purple cap tubes setup) | |
| --- | --- |
| Component | Volume |
| MH (Prewarmed) | 375 μL |
| Triton X-100 detergent (10X, 10%) (enhancer) | 50 μL (1X, 1%) |
| RNase Cocktail (50X) (degrader) | 1 μL (0.1X) |
| Antibiotic (50X), see ABX dilutions above (treated) (OR replace with NF Water in controls, (untreated) | 10 μL (1X) |
| $NaHCO_3$ (100 mM) | 5 μL (1 mM) |
| Ng Suspension (OD = 0.5) | 50 μL (OD = 0.05) |

2. Providing a sample containing bacteria

The bacteria were prepared according to the "NG Stock and Resuspension" description in the General Methods While cell pellet was suspending, the antibiotic exposure condition (everything except Ng suspension and ABX) was prepared.

Right before measuring OD, the tubes were set on the shaking heat block (set to 38° C. and 1000 rpm shaking).

3. Optionally, pre-process the sample containing bacteria

OD600 (dilute 1/10 in media) was measure and the, OD's below are corrected for the 1/10 dilution for the measurement. ng_30 OD=1.1 (before dilution). Adjust OD of suspension to OD=0.5 in prewarmed MHB+5 mM $NaHCO_3$ media 4. Split the sample into two or more parts 50 uL of the Ng suspension were withdrawn into a pipette 5. Combine sample with incubation media 50 uL of the Ng suspension were added into "treated" media, and 50 uL of the Ng suspension were added into untreated media. Note this addition can be performed sequentially or in parallel (using multichannel pipet) as will be understood by a skilled person 6. Incubate the treated and untreated samples at a controlled temperature for a short amount of time
Incubate at 37 C for 15 minutes
7. Extraction (at 15 minutes) of treated and untreated samples to purify RNA and DNA Extraction was performed following the procedure outlined herein for "Zymo Column Extraction (RNA)" in the General Methods. Eluted solution is referred to as "extraction"

8. Optionally splitting the extractions

In a variation of the experiments exemplified herein, the extractions can be split Splitting of the eluted nucleases into two parts. One part gets treated with DNaseI to remove the DNA (step 9). One part retains all extracted nucleic acids (RNA+DNA) without any further processing.

9. Optionally add degraders to a part of the extraction: DNase Treatment of (an aliquot) of extractions to remove DNA In a variation of the experiments exemplified herein, a DNase treatment (100 U/mL final concentration of NEB DNaseI) of an aliquot of the Zymo extracted nucleic acids can be performed to obtain a sample of RNA. In particular the DNAase treatment can be performed according to the following procedure.

10 min at 37° C. (actual incubation closer to 15 minutes—static incubation in 1.5 mL Eppendorf tubes on benchtop heating block set to 37° C.)
  a. dilute DNase to 1000 U/mL (10×)
    5 µL DNaseI+5 µL NF water
    add 1 µL of 1000 U/mL DNaseI to each prepared tube 10. Measurement of RNA and DNA by qRT-PCR Detection of RNA and DNA was performed by preparing a RT-qPCR mix and qPCR mix for the (−RT) controls. (see the "qRT-PCR" protocol in the General Methods). Primers were for the Ng 16S gene in each amplification. Samples were quantified for RNA (+RT), DNaseI-treated aliquots 11. Measurements of RNA and DNA by ddRT-PCR Detection of RNA was performed according to the "ddRT-PCR" protocol in General Methods, wherein primers were for the Ng 16S gene in each amplification, samples were quantified for total nucleic acid (+RT) and samples quantified for background DNA that was not digested (−RT)

12. Digital PCR analysis

Digital PCR analysis was performed with the ddRT-PCR concentrations reported corrected for dilutions prior to amplification. CT ratios were computed by dividing the concentrations measured with digital PCR.

13. qLAMP analysis

Detection by qLAMP analysis was performed according to the "qLAMP" protocol in General methods wherein the IsoAmp Buffer I was used with no adjustments from the commercial mix were done, this contains Tween, the transcription enzyme was Bst 2.0, the LAMP primers were for the Ng 16S gene and the mixt was 20× ng_16s_1 primer mix=P228/229 (4 uM), P230/231 (32 uM), P327/328 (8 uM). The RT-LAMP was run at 55° C. for 10 minutes and 68° C. for 20 seconds.

Figure 8:
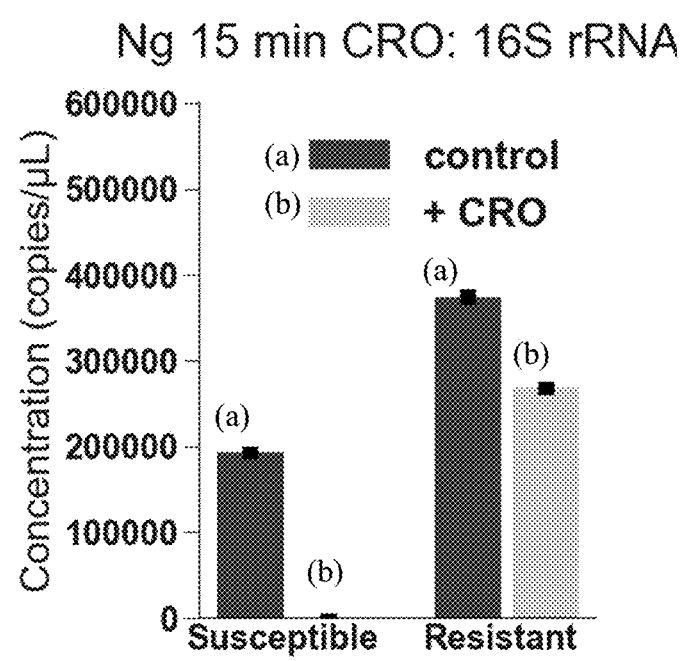
FIG. 8 shows a diagram illustrating the results of experiments, described in Example 5, directed to detect 16S rRNA concentration quantified with digital PCR, LAMP for antibiotic-susceptible and antibiotic-resistant Ng isolates in comparison to a control sample.

The results illustrated in FIG. 8, shows that accessible RNAs are degraded by the added RNases and RNases are inactivated during extraction with the Zymo Research Viral DNA/RNA kit. Due to the treatment with the lysis agent and antibiotics, the Susceptible-treated sample will have a lot of RNA degraded by the RNases, and shows a much lower concentration than the control. There is a small effect seen in the resistant-treated sample as well, but the effect is not as dramatic. Time to positive measurements are shown (10 minutes+TTP at 68° C.)

Figure 9:
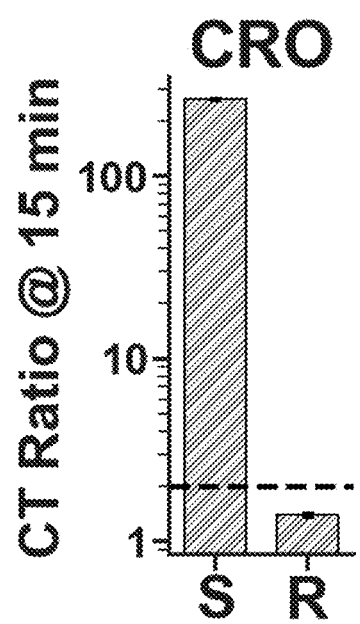
FIG. 9 shows a diagram illustrating the results of experiments, described in Example 5, directed to detect CT ratio for nucleic acid concentration, based on detection of 16S rRNA concentration quantified with digital PCR, LAMP for antibiotic-susceptible and antibiotic-resistant Ng isolates in comparison to a control sample as shown in FIG. 8.

Comparisons of the RNA concentrations can be shown with the CT ratio, as illustrated in FIG. 9 which shows the CT ratio of the RNA concentrations of the antibiotic-susceptible and antibiotic-resistant Ng isolates. Primers target NG 16S rRNA that has been reverse-transcribed. The ratio is calculated by dividing the concentrations obtained by digital PCR shown in the plot above.

Figure 10:
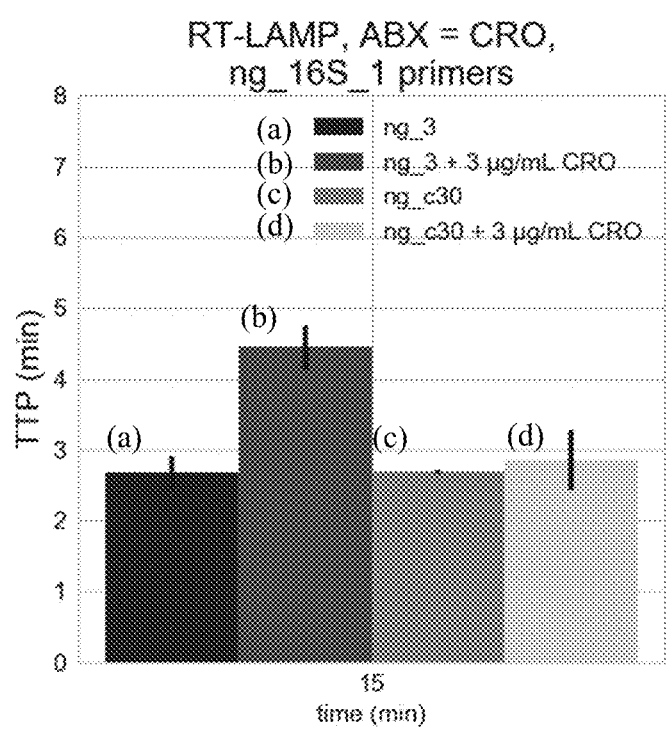
FIG. 10 shows a diagram illustrating the results of experiments, described in Example 5, directed to detect effects of antibiotic ceftriaxone (CRO) on RNA accessibility by quantification of the RNA through RT-LAMP with Ng 16S rRNA primers for ceftriaxone-susceptible Ng isolates (ng_3) and ceftriaxone-resistant Ng isolates (ng_30) in comparison to control samples.

The quantification of RNA through RT-LAMP with Ng 16S rRNA primers is illustrated in FIG. 10. In particular the illustration of FIG. 10, shows that RNA accessibility can show very large differences in nucleic acid concentrations that can be amplified quickly with LAMP. Error bars represent 95% confidence intervals from the qLAMP replicates. Time to positive measurements are shown (10 minutes+TTP at 68° C.), so a TTP of 3 minutes in the plot above, represents 13 minutes since the samples were mixed and added to the thermocylcer. The TTP difference between the treated and untreated samples can be used to differentiate susceptible and resistant isolates. An increase in the TTP of the antibiotic-treated sample corresponds to decreased quantity of detectable inaccessible nucleic acids The results of this example support the conclusion that RNA accessibility can be used for AST via adding an RNA degrading enzyme during the antibiotic incubation that was performed in the presence of an enhancing treatment that retains cell viability, such as 1% Triton X-100m to then detect the inaccessible RNA following cell lysis.

Digital RNA amplification can used for analysis and the CT ratio of computed from the RNA copies/µL can be used to differentiate between the susceptible and resistant isolates. In the CT ratio plotted in the results section, it suggests that this result can appear binary, the CT ratio is very large or it is around 1.0.

qLAMP amplification on extracted RNA can be used for analysis and the TTP differences could be used to differentiate between antibiotic susceptible and antibiotic resistant isolates. Amplification with bulk LAMP measurements allows for fast readouts.

It is noted that a skilled person will understand upon reading of the present disclosure step 1 can be performed before or after steps 2-4 of this example and that steps 1-7 (or 1-11) can be done on different days for each isolate as long as the comparisons of untreated and antibiotic-treated for one isolate are handled on the same day. It is also noted that step 13 of this example can be performed independently from steps 10-12 as will be understood by a skilled person upon reading of the present disclosure.

Example 6: AST Performed by Detecting Inaccessible RNA, with 1-Step Incubation (Media with Enhancer; Followed by Cell Lysis and NA Extraction) with RNA Quantified with Digital PCR Antibiotic susceptibility test was performed with methods herein described comprising one-step incubation of a sample with an enhancer with adding an RNA degrading enzyme The procedure used in this example is identical to the one of Example 5, up until the nucleic acid quantification which in this example is performed according to the following procedures.

Measurement of RNA and DNA by qRT-PCR

Measurement was performed by RT-qPCR mix and qPCR mix for the (−RT) controls. (see the "qRT-PCR" protocol in the General Methods). The primers were for the Ng 16S gene in each amplification. Samples quantified for total nucleic acid (+RT). The samples were quantified for RNA (+RT), DNaseI-treated aliquots. The samples quantified for DNA (−RT)

Measurements of RNA and DNA by ddRT-PCR

Measurement of RNA and DNA was performed following the "ddRT-PCR" protocol in General Methods. Primers were for the Ng 16S gene in each amplification. Samples were quantified for total nucleic acid (+RT) Samples quantified for DNA (−RT)

Digital PCR Analysis

Detection with digital PCR was performed with the ddPCR and ddRT-PCR concentrations reported are corrected for dilutions prior to amplification. For the RNA/DNA ratio the RNA concentrations were obtained by subtracting the concentration of DNA (extractions, without DNaseI treatment, quantified in ddPCR) from the total nucleic acid (extractions, without DNaseI treatment, quantified in ddRT-PCR in the presence of a reverse-transcriptase enzyme to amplify both DNA and RNA).

Figure 11A:
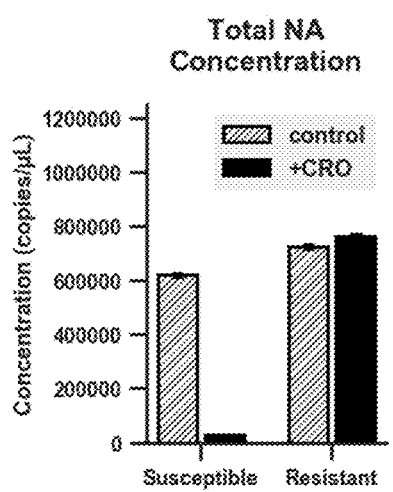
FIGS. 11A-11C show diagrams illustrating detection of nucleic acid concentrations following an AST performed according to exemplary methods of the disclosure.
Figure 11B:
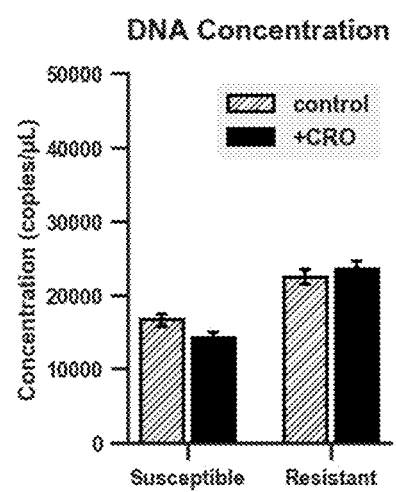
Figure 11C:
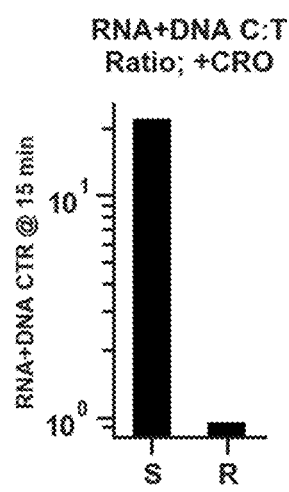

The results illustrated in FIGS. 11A to 11C show the total NA concentration, (NA=DNA+RNA) measured from the extraction (FIG. 11A) the total DNA concentration, middle (FIG. 11B). as well the C:T ratio computed from the total nucleic acid measurement (ddRT-PCR of extractions in the presence of a reverse-transcription enzyme) (FIG. 11C). The concentrations are quantified in digital PCR, see methods steps 11-12. The RNA concentration can be found by subtracting the DNA concentration from the total NA concentration. In the illustration of FIGS. 11A to 11C the RNA and DNA concentrations are used for the comparison. The DNA concentration is about the same for all four conditions since there is no extracellular DNase added to the tube, the DNA recovered is from both lysed and intact cells. However, the addition of RNase degrades any accessible RNAs.

Figures 12A, 12B:
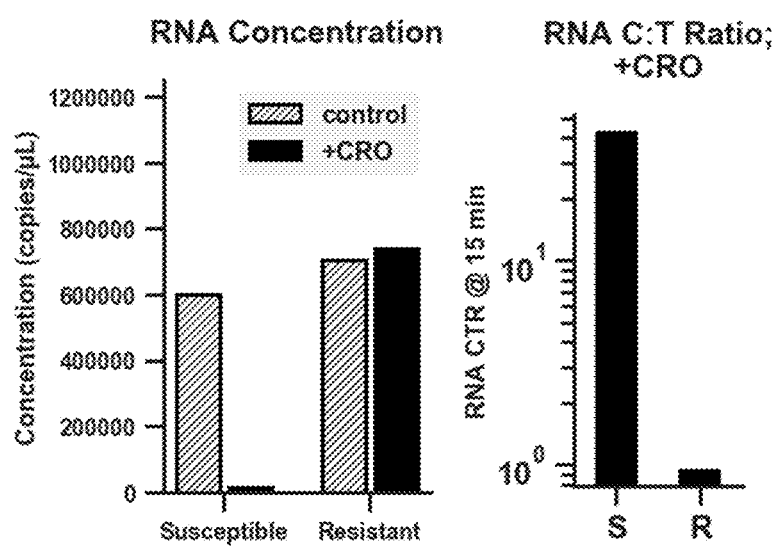
FIGS. 12A-12B show diagrams illustrating detection of RNA concentration and calculations of the related CT ratio. In particular

The RNA concentrations computed from the subtraction of the DNA from the total NA (as described above) are plotted in FIG. 12A. These concentrations can also be used to calculate a CT ratio (FIG. 12B) to differentiate between the susceptible and resistant isolates, giving a very similar readout to the CT ratio computed from the total RNA measurement and conclusions made as with previous DNA accessibility CT ratios. An RNA CT ratio was used since the degrader in the experimental setup includes RNases.

Figure 13:
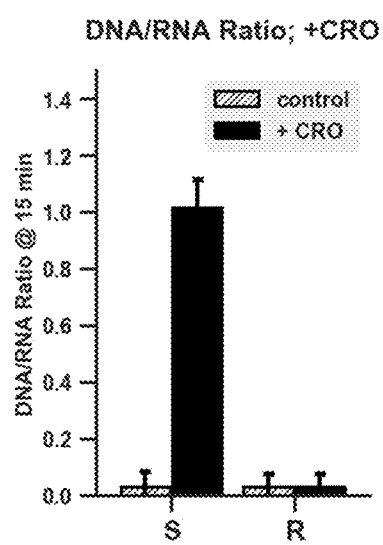
FIG. 13 shows a diagram illustrating the results of experiments described in Example 6, directed to detect the ratio of the measured DNA concentrations divided by the computed RNA concentration (total NA concentration minus DNA concentration) for ceftriaxone-susceptible Ng isolates (ng_3) and ceftriaxone-resistant Ng isolates (ng_30) in comparison to control samples.

The plot of FIG. 13 shows the ratio of the measured DNA concentrations divided by the computed RNA concentration (total NA concentration minus DNA concentration). The results illustrated in FIG. 13 shows that with one nucleic extraction a ratio can be computed to visualize the change in RNA concentration with respect to the unchanging DNA concentration. In a control case, it is expected for the RNA concentration to be much higher than the DNA concentration. In the case of the susceptible-treated, the RNA concentration is dropping due to the change in RNA accessibility and the presence of the RNases.

In general, the results of the experiments of this example support the conclusion that RNA accessibility can be used for AST via adding an RNA degrading enzyme during a 15-minute antibiotic incubation that can be performed in the presence of an enhancer, such as 1% Triton X-100. Total nucleic acid, total RNA+DNA that is extracted with the Zymo Research Viral DNA/RNA column can be used to generate a CT ratio to correctly characterize CRO susceptibility after 15 minutes of CRO exposure, shown in FIG. 11C.

The results of the experiments of this example support the conclusion that calculating RNA/DNA normalization may be used for AST without requiring splitting of the sample containing bacteria, and without requiring a control incubation. This is confirmed by plot titled "DNA/RNA Ratio+ CRO) (bottom). The control DNA/RNA ratios are plotted but are not needed to make the susceptibility call. Only the (+CRO) bars are needed, shown in FIG. 13.

The results of the experiments of this example further support the conclusions that digital NA amplification can be used for this analysis.

Example 7: AST Performed by Detecting Inaccessible DNA with gPCR and Static Incubation Antibiotic susceptibility test was performed with methods herein described relying on b-lactam-induced cellular lysis, or cell-wall damage, to generate differences in DNA accessibility between the unexposed and exposed tubes. No enhancing treatment is performed in this example. In this example DNaseI is used to degrade the DNA made accessible by beta-lactam induced damage over incubation times larger than what is tested in examples 1-6 (incubation times>30 minutes)

Figure 14:
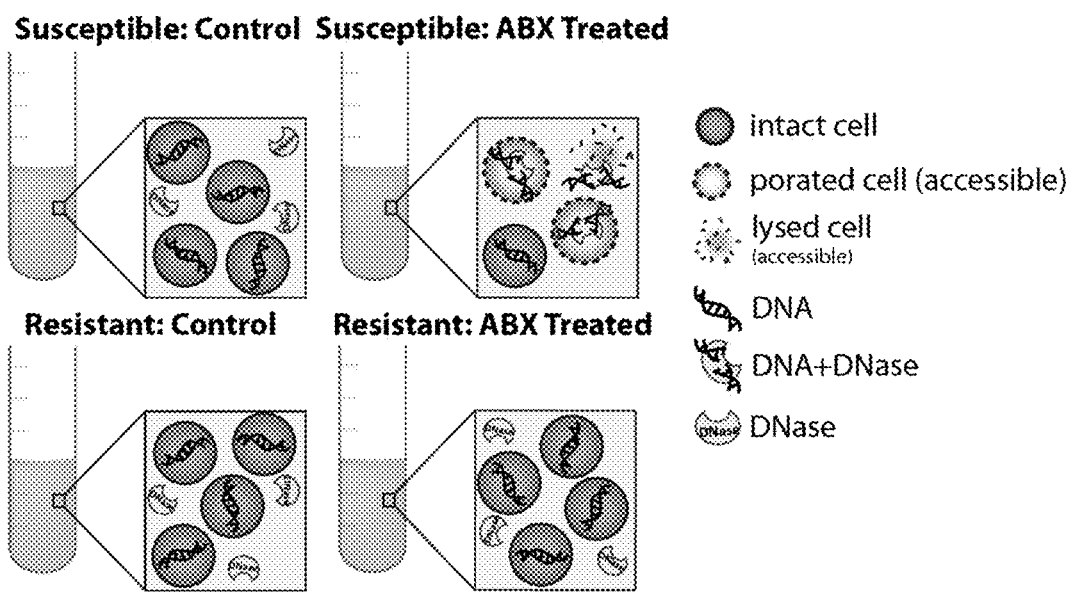
FIG. 14 shows a schematic illustration of an exemplary AST according to the disclosure in which a penicillin-susceptible isolate is incubated with penicillin for 15 min-6 hours.

The layout of this experiment is illustrated in FIG. 14 according to which a penicillin-susceptible isolate is incubated with penicillin for 15 min-6 hours. At each time point, DNaseI will be added to degrade the accessible DNA, then the DNaseI will be inactivated simultaneously with the lysis of the remaining cells. The quantified nucleic acids represent those from the cells with inaccessible DNA throughout the antibiotic exposure and incubation with DNaseI.

In particular, the detection was performed in outcome of the following procedure.

1. provide incubation media containing enhancer, accessibility, with and without an antibiotic for each isolate Several milliliters of media were prewarmed in a 37° C., 5% $CO_2$ incubator (media is MHB, see media preparation in general methods) for ≥45 minutes prior to use.

For each isolate, two incubation tubes were prepared in 12 mL BD Falcon culture tubes, following the chart below, titled "Antibiotic Exposure per 2 mL". Add $NaHCO_3$ (conditioner). Antibiotic was added when bacteria cells were incubating, so that the time from thawing the antibiotic stock was minimized before exposure (see step 4 of this example).

Primary Incubation: Antibiotic Exposure per 2 mL. (12 mL BD Falcon culture tubes)

| Component | Volume |
| --- | --- |
| MHB (Prewarmed) | 1,770 µL |
| Antibiotic (50X), see ABX dilutions above (treated) (OR replace with NF Water in controls, untreated) | 40 µL (1X) |
| $NaHCO_3$ (100 mM) | 90 µL (4.5 mM) |
| Ng Suspension (OD = 1) | 100 µL(OD = 0.05, 0.5 mM $NaHCO_3$) |

Secondary Incubation: DNAaseI Degradation Exposure per 50 µL. (200 µL capacity PCR tubes)

| Component | Volume |
| --- | --- |
| MHB (Prewarmed) | 22.5 µL |
| 10× NEB DNaseI Reaction Buffer | 5 µL (1X) |
| NEB DNaseI (2000 U/mL) | 2.5 µL (100 U/mL) |
| Ng sample from primary incubation | 20 µL |

2. Providing a sample containing bacteria

The isolate used was ng_15, a penicillin-susceptible isolate with an MIC of 0.015 μg/mL penicillin. (see the "Clinical Isolate MICs" table for *N. gonorrhoeae* for MICs in the General Methods).

The bacteria were prepared according to the "NG Stock and Resuspension" description in the General Methods section. While cell pellet was suspending, the antibiotic exposure condition (everything except Ng suspension and ABX) was prepared. Right before measuring OD, the tubes were set on the shaking block in the 37° C., 5% $CO_2$ incubator.

3. Optionally, pre-process the sample containing bacteria

In a variation of the procedure exemplified herein, the OD600 (dilute 1/10 in media) was measured and the OD of suspension to OD=0.5 in pre-warmed MHB+5 mM $NaHCO_3$ media was adjusted.

4. Add the antibiotic

Antibiotic dilutions were prepared from pre-made and frozen antibiotic stocks as follows: diluted 1 mg/mL ceftriaxone stock, were prepared according to "Preparing Antibiotic Stocks" description in the general methods, see penicillin.

In particular, 1 mg/mL penicillin stock was diluted to make a 50× stock for the experimental exposure. The 1 mg/mL stock can be stored at −80° C. in single-use aliquots prepared from penicillin G sodium salt. In particular 500 μL of 50× (1×1 μg/mL PEN→50 μg/mL=0.050 mg/mL PEN) penicillin were prepared with 25 μL (1.0 mg/mL stock)+475 μL nuclease-free water.

The antibiotic was added to the corresponding exposure tubes setup in step 1 of the present example.

5. Split the sample into two or more parts 100 uL of the Ng suspension were withdrawn into a pipette (following the chart for the primary exposure in step 1 of the present example).

6. Combine sample with incubation media

The timer was started and the Ng suspension were added to the sample. The time was recorded for Lab Notebook records. 100 uL of the Ng suspension were added into "treated" media, add 100 uL of the Ng suspension into untreated media. This addition can be performed sequentially or in parallel (using multichannel pipet) as will be understood by a skilled person.

Before transporting the tubes to the incubator, it was proceeded to steps 8-9 to take a "t0" sample. Tubes were incubated on the shaker (500 rpm) in 37° C., 5% $CO_2$ incubator for the duration of the experiment.

7. Incubate the treated and untreated samples at a controlled temperature for long amount of time (6 hours) taking aliquots for analysis, see steps 7-8, at defined time intervals The treated and untreated samples were incubated at 37 C for 15 minutes, 1 hr, 2 hr, 3 hr, 4 hr, 5 hr, 6 hr. At each time point, bring the culture tubes into the BSC and incubate an aliquot of the contents with DNaseI to degrade the accessible DNA.

8. Secondary incubation of treated and untreated samples to degrade accessible DNA 20 uL of the sample were withdrawn from the primary exposure into a pipette and transferred to the secondary incubation for accessible DNA degradation in a PCR tube. The caps were closed tightly, and the tubes were vortexed for a few seconds and centrifuged on a benchtop centrifuge to remove droplets from the caps.

These tubes were incubated for 5 min. incubation at 37° C. on a thermocylcer with a heated lid. The lid of the thermocylcer was lifted at 4 min to let the caps cool and bring tubes back into the BSC, vortex briefly, centrifuge 9. DNA extraction of treated and untreated samples from the secondary incubation, at each time point of primary exposure (at 0, 15 minutes; 1, 2, 3, 4, 5, 6 hours) to purify DNA DNA extraction was performed following the procedure outlined in "DEB Extraction" in the general methods section, using 10 μL of sample and 90 μL DEB in Eppendorf tubes. The extraction was stored at −20° C. until all time points were collected. The operator proceeded to step 10 to measure DNA from each time point.

10. Measurement of DNA by qPCR

DNA was measure by preparing a qPCR mix (see the "qPCR" protocol in the General Methods). The Primers were for the Ng 16S gene in each amplification, the samples were run in triplicate for 35 cycles at an annealing temperature of 62° C. Cqs measurements were used to calculate the CT ratio at each time point The results illustrated in FIGS. 15A to 15 C show that by relying on beta-lactam induced changes in accessibility (such as lysis or disruption of the cell envelope) without the addition of an enhancer or additional reagent (other than media, cells, antibiotic, and DNaseI) become detectable after several hours of exposure to the antibiotic. These figures show how the CTR magnitude changes with antibiotic exposure times. For the purposes of using this method to determine susceptibility, only one time would be needed. Based on these data, one isolate would require two DNA extractions, a control and a treated extraction ≥3 hours.

Figures 15A, 15B, 15C:
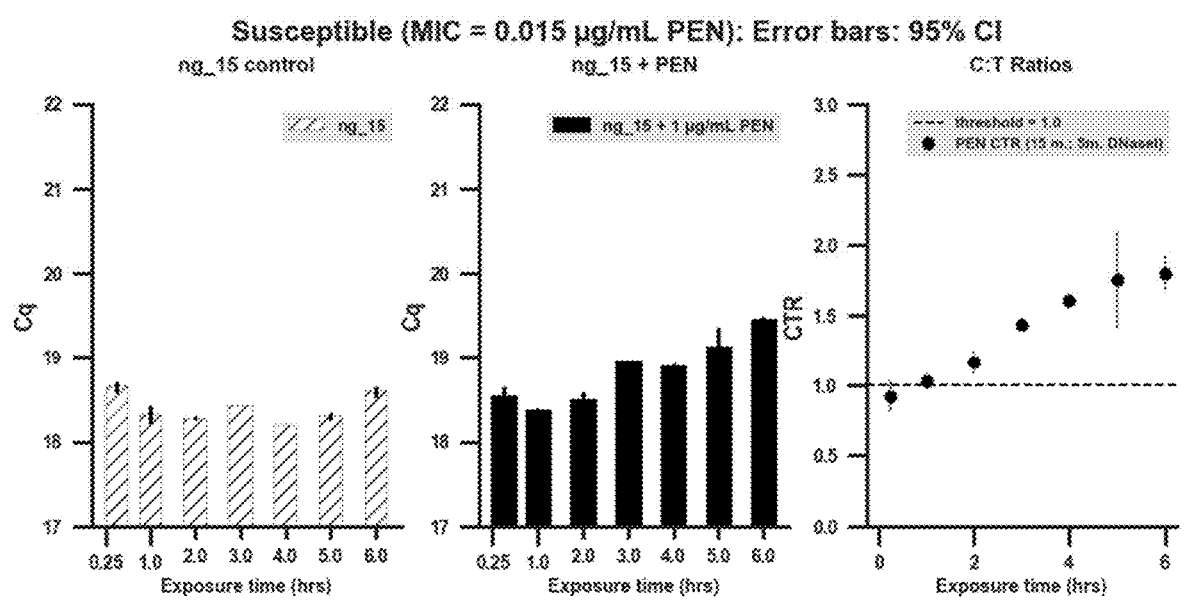
FIGS. 15A-15C show diagrams illustrating the results of an exemplary AST according to the disclosure in which beta-lactam treatment is performed in the absence of an enhancing treatment, as described in Example 7. Changes in nucleic acids between the untreated (FIG. 15A) and treated (FIG. 15B) shown as a CT ratio in FIG. 15C are a result of beta lactam exposure followed by a DNaseI degradation step to detect inaccessible nucleic acid.

The exemplary results illustrated in FIGS. 15A to 15 C support the conclusion that DNA accessibility with a degradation step (inclusion of DNaseI) help highlight the change in DNA accessibility caused by cell wall damage from the beta-lactam incubation; increase in Cq in the antibiotic-treated sample corresponds to decreased quantity of detectable inaccessible nucleic acids. MHB is not a media that sustains cell growth of NG over these time scales, supporting the conclusion that nucleic acids are made accessible by cell wall damage. DNaseI can be treated as a secondary step, but it could be included for the duration of the antibiotic exposure instead.

It is noted that step 1 of this example can be performed before or after steps 2-3 of this example, or in parallel with step 4 of this example as will be understood by a skilled person.

Example 8: AST Performed by Detecting Inaccessible DNA with Mechanical Disruption, after ABX Exposure Before Cell Lysis and NA Extraction Antibiotic susceptibility test was performed with methods herein described in which mechanical disruption by sonication is used as an enhancer for beta-lactam incubation, in combination with DNaseI as a degrader.

Figure 16:
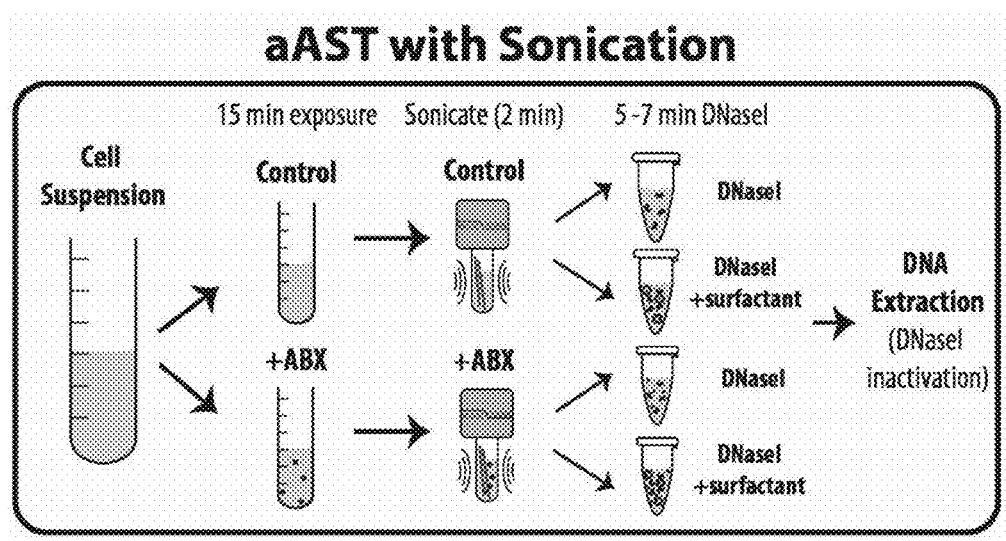
FIG. 16 shows a schematic illustration of an exemplary AST according to the disclosure in which a penicillin-susceptible isolate is incubated with penicillin for 15 minutes, sonicated on the Covaris M220 sonicator (such as 30 s, 120 s), followed by a third incubation with DNaseI to degrade the accessible DNA as described in Example 8.

The layout of the example is illustrated in FIG. 16 which provides a schematic representation of the experimental steps.

In particular, the detection was performed in outcome of to the following procedure 1. provide incubation media containing enhancer, accessibility, with and without an antibiotic for each isolate Several milliliters of media were prewarmed in a 37° C., 5% $CO_2$ incubator (media is MHB, see media preparation in general methods) for ≥45 minutes prior to use.

For each isolate, two incubation tubes were prepared in 2 mL purple cap tubes (VWR Cat #89004-298), following the chart below, titled "Primary Incubation (Antibiotic Exposure)". Add NaHCO$_3$ (conditioner). Antibiotic were added when bacteria cells were incubating, so that the time from thawing the antibiotic stock was minimized before exposure (see step 4 of this example).

| Primary Incubation (Antibiotic Exposure): (500 µL in screw-cap tube) | |
| --- | --- |
| Component | Volume |
| Ng Suspension (OD = 0.5) in MHB + 5 mM NaHCO$_3$ | 50 µL (OD = 0.05, 0.5 mM NaHCO$_3$) |
| MHB | 417.5 µL |
| NaHCO$_3$ (100 mM) | 22.5 µL (4.5 mM) |
| 50X ABX or NF water in control | 10 µL |

For each isolate, two incubation tubes were prepared of each secondary incubation. Each sample was added to a tube of each option so that the data can be compared with and without the second enhancer of the surfactant).

| Secondary Incubation (option 1): DNaseI digestion after sonication. (50 µL in PCR tube) | |
| --- | --- |
| Component | Volume |
| Ng Suspension (Post-Covaris Sonication) | 20 µL |
| NEB DNaseI (2000 U/mL) | 2.5 µL (100 U/mL) |
| 10× DNaseI Reaction Buffer | 5 µL |
| MHB | 22.5 µL |

| Secondary Incubation (option 2): DNaseI digestion in the presence of enhancer after sonication. (50 µL in PCR tube) | |
| --- | --- |
| Component | Volume |
| Ng Suspension (Post-Covaris Sonication) | 20 µL |
| NEB DNaseI (2000 U/mL) | 2.5 µL (100 U/mL) |
| 10× DNaseI Reaction Buffer | 5 µL |
| MHB | 20 µL |
| TNP (100 mM, 20X) | 2.5 µL (5 mM, 1X) |

2. Providing a sample containing bacteria ng_17 is a penicillin-susceptible isolates and ng_15 is a ceftriaxone-susceptible isolate were used. These isolates were exposed to an antibiotic concentration of 1.0 µg/mL penicillin or 4.0 µg/mL ceftriaxone (treated) and to nuclease-free water (control). (see the "Clinical Isolate MICs" table for *N. gonorrhoeae* for MICs in the General Methods).

The bacteria were prepared according to the "NG Stock and Resuspension" description in the General Methods section. While cell pellet was suspending, the antibiotic exposure condition and the secondary incubations in PCR tubes (everything except Ng suspension and ABX) was prepared as outlined in step 1 of this example.

Right before measuring OD, these tubes were set on the shaking block in the shaking heat block for incubation at 37° C.

3. Optionally, pre-process the sample containing bacteria

In a variation of the experimental procedure herein described the OD600 (dilute 1/10 in media) was measured and the OD of suspension was adjusted to OD=0.5 in pre-warmed MHB+5 mM NaHCO$_3$ media.

4. Add the antibiotic

Antibiotic dilutions were prepared from pre-made and frozen antibiotic stocks as follows. Diluted 1 mg/mL ceftriaxone or penicillin stock, was prepared according to "Preparing Antibiotic Stocks" description in the general methods, see penicillin and ceftriaxone.

In particular, 1 mg/mL penicillin stock was diluted to make a 50× stock for the experimental exposure. The 1 mg/mL stock was stored at −80° C. in single-use aliquots prepared from penicillin G sodium salt. In particular 500 µL of 50× (1×1 µg/mL PEN→50 µg/mL=0.050 mg/mL PEN) penicillin were prepared with 25 µL (1.0 mg/mL stock)+475 µL nuclease-free water.

1.0 mg/mL ceftriaxone stock was diluted, from −80° C. storage. In particular, 50× Stock (1×4 µg/mL CRO→200 µg/mL=0.200 mg/mL CRO) 250 µL of 0.200 mg/mL=50 µL (1.000 mg/mL stock)+200 µL NF water.

The antibiotic was added to the corresponding exposure tubes setup in step 1 of this example.

5. Split the sample into two or more parts 50 uL of the Ng suspension were withdrawn into a pipette (following the chart for the primary exposure in step 1 of this example)

6. Combine sample with incubation media

The timer was started and the Ng suspension was added. The time was recorded for the Lab Notebook records. 50 uL of the Ng suspension were added into "treated" media, and 100 uL of the Ng suspension were added into untreated media. This addition can be performed sequentially or in parallel (using multichannel pipet) as will be understood by a skilled person.

The tubes were staggered so that timing was more precise for each of and to give some timing for sonication, plating, and extractions of the tubes. The timer was started and the Ng suspension was added. The time was recorded for the Lab Notebook records. (at OD600=0.5 suspension, tubes were incubated on the shaker (1000 rpm) at 38° C. on the heat-shake block between the staggered exposure tubes).

7. Incubate for a short time (15 minutes) with antibiotics

The exposure tubes were incubated for 15-minutes on the heat-shake block set to 1000 rpm and 38° C.

8. Mechanical disruption by sonication

For each exposure tub, a 50 µL aliquot of the exposure tube was taken into a Covaris microTUBE-50. In cases like the one below, a separate 50 µL aliquot was taken for each sonication parameter. The chart below of Covaris Sonicating Conditions was followed to select the conditions for each sample. All samples were maintained at room temperature for the duration of the handling of the samples in parallel These steps were performed separately for the untreated and treated

| Covaris M220 Sonicating Conditions | | | | | |
| --- | --- | --- | --- | --- | --- |
| Sample Group | Peak Incident power (W) | Duty Factor (%) | Cycles per burst | Duration (s) | Temperature |
| 1-2 | N/A | N/A | N/A | N/A | N/A |
| 3-4 | 15 | 10 | 200 | 30 | 37° C. |
| 5-6 | 3 | 10 | 200 | 30 | 37° C. |

9. Secondary incubation of treated and untreated samples 20 uL of the sample were withdrawn from the primary exposure into a pipette and transfer to the secondary incubation for accessible DNA degradation in a PCR tube. Optionally, the sample prepared in step 8 can be divided into multiple secondary incubations (e.g. the two options prepared in step 1 of this example). The caps were closed tightly, the tubes were vortexed for a few seconds and centrifuged on a benchtop to remove droplets from the caps. These tubes were incubated for 5 min at 37° C. on a thermocylcer with a heated lid. The lid of the thermocylcer was lifted at 4 min to let the caps cool. The tubes were brought back into the BSC, vortex briefly, centrifuge 10. DNA extraction of treated and untreated samples from the secondary incubation to purify DNA DNA extraction was performed following the procedure outlined in "DEB Extraction" in the general methods section, using 10 µL of sample and 90 µL DEB in PCR tubes using the thermocylcer for heating steps. Since there were many samples that occur in parallel, a separate heat block was used for the DNaseI digestion steps in step 9 of this example as the DEB extraction steps in step 10.

11. Measurement of DNA by qPCR

Measurement of DNA was performed by preparing a qPCR mix (see the "qPCR" protocol in the General Methods). Primers were for the Ng 16S gene in each amplification. Samples were run in triplicate for 35 cycles at an annealing temperature of 62° C.

Cqs measurements were used to calculate the CT ratio at each time point

Figure 17A:
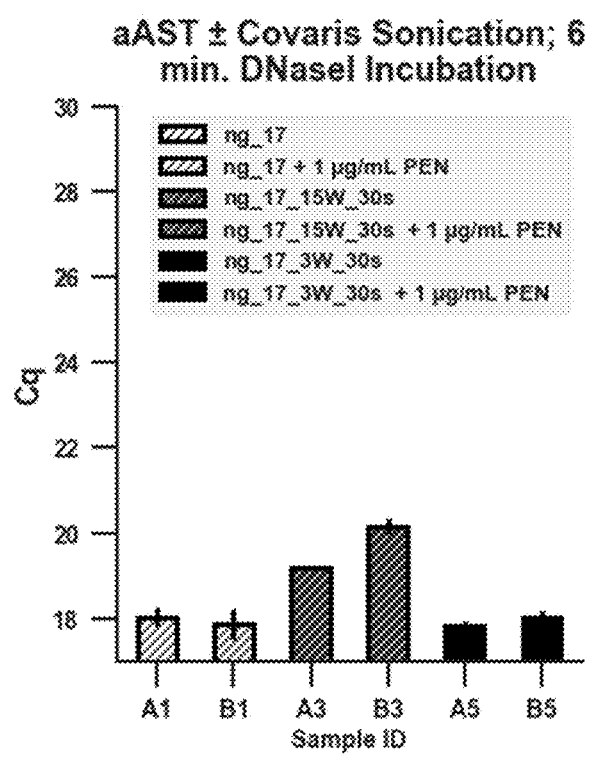
FIGS. 17A and 17B show diagrams illustrating the results of an exemplary AST according to the disclosure in which sonication is used an enhancement of the accessibility of DNA in a susceptible-treated sample compared to the susceptible-control sample. Experiments described in Example 8.
Figure 17B:
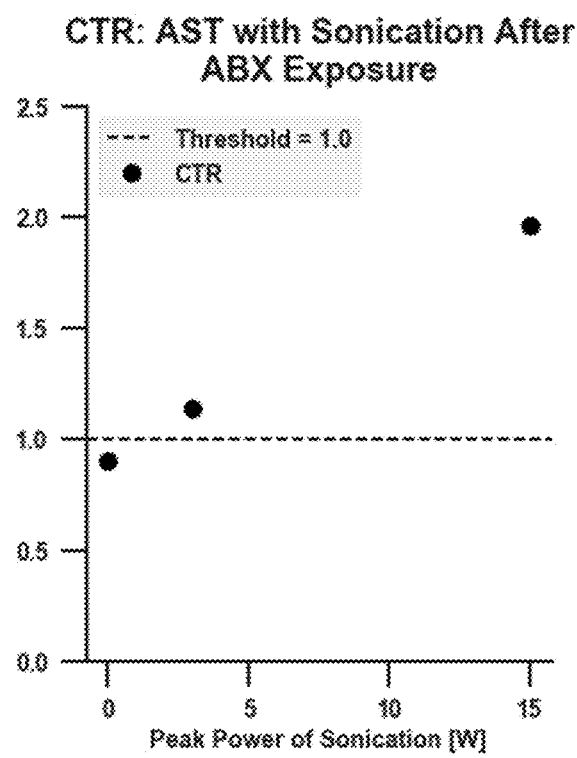

The results illustrated in FIGS. 17A and 17B, show that some sonication conditions allow for an enhancement of the accessibility of DNA in the susceptible-treated sample compared to the susceptible-control sample. In particular the results in the FIG. 17B labeled with the CTR points show that the readout of CTR depends on the sonication settings (here represented by the Peak Power of sonication in watts [W]).

A skilled person would understand that only one of these conditions screened could be used to determine the susceptibility to penicillin. This single point is obtained from steps (1-7, for step 8 only the third row of the "Covaris M220 Sonication Conditions" is needed to test, since the first two rows did not show a CT ratio>1, and steps 10-11).

Figures 18A, 18B, 18C:
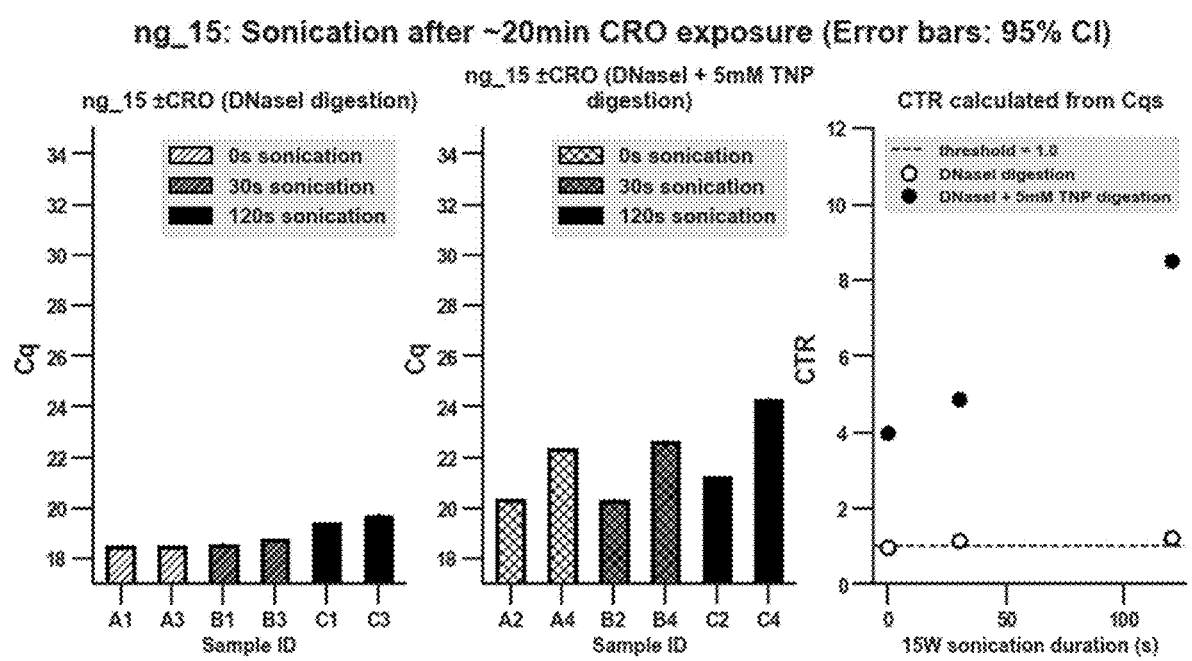
FIGS. 18A, 18B and 18C show diagrams illustrating the results of an exemplary AST according to the disclosure in which sonication is used an enhancement of the accessibility of DNA in a susceptible-treated sample compared to the susceptible-control sample. Experiments described in Example 9.

The results illustrated in FIGS. 18A to 18 C show sonication conditions that allow for enhancement of accessibility of DNA. These figures differ from FIGS. 17A and 17B in that the related results is a different antibiotic and a different isolate. Conditions might vary between antibiotics. The illustration of FIGS. 18A to 18C with isolate ng_15 and ceftriaxone shows little change with sonication+DNaseI digestion, but shows detectable signals with the combination of the enhancer sonication and the enhancer of surfactant TNP in the DNaseI digestion step.

In particular, the results in the FIG. 18C labeled with the CTR points show that the readout of CTR can be enhanced with the combination of sonication and a surfactant in the DNaseI digestion step. There are three potential conditions that could be used to determine the susceptibility to ceftriaxone if the enhancement step (under the conditions tested) happens after the 15 min antibiotic exposure. These conditions include the DNaseI digestion+5 mM TNP digestion with or without sonication.

In particular, for the CTR point at 0 s sonication with "DNaseI+5 mM TNP digestion" the following steps were performed Steps 1-7

(step 8 is "skipped" since the sonication refers to the first row of the table "Covaris M220 Sonicating Conditions" which is left intentionally empty, to indicate this step is skipped)

Steps 9-11

For the CTR point at 30 s sonication with "DNaseI+5 mM TNP digestion" the following steps were performed Steps 1-7

Step 8: with the second row of the table "Covaris M220 Sonicating Conditions"

Steps 9-11

For the CTR point at 120 s sonication "DNaseI+5 mM TNP digestion" the following steps were performed Steps 1-7

Step 8: with the third row of the table "Covaris M220 Sonicating Conditions"

Steps 9-11

The results illustrated in FIGS. 17A to 17 C support the conclusions that mechanical disruption by sonication after 15-minute penicillin exposure is a sufficient enhancer.

The results illustrated in FIGS. 18A to 18C also support the conclusions that mechanical disruption by sonication after 15-minute ceftriaxone exposure is done, followed by incubation with a second enhancer in the DNaseI digestion step (such as a 5-minute incubation with the surfactant TNP, at 5 mM, at 37° C.)

The results in FIGS. 18A to 18C illustrate that the combination of two enhancing treatments can give an even-bigger response, as measured by changes in the detectable inaccessible nucleic acids, which is shown in the figures as larger Cq differences. As with other qPCR representations and analysis, an increase in Cq in the antibiotic-treated sample corresponds to decreased quantity of detectable inaccessible nucleic acids.

The results illustrated in FIGS. 17A to 17 C and in FIGS. 18A to 18C further support the conclusions that qPCR is used for DNA measurements and data analysis and CT ratios computed from qPCR Cqs can be used to detect susceptibility. As with other qPCR representations and analysis, an increase in Cq in the antibiotic-treated sample corresponds to decreased quantity of detectable inaccessible nucleic acids It is noted that step 1 of this example can be performed before or after steps 2-3, of this example or in parallel with step 4 of this example as will be understood by a skilled person.

Example 9: AST Performed by Detecting Inaccessible DNA with Mechanical Disruption, DNA Accessibility AST Sonication During ABX Exposure Antibiotic susceptibility test was performed with methods herein described in which mechanical disruption by sonication is used as an enhancer for beta-lactam incubation, in combination with DNaseI as a degrader.

Figure 19:
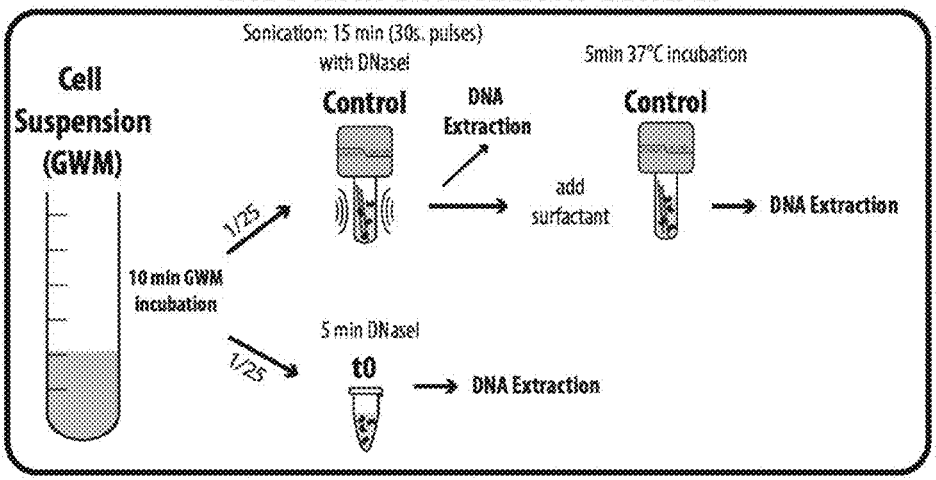
FIG. 19 shows a schematic illustration of an exemplary AST according to the disclosure in which a ceftriaxone-susceptible isolate is incubated with ceftriaxone and DNaseI for 15 minutes on a Covaris M220 sonicator (with a protocol of 30 s sonication, 30 s holding at 37° C.). From there, there are two options. One, the DNaseI is inactivated at the remaining cells are lysed, followed by qPCR. Two, there is an additional 5-minute incubation in the presence of surfactant (10 mM CHAPS) and DNaseI to degrade the accessible DNA. The DNaseI will be inactivated simultaneously with the lysis of the remaining cells. In both cases, the quantified nucleic acids represent those from the cells with inaccessible DNA throughout the antibiotic exposure, soncation, and incubation with DNaseI as described in Example 9.
Figure 19:
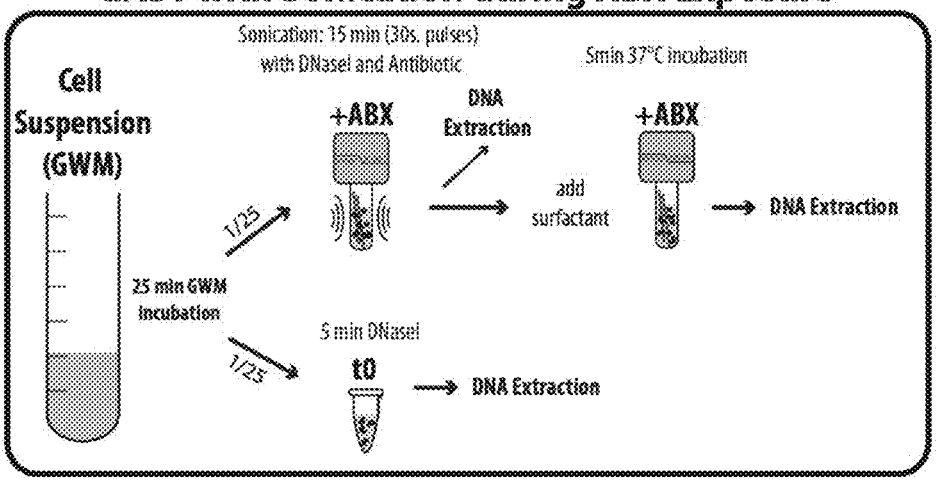

The layout of the example is illustrated in FIG. 19 which provides a schematic representation of the experimental steps.

In particular, FIG. 19 is a representation of the experimental steps, in which a ceftriaxone-susceptible isolate is incubated with ceftriaxone and DNaseI for 15 minutes on aCovaris M220 sonicator (with a protocol of 30 s sonication, 30 s holding at 37° C.). From there, there are two options. One, the DNaseI is inactivated at the remaining cells are lysed, followed by qPCR. Two, there is an additional 5 minute incubation in the presence of surfactant (10 mM CHAPS) and DNaseI to degrade the accessible DNA. The DNaseI will be inactivated simultaneously with the lysis of the remaining cells. In both cases, the quantified nucleic acids represent those from the cells with inaccessible DNA throughout the antibiotic exposure, sonication, and incubation with DNaseI.

In particular, the detection was performed according to the following procedure:

1. Provide incubation media containing enhancer, accessibility, with and without an antibiotic for each isolate Several milliliters (at least 14 mL) of media were pre-warmed in a 37° C., 5% $CO_2$ incubator (media is MHB, see media preparation in general methods) for >45 minutes prior to use.

For each isolate, two incubation tubes were prepared in screw-cap Covaris microtube-50, following the chart below, titled "Primary Incubation (Antibiotic Exposure)". $NaHCO_3$ (conditioner) was added. Wait to add antibiotic until bacteria cells are incubating, so that the time from thawing the antibiotic stock is minimized before exposure (see step 4 of this example).

| Primary Incubation (Antibiotic Exposure): (50 µL in screw-cap Covaris microTUBE) | |
|---|---|
| Component | Volume |
| Ng Suspension (OD = 1) in MHB + 5 mM $NaHCO_3$ | 10 µL (OD = 0.2, 0.5 mM $NaHCO_3$) |
| MHB | 27.75 µL |
| $NaHCO_3$ (100 mM) | 2.5 µL (4.5 mM) |
| 10X ABX or NF water in control | 5 µL |
| NEB DNaseI (2000 U/mL) | 5 µL (100 U/mL) |

For each isolate, two incubation tubes of each incubation below (each sample gets added to a tube of each option) were prepared. This way the data can be compared with and without the second enhancer of the surfactant).

| "t0" Incubation: DNaseI digestion of initial cell suspensions. (50 µL in PCR tube) | |
|---|---|
| Component | Volume |
| Ng Suspension (Post-Covaris Sonication) | 10 µL |
| NEB DNaseI (2000 U/mL) | 2.5 µL (100 U/mL) |
| MHB | 37.5 µL |

In some embodiments, after DEB extraction of 10 µL of the sonicated solution, additional steps are described to be taken to enhance the accessibility to DNA to the degrader (DNaseI) that is already present in the sample suspension. This is achieved by pipetting 2.1 µL of enhancer into the covaris microTUBE and incubating in a glass bead bath, such that the contents of the covaris microTUBE are kept at 37° C.

Step 1 can be performed before or after steps 2-3 or in parallel with step 4. as will be understood by a skilled person upon reading of the present disclosure.

| Secondary Incubation: DNaseI digestion in the presence of enhancer after sonication. (42.1 µL in screw-cap Covaris microTUBE) | |
|---|---|
| Component | Volume |
| Ng Suspension (Post-Covaris Sonication) | 40 µL (100 U/mL DNaseI, 1X ABX, 5 mM $NaHCO_3$) |
| CHAPS (200 mM, 20X) (enhancer) | 2.1 µL (10 mM, 1X) |

2. Providing a sample containing bacteria ng_19 is a ceftriaxone-susceptible isolate and ng_30 is a ceftriaxone-reduced-susceptible isolate. (see the "Clinical Isolate MICs" table for *N. gonorrhoeae* for MICs in the General Methods).

The bacteria were prepared according to the "NG Stock and Resuspension" description in the General Methods section with the following changes: incubate cell resuspension on shaker (1000 rpm) in 37° C., 5% $CO_2$ incubator (≥10 minutes).

The culture tube was then returned to the shaker in the incubator. This protocol requires the control and treated incubations to be staggered by 20 minutes.

While cell pellet is re-suspending, prepare the antibiotic exposure condition (everything except Ng suspension and ABX), see table below, and prewarm the tube in a glass bead bath so that the liquid inside the tube is 37° C. In the case of this lab setup, the bead bath was set to 40° C. and the temperature of an equivalent volume was measured to be 37° C. with a thermocouple.

3. Optionally, pre-process the sample containing bacteria

OD600 (dilute 1/10 in media) was measured. OD of suspension was adjusted to OD=1.0 in pre-warmed MHB media+5 mM $NaHCO_3$ 4. Add the antibiotic 1.0 mg/mL ceftriaxone (CRO) stock was diluted, from −80° C. storage. In particular, 10× Stock was prepared (1×1 µg/mL CRO→10 µg/mL=0.010 mg/mL CRO) in a 500 µL volume by mixing 5 µL (1.000 mg/mL stock)+495 µL NF water.

The antibiotic was added to the corresponding exposure tubes setup in step 1. Since the exposures are staggered by 20 minutes in this setup, the antibiotic dilution was stored on ice and was added within 10 minutes of beginning the exposure.

5. Split the sample into two or more parts 10 uL of the Ng suspension (from step 3) was withdrawn into a pipette (following the chart for the primary exposure in step 1)

6. Combine sample with incubation media

The time starts and the Ng suspension was added. The time is recorded for Lab Notebook records. 10 uL of the Ng suspension was added into "treated" or "untreated" media; this addition can be performed sequentially or in parallel (using multichannel pipet). The tubes were staggered so that timing can be more precise for each of and to give some timing for sonication, plating, and extractions of the tubes. Start the timer and add the Ng suspension. Record the time for Lab Notebook records. The screw-cap covaris microTUBE were sealed with parafilm.

7. Incubate for a short time (15 minutes) with antibiotics and mechanical disruption by covaris sonication The exposure tubes were incubated for 15-minutes in the covaris sonicator water bath set to 37° C. The sonicator was started to run the following protocol in the table below:

| Covaris Sonicating Conditions Sample Group | Peak Incident power (W) | Duty Factor (%) | Cycles per burst | Duration (s) | Temperature | Method Name |
|---|---|---|---|---|---|---|
| all | 75 | 2 | 100 | [30 s on, 30 s delay]*15 | 37° C. | Ng_test_713_C |

8. While running steps 6-7; run a parallel t0 exposure

Cells are added to the t0 tube (as with step 5) and the exposure tubes for the static incubation at the same time, then get vortexed, spun down and placed on the 37° C. heat block Benchmark Multi-Therm set to 37° C. and 0 rpm. Follow the Chart for the incubation tubes prepared in step 1.

9. DNA extract

DNA extraction was performed following the procedure outlined herein "DEB Extraction" in the general methods section, using 10 μL of sample (of the 50 μL total in the covaris microTUBE) and 90 μL DEB in PCR tubes using the thermocylcer for heating steps. Since there are many samples that occur in parallel, a separate heat block is used for the DNaseI digestion steps in step 8 and 9 as the DEB extraction steps here in step 10. Additionally, the samples in covaris microTUBEs cannot be vortexed, these steps were replaced by a mixing step by pipetting (pipetting up and down with a P100 set to 20 μL)

10. Secondary incubation of samples

At this point 10 μL of the 50 μL has been taken out for the condition without the additional enhancer
- add 2.1 uL of the enhancer to the covaris TUBE with the remaining 40 μL of sample
- Mix by pipetting up and down with a P100 set to 20 μL
- Screw the cap shut and ensure it is sealed with parafilm.
- Incubate these tubes for 5 min. in the glass bead bath (set to 40° C. but measured to be 37° C. inside these tubes)
- Return the sample to the BSC for an addition DEB extraction 11. DNA extraction of treated and untreated samples from the secondary incubation to purify DNA step 10 was repeated for the tube that incubated with the enhancer.

12. Repeat steps 3-11 for each condition of each isolate
13. Measurement of DNA by qPCR qPCR mix is prepared as follows (see the "qPCR" protocol in the General Methods):
- Primers were for the Ng 16S gene in each amplification
- Samples were run in triplicate
- 35 cycles
- Annealing temperature of 62° C.

Cqs measurements were used to calculate the CT ratio at each treated, untreated pair at the same conditions.

The results illustrated in FIGS. 20A-20C summarize three parts for a susceptible isolate. FIG. 20A shows the t0 qPCR measurements for the control (untreated) and the treated tubes; these qPCR measurements are used to normalize the AST measurements in FIG. 20B, since the control and treated incubations in FIG. 20B were taken 20 minutes apart. Four measurements are used in this example to compute a single t0-normalized CTR point.

The result in FIG. 20C labeled "[sonication]→DEB" can be used to determine susceptibility to ceftriaxone. This point is obtained from steps (1-9, and 13). In this case, the CTR close to 1.0 is indicative of no extra change from the treated condition, and this result shows the resistant phenotype.

The result in FIG. 20C labeled "[sonication]+5 min. CHAPS" is obtained from steps (1-8, and 10-13). As with the first data point in this panel, the CTR close to 1.0 is indicative of no additional change in accessibility from the treated condition, and this result shows the resistant phenotype.

The results shown in FIGS. 20A-20C support the conclusions that a differentiable CTR can be resolved with or without the surfactant digestion step when comparing the susceptible and resistant isolates.

In some embodiments, a CTR computed from the treated and untreated samples after a 15 minute antibiotic exposure with sonication can be sufficient to differentiate between the ceftriaxone-susceptible and ceftriaxone-resistant isolates shown in the above plots In some embodiments, a CTR computed from the treated and untreated samples after a 15 minute antibiotic exposure with sonication, followed by an additional incubation with another enhancer, can be used to differentiate between the ceftriaxone-susceptible and ceftriaxone-resistant isolates shown in the above plots In some embodiments, qPCR is used for DNA measurements and data analysis and CT ratios computed from qPCR Cqs can be used to detect susceptibility.

Example 10: Susceptibility Ratio Compared to Fold Change Before and After Incubation with ABX (Mechanical aAST Setup)

Antibiotic susceptibility test was performed with methods herein described in which mechanical disruption by sonication is used as an enhancer for beta-lactam incubation, in combination with DNaseI as a degrader.

Figure 21:
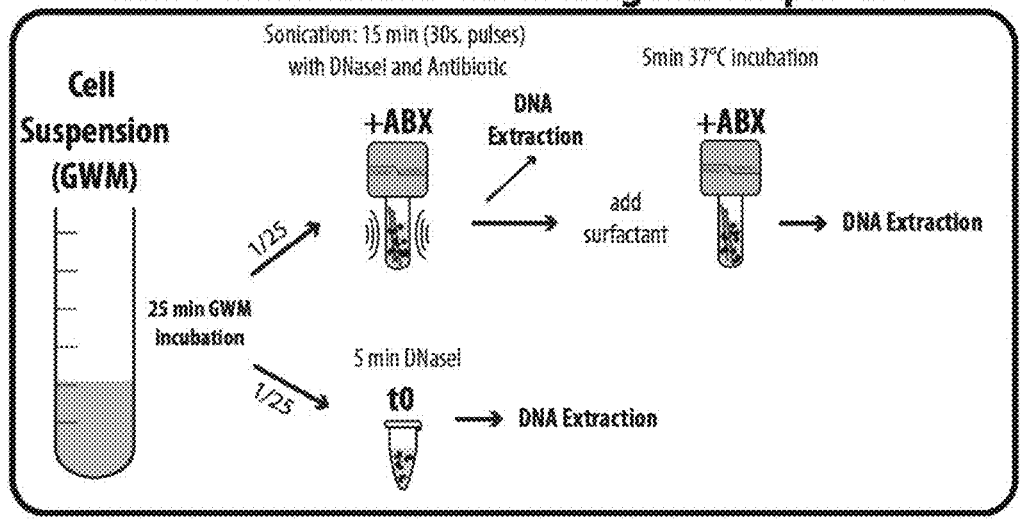
FIG. 21 shows a schematic illustration of an exemplary AST according to the disclosure in which a ceftriaxone-susceptible isolate is incubated with ceftriaxone and DNaseI for 15 minutes on a Covaris M220 sonicator (with a protocol of 30 s sonication, 30 s holding at 37° C.). From there, there are two options. One, the DNaseI is inactivated at the remaining cells are lysed, followed by qPCR. Two, there is an additional 5-minute incubation in the presence of surfactant (10 mM CHAPS) and DNaseI to degrade the accessible DNA. The DNaseI will be inactivated simultaneously with the lysis of the remaining cells. In both cases, the quantified nucleic acids represent those from the cells with inaccessible DNA throughout the antibiotic exposure, sonication, and incubation with DNaseI as described in Example 10.

The workflow of the example is illustrated in FIG. 21, which is the same as in Example 9, but the data analysis is slightly modified. This example only requires the "antibiotic-treated" tube and compared the fold change increase in DNA accessibility from before and after the antibiotic exposure.

DNaseI is used to degrade the DNA made accessible by the combination of beta-lactam induced damage and mechanical disruption by sonication. Cell suspensions are exposed to beta lactams for 15 minutes with 30-second pulses of sonication to selectively enhance the amount of DNA accessible in the susceptible-treated sample.

In some cases, and additional incubation step with a surfactant, such as CHAPS, are used to further enhance this signal.

DNaseI is inactivated during the DEB extraction and the nucleic acids of the cells that remained intact through the exposure protocol are quantified.

Isolates tested are: ng_19 and ng_30. ng_19 is a ceftriaxone-susceptible and penicillin-resistant isolate and ng_30 is a ceftriaxone reduced-susceptible isolate. Both exposed to an antibiotic concentration of 1.0 μg/mL ceftriaxone (treated).

In particular, as shown in FIG. 21, a ceftriaxone-susceptible isolate is incubated with ceftriaxone and DNaseI for 15 minutes on aCovaris M220 sonicator (with a protocol of 30 s sonication, 30 s holding at 37° C.). From there there are two options. One, the DNaseI is inactivated at the remaining cells are lysed, followed by qPCR. Two, there is an additional 5 minute incubation in the presence of surfactant (10 mM CHAPS) and DNaseI to degrade the accessible DNA. The DNaseI will be inactivated simultaneously with the lysis of the remaining cells. In both cases, the quantified nucleic acids represent those from the cells with inaccessible DNA throughout the antibiotic exposure, sonication, and incubation with DNaseI.

1. provide incubation media containing enhancer, accessibility, with and without an antibiotic for each isolate Several milliliters (at least 14 mL) of media were pre-warmed in a 37° C., 5% $CO_2$ incubator. The bacteria were prepared according to the "NG Stock and Resuspension" description in the General Methods section with the following changes: (media is MHB with 5 mM NaHCO$_3$, or GW media, see media preparation in general methods) for ≥45 minutes prior to use.

For each isolate, two incubation tubes screw-cap Covaris microtube-50 were prepared, following the chart below, titled "Primary Incubation (Antibiotic Exposure)". Add NaHCO$_3$ (conditioner). Wait to add antibiotic until bacteria cells are incubating, so that the time from thawing the antibiotic stock is minimized before exposure (see step 4 in this example).

| Primary Incubation (Antibiotic Exposure): (50 μL in screw-cap Covaris microTUBE) | |
|---|---|
| Component | Volume |
| Ng Suspension (OD = 1) in MHB + 5 mM NaHCO$_3$ | 10 μL (OD = 0.2, 0.5 mM NaHCO$_3$) |
| MHB (media) | 27.75 μL |
| NaHCO$_3$ (100 mM) | 2.5 μL (4.5 mM) |
| 10X ABX | 5 μL (1X) |
| NEB DNaseI (2000 U/mL) (degrader) | 5 μL (100 U/mL) |

For each isolate, one incubation tubes of the "t0" condition described below was prepared

| "t0" Incubation: DNaseI digestion of initial cell suspensions. (50 μL in PCR tube) | |
|---|---|
| Component | Volume |
| Ng Suspension (Post-Covaris Sonication) | 10 μL |
| NEB DNaseI (2000 U/mL) | 2.5 μL (100 U/mL) |
| MHB | 37.5 μL |

2. Providing a sample containing bacteria ng_19 is a ceftriaxone-susceptible/penicillin-resistant isolate and ng_30 is a ceftriaxone-reduced-susceptible isolate. (see the "Clinical Isolate MICs" table for *N. gonorrhoeae* for MICs in the General Methods).

Cell pellets were resuspended. Cell pellet was scraped with inoculating loop and twirl in 2 mL media (pre-warmed MHB+5 mM NaHCO$_3$ or GWM), and then incubated on shaker (1000 rpm) in 37° C., 5% CO$_2$ incubator (≥10 minutes).

While cell pellet is re-suspending, the antibiotic exposure condition (everything except Ng suspension and ABX) was prepared. The tube was prewarmed in a glass bead bath so that the liquid inside the tube is 37° C. In the case of this lab setup, the bead bath was set to 40° C. and the temperature of an equivalent volume was measured to be 37° C. with a thermocouple.

3. Optionally, pre-process the sample containing bacteria

OD600 (dilute 1/10 in media) was measured. OD of suspension was adjusted to OD=1.0 in pre-warmed MHB media+5 mM NaHCO$_3$ 4. Add the antibiotic The antibiotic dilutions are prepared below:

Ceftriaxone (CRO): Diluted 1.0 mg/mL ceftriaxone stock, from −80° C. storage. 10× Stock prepared (1×1 μg/mL CRO→10 μg/mL=0.010 mg/mL CRO) in a 500 μL volume by mixing 5 μL (1.000 mg/mL stock)+495 μL NF water Penicillin (PEN): Diluted 1.0 mg/mL penicillin stock, from −80° C. storage. 10× Stock prepared (1×1 μg/mL PEN→10 μg/mL=0.010 mg/mL CRO) in a 500 μL volume by mixing 5 μL (1.000 mg/mL stock)+495 μL NF water The antibiotic was added to the corresponding exposure tubes setup in step 1

5. Split the sample into two or more parts (steps 6-7 and step 8 represent this split into two parts)

10 uL of the Ng suspension (from step 3) was withdrawn into a pipette (following the chart for the primary exposure in step 1)

In this example, the sample will be split into a "t0" incubation and a "treated" incubation in step 6.

6. Combine sample with incubation media

The timer started and 10 uL of the Ng suspension was added into "treated" media of the Ng suspension. The time was recorded for Lab Notebook records.

The screw-cap covaris microTUBE was sealed with parafilm and the tube was transported to the covaris sonication (step 7).

7. Incubate for a short time (15 minutes) with antibiotics and mechanical disruption by covaris sonication The exposure tubes were incubated for 15-minutes in the covaris sonicator water bath set to 37° C. The sonicator was started to run the following protocol in the table below:

| Covaris Sonicating Conditions | | | | | |
|---|---|---|---|---|---|
| Sample Group | Peak Incident power (W) | Duty Factor (%) | Cycles per burst | Duration (s) | Temperature |
| all | 75 | 2 | 100 | [30 s on, 30 s delay] * 15 | 37° C. |

8. While running steps 6-7; run a parallel t0 exposure

Cells are added to the t0 tube (as with step 5) and the exposure tubes for the static incubation at the same time, then get vortexed, spun down and placed on the 37° C. heat block Benchmark Multi-Therm set to 37° C. and 0 rpm. Follow the Chart for the incubation tubes prepared in step 1.

9. DNA extract

DNA extraction was performed following the procedure outlined herein "DEB Extraction" in the general methods section, using 10 μL of sample (of the 50 μL total in the covaris microTUBE) and 90 μL DEB in PCR tubes using the thermocylcer for heating steps. The samples in covaris microTUBEs cannot be vortexed, these steps were replaced by a mixing step by pipetting (pipetting up and down with a P100 set to 20 μL)

10. Measurement of DNA by qPCR qPCR mix was prepared as follows (see the "qPCR" protocol in the General Methods):

Primers were for the Ng 16S gene in each amplification

Samples were run in triplicate 35 cycles

Annealing temperature of 62° C.

Cqs measurements were used to calculate the t0/TREATED ratio at each treated, t0 pair for each isolate-antibiotic condition.

Figures 22A, 22B:
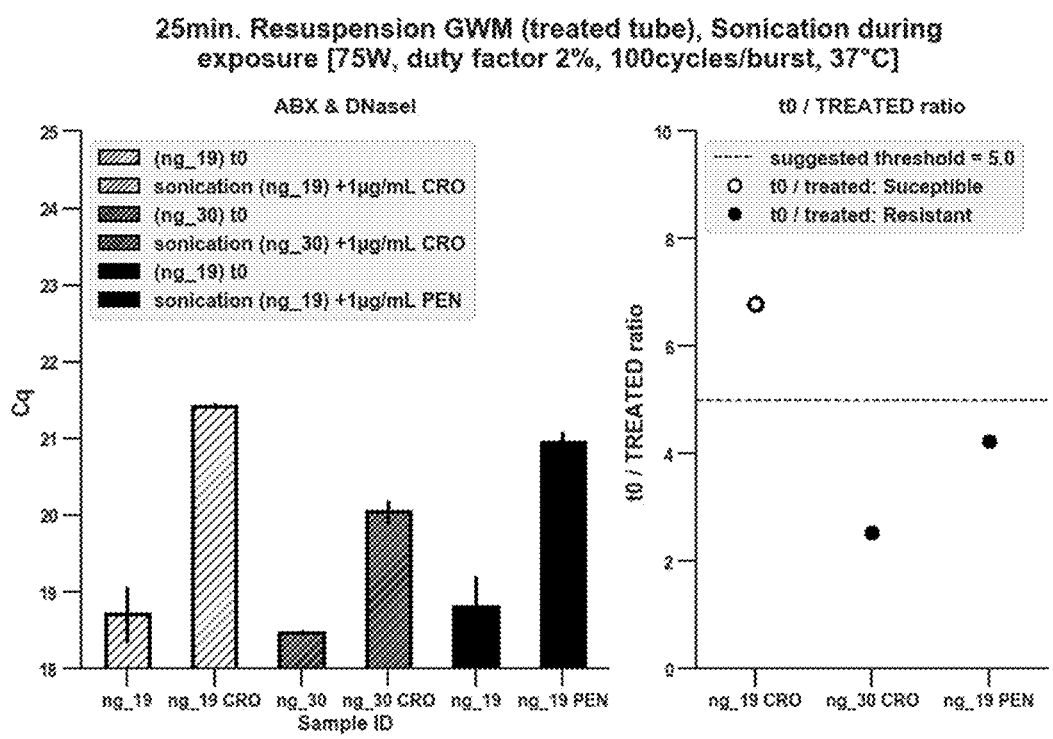
FIGS. 22A-22B show a diagram illustrating the results of an exemplary AST according to the schematic in FIG. 21 performed without using the sample with subsequent surfactant incubation for the measurements. Experiments described in Example 10. These data plotted represent an isolate, ng_19 which is susceptible to ceftriaxone (CRO) and resistant to penicillin (PEN), and an isolate, ng_30, which is resistant to ceftriaxone (CRO).

The results in FIGS. 22A-22B show a possible comparison of two samples to make a susceptibility call. The antibiotic-treated sample undergoes a sonication treatment as described above and the t0 reference undergoes only a DNaseI treatment but no enhancing treatment. The antibiotic-treated samples (the second bar in each pair) represent a sample that has undergone the combination treatment of sonication at 37° C. and incubation with either CRO or PEN antibiotics. In each case the second bar is higher than the initial amount of inaccessible nucleic acids. FIG. 22B shows the conversion of the raw qPCR measurements into a ratio that could be used to predict susceptibility. The t0/TREATED ratio is a representation of how much the accessibility of DNA has changed with the enhancement treatment and the antibiotic treatment. A suggested threshold of susceptibility of a t0/TREATED ratio of 5.0 is represented as a dashed line, in which the susceptible incubations would be expected to fall above this line and the resistant incubations would be expected to fall below this line.

The results illustrated in FIGS. 22A-22B support the conclusion that it is possible to simplify the measurement of susceptibility for the sonication-during-exposure to include only two extractions per measurement (whereas Example 9 required four extractions per measurement) if the t0 and the treated tubes are compared.

Example 11: Two-Step aAST with Surfactant Only in the Secondary Exposure

This example was performed using a two-step exposure in which the first step is exposure to a beta-lactam antibiotic and the second step is a 1:1 dilution into DNaseI treatment in the presence of a surfactant.

The inclusion of the surfactant enhances the accessible nucleic acids made available by short (15 minute) b-lactam exposure by adding a second incubation step with a surfactant. Differences in DNA accessibility between the unexposed and exposed tubes are enhanced. DNaseI is used to degrade the DNA made accessible by beta-lactam treatment and the surfactant.

DNaseI is inactivated during the DEB extraction and the nucleic acids of the cells that remained intact through the exposure protocol are quantified.

ng_15 is a ceftriaxone-susceptible isolate with an MIC≤0.008 µg/mL ceftriaxone. ng_17 is a ceftriaxone-susceptible isolate with an MIC≤0.008 µg/mL ceftriaxone. ng_19 is a ceftriaxone-susceptible isolate with an MIC=0.015 µg/mL ceftriaxone. ng_30 is an isolate with reduced-susceptibility to ceftriaxone with an MIC=0.05 µg/mL ceftriaxone. All isolates are exposed to an antibiotic concentration of 1.0 µg/mL ceftriaxone (treated) and nuclease-free water (control)

Figure 23:
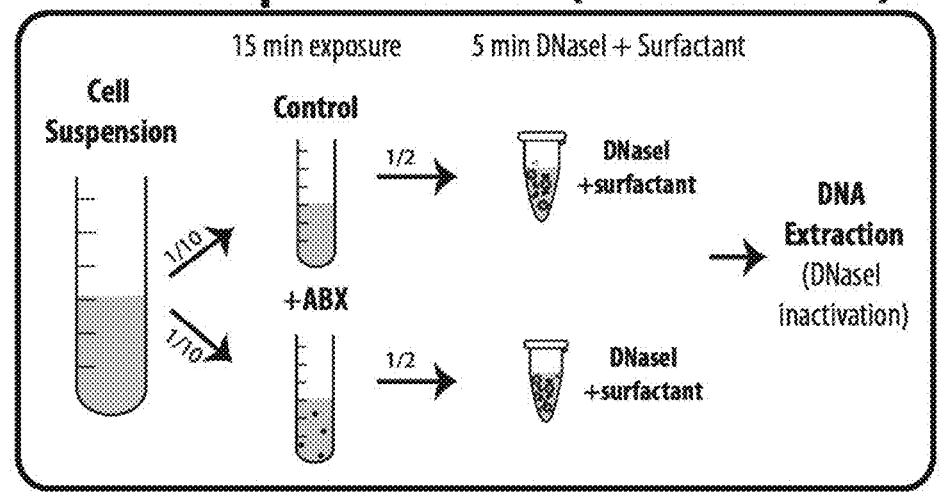
FIG. 23 shows a schematic illustration of an exemplary AST according to the disclosure in which an NG isolate is incubated with a beta-lactam antibiotic for 15 minutes, followed by a DNaseI digestion step in the presence of surfactant. At each time point, DNaseI will be added to degrade the accessible DNA, then the DNaseI will be inactivated simultaneously with the lysis of the remaining cells. The quantified nucleic acids represent those inaccessible from the DNaseI throughout the exposure protocol.

FIG. 23 describes the layout of this experiment. An NG isolate is incubated with a beta-lactam antibiotic for 15 minutes, followed by a DNaseI digestion step in the presence of surfactant. At each time point, DNaseI will be added to degrade the accessible DNA, then the DNaseI will be inactivated simultaneously with the lysis of the remaining cells. The quantified nucleic acids represent those inaccessible from the DNaseI throughout the exposure protocol.

1. provide incubation media containing enhancer, accessibility, with and without an antibiotic for each isolate Several milliliters (at least 14 mL) of media were pre-warmed in a 37° C., 5% $CO_2$ incubator (media is GWM) for ≥45 minutes prior to use.

For each isolate, two incubation tubes were prepared in PCR tubes (or two tubes in a 8-tube strip of PCR tubes), following the chart below, titled "Primary Incubation (Antibiotic Exposure)". Add $NaHCO_3$ (conditioner), DNaseI (degrader). Wait to add antibiotic until bacteria cells are incubating, so that the time from thawing the antibiotic stock is minimized before exposure (see step 4).

| Primary Incubation (Antibiotic Exposure): (100 µL in PCR tubes) | |
|---|---|
| Component | Volume |
| Ng Suspension in GWM | 10 µL |
| MHB (media) | 75.5 µL |
| $NaHCO_3$ (100 mM) | 4.5 µL (4.5 mM) |
| 10X ABX (treated) or NF water in control (untreated) | 5 µL |
| NEB DNaseI (2000 U/mL) (degrader) | 5 µL (100 U/mL) |

Enhancement of accessibility after the primary incubation is done in this example with the surfactant CHAPS as the enhancer.

| Secondary Incubation: DNaseI digestion in the presence of enhancer (50 µL in PCR tubes) | |
|---|---|
| Component | Volume |
| Ng Suspension (from primary incubation) | 25 µL (50 U/mL DNaseI, 0.5X ABX, 2.5 mM $NaHCO_3$) |
| CHAPS (200 mM, 20X) (enhancer) | 2.5 µL (10 mM, 1X) |
| $NaHCO_3$ (100 mM) | 2.5 µL (2.5 mM) |
| NEB DNaseI (degrader) | 1.25 µL (50 U/mL) |
| MHB (media) | 18.75 µL |

Step 1 can be performed before or after steps 2-3, or in parallel with step 4 as will be understood by a person skilled in the art upon reading of the current disclosure.

2. Providing a sample containing bacteria ng_5, ng_17, and ng_19 are ceftriaxone-susceptible isolates and ng_30 is a ceftriaxone-reduced-susceptible isolate. (see the "Clinical Isolate MICs" table for *N. gonorrhoeae* for MICs in the General Methods).

The bacteria were prepared according to the "NG Stock and Resuspension" description in the General Methods section with the following changes: media (GWM). incubate on shaker (1000 rpm) in 37° C., 5% $CO_2$ incubator (120 minutes).

While cell pellet is re-suspending, the antibiotic exposure condition (everything except Ng suspension and ABX) was prepared (see table below), and the tubes were prewarmed on a thermocycler set to 37° C. so the liquid inside the tube reaches 37° C.

3. Optionally, pre-process the sample containing bacteria

OD600 (dilute 1/10 in media) was measured. OD of suspension was adjusted to OD=0.5 in pre-warmed MHB media+5 mM $NaHCO_3$ 4. Add the antibiotic Ceftriaxone (CRO) was prepared as follows. 1.0 mg/mL ceftriaxone stock was diluted, from −80° C. storage. 20× Stock prepared (1×1 µg/mL CRO→10 µg/mL=0.020 mg/mL CRO) in a 500 µL volume by mixing 10 µL (1.000 mg/mL stock)+490 µL NF water The antibiotic was then added to the corresponding exposure tubes setup in step 1.

5. Split the sample into two or more parts 10 uL of the Ng suspension (from step 3) was withdrawn into a pipette (following the chart for the primary exposure in step 1).

6. Combine sample with incubation media

The timer started and the Ng suspension was added. The time was recorded for Lab Notebook records. 10 uL of the Ng suspension was added into "treated" or "untreated" media; this addition can be performed sequentially or in parallel (using multichannel pipet).

7. Incubate the treated and untreated samples at a controlled temperature for a short amount of time. (15 minutes; primary incubation)

Close primary incubation tubes, spray with 70% EtOH
Vortex briefly (2-4 seconds)
Centrifuge to remove droplets from the caps
Spray with 70% EtOH
Transport the tubes to the thermocycler (set to 37° C.)

8. Dilution of treated and untreated samples into a secondary incubation for a short amount of time (5 minutes; secondary incubation)

The samples were mixed before transferring 25 μL of the sample to the prepared secondary incubation (enhancer) tubes. Follow the charts in step 1 to add the appropriate volume of cells to each tube.

Close tubes, spray with 70% EtOH
Vortex briefly
Centrifuge to remove droplets from the caps
Spray with 70% EtOH
Return to the thermocylcer for incubation at 37° C. (for 5 minutes)

9. Extraction (at 30 minutes) of treated and untreated samples to purify DNA

Extraction was performed by following "DEB Extraction" description in the general methods using PCR tubes, and then transferring 10 μL of the contents to 90 μL of the extraction buffer.

10. Measurement of DNA by qPCR qPCR mix was prepared as follows (see the "qPCR" protocol in the General Methods):

Primers were for the Ng 16S gene in each amplification
Samples were run in triplicate
35 cycles
Annealing temperature of 62° C.

Cqs measurements were used to calculate the CT ratio at each treated, untreated pair at the same conditions.

Figures 24A, 24B:
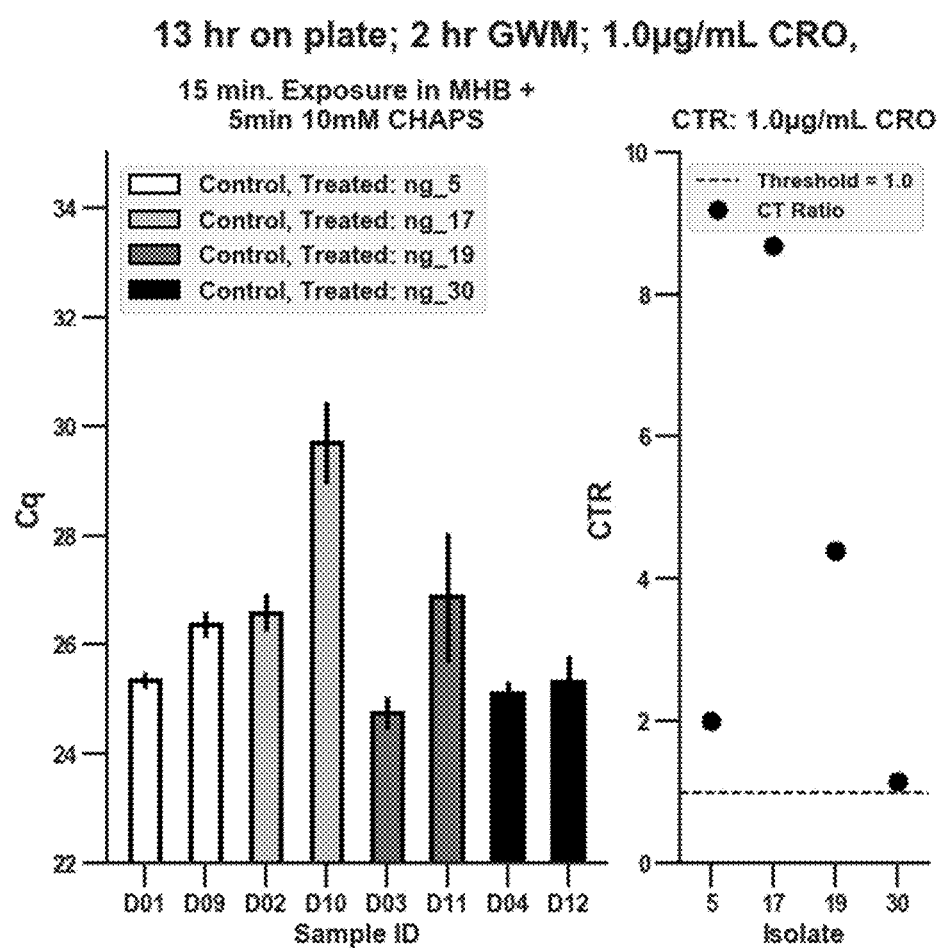
FIGS. 24A-24B show diagrams comparing the accessibility AST results for four isolates treated with 1 μg/mL ceftriaxone. Isolates ng_5, ng_17, and ng_19 are all susceptible to ceftriaxone, whereas, isolate ng_30 has reduced-susceptibility to ceftriaxone. The CT ratios can be used to differentiate between the antibiotic-susceptible (CT>1.5) and the antibiotic-resistant (CTR<1.5).

FIGS. 24A-24B compare the accessibility AST results for four isolates treated with 1 μg/mL ceftriaxone. Isolates ng_5, ng_17, and ng_19 are all susceptible to ceftriaxone, whereas, isolate ng_30 has reduced-susceptibility to ceftriaxone. The CT ratios can be used to differentiate between the antibiotic-susceptible (CT>1.5) and the antibiotic-resistant (CTR<1.5).

The results illustrate that a two-step incubation with a primary incubation of 15 min.±CRO and a secondary incubation with an enhancer of 10 mM CHAPS with DNaseI successfully differentiates between the CRO-susceptible and CRO-resistant isolates screened.

Example 12: AST Based on Nucleic Acid Accessibility, with 1-Step Incubation in Non-Lysing Conditions, Quantified Using Direct LAMP without Enhancer Present During Amplification AST was performed based on nucleic acid accessibility, with 1-step incubation in non-lysing conditions, quantified using direct LAMP without enhancer present during amplification In some embodiments, AST may be performed based on nucleic acid accessibility to polymerase during the nucleic acid amplification step. In some embodiments, antibiotic exposure is performed in non-lysing conditions. Bacteria can be added directly to the nucleic acid amplification mix after antibiotic exposure. In some embodiments, the nucleic acid amplification mix is not fully lysing. The nucleic acid amplification mix can contain RNase or reverse transcriptase.

In this example, the AST was performed following the steps below:

1. Provide a sample containing bacteria
   a. Isolates and antibiotics; in this example, AST was performed using ec_1, ec_4, ec_38, and ec_39, antibiotic used was ertapenem
   b. Cell resuspension; resuspended small clump of each isolate scraped from plate in 400 uL BHI (37° C.) in 2 mL screw cap polypropylene tubes by pipetting
   c. Cell growth; for each isolate added 20 uL of cell suspension to 2 mL BHI (37° C.) in 15 mL polypropylene falcon tubes, incubated with 500 rpm shaking at 37° C.+5% CO2 for ~4 hrs 2. Optionally, pre-process the sample containing bacteria
   d. Measurement of OD; diluted all cell suspensions 10× (60 uL into 540 uL pre-warmed BHI) in 1 cm path length polystyrene disposable cuvettes, measured OD at 600 nm using portable spectrophotometer (BioChrom cat. no. 80-2116-30), ODs listed below (corrected for 10× dilution), ec_1 OD=3.3, ec_4 OD=3.4, ec_38 OD=3.5, ec_39 OD=3.3
   e. Cell dilution; diluted starter cultures 150× (10 uL into 1.5 mL BHI), incubated with 500 rpm shaking at 37° C.+5% CO2 for 55 min 3. Provide non-lytic incubation media with and without antibiotic
   f. Preparation of exposure condition; prepared 100 uL of exposure conditions (not including cell suspension volume) with and without antibiotic according to list below in 8-tube PCR tube strips (USA Scientific 1402-2700); tubes were pre-warmed at 37° C.+5% CO2 for 6 min

| Component | Volume |
|---|---|
| MHB | 70 uL |
| ABX stock (20 ug/mL) | 2.5 uL |
| NF-H2O | 7.5 uL |
| Cell suspension | 20 uL |

4. Split the sample into two or more parts
   g. Cell transfer; transferred 150 uL of cell suspensions to appropriate tubes of 8-tube PCR tube strip so that transfer to exposure condition could be performed with multi-channel pipette 5. Combine sample with incubation media
   h. Transfer to exposure; used multi-channel pipette to transfer cell suspensions from 8-tube PCR tube strip into exposure condition tube strips, exposure PCR tube strips were closed, vortexed, quick spun, and transferred to pre-warmed thermocycler 6. Incubate the treated and untreated samples at a controlled temperature for a short amount of time
   i. Exposure; exposure performed at 37° C. on BioRad CT1000 thermocycler for 15 minutes 7. Provide amplification mix, optionally containing RNase or reverse transcriptase
   j. Prepared LAMP mix on ice according to the general protocol
   k. Prepared qPCR mix on ice according to the general protocol 8. Combine incubation media containing sample with amplification mixes
   l. Addition to LAMP mix; immediately after exposure, samples were added to LAMP mix (already aliquoted into plate and on ice) in triplicate using multichannel pipette m. Addition to qPCR mix; immediately after addition to LAMP mix, samples were added to qPCR mix (already aliquoted into plate and on ice) in triplicate using multichannel pipette
9. Quantify nucleic acids using qPCR and qLAMP
   n. LAMP was run on BioRad CFX96 instrument according to the general protocol
   o. qPCR was run on Roche LightCycler 96 instrument according to the general protocol
10. Analyze data and make susceptibility call
    p. Time-to-positive (TTP) for each sample is determined by setting an amplification threshold and determining the time at which the amplification curve of each sample crosses this threshold. The average TTP for each sample is then determined.
    q. The average TTPs of the treated sample is then subtracted from the average TTP of the control sample to determine a TTP Difference value. If this value is greater than the pre-determined threshold for the organism/antibiotic combination being tested, the sample is susceptible. If the value is smaller than the pre-determined threshold then the sample is resistant.

Figure 25:
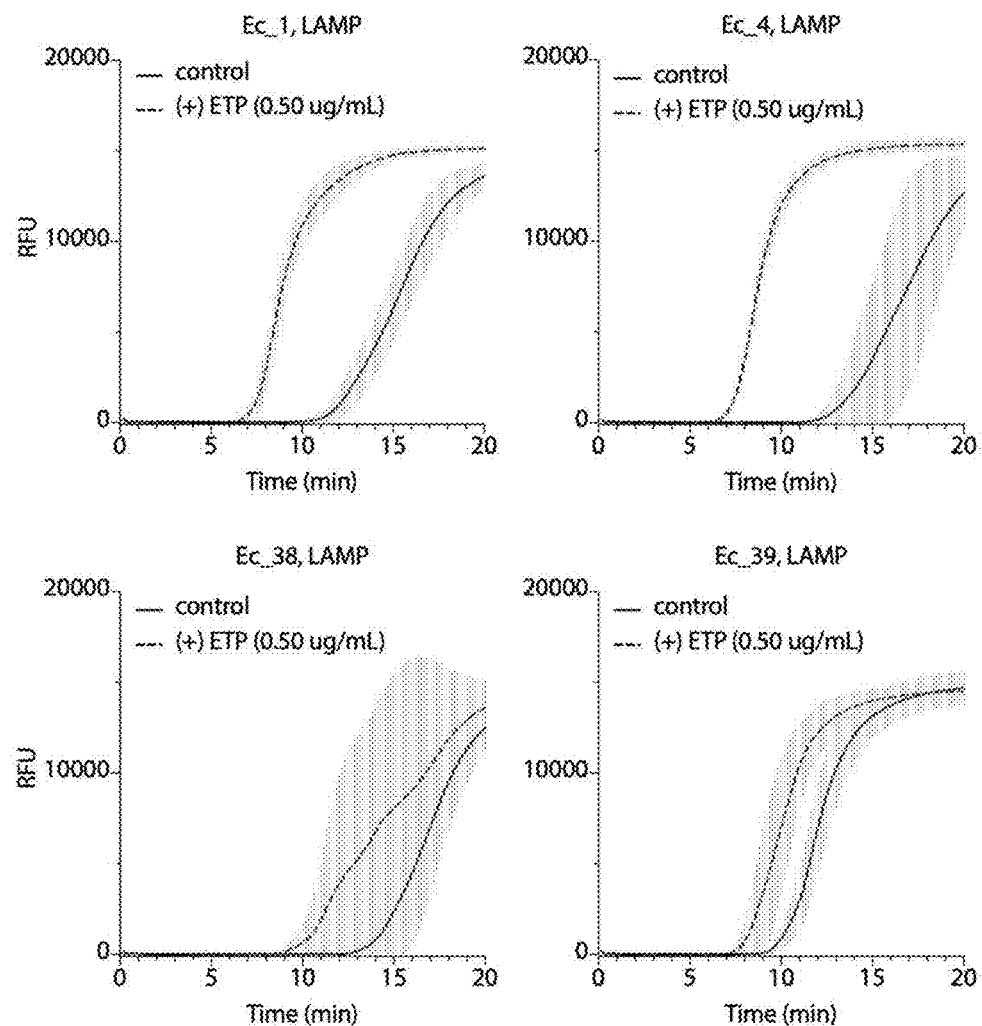
FIG. 25 shows LAMP amplification curves for four isolates as described in Example 12.
Figure 26:
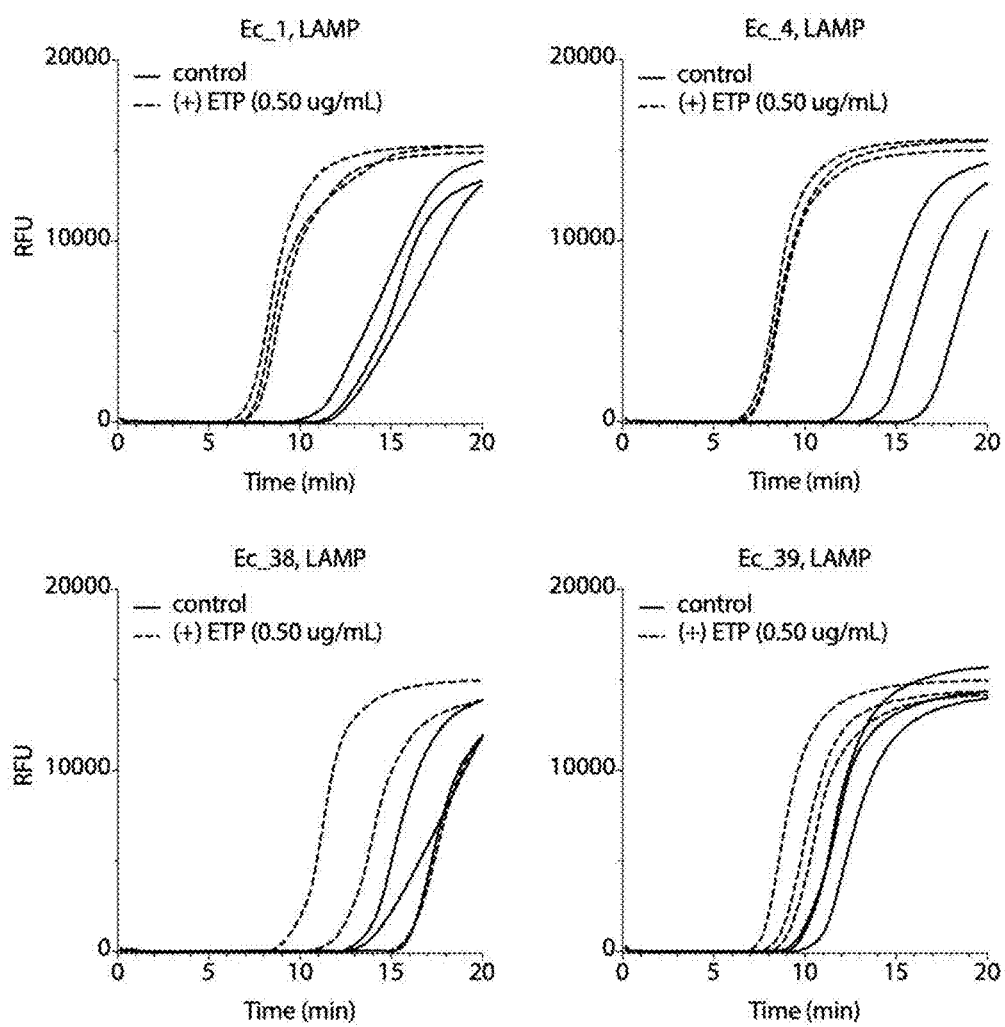
FIG. 26 shows individual LAMP amplification curves for each sample as described in Example 12.

FIGS. 25-26 represents the average control (solid lines) and average treated (dashed lines). FIG. 25 shows LAMP amplification curves for four isolates. Gray error bars represent standard deviation of triplicate samples for each time point where fluorescence was measured. The individual LAMP amplification curves for each sample are plotted in FIG. 26. LAMP can be performed without enhancer present during amplification. The control and treated curves can be used for comparison. LAMP is not a fully lytic amplification method and therefore when amplification occurs depends on the accessibility of template NA molecules (NA=DNA+RNA). In susceptible isolates (top two plots in FIG. 25), the sample treated with antibiotic amplifies earlier because NAs are more accessible.

Figure 27:
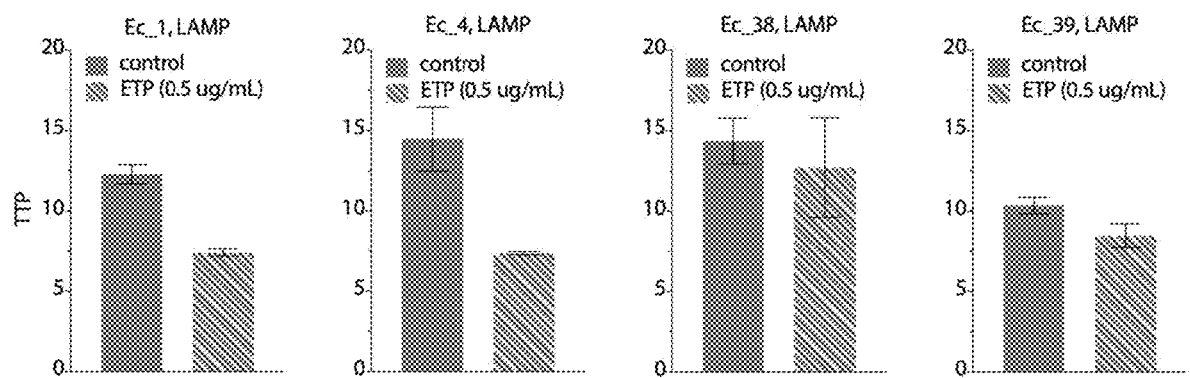
FIG. 27 shows diagrams illustrating the average time-to-positive for LAMP amplification for each sample as described in Example 12.

FIG. 27 represents the average time-to-positive for LAMP amplification for each sample as determined from setting an amplification threshold and measuring the time at which the amplification curve crosses the threshold. In susceptible isolates (left two plots), the sample treated with antibiotic amplifies earlier because NAs are more accessible. This results in a larger difference between the average TTP of the control and treated samples than observed in samples resistant to the antibiotic (right two plots).

Figure 28:
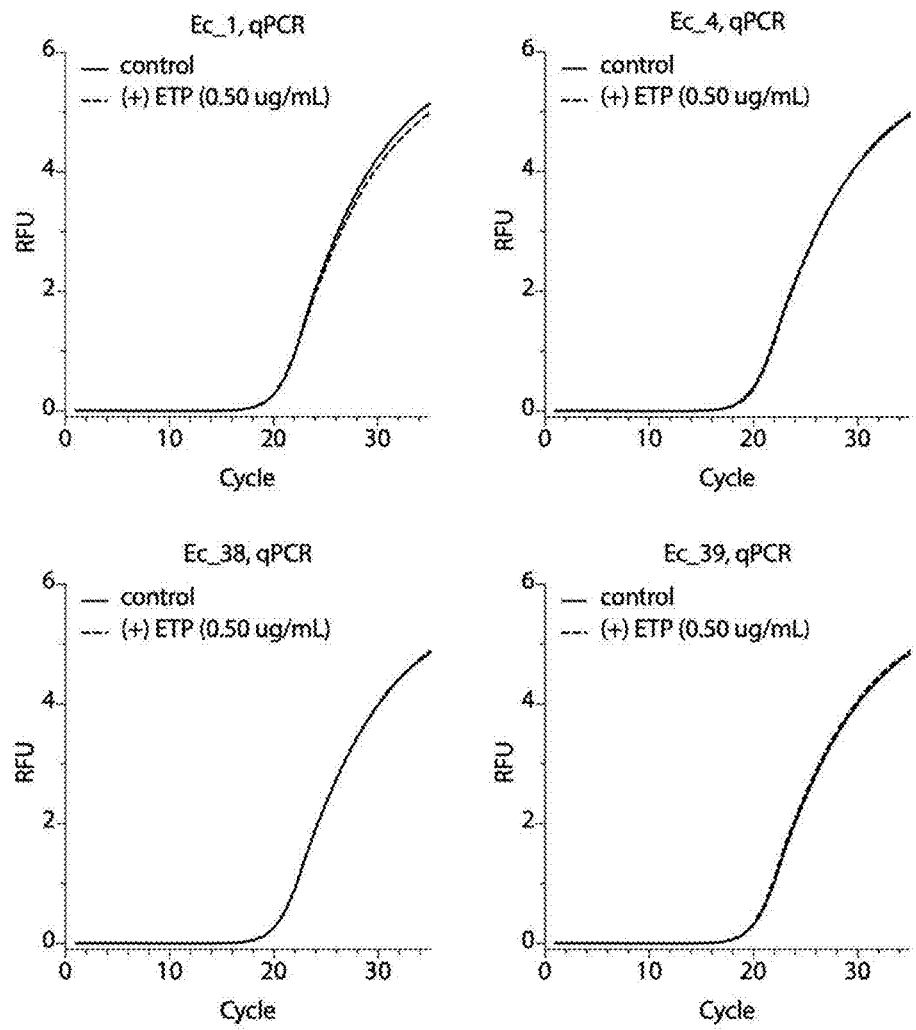
FIG. 28 shows the average control (solid lines) and treated (dashed lines) PCR amplification curves for four isolates.

FIG. 28 represents the average control (solid lines) and treated (dashed lines) PCR amplification curves for four isolates. The control and treated can be used for comparison. PCR is a lytic amplification method and therefore when amplification occurs does not depend on accessibility of template NA molecules (NA=DNA+RNA).

Figure 29:
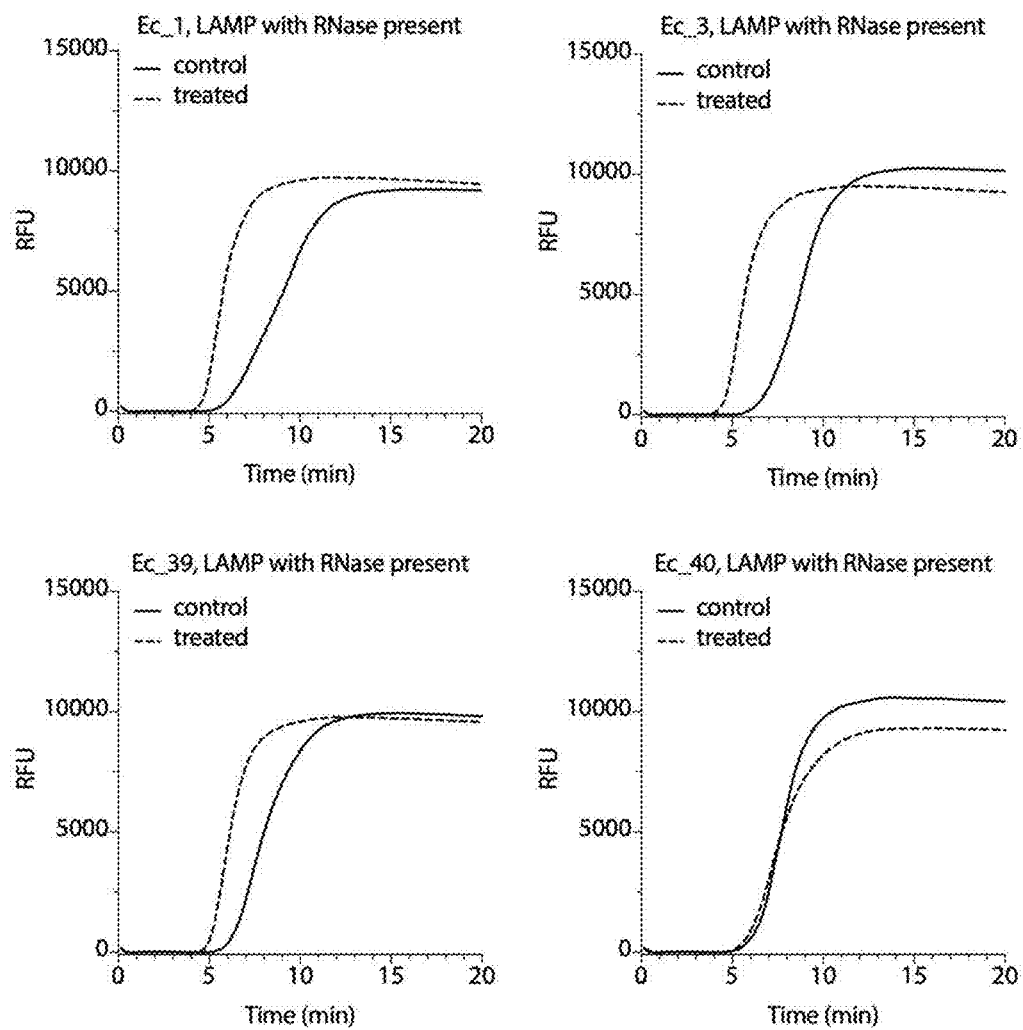
FIG. 29 shows the average control (solid lines) and treated (dashed lines) LAMP amplification curves for four isolates with RNase present.

FIG. 29 represents the average control (solid lines) and treated (dashed lines) LAMP amplification curves for four isolates. LAMP can be performed with RNase present during amplification to degrade RNA (as shown in this figure). The control and treated curves can be used for comparison. LAMP is not a fully lytic amplification method and therefore when amplification occurs depends on the accessibility of template NA molecules (NA=DNA+RNA). In susceptible isolates (top two plots), the sample treated with antibiotic amplifies earlier because NAs are more accessible.

Figure 30:
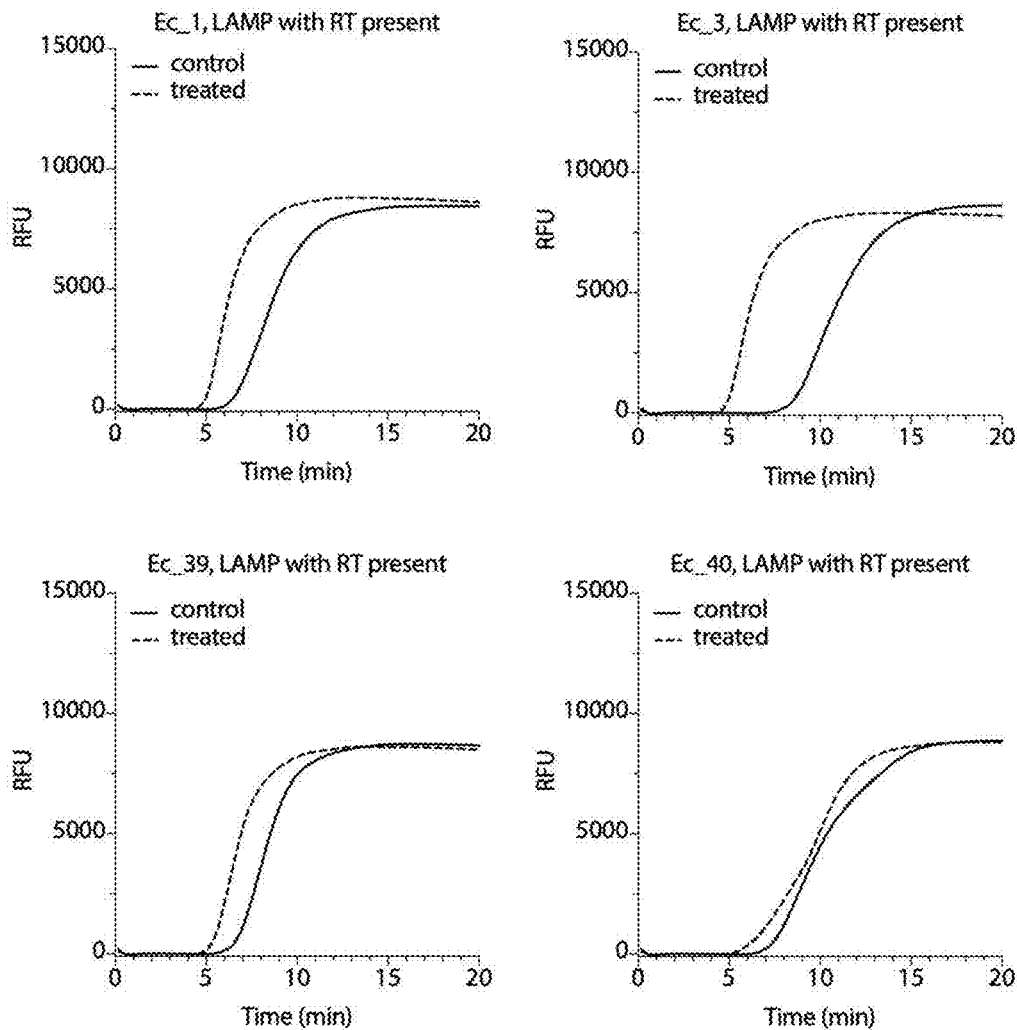
FIG. 30 shows the average control (solid lines) and treated (dashed lines) LAMP amplification curves for four isolates with RT present.

FIG. 30 represents the average control (solid lines) and treated (dashed lines) LAMP amplification curves for four isolates. LAMP can be performed with reverse transcriptase (RT) present during amplification to reverse transcribe RNA into DNA, which is then amplified using LAMP (as shown in this figure). The control and treated curves can be used for comparison. LAMP is not a fully lytic amplification method and therefore when amplification occurs depends on the accessibility of template NA molecules (NA=DNA+RNA). In susceptible isolates (top two plots), the sample treated with antibiotic amplifies earlier because NAs are more accessible.

The results illustrated in this example support the conclusion that AST may be performed based on nucleic acid accessibility to polymerase during the nucleic acid amplification step. This is observed in FIG. 27, showing that the magnitude of the difference in TTP between the control and treated samples correctly predicts ETP susceptibility or resistance after 15 minutes of ETP exposure.

Example 13: AST Based on Nucleic Acid Accessibility, with Enhancer Present During Incubation, Quantified Using Direct LAMP without Enhancer Present During Amplification In this example, AST is performed based on nucleic acid accessibility with enhancer present during incubation, quantified using direct LAMP without enhancer present during amplification. Antibiotic exposure can be performed in the presence of an enhancer. Bacteria can be added directly to the nucleic acid amplification mix after antibiotic exposure. The nucleic acid amplification mix can be selectively lysing.

In this example, the AST was performed following the steps below:

1. Provide a sample containing bacteria

AST was performed using ec_2, ec_3, ec_40, and ec_41, antibiotic used was ertapenem. Small clump of each isolate scraped from plate was resuspended in 400 uL BHI (37° C.) in 2 mL screw cap polypropylene tubes by pipetting. For each isolate, 20 uL of cell suspension was added to 2 mL BHI (37° C.) in 15 mL polypropylene falcon tubes, and incubated with 500 rpm shaking at 37° C.+5% CO2 for ~4 hrs 2. Optionally, pre-process the sample containing bacteria All cell suspensions were diluted 10× (60 uL into 540 uL pre-warmed BHI) in 1 cm path length polystyrene disposable cuvettes, OD was measured at 600 nm using portable spectrophotometer (BioChrom cat. no. 80-2116-30), ODs listed below (corrected for 10× dilution), ec_2 OD=3.6, ec_3 OD=3.3, ec_40 OD=3.5, ec_41 OD=3.7.

Starter cultures were diluted 150× (10 uL into 1.5 mL BHI), incubated with 500 rpm shaking at 37° C.+5% CO2 while preparing initial exposure conditions, secondary exposure conditions, and LAMP mix (60 min)

3. Provide non-lytic incubation media with and without antibiotic 100 uL of exposure condition (not including cell suspension volume) was prepared according to list below in 8-tube PCR tube strips (USA Scientific 1402-2700); tubes were pre-warmed at 37° C.+5% CO2 for 6 min

| Component | Volume |
|---|---|
| MHB | 70 uL |
| ABX stock (40 ug/mL) | 2.5 uL |
| NF-H2O | 7.5 uL |
| Cell suspension | 20 uL |

4. Optionally provide lytic incubation media 100 uL of exposure condition (not including cell suspension volume) was prepared according to list below in 8-tube PCR tube strips (USA Scientific 1402-2700); tubes were pre-warmed at 37° C.+5% CO2 for 6 min

| Component | Volume |
|---|---|
| MHB | 70 uL |
| CHAPS (100 mM) | 20 uL |
| NF-H2O | 10 uL |

5. Split the sample into two or more parts 150 uL of cell suspensions were transferred to appropriate tubes of 8-tube PCR tube strip so that transfer to initial exposure condition could be performed with multi-channel pipette.

6. Combine sample with non-lytic incubation media

Multi-channel pipette was used to transfer cell suspensions from 8-tube PCR tube strip into initial exposure condition tube strips. Initial exposure PCR tube strips were closed, vortexed, quick spun, and transferred to pre-warmed thermocycler.

7. Incubate the treated and untreated samples at a controlled temperature for a short amount of time Antibiotic exposure was performed at 37° C. on BioRad CT1000 thermocycler for 15 min.

8. Optionally combine sample with lytic incubation media 20 uL of all samples was transferred to incubation media containing enhancer, samples were vortexed and quick spun.

9. Incubate the treated and untreated samples at a controlled temperature for a short amount of time Exposure was performed at 37° C. on BioRad CT1000 thermocycler for 5 min.

10. Provide amplification mix

LAMP mix was prepared on ice according to general protocol

11. Combine incubation media containing sample with amplification mixes

Immediately after exposure, samples were added to LAMP mix (already aliquoted into plate and on ice) in triplicate using multichannel pipette.

12. Quantify nucleic acids using qLAMP

LAMP was run on BioRad CFX96 instrument according to general protocol

Figure 31:
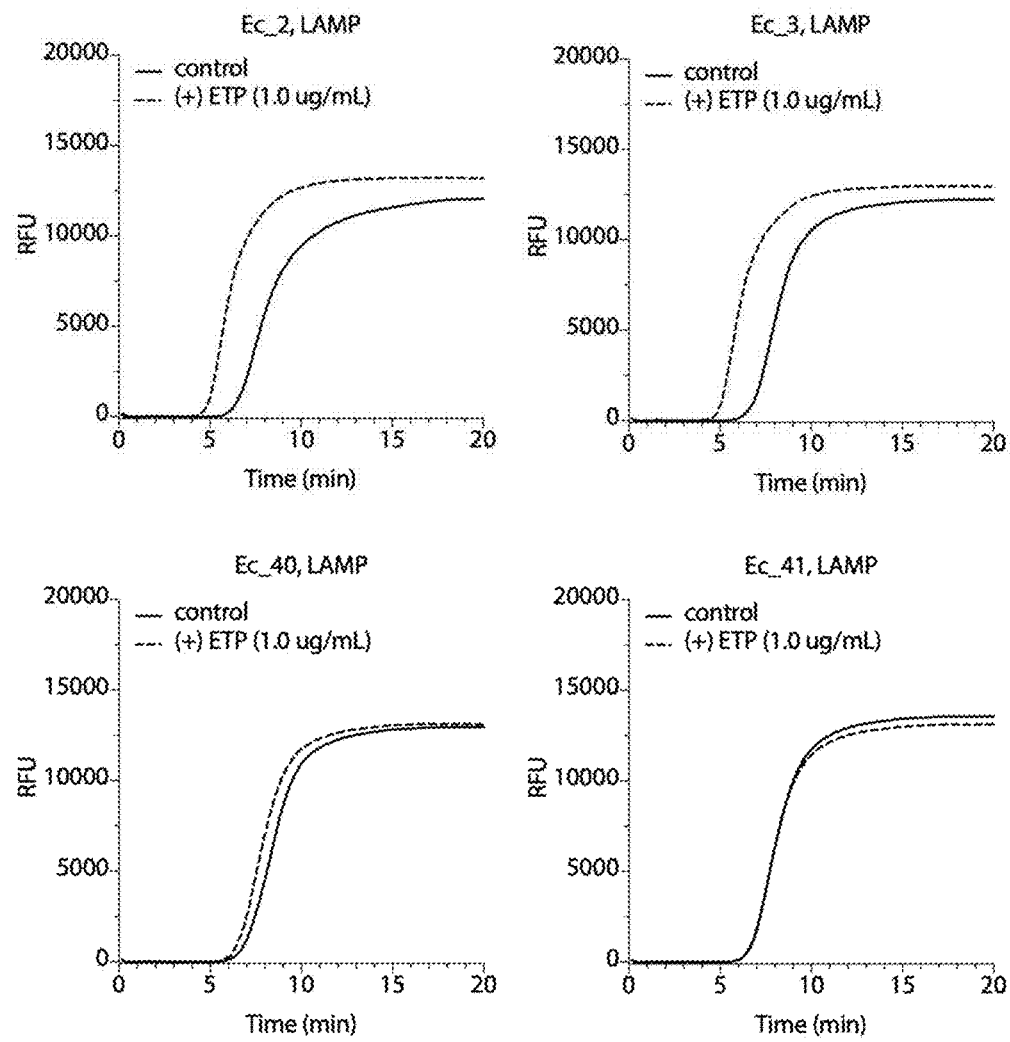
FIG. 31 shows average control (solid lines) and treated (dashed lines) LAMP amplification curves for four isolates as described in Example 13.

FIG. 31 represents the average control (solid lines) and treated (dashed lines) LAMP amplification curves for four isolates. Incubation can be performed with enhancer present. LAMP can be performed without enhancer present during amplification. The control and treated curves can be used for comparison. LAMP is not a fully lytic amplification method and therefore when amplification occurs depends on the accessibility of template NA molecules (NA=DNA+RNA). In susceptible isolates (top two plots), the sample treated with antibiotic amplifies earlier because NAs are more accessible.

Figure 32:
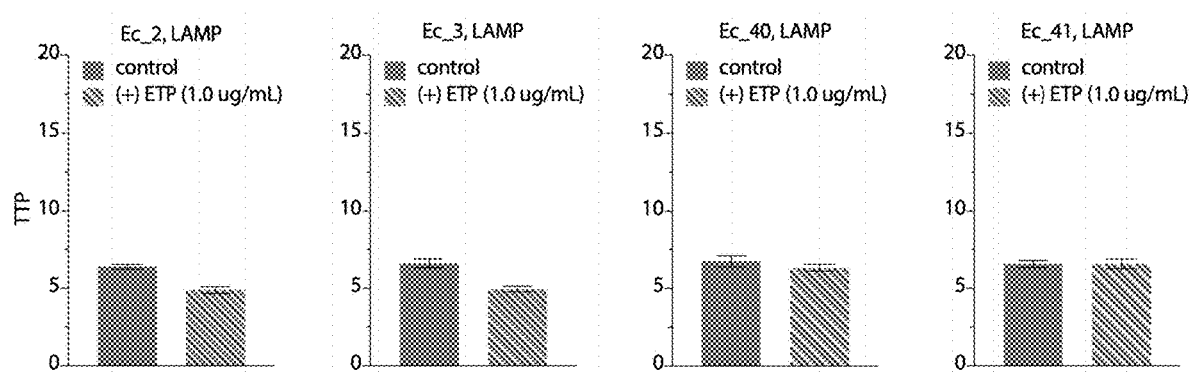
FIG. 32 shows diagrams illustrating the average time-to-positive for LAMP amplification as described in Example 13.

FIG. 32 represents the average time-to-positive for LAMP amplification as determined from setting an amplification threshold and measuring the time at which the amplification curve crosses the threshold. In susceptible isolates (left two plots), the sample treated with antibiotic amplifies earlier because NAs are more accessible. This results in a larger difference between the average TTP of the control and treated samples than observed in samples resistant to the antibiotic (right two plots).

The results illustrated in this example support the conclusion that AST may be performed based on nucleic acid accessibility to polymerase during the nucleic acid amplification step. This is observed in FIG. 32, showing that the magnitude of the difference in TTP between the control and treated samples correctly predicts ETP susceptibility or resistance after 15 minutes of ETP exposure. FIG. 31 also shows that susceptible samples treated with antibiotic amplify earlier relative to their controls than resistant samples.

Example 14: AST Based on Nucleic Acid Accessibility, with 1-Step Incubation in Non-Lysing Conditions Followed by Filtering, Quantified Using Direct LAMP without Enhancer Present During Amplification In this example, AST was performed based on nucleic acid accessibility, with 1-step incubation in non-lysing conditions followed by filtering, quantified using direct LAMP without enhancer present during amplification.

Antibiotic exposure is performed in non-lysing conditions. AST may be performed based on NA release during the incubation step. Samples can be filtered after antibiotic exposure to select for released NAs. Eluate from filtration can be added directly to the nucleic acid amplification mix after antibiotic exposure. Bulk qualitative, semi-quantitative, or quantitative NA quantification methods can be used to determine susceptibility based on stochasticity of replicate samples.

In this example, the AST was performed following the steps below:

1. Provide a sample containing bacteria

AST was performed using ec_2, ec_3, ec_40, and ec_41, antibiotic used was ertapenem. Small clump of each isolate scraped from plate was resuspended in 400 uL BHI (37° C.) in 2 mL screw cap polypropylene tubes by pipetting. For each isolate, 20 uL of cell suspension was added to 2 mL BHI (37° C.) in 15 mL polypropylene falcon tubes, incubated with 500 rpm shaking at 37+5% CO2 for ~4 hrs 2. Optionally, pre-process the sample containing bacteria All cell suspensions were diluted 10× (60 uL into 540 uL pre-warmed BHI) in 1 cm path length polystyrene disposable cuvettes, OD was measured at 600 nm using portable spectrophotometer (BioChrom cat. no. 80-2116-30), ODs listed below (corrected for 10× dilution), ec_2 OD=4.3, ec_3 OD=3.8, ec_40 OD=3.3, ec_41 OD=4.0. Starter cultures were diluted 150× (10 uL into 1.5 mL BHI), incubated with 500 rpm shaking at 37° C.+5% CO2 while preparing initial exposure conditions, secondary exposure conditions, and LAMP mix (60 min)

3. Provide non-lytic incubation media with and without antibiotic 100 uL of exposure condition (not including cell suspension volume) was prepared according to list below in 8-tube PCR tube strips (USA Scientific 1402-2700); tubes were pre-warmed at 37° C.+5% CO2 for 5 min

| Component | Volume |
|---|---|
| MHB | 70 uL |
| ABX stock (40 ug/mL) | 2.5 uL |
| NF-H2O | 7.5 uL |
| Cell suspension | 20 uL |

4. Split the sample into two or more parts 150 uL of cell suspensions was transferred to appropriate tubes of 8-tube PCR tube strip so that transfer to initial exposure condition could be performed with multi-channel pipette 5. Combine sample with incubation media Multi-channel pipette was used to transfer cell suspensions from 8-tube PCR tube strip into initial exposure condition tube strips, initial exposure PCR tube strips were closed, vortexed, quick spun, and transferred to pre-warmed thermocycler 6. Incubate the treated and untreated samples at a controlled temperature for a short amount of time Exposure was performed at 37° C. on BioRad CT1000 thermocycler for 15 min.

Figure 33:
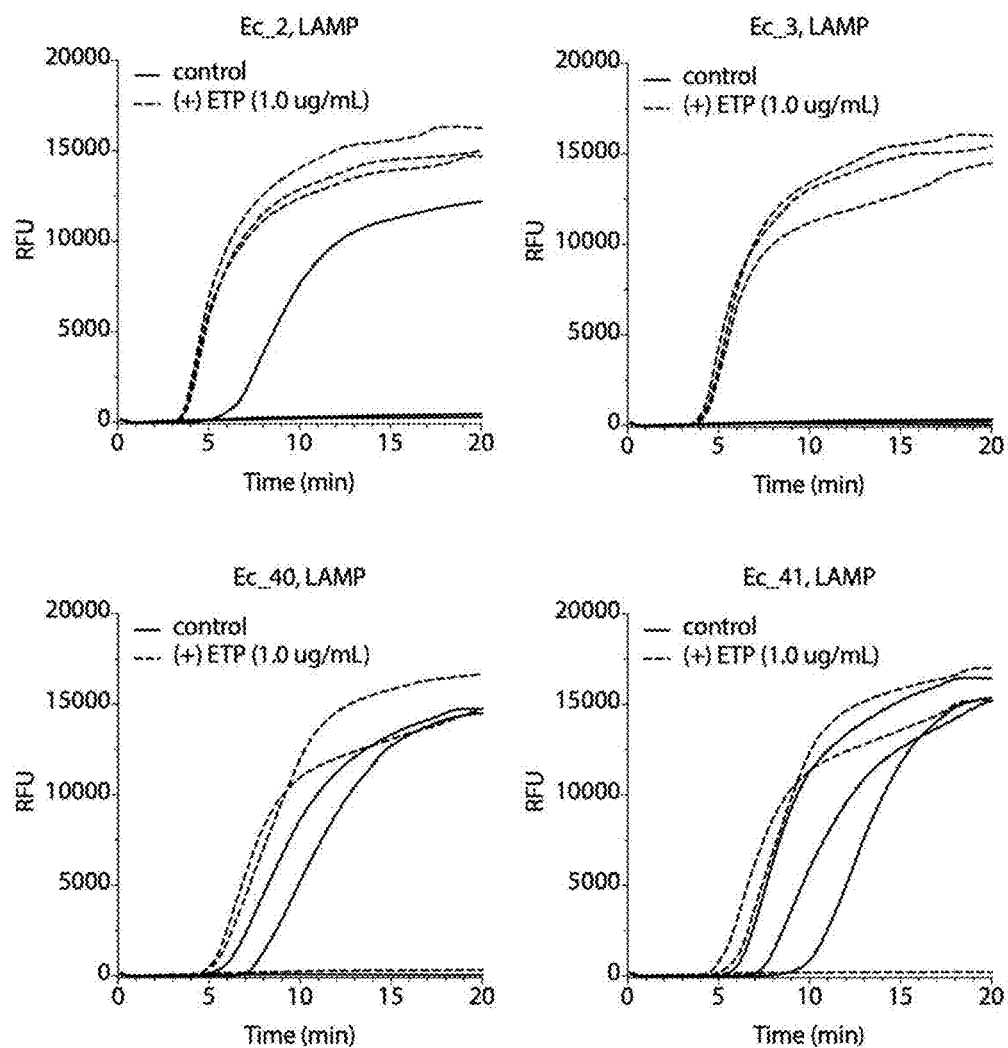
FIG. 33 shows triplicate control (solid lines) and triplicate treated (dashed lines) LAMP amplification curves for four isolates as described in Example 14.

7. Filtration; immediately after initial exposure samples were filtered through 0.2 uM cellulose acetate filters 40 uL of each sample was added to center of Costar Spin-X 0.22 uM cellulose acetate centrifuge filter (Sigma cat no. 8160, lot no. 08218000) using adjustable-width multi-channel pipette. All samples were centrifuged at 1000 rcf for 30 sec in aerosol-tight benchtop centrifuge 8. Provide amplification mix LAMP mix was prepared on ice according to general protocol 9. Combine filter eluate with amplification mix Immediately after filtration, samples were added to LAMP mix (already aliquoted into plate and on ice) in triplicate using multichannel pipette 10. Quantify nucleic acids using qLAMP LAMP was run on BioRad CFX96 instrument according to general protocol FIG. 33 represents triplicate control (solid lines) and triplicate treated (dashed lines) LAMP amplification curves for four isolates. The control and treated curves can be used for comparison. The number of treated replicates that amplify can also be used for comparison. Because the samples are filtered, only NAs that have been released during sample incubation will be amplified. In susceptible isolates (top two plots), the sample treated with antibiotic shows more replicates amplifying because more NAs have been released during sample incubation.

As shown in this example, bulk qualitative, semi-quantitative, or quantitative NA quantification methods can be used to determine susceptibility based on stochasticity of replicate samples. This is observed in FIG. 33, showing that the number of replicate bulk LAMP samples that amplify can correctly predict ETP susceptibility or resistance after 15 minutes of exposure to ETP and filtration of samples.

Example 15: AST Based on Percentage of NAs Released During Incubation, Quantified Using Digital Nucleic Acid Amplification In this example, AST was performed based on percentage of NAs released during incubation, quantified using digital nucleic acid amplification.

AST can be performed based on measurement DNA release during incubation with antibiotics. AST can be performed based on measurement RNA release during incubation with antibiotics. Incubation can be performed in the presence of an enhancer.

In this example, the AST was performed following the steps below:

1. Provide a sample containing bacteria

AST was performed using ec_4, ec_39, antibiotic used was ertapenem. Small clump of each isolate scraped from plate was resuspended in 400 uL BHI (37° C.) in 2 mL screw cap polypropylene tubes by pipetting. For each isolate, 20 uL of cell suspension was added to 2 mL BHI (37° C.) in 15 mL polypropylene falcon tubes, incubated with 500 rpm shaking at 37° C.+5% CO2 for ~3 hrs 2. Optionally, pre-process the sample containing bacteria All cell suspensions was diluted 10× (60 uL into 540 uL pre-warmed BHI) in 1 cm path length polystyrene disposable cuvettes, OD measured at 600 nm using portable spectrophotometer (BioChrom cat. no. 80-2116-30), ODs listed below (corrected for 10× dilution), ec_4 OD=2.7, ec_39 OD=2.6. Starter cultures was diluted 150× (10 uL into 1.5 mL BHI), incubated with 500 rpm shaking at 37° C.+5% CO2 while preparing initial exposure conditions (40 min)

3. Provide non-lytic incubation media with and without antibiotic 100 uL of exposure condition (not including cell suspension volume) was prepared according to list below in 8-tube PCR tube strips (USA Scientific 1402-2700); tubes were pre-warmed at 37° C.+5% CO2 for 6 min

| Component | Volume |
| --- | --- |
| BHI | 70 uL |
| ETP (10 ug/mL) | 10 uL |
| Cell suspension | 20 uL |

4. Optionally provide lytic incubation media 100 uL of exposure condition (not including cell suspension volume) was prepared according to list below in 8-tube PCR tube strips (USA Scientific 1402-2700); tubes were pre-warmed at 37° C.+5% CO2 for 20 min

| Component | Volume |
| --- | --- |
| BHI | 55 uL |
| TNP (50 mM) | 10 uL |
| ETP (10 ug/mL) | 10 uL |
| NF-H2O | 5 |
| Sample from initial exposure | 20 uL |

5. Split the sample into two or more parts 150 uL of cell suspensions was transferred to appropriate tubes of 8-tube PCR tube strip so that transfer to initial exposure condition could be performed with multi-channel pipette.

6. Combine sample with non-lytic incubation media

Multi-channel pipette was used to transfer cell suspensions from 8-tube PCR tube strip into initial exposure condition tube strips, initial exposure PCR tube strips were closed, vortexed, quick spun, and transferred to pre-warmed thermocycler 7. Incubate the treated and untreated samples at a controlled temperature for a short amount of time Exposure was performed at 37° C. on BioRad CT1000 thermocycler for 15 min.

8. Optionally combine sample with lytic incubation media 20 uL of all samples was transferred to incubation media containing enhancer, samples were vortexed and quick spun 9. Incubate the treated and untreated samples at a controlled temperature for a short amount of time Exposure was performed at 37° C. on BioRad CT1000 thermocycler for 5 min.

10. Filtration; immediately after initial exposure samples were filtered through 0.2 uM cellulose acetate filters 40 uL of each sample was added to center of Costar Spin-X 0.22 uM cellulose acetate centrifuge filter (Sigma cat no. 8160, lot no. 08218000) using adjustable-width multichannel pipette. All samples were centrifuged at 1000 rcf for 1 minute in aerosol-tight benchtop centrifuge 11. Quantify nucleic acids using digital nucleic acid quantification DNA was quantified using ddPCR according to the general protocol. RNA was quantified using RT-ddPCR according to the general protocol.

Figure 34:
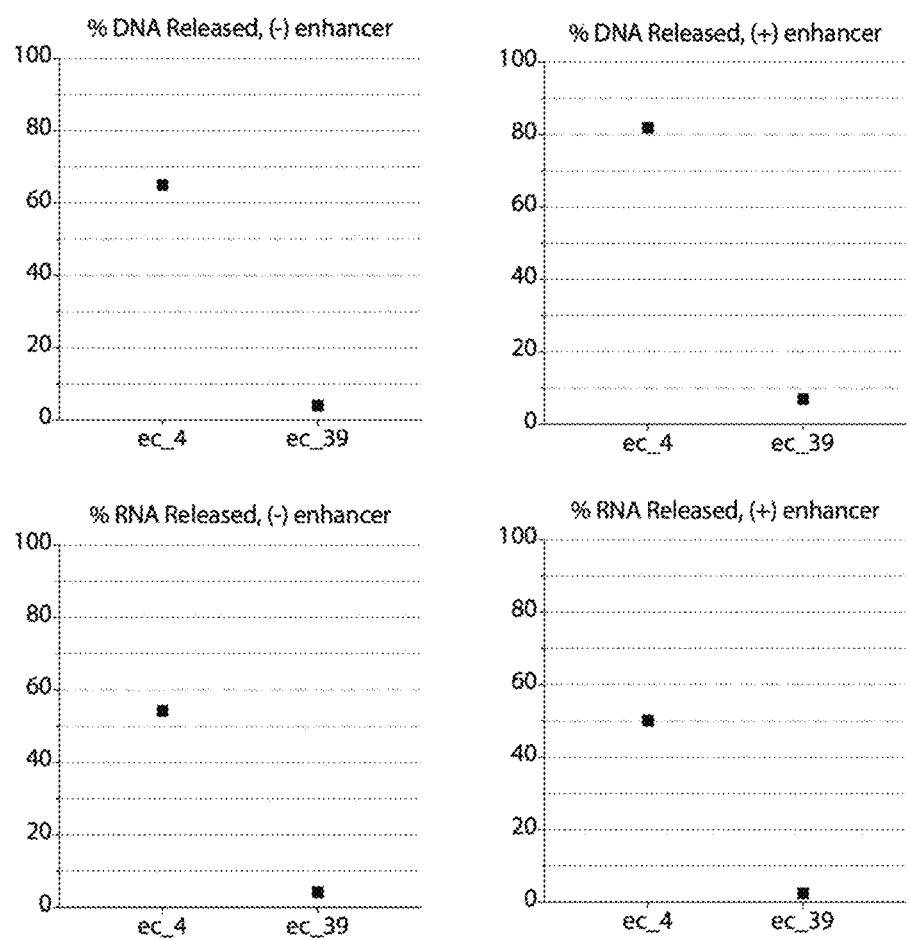
FIG. 34 shows diagrams illustrating the percentage of DNA (top two plots) and RNA (bottom two plots) released after a 15 minutes incubation with ertapenem. The percentages were calculated relative to the total DNA and RNA concentration respectively.

FIG. 34 represents the percentage of DNA (top two plots) and RNA (bottom two plots) released after a 15 minute incubation with ertapenem. A second incubation can be performed with enhancer present. DNA and RNA concentration before and after filtration is determined using digital nucleic acid quantification and can be used to determine percentage of NAs released after incubation with antibiotic or after optional additional incubation with enhancer (percentage is calculated by dividing the DNA in the eluate by the total DNA or by dividing the RNA in the eluate by the total RNA). In susceptible isolates, a significantly larger percentage of NAs is released as a result of antibiotic exposure.

As shown FIG. 34 (top two plots), the percentage of DNA released (calculated relative to the total DNA concentration) correctly predicts susceptibility to ETP after 15 min of ertapenem exposure. As shown in FIG. 34 (bottom two plots), the percentage of RNA released (calculated relative to the total RNA concentration) also correctly predicts susceptibility to ETP after 15 min of ertapenem exposure.

Example 16: AST Performed with the Use of Sonication to Enhance Accessibility Differences Caused by Ertapenem Antibiotics in E. coli This example uses sonication to increase the fraction of accessible bacterial genomes and filtration to decrease the amplification of inaccessible bacterial genomes and increase the difference between antibiotic-treated and antibiotic-untreated samples. The latter quantity is used to determine susceptibility in our AST method. The organism used in this example is the K12 MG1655 laboratory strain of *Escherichia coli*, which is a member of the Enterobacteriaceae and the same species as pathogenic *Escherichia coli*. Ertapenem is a representative carbapenem antibiotic used in current clinical practice.

In this example, the AST was performed following the steps below.
1. Obtain a log phase culture of *E. coli* at an optical density (OD) between 0.3 and 0.6, then dilute the culture to $5 \times 10^7$ colony forming units (CFU) per mL. This diluted culture will be tube A.
2. Prepare four exposure solutions, "B1" through "B4", comprising
    a. 65% rich bacteria growth medium (such as Brain Heart Infusion medium) in molecular biology-grade water
    b. A final concentration of 0 (for B1-B2) or 1 ug/mL (for B3-B4) of beta-lactam antibiotic. Here, ertapenem was used.
3. Spike into tube "A" a known amount of DNA molecules "L" with identical sequences and whose sequences are not found in bacterial genomes, such as commercially available lambda phage DNA. The extracellular "L" molecules serve as a control to detect errors in volumetric pipette measurements in subsequent steps. Mix tube A well.
4. Start a timer. Using a multichannel pipette, add 10 uL of tube A to each of tubes B1 through B4, noting the time of addition. Incubate tubes B1-4 at 37 Celsius.
5. After 15 minutes of incubation, sonicate tubes B2 and B4. Sonicate for 10 seconds with a peak power of 15 Watt, a duty cycle of 0.1, and a frequency of 50 cycles/burst.
6. Immediately after sonication (preferably no more than 20 minutes after the addition of A to B1-4), pass 50 uL of each of tubes B1-4 through a 0.2 micron cellulose acetate filter. This can be done by centrifuging the filters at 500 to 1000 relative centrifugal forces (rcf). Collect the filtrate for each of tubes B1-4 and call these tubes C1-C4.
7. Measure the concentrations of *E. coli* DNA and the spike-in DNA control in tubes B1-4 and C1-4 by performing ddPCR reactions with primers for a single-copy *E. coli* gene (e.g. uidA) or for the spike-in control.
8. Choose the spike-in control concentration of one of the tubes to be the standard control concentration. Then, normalize the concentration of *E. coli* DNA in a given tube by dividing the *E. coli* concentration by the amount of spike-in then multiplying by the standard control concentration.
9. Lastly, calculate the fraction of DNA that was released by antibiotic by dividing the normalized *E. coli* DNA concentration in the filtrate tubes (C1-4) by the normalized *E. coli* DNA concentrations in the corresponding feed tubes B1-4.

Figure 35:
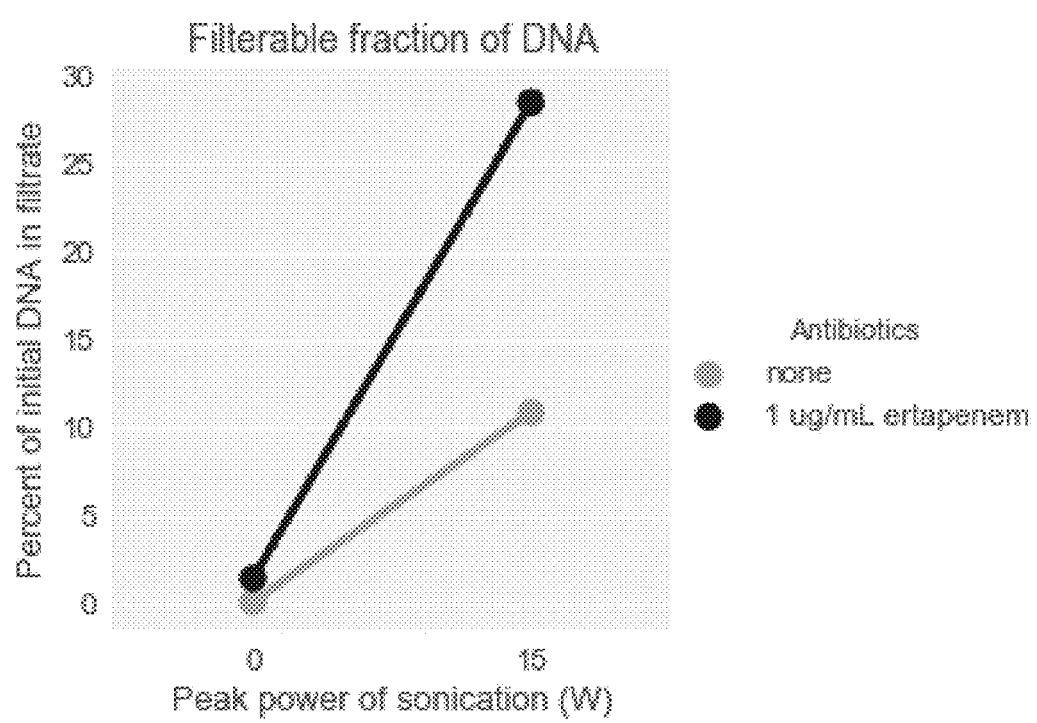
FIG. 35 shows, for one *E. coli* strain, percentages of DNA detected by dPCR after filtration. The percentage was calculated relative to the total DNA concentration. The filtration was performed on four samples that underwent different exposure conditions, as described in Example 16.

The above protocol was performed with *Escherichia coli* K12 MG1655 and a lambda DNA control from New England Biolabs. The results are shown in FIG. 35.

In this experimental design, only DNA that has been released from the cell cytoplasm upon lysis of the cell will be recovered after filtration. The strain used is susceptible to the concentration of ertapenem used. On the left column, where peak sonication power was 0 watt because sonication was not performed, the percentage of DNA released is less than the percentage released when sonication at a peak power of 15 watt occurred (right column). The percentages released are less than 90% and leave enough un-released DNA for a difference between antibiotic conditions to be measurable by the read-out method. The preceding characteristics indicate that sonication acted as an enhancing treatment. The combination of antibiotic exposure followed by sonication yielded an amount of DNA release that is greater than the sum of the release following antibiotic exposure alone and following sonication alone. This indicates that sonication increases the magnitude of the difference between an antibiotic-treated sample and a reference sample not treated with antibiotics.

Example 17: AST Performed Using Heating, Sonication or Detergent to Increase the Fraction of Bacterial Genomes Released after 15 Minutes of Beta-Lactam Action In this example, AST was performed using heating (or pasteurization), sonication, or detergent exposure to increase the fraction of accessible bacterial genomes. This example also describes the use of filtration to decrease the amplification of inaccessible bacterial genomes and increase the difference between antibiotic-treated and antibiotic-untreated samples. The latter quantity is used to determine susceptibility in the AST method. The organism used in this example is the K12 MG1655 laboratory strain of *Escherichia coli*, which is a member of the Enterobacteriaceae and the same species as pathogenic *Escherichia coli*. Ertapenem is a representative carbapenem antibiotic used in current clinical practice.

The example was performed according to the following steps:

1. Obtain a log phase culture of *E. coli* at an optical density (OD) between 0.3 and 0.6, then dilute the culture to 5×10^7 colony forming units (CFU) per mL. This diluted culture will be tube A.
2. Prepare six exposure solutions as follows:

| Tube Name | B1 | B2 | B3 | B4 | B5 | B6 |
|---|---|---|---|---|---|---|
| Brain Heart Infusion broth | 65% by volume in water | 65% by volume in water | 65% by volume in water | 65% by volume in water | 65% by volume in water | 65% by volume in water |
| ertapenem | | 1.0 ug/mL | | 1.0 ug/mL | | 1.0 ug/mL |
| Molecular biology grade water | Fill to 90 uL | Fill to 90 uL | Fill to 90 uL | Fill to 90 uL | Fill to 90 uL | Fill to 90 uL |

3. Prepare six perturbation solutions as follows:

| Tube Name | C1 | C2 | C3 | C4 | C5 | C6 |
|---|---|---|---|---|---|---|
| Tris pH 7.0 | 50 mM | 50 mM | | | | |
| Brain Heart Infusion broth | | | 65% by volume in water | 65% by volume in water | 65% by volume in water | 65% by volume in water |
| Tergitol NP 10 | | | | | 5 mM | 5 mM |
| Molecular biology grade water | Fill to 90 uL | Fill to 90 uL | Fill to 90 uL | Fill to 90 uL | Fill to 90 uL | Fill to 90 uL |

4. Start a timer. Add 10 uL of tube A to each of tubes B1 through B6, noting the time of addition. Immediately incubate tubes B1-B6 at 37 degrees Celsius.
5. After 15 minutes of incubation, move 10 uL of tubes B1-B6 to tubes C1-C6, such that B1 is transferred to C1, B2 to C2, and so forth. Vortex and spin C1-C6.
6. Perform these three series of actions simultaneously on tubes C1-C6:
7. Heat tubes C1-C2 to 80 degrees Celsius for 20 minutes. Immediately after heating, filter half of the tubes' contents through cellulose acetate filters with a 0.2 micron pore size, one filter per tube. Then move 10 uL of the filtrate from that filtering process into tubes of DNA extraction buffer, one tube per filtration. Vortex and briefly spin the extraction tubes. Heat the DNA extraction buffer tubes to 65 degrees Celsius for 6 minutes and then to 98 degrees Celsius for 4 minutes.
8. Sonicate tubes C3-C4 for 30 seconds with a peak power of 2.5 Watt, a duty cycle of 0.05, and a frequency of 50 cycles/burst. Immediately after sonication, filter half of the tubes' contents through cellulose acetate filters with a 0.2 micron pore size, one filter per tube. Then move 10 uL of the filtrate from that filtering process into tubes of DNA extraction buffer, one tube per sonication. Heat the DNA extraction buffer tubes to 65 degrees Celsius for 6 minutes and then to 98 degrees Celsius for 4 minutes.
9. Incubate tubes C5-C6 at 37 degrees Celsius for 5 minutes. Immediately after incubation, filter half of the tubes' contents through cellulose acetate filters with a 0.2 micron pore size, one filter per tube. Then move 10 uL of the filtrate from that filtering process into tubes of DNA extraction buffer, one tube per incubation. Heat the DNA extraction buffer to 65 degrees Celsius for 6 minutes and then to 98 degrees Celsius for 4 minutes.
10. Measure the concentrations of *E. coli* DNA and the spike-in DNA control in tubes B1-4 and C1-4 by performing ddPCR reactions with primers for a single-copy *E. coli* gene (e.g. uidA) or for the spike-in control.
11. Choose the spike-in control concentration of one of the tubes to be the standard control concentration. Then, normalize the concentration of *E. coli* DNA in a given tube by dividing the *E. coli* concentration by the amount of spike-in then multiplying by the standard control concentration.
12. Lastly, calculate the fraction of DNA that was released by antibiotic by dividing the normalized *E. coli* DNA concentration in the filtrate tubes (C1-4) by the normalized *E. coli* DNA concentrations in the corresponding feed tubes B1-4.

Figure 36:
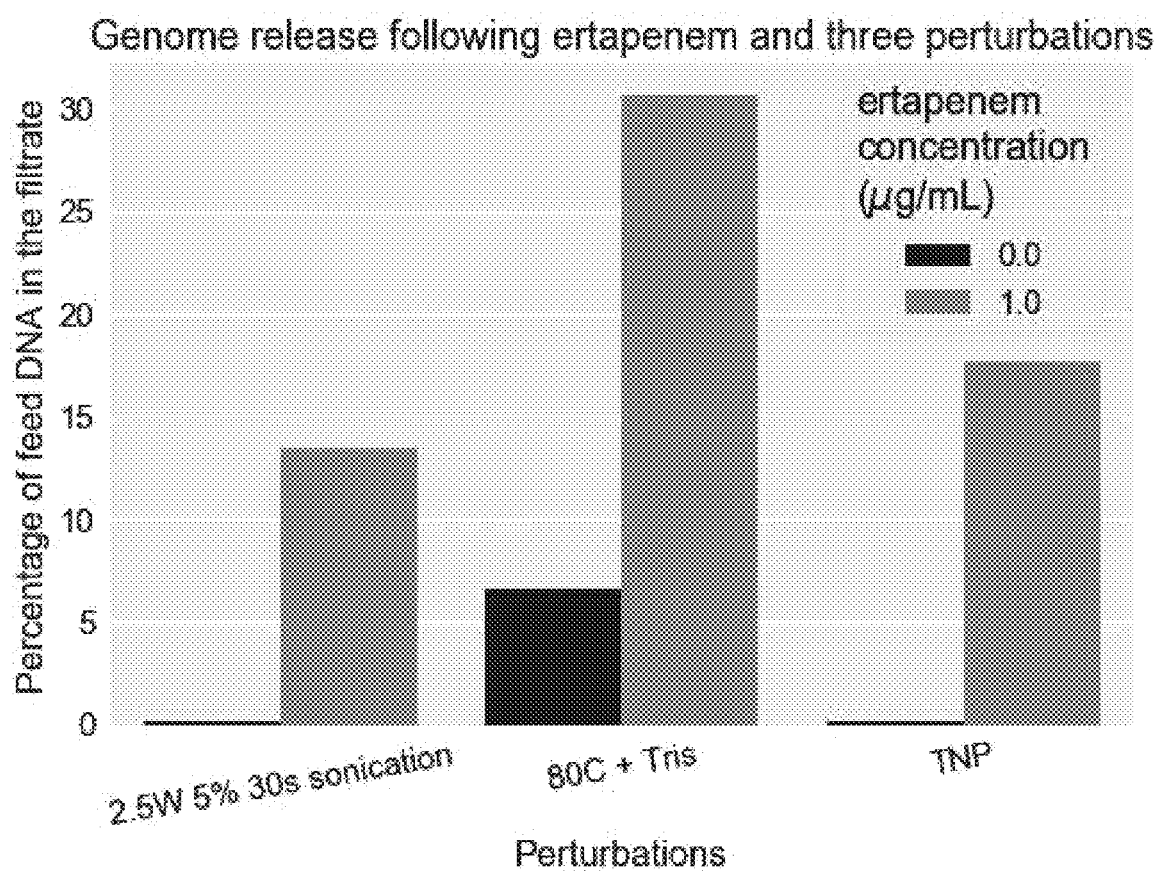
FIG. 36 shows, for one *E. coli* strain, the percentage of DNA detected by dPCR after filtration. The percentage was calculated relative to the total DNA concentration. The filtration was performed on six samples that underwent different exposure conditions. The conditions involved contact or no contact with ertapenem, followed by one of sonication, heating, or contact with detergents. The conditions are described in Example 17.

The results are shows in FIG. 36.

In this experimental design, only DNA that has been released from the cytoplasm upon lysis of the cell will be recovered after filtration. The strain used is susceptible to the concentration of ertapenem used. In all three conditions, the fraction of DNA detected in the filtrate is larger after antibiotic exposure than without antibiotic exposure. This indicates that antibiotic exposure increases the amount of accessible DNA of the target microorganism. All the percentages are less than 90% and leave enough un-released DNA for a difference between antibiotic conditions to be measurable by the read-out method. The preceding characteristics indicate that sonication, heating, and contact with TNP detergent all act as enhancing treatments.

Example 18: AST Based on Nucleic Acid Accessibility, with 1-Step Incubation in Non-Lysing Conditions, Quantified Using Direct LAMP with Enhancer Present During Amplification In this example, AST was performed based on nucleic acid accessibility, with 1-step incubation in non-lysing conditions, quantified using direct LAMP with enhancer present during amplification AST may be performed based on nucleic acid accessibility to polymerase during the nucleic acid amplification step. Antibiotic exposure can be performed in non-lysing conditions. Bacteria can be added directly to the nucleic acid amplification mix after antibiotic exposure. The nucleic acid amplification mix can be partially lysing. The nucleic acid amplification mix contains an enhancer.

The example was performed according to the following steps.

1. Provide a sample containing bacteria

AST was performed using ec_2, ec_4, ec_38 and ec_41, the antibiotic used was ertapenem. Small clump of each isolate scraped from plate was resuspended in 400 uL BHI (37° C.) in 2 mL screw cap polypropylene tubes by pipetting. For each isolate 20 uL of cell suspension was added to 2 mL BHI (37° C.) in 15 mL polypropylene falcon tubes, incubated with 500 rpm shaking at 37° C.+5% CO2 for ~3.5 hrs.

2. Optionally, pre-process the sample containing bacteria

All cell suspensions were diluted 10× (60 uL into 540 uL pre-warmed BHI) in 1 cm path length polystyrene disposable cuvettes, OD measured at 600 nm using portable spectrophotometer (BioChrom cat. no. 80-2116-30), ODs listed below (corrected for 10× dilution), ec_2 OD=2.4, ec_38 OD=3.2. Starter cultures were diluted 150× (10 uL into 1.5 mL BHI), incubated with 500 rpm shaking at 37° C.+5% CO2 for 80 min.

3. Provide non-lytic incubation media with and without antibiotic 100 uL of exposure conditions (not including cell suspension volume) was prepared with and without antibiotic according to list below in 8-tube PCR tube strips (USA Scientific 1402-2700); tubes were pre-warmed at 37° C.+5% CO2 for 5 min.

| Component | Volume |
|---|---|
| MHB | 80 uL |
| ABX stock (20 ug/mL) | 2.5 uL |
| NF-H2O | 7.5 uL |
| Cell suspension | 10 uL |

4. Split the sample into two or more parts 150 uL of cell suspensions were transferred to appropriate tubes of 8-tube PCR tube strip so that transfer to exposure condition could be performed with multi-channel pipette 5. Combine sample with incubation media Multi-channel pipette was used to transfer cell suspensions from 8-tube PCR tube strip into exposure condition tube strips, exposure PCR tube strips were closed, vortexed, quick spun, and transferred to pre-warmed thermocycler.

6. Incubate the treated and untreated samples at a controlled temperature for a short amount of time Exposure was performed at 37° C. on BioRad CT1000 thermocycler for 15 minutes 7. Provide amplification mix, optionally containing enhancer LAMP mix was prepared on ice according to the general protocol 8. Combine incubation media containing sample with amplification mixes.

Figure 37:
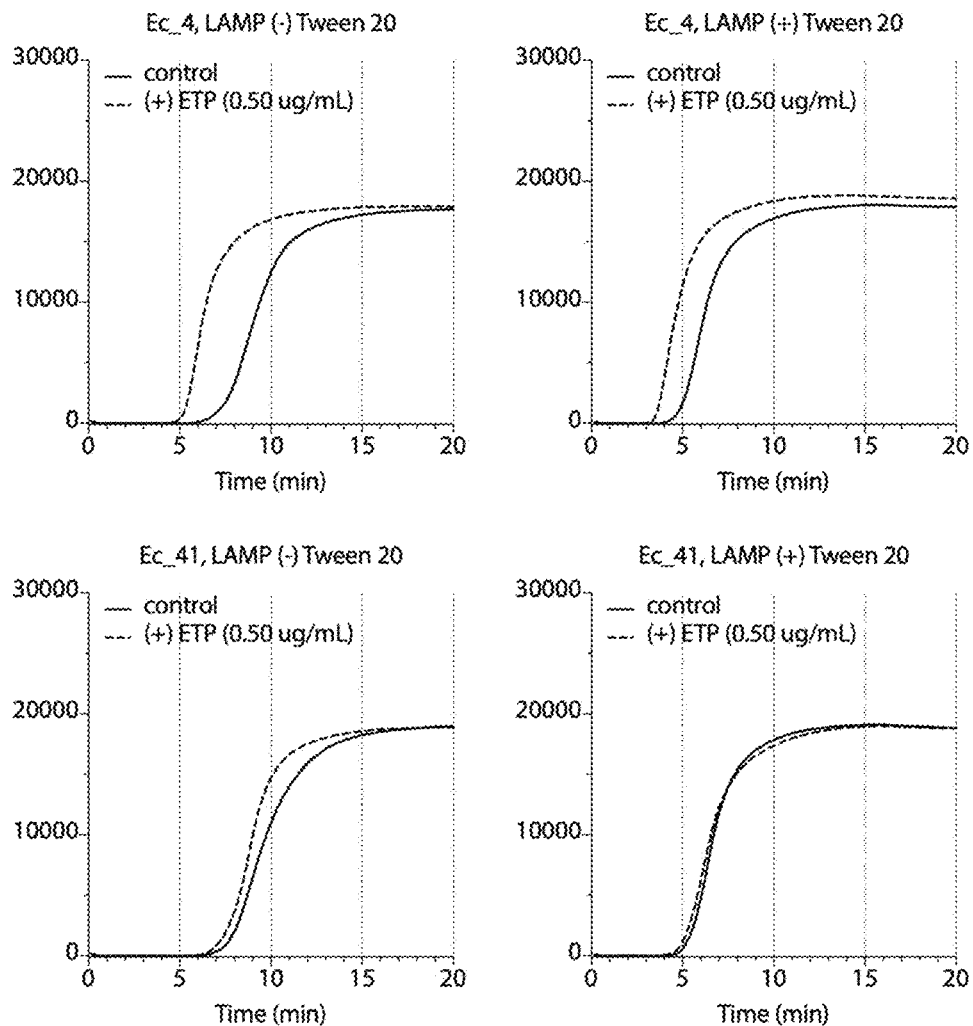
FIG. 37 shows the average control (solid lines) and treated (dashed lines) LAMP amplification curves for two isolates as described in Example 18.

Immediately after exposure, samples were added to LAMP mix (already aliquoted into plate and on ice) in triplicate using multichannel pipette. Immediately after exposure, samples were added to LAMP mix containing enahancer (already aliquoted into plate and on ice) in triplicate using multichannel pipette 9. Quantify nucleic acids qLAMP with and without enhancer LAMP was run on BioRad CFX96 instrument according to the general protocol FIG. 37 represents the average control (solid lines) and treated (dashed lines) LAMP amplification curves for two isolates. LAMP can be performed with enhancer (right two plots) or without enhancer present during amplification (left two plots). The control and treated curves can be used for comparison. LAMP is not a fully lytic amplification method and therefore when amplification occurs depends on the accessibility of template NA molecules (NA=DNA+RNA). In susceptible isolates (top two plots), the sample treated with antibiotic amplifies earlier because NAs are more accessible.

Figure 38:
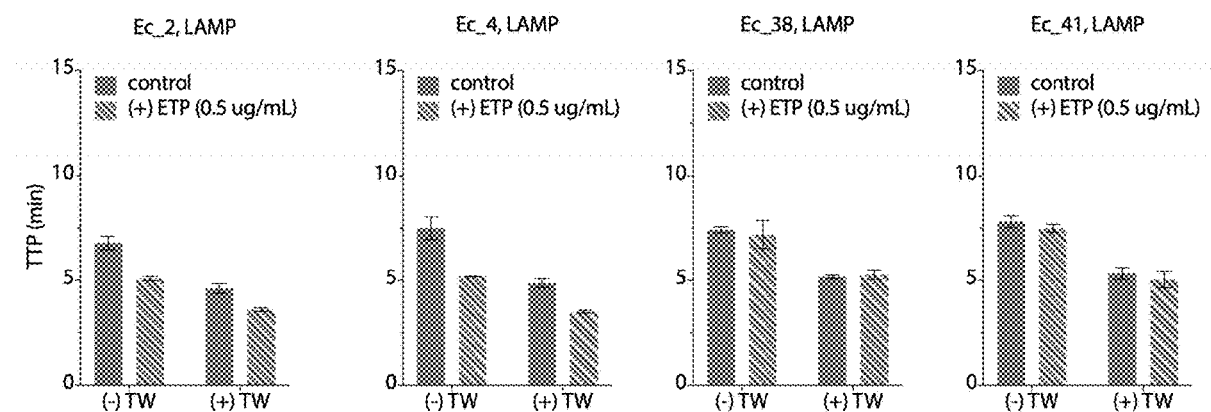
FIG. 38 shows diagrams illustrating the average time-to-positive for LAMP amplification as described in Example 18.

FIG. 38 represents the average time-to-positive for LAMP amplification as determined from setting an amplification threshold and measuring the time at which the amplification curve crosses the threshold. In susceptible isolates (left two plots), the sample treated with antibiotic amplifies earlier because NAs are more accessible. This results in a larger difference between the average TTP of the control and treated samples than observed in samples resistant to the antibiotic (right two plots). In all samples, amplification is enhanced (occurs more rapidly) with Tween present as an enhancer.

As shown in this example, AST may be performed based on nucleic acid accessibility to polymerase during the nucleic acid amplification step. This is observed in FIG. 38, showing that the magnitude of the difference in TTP between the control and treated samples correctly predicts ETP susceptibility or resistance after 15 minutes of ETP exposure. In some embodiments, the nucleic acid amplification mix is not fully lysing. This is confirmed by FIG. 37 showing that susceptible samples treated with antibiotic amplify earlier relative to their controls than resistant samples. This example also shows that including Tween as an enhancer during amplification increases the speed of amplification.

Example 19: AST Based on Nucleic Acid Accessibility, with 1-Step Incubation in Non-Lysing Conditions, Quantified Using Direct LAMP with Enhancer Present During Amplification and Normalized to Lysing Extraction Condition In this example, AST was performed based on nucleic acid accessibility, with 1-step incubation in non-lysing conditions, quantified using direct LAMP with enhancer present during amplification and normalized to lysing extraction condition.

AST may be performed based on nucleic acid accessibility to polymerase during the nucleic acid amplification step. Antibiotic exposure can be performed in non-lysing conditions. Bacteria can be added directly to the nucleic acid amplification mix after antibiotic exposure. The nucleic acid amplification mix is not fully lysing. Quantification is normalized to a lysing extraction condition.

The example was performed according to the following steps.

1. Provide a sample containing bacteria

AST was performed using ec_2, ec_4, ec_39, and ec_40, antibiotics used were ampicillin, ceftriaxone, and ertapenem. Small clump of each isolate scraped from plate was resuspended in 2 mL BHI (37° C.) in 15 mL polypropylene falcon tubes, incubated with 500 rpm shaking at 37° C.+5% CO2 for ~2 hrs.

2. Optionally, pre-process the sample containing bacteria

All cell suspensions were diluted 10× (60 uL into 540 uL pre-warmed BHI) in 1 cm path length polystyrene disposable cuvettes, OD measured at 600 nm using portable spectrophotometer (BioChrom cat. no. 80-2116-30), ODs listed below (corrected for 10× dilution), ec_2 OD=1.7, ec_4 OD=2.1, ec_39 OD=1.9, ec_40 OD=1.3. Starter cultures were diluted 150× (10 uL into 1.5 mL BHI), incubated with 500 rpm shaking at 37° C.+5% CO2 for 90 min.

3. Provide non-lytic incubation media with and without antibiotic 100 uL of exposure conditions (not including cell suspension volume) were prepared with and without antibiotic according to list below in 8-tube PCR tube strips (USA Scientific 1402-2700); tubes were pre-warmed at 37° C.+5% CO2 for 5 min, 20× antibiotic stock in below list was 320 ug/mL ampicillin or 40 ug/mL ceftriaxone or 10 ug/mL ertapenem

| Component | Volume |
| --- | --- |
| MHB | 80 uL |
| ABX stock (20X) | 5 uL |
| NF-H2O | 5 uL |
| Cell suspension | 10 uL |

4. Split the sample into two or more parts 150 uL of cell suspensions were transferred to appropriate tubes of 8-tube PCR tube strip so that transfer to exposure condition could be performed with multi-channel pipette.

5. Combine sample with incubation media

Multi-channel pipette was used to transfer cell suspensions from 8-tube PCR tube strip into exposure condition tube strips, exposure PCR tube strips were closed, vortexed, quick spun, and transferred to pre-warmed thermocycler.

6. Incubate the treated and untreated samples at a controlled temperature for a short amount of time Exposure was performed at 37° C. on BioRad CT1000 thermocycler for 15 minutes 7. Provide amplification mix, optionally containing enhancer
   a. LAMP mix was prepared on ice according to the general protocol 8. Combine incubation media containing sample with amplification mixes Immediately after exposure, samples were added to LAMP mix (already aliquoted into plate and on ice) in triplicate using multichannel pipette 9. Optionally extract using fully lysing conditions according to the general protocol.

This step can be performed during sample incubation or after as will be understood by a skilled person upon reading of the current disclosure.

10. Quantify nucleic acids using qLAMP

Figure 39:
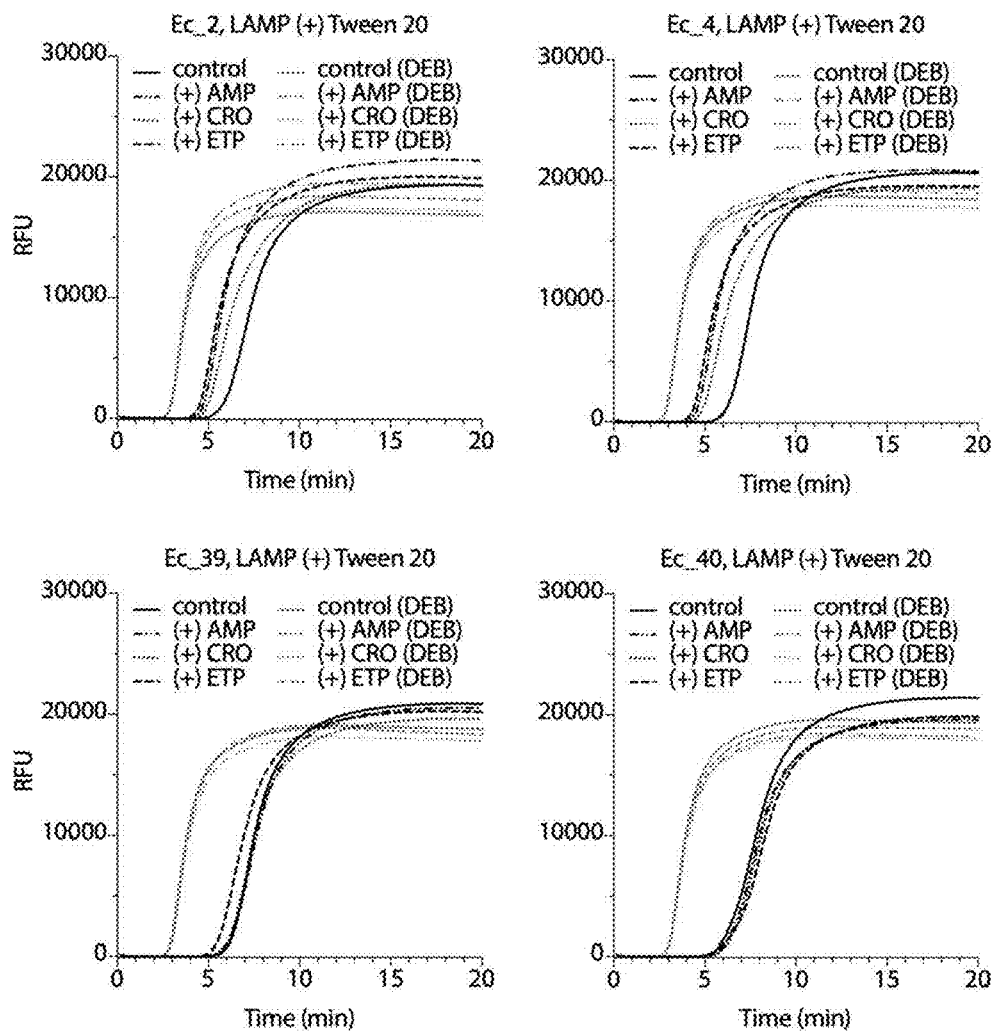
FIG. 39 shows the average control (black solid lines) and treated (black dashed lines) LAMP amplification curves for four isolates as described in Example 19.

LAMP was run on BioRad CFX96 instrument according to the general protocol. Samples extracted using the fully lysing condition can be quantified with samples added directly to LAMP mix or separately after FIG. 39 represents the average control (black solid lines) and treated (black dashed lines) LAMP amplification curves for four isolates. Also shown are average control (gray solid lines) and treated (gray dashed lines) LAMP amplification curves for each sample extracted using a fully lysing condition. The control and treated curves can be used for comparison and can be normalized to the amplification curves from the fully lysed and extracted samples. LAMP is not a fully lytic amplification method and therefore when amplification occurs depends on the accessibility of template NA molecules (NA=DNA+RNA). In susceptible isolates (top two plots), the sample treated with antibiotic amplifies earlier because NAs are more accessible.

Figure 40:
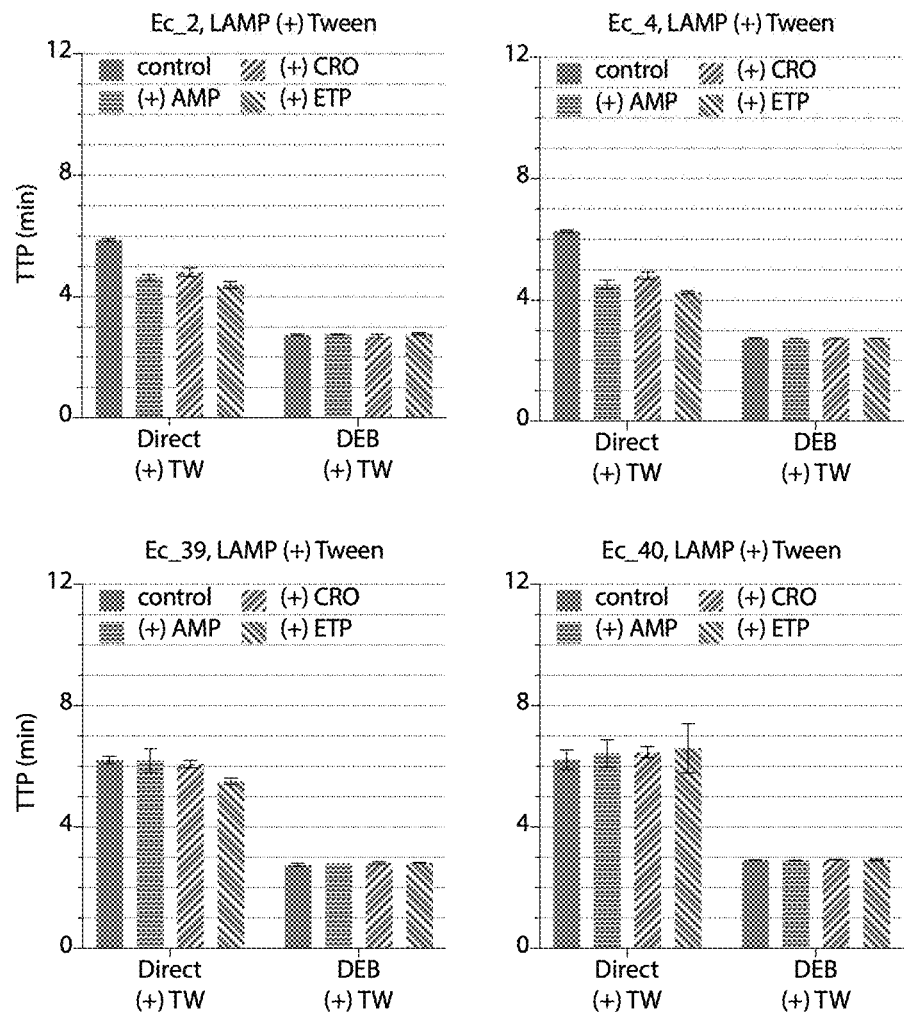
FIG. 40 shows the average time-to-positive for LAMP amplification with samples extracted using the fully lysing condition as determined from setting an amplification threshold and measuring the time at which the amplification curve crosses the threshold as described in Example 19.
Figure 41:
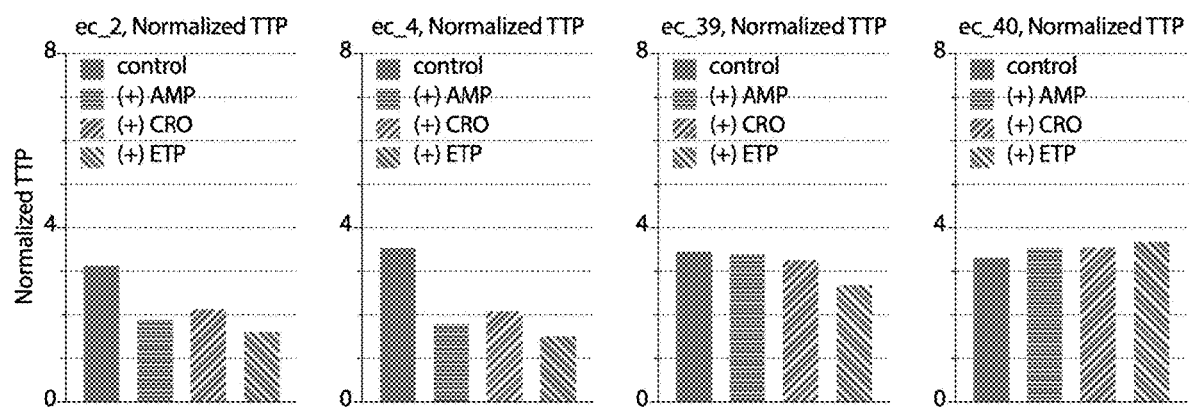
FIG. 41 shows the average time-to-positive for each sample amplified directly in LAMP mix normalized to the fully lysing condition as described in Example 19.

FIG. 40 represents the average time-to-positive for LAMP amplification with samples extracted using the fully lysing condition as determined from setting an amplification threshold and measuring the time at which the amplification curve crosses the threshold. FIG. 41 shows the average time-to-positive for each sample amplified directly in LAMP mix normalized to the fully lysing condition. Normalization to this condition can be used for analysis and comparison. In susceptible isolates (ec_2 and ec_4), the sample treated with antibiotic amplifies earlier because NAs are more accessible. This results in a larger difference between the average TTP of the control and treated samples than observed in samples resistant to the antibiotic (e_39 and ec_40).

As shown in this example, AST can be performed based on nucleic acid accessibility to polymerase during the nucleic acid amplification step. This is observed FIG. 41, showing that the magnitude of the difference in TTP between the control and treated samples correctly predicts AMP, CRO, and ETP susceptibility or resistance after 15 minutes of ETP exposure. As seen in FIG. 40 showing that susceptible samples treated with antibiotic amplify earlier relative to their controls than resistant samples, the nucleic acid amplification mix is not fully lysing.

This example also shows that quantification is normalized to a lysing extraction condition. In particular, as seen in FIG. 41, the TTPs of samples added directly to amplification mix is normalized to the TTPs of the same samples extracted under fully lysing conditions. After normalization, susceptibility can be determined by comparing the magnitude of the difference between normalized control and treated samples.

Example 20: AST Based on Nucleic Acid Accessibility Using Spiked Urine Samples in Less than 30 Min Sample-to-Answer, with 1-Step Incubation in Non-Lysing Conditions, Quantified Using Direct LAMP with Enhancer Present During Amplification In this example, AST is performed based on nucleic acid accessibility using spiked urine samples in less than 30 min sample-to-answer, with 1-step incubation in non-lysing conditions, quantified using direct LAMP with enhancer present during amplification.

AST may be performed based on nucleic acid accessibility to polymerase during the nucleic acid amplification step. Antibiotic exposure can be performed in non-lysing conditions. Bacteria can be added directly to the nucleic acid amplification mix after antibiotic exposure. The nucleic acid amplification mix can be selectively lysing. Sample matrix used in this example is urine containing bacteria. All steps from sample-to-answer are performed in less than 30 min.

The example was performed according to the following steps.

1. Provide a sample containing bacteria

AST was performed using ec_4, ec_40, kp_2, and kp_8, antibiotic used was ertapenem. Small clump of each isolate scraped from plate was resuspended in 2 mL BHI (37° C.) in 15 mL polypropylene falcon tubes, incubated with 500 rpm shaking at 37° C.+5% CO2 for ~2.2 hrs.

2. Optionally, pre-process the sample containing bacteria

All cell suspensions were diluted 10× (60 uL into 540 uL pre-warmed BHI) in 1 cm path length polystyrene disposable cuvettes, OD measured at 600 nm using portable spectrophotometer (BioChrom cat. no. 80-2116-30), ODs listed below (corrected for 10× dilution), ec_4 OD=2.4, ec_40 OD=1.8, kp_2 OD=2.7, kp_8 OD=2.8

3. Optionally, spike urine sample with bacteria 10 uL of ec_4, kp_2, and kp_8 samples were added to pre-filtered pooled human urine, 14 uL of ec_40 sample added to pre-filtered pooled human urine, incubated with 500 rpm shaking at 37° C.+5% CO2 for 31 min 4. Provide non-lytic incubation media with and without antibiotic 100 uL of exposure conditions (not including cell suspension volume) were prepared with and without antibiotic according to list below in 8-tube PCR tube strips (USA Scientific 1402-2700); tubes were pre-warmed at 37° C.+5% CO2 for 11 min, 20×ABX stock listed below=10 ug/mL for Ec samples and 20 ug/mL for Kp samples

| Component | Volume |
|---|---|
| MHB | 80 uL |
| ABX stock (20X) | 5 uL |
| NF-H2O | 5 uL |
| Cell suspension in urine | 10 uL |

5. Split the sample into two or more parts 150 uL of cell suspensions in urine were transferred to appropriate tubes of 8-tube PCR tube strip so that transfer to exposure condition could be performed with multi-channel pipette.

6. Start timer

Timer is started to record sample-to-answer time of all steps. This step can be performed immediately before or after combining samples with incubation media.

7. Combine sample with incubation media

Multi-channel pipette was used to transfer cell suspensions from 8-tube PCR tube strip into exposure condition tube strips, exposure PCR tube strips were closed, vortexed, quick spun, and transferred to pre-warmed thermocycler 8. Incubate the treated and untreated samples at a controlled temperature for a short amount of time Exposure was performed at 37° C. on BioRad CT1000 thermocycler for 13 minutes.

9. Provide amplification mix

LAMP mix was prepared on ice according to the general protocol

10. Combine incubation media containing sample with amplification mixes

Immediately after exposure, samples were added to LAMP mix (already aliquoted into plate and on ice) in triplicate using multichannel pipette.

11. Quantify nucleic acids using qLAMP

LAMP was run on BioRad CFX96 instrument according to the general protocol

12. Analyze once amplification curves have crossed given threshold

Once all samples have amplified to a fluorescence value greater than set threshold (here 1000 RFU was used), amplification is stopped and time-to-positive values are determined by copying values from instrument to data analysis spreadsheet.

Susceptibility calls are returned according to magnitude of difference in TTPs between control and treated samples.

13. Stop timer

Timer is stopped and sample-to-answer time recorded

Figure 42:
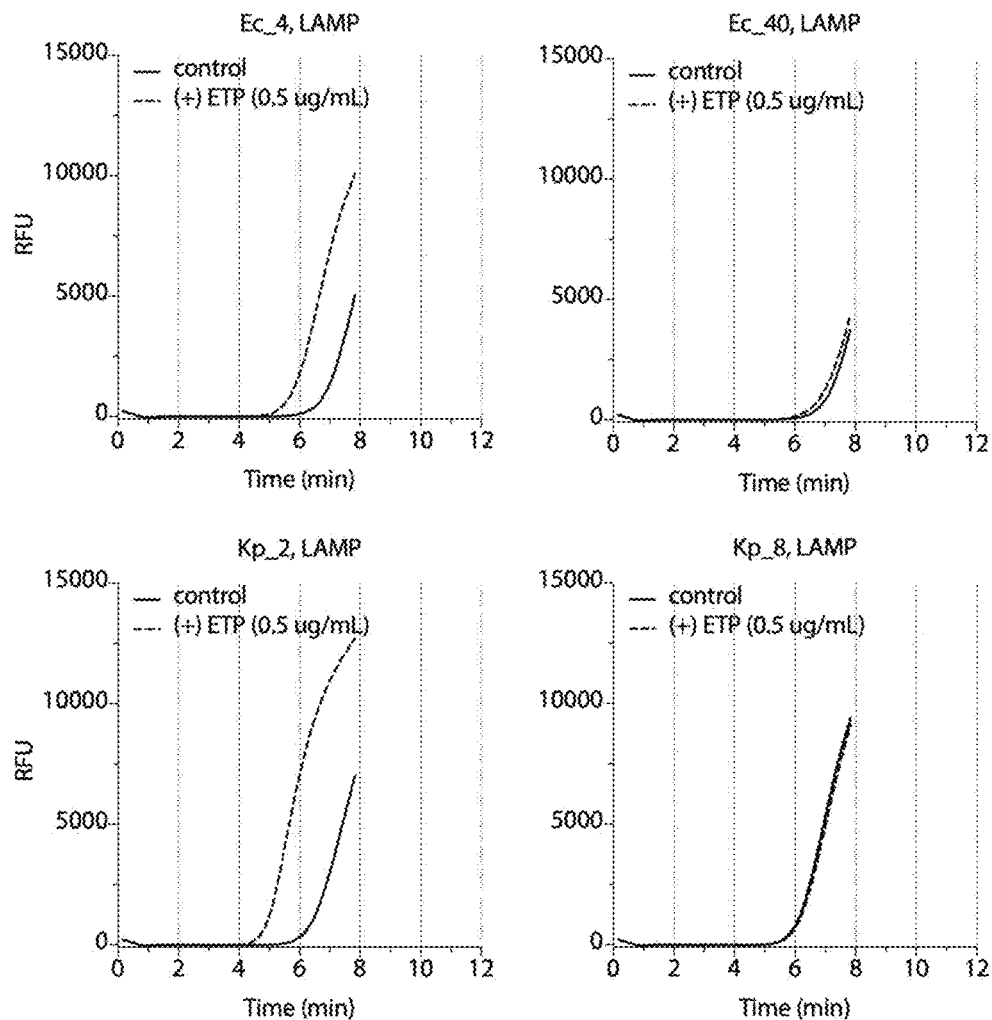
FIG. 42 shows the average control (solid lines) and treated (dashed lines) LAMP amplification curves for four isolates as described in Example 20.

FIG. 42 represents the average control (solid lines) and treated (dashed lines) LAMP amplification curves for four isolates. The control and treated curves can be used for comparison. LAMP is not a fully lytic amplification method and therefore when amplification occurs depends on the accessibility of template NA molecules (NA=DNA+RNA). In susceptible isolates (left two plots), the sample treated with antibiotic amplifies earlier because NAs are more accessible.

Figure 43:
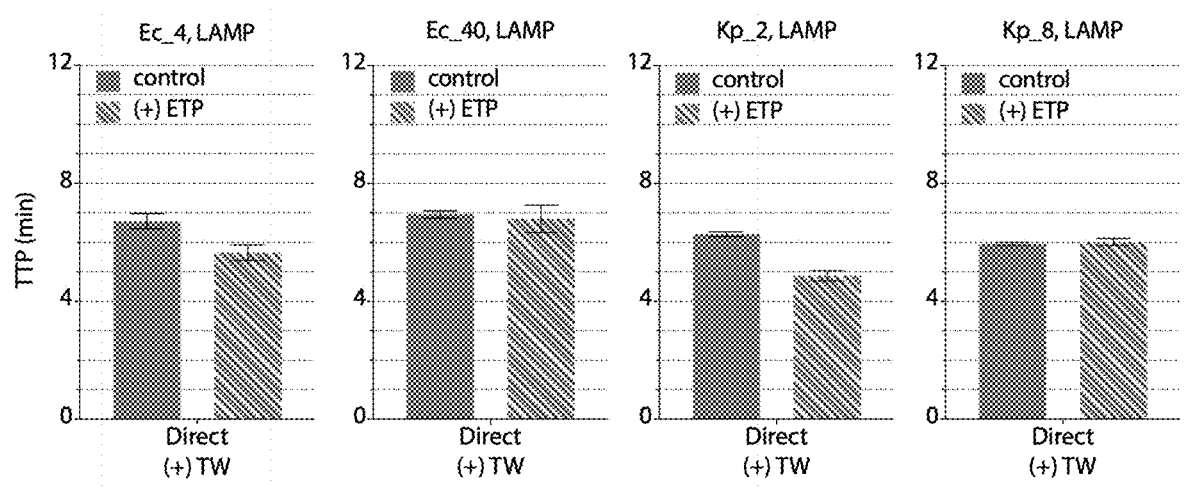
FIG. 43 shows diagrams illustrating the average time-to-positive for LAMP amplification as determined from setting an amplification threshold and measuring the time at which the amplification curve crosses the threshold as described in Example 20.

FIG. 43 represents the average time-to-positive for LAMP amplification as determined from setting an amplification threshold and measuring the time at which the amplification curve crosses the threshold. In susceptible isolates (first and third plots), the sample treated with antibiotic amplifies earlier because NAs are more accessible. This results in a larger difference between the average TTP of the control and treated samples than observed in samples resistant to the antibiotic (second and fourth plots).

As shown in this example, AST can be performed based on nucleic acid accessibility to polymerase during the nucleic acid amplification step. This is observed in FIG. 43, showing that the magnitude of the difference in TTP between the control and treated samples correctly predicts ETP susceptibility or resistance after 15 minutes of ETP exposure. FIGS. 42-43 also demonstrate that spiked urine samples can be used as the sample type and the correct susceptibility call is still made after 15 minutes of exposure to ETP. Furthermore, the total sample-to-answer time for all steps in the above example was recorded using a timer and summed to 29.5 min.

Example 21: AST Based on Nucleic Acid Accessibility, with 1-Step Incubation and Non-Lysing Conditions Quantified with Direct LAMP, Normalized to a Fully-Lysed Sample with gLAMP Measurement In this example, AST was performed based on nucleic acid accessibility, with 1-step incubation and non-lysing conditions quantified with direct LAMP, normalized to a fully-lysed sample with qLAMP measurement AST may be performed with a treated sample (direct-into-qLAMP without lysis) and the DEB extracted sample (lysed sample) in qLAMP. Data may be collected on different days and data compiled. It is important to note that each DEB extracted sample and direct-to-LAMP sample must be completed in the same experiment to make the comparison for AST.

The example was performed according to the following steps.

1. Provide a sample containing bacteria

AST was performed as follows:
  i. kp_1, kp_2, kp_7, kp_8 (CRO, ETP, MEM)
  ii. ec_2, ec_4, ec_39, ec_40 (AMP)
  iii. ec_1, ec_2, ec_3, ec_4, ec_39, ec_40, ec_44, ec_45 (CRO)
  iv. ec_1, ec_2, ec_3, ec_4, ec_38, ec_39, ec_40, ec_41, ec_44, ec_45 (ETP)
  v. ec_1, ec_3, ec_44, ec_45 (MEM)

Small clump of each isolate scraped from plate was resuspended in 2 mL BHI (37° C.) in 15 mL polypropylene falcon tubes, incubated with 500 rpm shaking at 37° C.+5% CO2 for ~2 hrs 2. Optionally, pre-process the sample containing bacteria All cell suspensions were diluted 10× (60 uL into 540 uL pre-warmed BHI) in 1 cm path length polystyrene disposable cuvettes, measured OD at 600 nm using portable spectrophotometer (BioChrom cat. no. 80-2116-30), ODs listed below (corrected for 10× dilution), ec_2 OD=1.7, ec_4 OD=2.1, ec_39 OD=1.9, ec_40 OD=1.3.

Starter cultures were diluted 150× (10 uL into 1.5 mL BHI), incubated with 500 rpm shaking at 37° C.+5% CO2 for 90 min 3. Provide non-lytic incubation media with and without antibiotic 100 uL of exposure conditions (not including cell suspension volume) were prepared with and without antibiotic according to list below in 8-tube PCR tube strips (USA Scientific 1402-2700); tubes were pre-warmed at 37° C.+5% CO2 for 5 min, 20× antibiotic stock in below list was 320 ug/mL ampicillin or 40 ug/mL ceftriaxone or 10 ug/mL ertapenem

| Component | Volume |
|---|---|
| MHB | 80 uL |
| ABX stock (20X) | 5 uL |
| NF-H2O | 5 uL |
| Cell suspension | 10 uL |

4. Split the sample into two or more parts 150 uL of cell suspensions were transferred to appropriate tubes of 8-tube PCR tube strip so that transfer to exposure condition could be performed with multi-channel pipette 5. Combine sample with incubation media Multi-channel pipette was used to transfer cell suspensions from 8-tube PCR tube strip into exposure condition tube strips, exposure PCR tube strips were closed, vortexed, quick spun, and transferred to pre-warmed thermocycler.

6. Incubate the treated samples at a controlled temperature for a short amount of time Exposure was performed at 37° C. on BioRad CT1000 thermocycler for 15 minutes 7. Provide amplification mix, optionally containing enhancer LAMP mix was prepared on ice according to the general protocol 8. Combine incubation media containing sample with amplification mixes Immediately after exposure, samples were added to LAMP mix (already aliquoted into plate and on ice) in triplicate using multichannel pipette 9. Extract using fully lysing conditions according to the general protocol This step can be performed during sample incubation (step 6) or after 10. Quantify nucleic acids using qLAMP LAMP was run on BioRad CFX96 instrument according to the general protocol (with tween in the amplification mix). Samples extracted using the fully lysing condition can be quantified with samples added directly to LAMP mix or separately after on a separate plate. Both TTP measurements are needed for this specific readout.

Step 9 and 10(b) can be carried out before, after, or in parallel with steps 5-7.

Figure 44A:
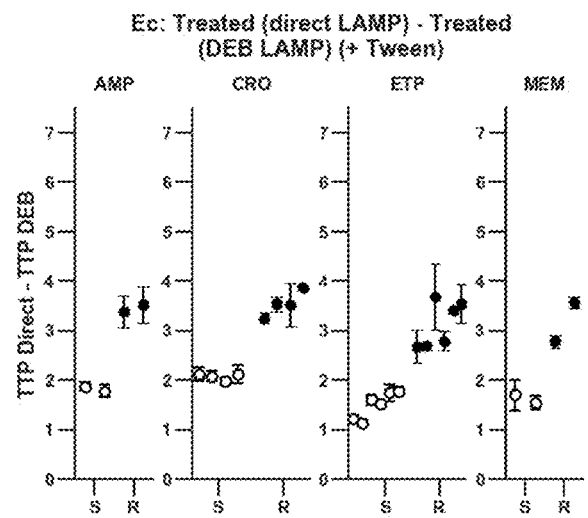
FIGS. 44A-44B show diagrams illustrating the experimental results and data analysis methods as describe in Example 21.
Figure 44B:
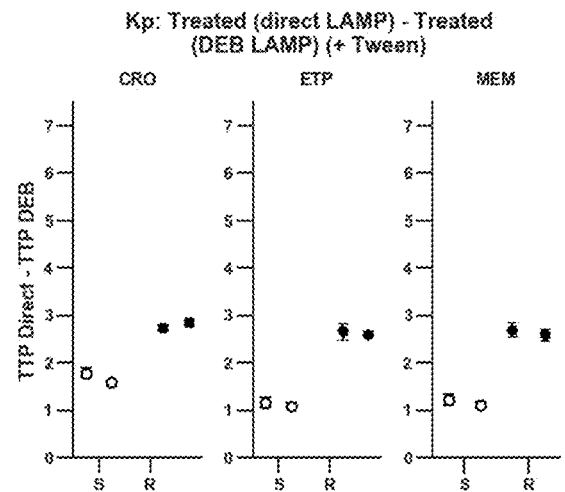

FIGS. 44A-44B show the results for the AST for several *E. coli* and *K. pneumoniae* isolates with different beta lactam antibiotics. The differences between the time to positive (TTP) for the treated sample that was measured directly-into-qLAMP mix and the DEB extracted sample run in qLAMP. The DEB sample is a normalization that accounts for the total measurable nucleic acids from a fully-lysed sample and the direct LAMP measurement assesses the amount of the nucleic acids accessible to the polymerases. Differentiable AST results are obtained between the susceptible and resistant isolates when looking at the TTP Direct-TTP DEB readout. The error bars represent the error between the qLAMP triplicate wells (with standard propagation of error methods to account for the comparison of the two measurements).

As seen in this example, AST can be performed with a 1-step incubation in non-lysing conditions of a treated sample if it is compared to a fully-lysed-sample (DEB extracted) from the same initial cell suspension. Some samples are added directly to the nucleic acid amplification mix after antibiotic exposure.

Example 22: AST Performed with Calling of Susceptible Ng Samples after 15 Minutes of Antibiotic Exposure Followed by Extended Exposure to Determine Susceptibility of Samples not Called at 15 Minutes In this example, AST was performed with calling of susceptible Ng samples after 15 minutes of antibiotic exposure followed by extended exposure to determine susceptibility of samples not called at 15 minutes.

An initial susceptibility call can be made for susceptible samples that respond after 15 min of antibiotic exposure. An extended antibiotic exposure (30 minutes total) is then used to determine susceptibility of samples, including those that do not respond to antibiotics after 15 minutes. The data in this example was obtained using the protocol described in Example 11 (two-step exposure with enhancer present during second step). In some embodiments, data may be collected on different days and data compiled.

A workflow can be designed as follows. Sample believed to contain target bacteria is incubated with antibiotic (optionally split and incubated, optionally control sample is incubated with media) for the first period of time (e.g. 15 minutes). Nucleic acid Accessibility is rapidly measured on a portion of the exposed sample, (while another portion of the sample continues to be incubated with the ABX). Optionally measuring control sample takes place. If sufficiently strong response is observed to consider the bacteria in the sample as susceptible, the test is stopped (and action is taken, for example to treat the patient). If sufficiently strong response is not observed, then after the next period of time (e.g. additional 15 minutes, or 30 minutes total ABX exposure) another portion of the treated sample is analyzed; if susceptible call is made, the test is stopped. Optionally, the cycle can continue for one or more exposure periods until the resistant, intermediate, or reduced susceptibility call can be made reliably. Rapid analysis, such as by LAMP, that can be completed in a short amount of time (e.g. within 15 minutes) is important to enable this workflow.

The same method/protocol described in Example 11 was used in this example, except for the following changes.

All samples were grown on plate for 8 hours or less. All samples were resuspended in GWM for >3 hours. Surfactant exposure time was 6.5 minutes or less. During step 8, the portion of the sample not transferred to the secondary incubation was left to incubate in the initial incubation (with antibiotic) for an additional 15 minutes (30 minutes total), after this extended incubation, a portion of this extended incubation sample was removed and handled as described in the remaining steps of the protocol (diluted into secondary incubation, etc.).

To conduct the analysis, samples were quantified using qPCR and analyzed as described in Example 11, with a percent increase in accessibility value being determined and compared to a pre-determined threshold to make the susceptibility call. The threshold used to determine susceptibility depends on the antibiotic used and the exposure time.

Figures 45A, 45B, 45C:
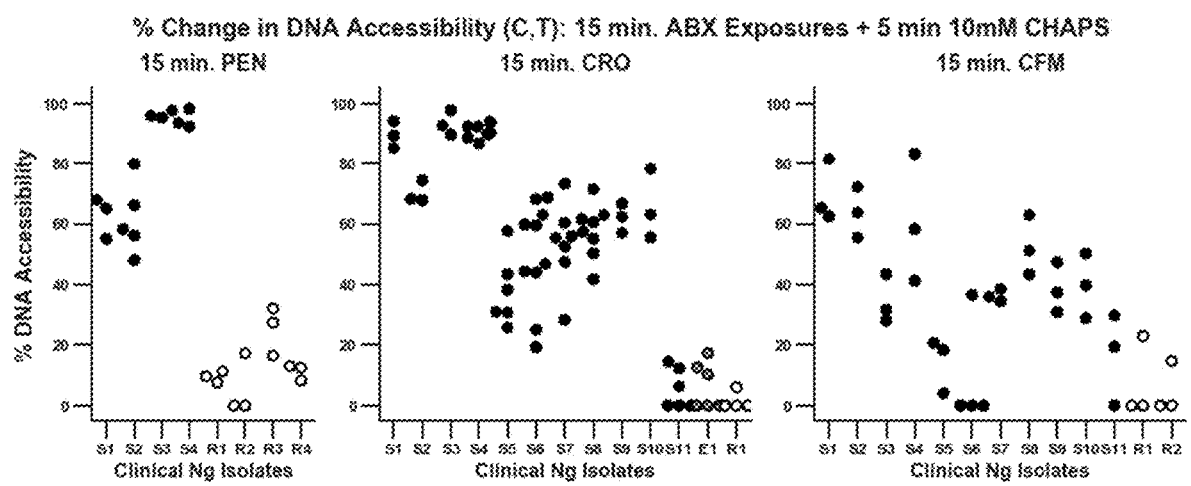
FIGS. 45A-45C show percentage change in DNA accessibility between the untreated and treated samples, at 15 min antibiotic exposure with PEN, CRO, and CFM as described in Example 22. All measurements were made in qPCR and the percent change was computed from the Cq difference in the untreated and treated samples. In each incubation a 15-minute antibiotic exposure is followed by an enhancing treatment for 5 minutes with 10 mM CHAPS. In the figure, all black circles represent measurements of antibiotic-susceptible isolates and open circles represent antibiotic-resistant isolates.

FIGS. 45A-45C show compiled data for multiple samples exposed to different antibiotics for 15 minutes. Only those samples with a % DNA accessibility value above the predetermined threshold are called susceptible. The percentage of isolates that can be called at 15 minutes depends on the antibiotic being tested.

Figures 46A, 46B, 46C:
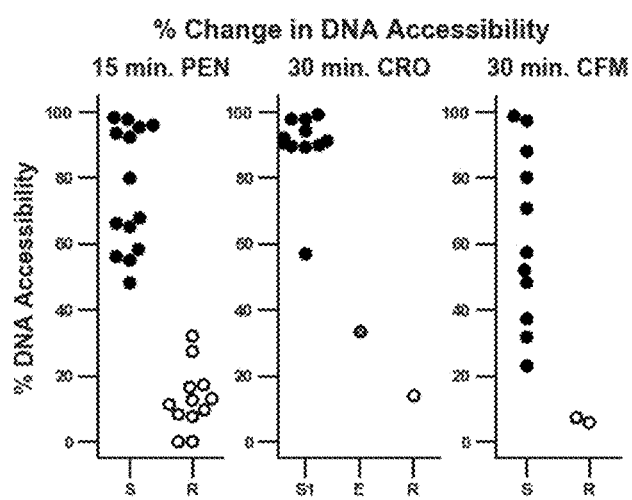
FIGS. 46A-46C show percentage change in DNA accessibility at 15 min PEN treatment (FIG. 46A), 30 min CRO treatment (FIG. 46 B) and 30 min CFM treatment (FIG. 46 C) for susceptible and resistant strains as described in Example 22. The plots are organized by the same layout and logic as FIG. 45, utilizing the same abbreviations for antibiotics and categorization of susceptible, elevated MIC, and resistant clinical isolates.

FIGS. 46A-46C show compiled data for multiple samples exposed to different antibiotics for 15 minutes. Only those samples with a % DNA accessibility value above the predetermined threshold are called susceptible. The percentage of isolates that can be called at 15 minutes depends on the antibiotic being tested.

This example supports the conclusion that an initial susceptibility call can be made for susceptible samples that respond after 15 min of antibiotic exposure. This is shown in FIGS. 45A-45C where only a portion of the samples have a % DNA accessibility value large enough to be called susceptible after 15 minutes of antibiotic exposure. The example also confirms that an extended antibiotic exposure (30 minutes total) can used to determine susceptibility of samples that do not respond to antibiotics after 15 minutes. This is shown in FIGS. 46A-46C, which shows that all samples can be called after 30 minutes of antibiotic exposure. The example further verifies that AST can be carried out with data collected on different days and with compiled data. The data shown in FIGS. 45A-45C-46A-46C is a compilation of data from different days and experiments which all meets the conditions described in the methods.

Example 23: Treatment Media for Testing Procedures

In some of the experiments described herein with reference to *N. gonorrhoeae*, the treatment media used was Mueller Hinton Broth (MHB) from BBL Mueller Hinton II Broth Cation Adjusted (BBL cat no. 212322), which is prepared according to manufacturer instructions and autoclaved to sterilize before use, is comprised of beef extract, acid hydrolysate of casein, and starch. Mueller Hinton II Broth is cation-adjusted for calcium and magnesium ions and is used for quantitative susceptibility testing of gram-negative and gram-positive aerobic bacteria with a variety of antimicrobial agents. It is formulated to have a low thymine and thymidine content and is adjusted to the calcium and magnesium ion concentrations recommended in the CLSI standard M7-A7 (see the document available on the web page legacy.bd.com/ds/technicalCenter/inserts/L007475 (13).pdf, or the document available on the web page fish-ersci.com/shop/products/bd-bbl-dehydrated-culture-media-mueller-hinton-ii-broth-cation-adjusted-mueller-hinton-ii-broth-cation-adjusted-500g/b12322) at the filing date of the present disclosure)

In experiments described herein with reference to *N. gonorroheae* the resuspension or growing media used was HFB, MHB, or Graver-Wade Media (All concentrations based on volumes and reported concentration in Wade et al. 2007 paper) M199 cell culture medium was prepared by dissolving M199 salts (Sigma cat no. M3769, lot no. SLBW4106) in 1 L milliQ H2O. Graver-Wade salt additions to 667 mL M199 cell culture medium (final volume 1.0 L) are as follows, with the molar concentrations listed as the final concentration in the volume, 37 mM glucose, 17 mM ammonium bicarbonate, 4.9 mM Sodium acetate, 3.4 mM L-glutamine, 0.92 mM spermidine, 0.38 mM L-arginine, 0.25 mM hypoxanthine, 0.3 mM uracil, 0.25 oxaloacetate, 0.1 mM Thiamine hydrochloride, 0.04 mM L-orithine, 0.01 mM Nicotinamide adenine dinucleotide, NAD+, and ~13 mM DL-lactate, all added to miliQ- or nuclease-free water.

In experiments described herein with reference to carbapenem-resistant Enterobacteriaceae (CREs) including *E. coli* and *K. pneumoniae*, MHB can be used for exposure media. For example, in some of the experiments described herein with reference to carbapenem-resistant Enterobacteriaceae (CREs) including *E. coli* and *K. pneumoniae*, Brain Heart Infusion (BHI) media is used for the resuspension or growth media. BHI media can be purchased as prepared, liquid media, or as dehydrated media (BD catalog number 237500). Brain Heart Infusion (BHI) is a general-purpose liquid medium used in the cultivation of fastidious and nonfastidious microorganisms, including aerobic and anaerobic bacteria, from a variety of clinical and nonclinical materials. It serves as a base for supplemented media containing 0.1% agar, Fildes enrichment or 6.5% sodium chloride see the document available on the web page (bd.com/europe/regulatory/Assets/IFU/Difco_BBL/237500.pdf) at the filing date of the present disclosure.

In summary, described herein is an antibiotic susceptibility test and related compositions, methods and systems based on detection of a nucleic acid from a target microorganism in a sample in presence or absence of a lysis treatment of the sample.

The examples set forth above are provided to give those of ordinary skill in the art a complete disclosure and description of how to make and use the embodiments of the compounds, compositions, systems and methods of the disclosure, and are not intended to limit the scope of what the inventors regard as their disclosure. All patents and publications mentioned in the specification are indicative of the levels of skill of those skilled in the art to which the disclosure pertains.

The entire disclosure of each document cited (including webpages patents, patent applications, journal articles, abstracts, laboratory manuals, books, or other disclosures) in the Background, Summary, Detailed Description, and Examples is hereby incorporated herein by reference. All references cited in this disclosure, including references cited in any one of the Appendices, are incorporated by reference to the same extent as if each reference had been incorporated by reference in its entirety individually. However, if any inconsistency arises between a cited reference and the present disclosure, the present disclosure takes precedence.

Further, the computer readable form of the sequence listing of the ASCII text file P2283-US-Sequence-listing-ST25 created on Jan. 9, 2019 and having a size of 2000 bytes measured on Windows Server 2016 Standard is incorporated herein by reference in its entirety.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified may be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein may be excluded from a claim of this disclosure. The disclosure illustratively described herein suitably may be practiced in the absence of any element or elements, limitation or limitations which is not specifically disclosed herein.

A number of embodiments of the disclosure have been described. The specific embodiments provided herein are examples of useful embodiments of the invention and it will be apparent to one skilled in the art that the disclosure can be carried out using a large number of variations of the devices, device components, methods steps set forth in the present description. As will be obvious to one of skill in the art, methods and devices useful for the present methods may include a large number of optional composition and processing elements and steps.

In particular, it will be understood that various modifications may be made without departing from the spirit and scope of the present disclosure. Accordingly, other embodiments are within the scope of the following claims.

REFERENCES

1. Song, J. and C. Yi, *Chemical Modifications to RNA: A New Layer of Gene Expression Regulation*. ACS Chem Biol, 2017. 12(2): p. 316-325.
2. Jackman, J. E. and J. D. Alfonzo, *Transfer RNA modifications: Nature's combinatorial chemistry playground*. Wiley interdisciplinary reviews. RNA, 2013. 4(1): p. 35-48.
3. Skerman, V., V. McGowan, and P. Sneath, *Approved Lists of Bacterial Names (Amended)*. 1989: ASM Press.
4. Winn, W. C. and E. W. Koneman, *Koneman's color atlas and textbook of diagnostic microbiology*. 2006: Philadelphia: Lippincott Williams & Wilkins.
5. Wagner, G. P., K. Kin, and V. J. Lynch, *Measurement of mRNA abundance using RNA-seq data: RPKM measure is inconsistent among samples*. Theory Biosci, 2012. 131(4): p. 281-5.
6. Sambrook, J., Fritsch, E. F., & Maniatis, T., *Molecular cloning: a laboratory manual*. Cold Spring Harbor: Cold Spring Harbor Laboratory Press., 2012.
7. Chen, C. Y., G. W. Nace, and P. L. Irwin, *A 6×6 drop plate method for simultaneous colony counting and MPN enumeration of Campylobacter jejuni, Listeria monocytogenes, and Escherichia coli*. J Microbiol Methods, 2003. 55(2): p. 475-9.
8. Conesa, A., et al., *A survey of best practices for RNA-seq data analysis*. Genome Biol, 2016. 17: p. 13.
9. Devore, J. L., *Probability and Statistics for Engineering and the Sciences*. 9th ed. 2016: Cengage.
10. Kreutz, J. E., et al., *Theoretical design and analysis of multivolume digital assays with wide dynamic range validated experimentally with microfluidic digital PCR*. Anal Chem, 2011. 83(21): p. 8158-68.
11. Marsland, S., *Machine learning: an algorithmic perspective*. 2015: Chapman and Hall/CRC.
12. Chakravorty, S., et al., *A detailed analysis of 16S ribosomal RNA gene segments for the diagnosis of pathogenic bacteria*. J Microbiol Methods, 2007. 69(2): p. 330-9.
13. Ye, J., et al., *Primer-BLAST: a tool to design target-specific primers for polymerase chain reaction*. BMC bioinformatics, 2012. 13(1): p. 134.
14. Gootenberg, J. S., et al., *Nucleic acid detection with CRISPR-Cas13a/C2c2*. Science, 2017. 356(6336): p. 438-442.
15. Myhrvold, C., et al., *Field-deployable viral diagnostics using CRISPR-Cas13*. Science, 2018. 360(6387): p. 444-448.
16. Gootenberg, J. S., et al., *Multiplexed and portable nucleic acid detection platform with Cas13, Cas12a, and Csm6*. Science, 2018. 360(6387): p. 439-444.
17. Matsuda, K., et al., *Sensitive quantitative detection of commensal bacteria by rRNA-targeted reverse transcription-PCR*. Appl Environ Microbiol, 2007. 73(1): p. 32-9.
18. Lee, S. R., J. M. Chung, and Y. G. Kim, *Rapid one step detection of pathogenic bacteria in urine with sexually transmitted disease (STD) and prostatitis patient by multiplex PCR assay (mPCR)*. J Microbiol, 2007. 45(5): p. 453-9.
19. Schoepp, N. G., et al., *Rapid pathogen-specific phenotypic antibiotic susceptibility testing using digital LAMP quantification in clinical samples*. Sci Transl Med, 2017. 9(410).

The invention claimed is:

1. A method to detect a nucleic acid of a microorganism in a sample of an isolate or specimen including the microorganism, the method comprising
   contacting the sample with an antibiotic to provide an antibiotic-treated sample,
   quantitatively detecting in the antibiotic-treated sample an accessible nucleic acid of the microorganism, the detecting performed
      in the absence of a lysis treatment of the antibiotic-treated sample targeting the microorganism; or
      in the presence of a lysis treatment of the antibiotic-treated sample targeting the microorganism, the lysis treatment following pre-lysis mechanical separation of cells from the nucleic acid in the antibiotic-treated sample to remove the inaccessible nucleic acids from the sample,
the contacting and the quantitatively detecting performed to obtain a detected accessible antibiotic-treated nucleic acid concentration value of the microorganism in the antibiotic-treated sample.

2. The method of claim 1, wherein the method further comprises concurrently or after the contacting and before the detecting:
   performing an enhancing treatment of the antibiotic-treated sample.

3. The method of claim 1, the method further comprising detecting an accessible nucleic acid concentration ratio in the sample by
   comparing the detected accessible antibiotic-treated nucleic acid concentration value with a detected reference nucleic acid concentration value of a nucleic acid concentration parameter of the microorganism in the sample.

4. The method of claim 3, wherein the reference nucleic acid concentration value of the nucleic acid concentration parameter is an accessible control nucleic acid concentration value obtained by
   detecting an accessible nucleic acid concentration for the nucleic acid of the microorganism in a control sample of the isolate or specimen comprising the microorganism, the detecting in the control sample performed
      in the absence of a lysis treatment of the control sample when the detecting in the antibiotic-treated sample is performed in the absence of a lysis treatment of the antibiotic-treated sample; or
      in the presence of a lysis treatment of the control sample following pre-lysis mechanical separation of microorganism from the nucleic acid in the antibiotic-treated sample,
      when the detecting in the antibiotic-treated sample is performed in the presence of a lysis treatment of the antibiotic-treated sample following pre-lysis mechanical separation of the microorganism from the nucleic acid in the antibiotic-treated sample,
   the detecting an accessible nucleic acid concentration in the control sample is performed to provide the accessible control nucleic acid concentration value for the nucleic acid of the microorganism.

5. The method of claim 3, wherein the accessible reference nucleic acid concentration value is a total nucleic acid concentration value obtained by
   detecting the total nucleic acid concentration of the microorganism in a control sample of an isolate or specimen comprising the microorganism and either treated or not treated with the antibiotic, to provide the total nucleic acid concentration value for the nucleic acid of the microorganism.

6. The method of claim 3, wherein the detecting is performed in the presence of a lysis treatment of the antibiotic-treated sample targeting the microorganism, the lysis treatment following pre-lysis mechanical separation of the microorganism from the nucleic acid in the antibiotic-treated sample, and the method further comprises establishing susceptibility of the microorganism to the antibiotic when the accessible nucleic acid concentration ratio is above an accessible threshold of susceptibility.

7. The method of claim 6, wherein the reference nucleic acid concentration value of the nucleic acid concentration parameter is an accessible control nucleic acid concentration and wherein the accessible nucleic acid concentration ratio is more than 2 or less than 0.5.

8. The method of claim 7, wherein the duration of the contacting of the sample with an antibiotic is 20 minutes or less, and wherein the nucleic acid concentration ratio is alternatively selected from more than 2 or less than 0.5, more than 3 or less than 0.33, more than 5 or less than 0.2, more than 10 or less than 0.1, more than 15 or less than 0.067, or more than 20 or less than 0.05.

9. The method of claim 8, wherein the nucleic acid is DNA.

10. The method of claim 8, wherein the nucleic acid is RNA.

11. The method of claim 7, wherein the contacting of the sample with an antibiotic is performed for 30 minutes or less, and wherein the nucleic acid concentration ratio is more than 3 or less than 0.33, more than 5 or less than 0.2, more than 10 or less than 0.1, more than 15 or less than 0.067, or more than 20 or less than 0.05.

12. The method of claim 11, wherein the nucleic acid is DNA.

13. The method of claim 11, wherein the nucleic acid is RNA.

14. The method of claim 6, wherein the pre-lysis mechanical separation is performed by filtering the microorganism from the nucleic acid in the antibiotic-treated sample.

15. The method of claim 6, wherein the method further comprises purifying or extracting the nucleic acid from the antibiotic-treated sample before the detecting.

16. The method of claim 3, wherein the detecting is performed in the presence of a lysis treatment of the antibiotic-treated sample targeting the microorganism, the lysis treatment following pre-lysis separation of the microorganism from the nucleic acid in the antibiotic-treated sample, and the method further comprises establishing resistance of the microorganism to the antibiotic when the accessible nucleic acid concentration ratio is below a second accessible threshold of resistance.

17. The method of claim 1, wherein the quantitatively detecting is performed by performing RNA-seq and obtaining the accessible antibiotic-treated nucleic acid concentration value based on the sequence data.

18. The method of claim 1, wherein the quantitatively detecting is performed by performing DNA-seq and obtaining nucleic acid concentration ratio based on the sequence data.

19. The method of claim 1, wherein contacting the sample with an antibiotic is performed for up to 90 minutes.

20. The method of claim 1, wherein contacting the sample with an antibiotic is performed for up to 45 minutes.

21. The method of claim 1, wherein contacting the sample with an antibiotic is performed for up to 30 minutes.

22. The method of claim 1, wherein contacting the sample with an antibiotic is performed for up to 15 minutes.

23. The method of claim 1, wherein contacting the sample with an antibiotic is performed for up to 5 minutes.

24. The method of claim 1, wherein the detecting is performed by contacting the sample with a probe specific for a nucleic acid of the microorganism and/or for any nucleic acid complementary to the nucleic acid of the microorganism.

25. The method of claim 1, wherein the antibiotic is a beta-lactam.

26. The method of claim 1, wherein the antibiotic is a carbapenem.

27. The method of claim 1, wherein the contacting results in the antibiotic disrupting a cell envelope of the microorganism.

28. The method of claim 1, wherein the microorganism is *Neisseria gonorrhoeae*.

29. The method of claim 1, wherein the microorganism belongs to the family Enterobacteriaceae.

\* \* \* \* \*

SEQUENCE LISTING

```
<160> NUMBER OF SEQ ID NOS: 4

<210> SEQ ID NO 1
<211> LENGTH: 22
<212> TYPE: DNA
<213> ORGANISM: Artificial Sequence;
<220> FEATURE:
<223> OTHER INFORMATION: Synthetic polynucleotide

<400> SEQUENCE: 1
```

| | | |
|---|---|---|
| tgccgtaact tcgggagaag gc | | 22 |

<210> SEQ ID NO 2
<211> LENGTH: 18
<212> TYPE: DNA
<213> ORGANISM: Artificial Sequence;
<220> FEATURE:
<223> OTHER INFORMATION: Synthetic polynucleotide

<400> SEQUENCE: 2

| | | |
|---|---|---|
| ggcggtcaat ttcacgcg | | 18 |

<210> SEQ ID NO 3
<211> LENGTH: 22
<212> TYPE: DNA
<213> ORGANISM: Artificial Sequence;
<220> FEATURE:
<223> OTHER INFORMATION: Synthetic polynucleotide

<400> SEQUENCE: 3

| | | |
|---|---|---|
| tcaaggctca atgttcagtg tc | | 22 |

<210> SEQ ID NO 4
<211> LENGTH: 20
<212> TYPE: DNA
<213> ORGANISM: Artificial Sequence;
<220> FEATURE:
<223> OTHER INFORMATION: Synthetic polynucleotide

<400> SEQUENCE: 4

| | | |
|---|---|---|
| actgcgttct gaactgggtg | | 20 |